US011584748B2

(12) United States Patent
Nasveschuk et al.

(10) Patent No.: US 11,584,748 B2
(45) Date of Patent: Feb. 21, 2023

(54) SPIROCYCLIC COMPOUNDS

(71) Applicant: C4 Therapeutics, Inc., Watertown, MA (US)

(72) Inventors: Christopher G. Nasveschuk, Stoneham, MA (US); Fabian Dey, Basel (CH); Annick Goergler, Basel (CH); Bernd Kuhn, Reinach BL (CH); Roger Norcross, Basel (CH); Stephan Roever, Basel (CH); Philipp Schmid, Basel (CH)

(73) Assignee: C4 Therapeutics, Inc., Watertown, MA (US)

( * ) Notice: Subject to any disclaimer, the term of this patent is extended or adjusted under 35 U.S.C. 154(b) by 0 days.

(21) Appl. No.: 17/072,896

(22) Filed: Oct. 16, 2020

(65) Prior Publication Data
US 2021/0032245 A1 Feb. 4, 2021

Related U.S. Application Data

(63) Continuation of application No. PCT/US2019/027747, filed on Apr. 16, 2019.

(30) Foreign Application Priority Data

Apr. 16, 2018 (EP) .................................... 18167561
Apr. 19, 2018 (EP) .................................... 18168269

(51) Int. Cl.
C07D 471/10 (2006.01)
A61K 31/438 (2006.01)
C07D 519/00 (2006.01)

(52) U.S. Cl.
CPC ......... *C07D 471/10* (2013.01); *C07D 519/00* (2013.01)

(58) Field of Classification Search
CPC ...... C07D 471/10; A61K 31/438; A61P 35/00
USPC ............................................ 546/16; 514/278
See application file for complete search history.

(56) References Cited

U.S. PATENT DOCUMENTS

| | | | |
|---|---|---|---|
| 5,635,517 A | 6/1997 | Muller et al. | |
| 6,045,501 A | 4/2000 | Elsayed et al. | |
| 6,306,663 B1 | 10/2001 | Kenten et al. | |
| 6,315,720 B1 | 11/2001 | Williams et al. | |
| 6,395,754 B1 | 5/2002 | Muller et al. | |
| 6,561,976 B2 | 5/2003 | Elsayed et al. | |
| 6,561,977 B2 | 5/2003 | Williams et al. | |
| 6,755,784 B2 | 6/2004 | Williams et al. | |
| 6,869,399 B2 | 3/2005 | Williams et al. | |
| 6,908,432 B2 | 6/2005 | Elsayed et al. | |
| 7,041,298 B2 | 5/2006 | Deshaies et al. | |
| 7,141,018 B2 | 11/2006 | Williams et al. | |
| 7,208,157 B2 | 4/2007 | Deshaies et al. | |
| 7,230,012 B2 | 6/2007 | D-Angio et al. | |
| 7,820,697 B2 | 10/2010 | Man et al. | |
| 7,874,984 B2 | 1/2011 | Elsayed et al. | |
| 7,959,566 B2 | 6/2011 | Williams et al. | |
| 8,204,763 B2 | 6/2012 | Elsayed et al. | |
| 8,315,886 B2 | 11/2012 | Williams et al. | |
| 8,589,188 B2 | 11/2013 | Elsayed et al. | |
| 8,626,531 B2 | 1/2014 | Williams et al. | |
| 8,673,939 B2 | 3/2014 | Zeldis | |
| 8,735,428 B2 | 5/2014 | Zeldis | |
| 8,741,929 B2 | 6/2014 | Zeldis | |
| 8,828,427 B2 | 9/2014 | Tutino et al. | |
| 9,056,120 B2 | 6/2015 | Zeldis | |
| 9,101,621 B2 | 8/2015 | Zeldis | |
| 9,101,622 B2 | 8/2015 | Zeldis | |
| 9,125,915 B2 | 9/2015 | Miyoshi et al. | |
| 9,206,142 B2 | 12/2015 | Shipps, Jr. et al. | |
| 9,249,161 B2 | 2/2016 | Albrecht et al. | |
| 10,351,568 B2 | 7/2019 | Finley et al. | |
| 10,646,575 B2 | 5/2020 | Phillips et al. | |
| 10,660,968 B2 | 5/2020 | Phillips et al. | |
| 10,849,982 B2 | 12/2020 | Phillips et al. | |
| 10,905,768 B1 | 2/2021 | Phillips et al. | |
| 2006/0069067 A1 | 3/2006 | Bhatnagar et al. | |
| 2012/0071459 A1 | 3/2012 | Christensen, IV et al. | |
| 2013/0190340 A1 | 7/2013 | Hedstrom et al. | |
| 2014/0302523 A1 | 10/2014 | Crews et al. | |
| 2014/0356322 A1 | 12/2014 | Crews et al. | |
| 2015/0119435 A1 | 4/2015 | Crews et al. | |
| 2015/0274738 A1 | 10/2015 | Gray et al. | |
| 2015/0291562 A1 | 10/2015 | Crew et al. | |
| 2016/0016966 A1 | 1/2016 | Amans et al. | |

(Continued)

FOREIGN PATENT DOCUMENTS

BR PI1100318 A2 5/2013
CN 103421061 A 12/2013

(Continued)

OTHER PUBLICATIONS

Agafonov Roman et al., Poster Presentation titled "Quantitative and high throughput method for measuring complex formation between target proteins and E3 ubiquitin ligase", EMBO, Sep. 16, 2017.
Bartlett, et al. "The evolution of thalidomide and its IMiD derivatives as anticancer agents." Nat Rev Cancer 2004, 4(4):312-322.
Berndsen et al. "New insights into ubiquitin E3 ligase mechanism" Nat. Struct. Mol. Biol. 2014, 21:301-307.
Bondeson et al. "Catalytic in vivo protein knockdown by small-molecule PROTACs" Nature Chemical Biology 2015, 11:611-617.
Buckley et al. "HaloPROTACS: use of small molecule protacs to induce degradation of halotag fusion proteins" ACS Chemical Biology 2015, 10:1831-1837.

(Continued)

*Primary Examiner* — Charanjit Aulakh
(74) *Attorney, Agent, or Firm* — Knowles Intellectual Property Strategies, LLC

(57) ABSTRACT

The present invention provides compounds which bind to the ubiquitously expressed E3 ligase protein cereblon (CRBN) and their use for the treatment of abnormal cellular proliferation. The present invention also provides compounds that may be used as synthetic intermediates in the synthesis of bifunctional compounds used for targeted protein degradation.

11 Claims, No Drawings

(56) References Cited

U.S. PATENT DOCUMENTS

| | | |
|---|---|---|
| 2016/0022642 A1 | 1/2016 | Crews et al. |
| 2016/0045607 A1 | 2/2016 | Crew et al. |
| 2016/0046661 A1 | 2/2016 | Gray et al. |
| 2016/0058872 A1 | 3/2016 | Crew et al. |
| 2016/0176916 A1 | 6/2016 | Bradner et al. |
| 2016/0214972 A1 | 7/2016 | Jin et al. |
| 2016/0272639 A1 | 9/2016 | Crew et al. |
| 2017/0008904 A1 | 1/2017 | Crew et al. |
| 2017/0037004 A1 | 2/2017 | Crew et al. |
| 2017/0065719 A1 | 3/2017 | Qian et al. |
| 2018/0015087 A1 | 1/2018 | Liu et al. |
| 2018/0085465 A1 | 3/2018 | Bradner et al. |
| 2020/0140456 A1 | 5/2020 | Phillips et al. |
| 2020/0207733 A1 | 7/2020 | Norcross et al. |
| 2020/0207764 A1 | 7/2020 | Norcross et al. |
| 2020/0207783 A1 | 7/2020 | Norcross et al. |
| 2021/0009559 A1 | 1/2021 | Henderson et al. |

FOREIGN PATENT DOCUMENTS

| | | |
|---|---|---|
| WO | WO 1998/011111 A1 | 3/1998 |
| WO | WO 2002/059106 A1 | 8/2002 |
| WO | WO 2003/020721 A1 | 3/2003 |
| WO | WO 2006/102557 A2 | 9/2006 |
| WO | WO 2008/027542 A2 | 3/2008 |
| WO | WO 2008/033567 A1 | 3/2008 |
| WO | WO 2008/039489 A2 | 4/2008 |
| WO | WO 2008/115516 A2 | 9/2008 |
| WO | WO 2008/122038 A1 | 10/2008 |
| WO | WO 2009/042177 A1 | 4/2009 |
| WO | WO 2009/139880 A1 | 11/2009 |
| WO | WO 2009/145899 A1 | 12/2009 |
| WO | WO 2010/053732 A1 | 5/2010 |
| WO | WO 2010/107485 A1 | 9/2010 |
| WO | WO 2011/025690 A1 | 3/2011 |
| WO | WO 2011/097218 A1 | 8/2011 |
| WO | WO 2011/143669 A2 | 11/2011 |
| WO | WO 2012/079022 A1 | 6/2012 |
| WO | WO 2012/176123 A1 | 12/2012 |
| WO | WO 2012/178208 A2 | 12/2012 |
| WO | WO 2013/020557 A1 | 2/2013 |
| WO | WO 2013/059215 A1 | 4/2013 |
| WO | WO 2013/063560 A2 | 5/2013 |
| WO | WO 2013/106643 A2 | 7/2013 |
| WO | WO 2013/106646 A2 | 7/2013 |
| WO | WO 2013/124026 A1 | 8/2013 |
| WO | WO 2013/170147 A1 | 11/2013 |
| WO | WO 2014/145887 A1 | 9/2014 |
| WO | WO 2015/031036 A1 | 3/2015 |
| WO | WO 2015/160845 A1 | 10/2015 |
| WO | WO 2016/011906 A1 | 1/2016 |
| WO | WO 2016/022644 A1 | 2/2016 |
| WO | WO 2016/065139 A1 | 4/2016 |
| WO | WO 2016/105518 A1 | 6/2016 |
| WO | WO 2016/118666 A1 | 7/2016 |
| WO | WO 2016/146985 A1 | 9/2016 |
| WO | WO 2016/149668 A1 | 9/2016 |
| WO | WO 2016/169989 A1 | 10/2016 |
| WO | WO 2016/191178 A1 | 12/2016 |
| WO | WO 2016/197032 A1 | 12/2016 |
| WO | WO 2016/197114 A1 | 12/2016 |
| WO | WO 2017/007612 A1 | 1/2017 |
| WO | WO 2017/011371 A1 | 1/2017 |
| WO | WO 2017/011590 A1 | 1/2017 |
| WO | WO 2017/024317 A2 | 2/2017 |
| WO | WO 2017/024318 A1 | 2/2017 |
| WO | WO 2017/024319 A1 | 2/2017 |
| WO | WO 2017/030814 A1 | 2/2017 |
| WO | WO 2017/046036 A1 | 3/2017 |
| WO | WO 2017/079267 A1 | 5/2017 |
| WO | WO 2017/117473 A1 | 7/2017 |
| WO | WO 2017/161119 A1 | 9/2017 |
| WO | WO 2017/176708 A1 | 10/2017 |
| WO | WO 2017/176957 A1 | 10/2017 |
| WO | WO 2017/176958 A1 | 10/2017 |
| WO | WO 2017/180417 A1 | 10/2017 |
| WO | WO 2017/189386 A1 | 11/2017 |
| WO | WO 2017/197036 A1 | 11/2017 |
| WO | WO 2017/197046 A1 | 11/2017 |
| WO | WO 2017/197051 A1 | 11/2017 |
| WO | WO 2017/197055 A1 | 11/2017 |
| WO | WO 2017/197056 A1 | 11/2017 |
| WO | WO 2017/197240 A1 | 11/2017 |
| WO | WO 2017/201069 A1 | 11/2017 |
| WO | WO 2017/201449 A1 | 11/2017 |
| WO | WO 2018/005591 A1 | 1/2018 |
| WO | WO 2018/023029 A1 | 2/2018 |
| WO | WO 2018/051107 A1 | 3/2018 |
| WO | WO 2018/052945 A1 | 3/2018 |
| WO | WO 2018/052949 A1 | 3/2018 |
| WO | WO 2018/053354 A1 | 3/2018 |
| WO | WO 2018/071606 A1 | 4/2018 |
| WO | WO 2018/085247 A1 | 5/2018 |
| WO | WO 2018/102067 A2 | 6/2018 |
| WO | WO 2018/102725 A1 | 6/2018 |
| WO | WO 2018/118598 A1 | 6/2018 |
| WO | WO 2018/118947 A1 | 6/2018 |
| WO | WO 2018/119357 A1 | 6/2018 |
| WO | WO 2018/119441 A1 | 6/2018 |
| WO | WO 2018/119448 A1 | 6/2018 |
| WO | WO 2018/140809 A1 | 8/2018 |
| WO | WO 2018/144649 A1 | 8/2018 |
| WO | WO 2018/169777 A1 | 9/2018 |
| WO | WO 2018/183411 A1 | 10/2018 |
| WO | WO 2018/189554 A1 | 10/2018 |
| WO | WO 2018/191199 A1 | 10/2018 |
| WO | WO 2018/226542 A1 | 12/2018 |
| WO | WO 2018/237026 A1 | 12/2018 |
| WO | WO 2019/032632 A1 | 2/2019 |
| WO | WO 2019/060693 A1 | 3/2019 |
| WO | WO 2019/060742 A1 | 3/2019 |
| WO | WO 2019/140387 A1 | 7/2019 |
| WO | WO 2019/152440 A1 | 8/2019 |
| WO | WO 2019/165229 A1 | 8/2019 |
| WO | WO 2019/199816 A1 | 10/2019 |
| WO | WO 2019/213005 A1 | 11/2019 |
| WO | WO 2020/006262 A1 | 1/2020 |
| WO | WO 2020/006264 A1 | 1/2020 |
| WO | WO 2020/006265 A1 | 1/2020 |
| WO | WO 2020/010227 A1 | 1/2020 |
| WO | WO 2020/023851 A1 | 1/2020 |
| WO | WO 2020/041331 A1 | 2/2020 |
| WO | WO 2020/051564 A1 | 3/2020 |
| WO | WO 2020/081450 A1 | 4/2020 |

OTHER PUBLICATIONS

Buckley et al. "Small-molecule control of intracellular protein levels through modulation of the ubiquitin proteasome system" Angewandte Reviews, 2014, 53:2312-2330.

Buckley et al. "Targeting the Von Hippel-Lindau E3 ubiquitin ligase using small molecules to disrupt the Vhl/Hif-1alpha interaction" J. Am. Chem. Soc. 2012, 134:4465-4468.

Burkhard et al. "Synthesis and stability of oxetane analogs of thalidomide and lenalidomide" Organic Letters 2013, 15(7):4312-4315.

Chamberlain et al. "Structure of the human cereblon-DDB1-lenalidomide complex reveals basis for responsiveness to thalidomide analogs" Nature Structural and Molecule Biology, 2014, 21(9):803-809.

Chang, X. and Stewart, K. A. "What is the functional role of the thalidomide binding protein cereblon?" Int J Biochem Mol Bio. 2011, 2(3):287-294.

Contino-Pepin, et al., "Preliminary biological evaluations of new thalidomide analogues for multiple sclerosis application", Bioorganic & Medicinal Chemistry Letters, 2009, 19(3), 878-881.

Crews, C. M. "Targeting the undruggable proteome: the small molecules of my dreams" Chemistry and Biology 2010, 17(6):551-555.

Deshaies et al. "Ring domain E3 ubiquitin ligases." Ann. Rev. Biochem. 2009, 78:399-434.

(56) References Cited

OTHER PUBLICATIONS

Elam W.A., et al, Poster Presentation titled "Application of biophysical techniques to the targeted protein degradation therapeutic strategy", Sep. 24, 2017.
Faden et al. "Generic tools for conditionally altering protein abundance and phenotypes on demain" Biol. Chem. 2014, 395(7-8):737-762.
Fischer et al. "Structure of the DDB1-CRBN E3 ubiquitin ligase in complex with thalidomide" Nature 2014, 512:49-53.
Fischer et al. "The molecular basis of CRL4DDB2/CSA ubiquitin ligase architecture, targeting, and activation," Cell 2011, 147:1024-1039.
Fisher S., Presentation titled "Targeted protein degradation", Targeted Protein Degradation Summit, Boston, MA, Oct. 24-25, 2018.
Fisher et al., "Targeted protein degradation and the enzymology of degraders", Current Opinion of Chemical Biology, 2018, 44, 47-55.
Gosink et al. "Redirecting the specificity of ubiquitination by modifying ubiquitin-conjugating enzymes" Proc. Natl. Acad. Sci. USA 1995, 92:9117-9121.
Gustafson et al. "Small-molecule-mediated degradation of the androgen receptor through hydrophobic tagging" angewandte chemie 2015, 54:9659-9662.
Henderson C., Presentation titled "Development of AchillesTAG degradation systems and their application to control CAR-T activity", ChemBio in the hub, Cambridge, MA. Oct. 22, 2018.
Hines et al. "Posttranslational protein knockdown couple to receptor tyrosine kinase activation with phosphoPROTACs" PNAS 2013, 110(22):8942-8947.
International Search Report and Written Opinion for PCT/US2019/027747 dated Jul. 25, 2019.
Ito et al., "Identification of a Primary Target of thalidomide teratogenicity", Science, 2010, 327(5971), 1345-1350, XP0055062167.
Itoh et al. "Protein knockdown using methyl bestatin-ligand hybrid molecules: design and synthesis of inducers of ubiquitination-mediated degradation of cellular retinoic acid-binding proteins" Journal of the American Chemical Society 2010, 132(16), 5820-5826.
Jacques et al. "Differentiation of anti-inflammatory and antitumorigenic properties of stabilized enantiomers of thalidomide analogs" PNAS, 2015, 112(12): E1471-E1479.
Kronke et al. "Lenalidomide causes selective degradation of IKZF1 and IKZF3 in Multiple Myeloma Cells" Science 2014, 343(6168):301-305.
Kronke et al. "Lenalidomide induces ubiquitination and degradation of CDK1[alpha] in del(5q) MDS" Nature 2015, 523(7559):183-188.
Lai et al. "Modular PROTAC design for the degradation of oncogenic BCR-ABL" Angewandte Chemie International Edition 2016, 55:807-810.
Lee et al. "Targeted degradation of the aryl hydrocarbon receptor by the PROTAC approach: a useful chemical genetic tool" ChemBioChem 2007, 8:2058-2062.
Li et al. "Genome-wide and functional annotation of human E3 ubiquitin ligases identifies MULAN, a mitochondrial E3 that regulates the organelle's dynamics and signaling" PLOS One 2008, 3:1487.
Liu et al. "Design and biological characterization of hybrid compounds of curcumin and thalidomide for multiple myeloma" Organic and Biomolecular Chemistry 2013, 11:4757.
Lu et al. "Hijacking the E3 Ubiquitin ligase cereblon to efficiently target BRD4" Chemistry and Biology 2015, 22(6):755-763.
Lu et al. "The myeloma drug lenalidomide promotes the cereblon-dependent destruction of Ikaros proteins" Science 2014, 343:305-309.
Martiniani, R. et al., "Biological activity of lenalidomide and its underlying therapeutic effects in multiple myeloma", Adv Hematol, 2012, 2012, 842945.
Nasveschuk C., Presentation titled "Advances in the medicinal chemistry of targeted protein degradation", Aug. 7, 2018.

Nawaz et al. "Proteasome-Dependent Degradation of the Human Estrogen Receptor" Proc. Natl. Acad. Sci. USA 1999, 96:1858-1862.
Neklesa et al. "Small-molecule hydrophobic tagging-induced degradation of HaloTag fusion proteins." Nat Chem Biol 2011, 7(8):538-543.
Patel, J., Poster Presentation titled "Diverse Utility of Targeted Protein Degradation at C4 Therapeutics", Sep. 17, 2017.
Phillips A., Presentation titled "Targeted Protein Degradation", Applied Pharmaceutical Chemistry, Cambridge, MA. Apr. 5, 2018.
Phillips A., Presentation titled "Small molecule driven targeted protein degradation", ChemBio in the hub, Cambridge, MA. Oct. 22, 2018.
Raina et al. "Chemical Inducers of Targeted Protein Degradation" Journal of Biological Chemistry 2010, 285:11057-11060.
Rodriguez-Gonzalez et al. "Targeting steroid hormone receptors for ubiquitination and degradation in breast and prostate cancer" Oncogene 2008, 27:7201-7211.
Ruchelman et al. "Isosteric analogs of lenalidomide and pomalidomide: Synthesis and biological activity" Bioorganic and Medicinal Chemistry Letters 2012, 23:360-365.
Sakamoto et al. "Development of Protacs to Target Cancer-Promoting Proteins for Ubiquitination and Degradation" Molecular and Cellular Proteomics 2003, 2(12):1350-1357.
Sakamoto et al. "Protacs: chimeric molecules that target proteins to the Skp1-Cullin-F box complex for ubiquitination and degradation" PNAS 2001, 98(15):8554-8559.
Schneekloth et al. "Chemical approaches to controlling intracellular protein degradation" Chembiochem 2005, 6(1):40-46.
Schneekloth et al. "Chemical genetic control of protein levels: selective in vivo targeted degradation" Journal of the American Chemical Society 2004, 126(12):3748-3754.
Schneekloth et al. "Targeted intracellular protein degradation induced by a small molecule: en route to chemical proteomics" Bioorganic and Medicinal Chemistry Letters 2008, 18:5904-5908.
Shoji, et al., "Modified DNA aptamer that binds the (r)-isomer of a thalidomide derivative with high enantioselectivity", J. Am. Chem. Soc., 2007, 129, 1456-1464.
Smith et al. "Targeted intracellular protein degradation induced by a small molecule: en route to chemical proteomics" Bioorg. Med. Chem. Lett. 2008, 18(22):5904-5908.
Spratt et al. "RBR E3 ubiquitin ligases: new structures, new insights, new questions." Biochem. 2014, 458:421-437.
Terpos, E. et al., "Pomalidomide: a novel drug to treat relapsed and refractory multiple myeloma", Oncotargets and Therapy, 2013, 6, 531-538.
Toure et al. "Small-Molecule PROTACs: New Approaches to Protein Degradation" Angewandte Chemie International Edition 2016, 55:1966-1973.
Vassilev et al. "In Vivo Activation of the P53 pathway by small-molecule antagonists of MDM2" Science 2004, 303:844-848.
Vieux Ellen et al., Poster Presentation titled "Measuring Small Molecule Induced Ubiquitination of Proteins", EMBO, Sep. 18, 2017.
Wang et al. "Roles of F-box proteins in cancer." Nat. Rev. Cancer 2014, 14:233-347.
Winter et al. "Phthalimide conjugation as a strategy for in vivo target protein degradation", Science, 2015, 348(6241):1376-1381.
Zeid Rhamy Presentation titled "Targeted protein degradation as a novel therapeutic approach", Gordon Research Conference, Jun. 26, 2017.
Zengerle et al. "Selective small molecule induced degradation of the bet bromodomain protein BRD4," ACS Chem. Biol., 2015, 10:1770-1777.
Zhou et al. "Harnessing the ubiquitination machinery to target the degradation of specific cellular proteins" Molecular Cell, 2000, 6:751-756.
U.S. Appl. No. 16/874,475, filed May 15, 2020, Phillips et al.
U.S. Appl. No. 16/882,236, filed May 22, 2020, Phillips et al.
U.S. Appl. No. 17/103,621, filed Nov. 24, 2020, Nasveschuk et al.
U.S. Appl. No. 17/107,781, filed Nov. 30, 2020, Phillips et al.
U.S. Appl. No. 17/121,389, filed Dec. 14, 2020, Phillips et al.
U.S. Appl. No. 17/164,446, filed Feb. 1, 2021, Phillips et al.

(56) References Cited

OTHER PUBLICATIONS

U.S. Appl. No. 17/192,634, filed Mar. 4, 2021, Nasveschuk et al.
C4 Therapeutics Presentation Patel—"Advances in the Medicinal Chemistry of Targeted Protein Degradation," 24 pages, Sep. 27, 2018.
Corson et al. "Design and applications of bifunctional small molecules: Why two heads are better than one" ACS Chemical Biology 2008, 3(11): 677-692.
International Application No. PCT/US19/35223, filed Jun. 3, 2019; International Search Report and Written Opinion dated Oct. 31, 2019, 10 pages.
Prevet et al. "Microwave-assisted synthesis of functionalized spirohydantoins as 3-D privileged fragments for scouting the chemical space," Tetrahedron Letters, May 18, 2016, vol. 57, pp. 2888-2894.
Pubmed Compound Summary for CID 51072057, Tert-butyl 4-[9-(4-cyanophenyl)-3-(3,5-dichlorophenyl)-1-methyl-2,4-dioxo-1,3,7-triazaspiro[4,4]nonan-7-yl]benzoate, U.S. National Library of Medicine, May 3, 2011; pp. 1-17; p. 2 (https://pubchem.ncbi.nlm.nih.gov/compound/51072057).
Pubmed Compound Summary for CID 45792656, 7-Cyclopropyl-1,3,7-triazaspiro[4,4]nonane-2m4-dione, U.S. National Library of Medicine, Jun. 21, 2010, pp. 1-13; (https://pubchem.ncbi.nlm.nih.gov/compound/45792656).
Pubmed Compound Summary for CID 70731020, 7-(1,2,4)Triazolo[4,3-a]pyridine-3-yl)-2,7-diazaspiro[4,4]nonane-1,3-dione, U.S. National Library of Medicine, Mar. 4, 2013, pp. 1-11; (https://pubchem.ncbi.nlm.nih.gov/compound/70731020).
U.S. Appl. No. 17/351,935, filed Jun. 18, 2021, Phillips et al.
U.S. Appl. No. 17/465,583, filed Sep. 2, 2021, Nasveschuk et al.
U.S. Appl. No. 17/498,617, filed Oct. 11, 2021, Henderson et al.
U.S. Appl. No. 17/524,558, filed Nov. 11, 2021, Phillips et al.
U.S. Appl. No. 17/576,582, filed Jan. 14, 2022, Norcross et al.
U.S. Appl. No. 17/723,199, filed Apr. 18, 2022, Henderson et al.
U.S. Appl. No. 16/882,236, filed Nov. 30, 2020, Philips et al.
U.S. Appl. No. 16/903,237, filed Oct. 1, 2020, Jaeschke et al.
U.S. Appl. No. 17/103,621, filed Mar. 11, 2021, Nasveschuk et al.
U.S. Appl. No. 17/192,634, filed Jul. 1, 2021, Nasveschuk et al.
U.S. Appl. No. 17/541,035, filed Mar. 31, 2022, Nasveschuk et al.

SPIROCYCLIC COMPOUNDS

CROSS-REFERENCE TO RELATED APPLICATIONS

This application is a continuation of International Application No. PCT/US2019/027747, filed in the International Patent Cooperation Treaty, U.S. Receiving Office on Apr. 16, 2019, which claims the benefit of European Patent Application No. EP18167561, filed Apr. 16, 2018, and European Patent Application No. EP18168269, filed Apr. 19, 2018. The entirety of these applications is hereby incorporated by reference herein for all purposes.

FIELD OF THE INVENTION

The present invention provides compounds which bind to the ubiquitously expressed E3 ligase protein cereblon (CRBN), which can alter the substrate specificity of the CRBN E3 ubiquitin ligase complex, resulting in breakdown of intrinsic downstream proteins. The present invention also provides compounds that can be used as synthetic intermediates in the preparation of bifunctional compounds for use in targeted protein degradation. The present compounds are thus useful for the treatment or prophylaxis of abnormal cellular proliferation, including tumors and cancer.

BACKGROUND OF THE INVENTION

Protein degradation is a highly regulated and essential process that maintains cellular homeostasis. The selective identification and removal of damaged, misfolded, or excess proteins is achieved via the ubiquitin-proteasome pathway (UPP). The UPP is central to the regulation of almost all cellular processes, including antigen processing, apoptosis, biogenesis of organelles, cell cycling, DNA transcription and repair, differentiation and development, immune response and inflammation, neural and muscular degeneration, morphogenesis of neural networks, modulation of cell surface receptors, ion channels and the secretory pathway, the response to stress and extracellular modulators, ribosome biogenesis and viral infection.

Covalent attachment of multiple ubiquitin molecules by an E3 ubiquitin ligase to a terminal lysine residue marks the protein for proteasome degradation, where the protein is digested into small peptides and eventually into its constituent amino acids that serve as building blocks for new proteins. Defective proteasomal degradation has been linked to a variety of clinical disorders including Alzheimer's disease, Parkinson's disease, Huntington's disease, muscular dystrophies, cardiovascular disease, and cancer among others.

There are over 600 E3 ubiquitin ligases which facilitate the ubiquitination of different proteins in vivo, which can be divided into four families: HECT-domain E3s, U-box E3s, monomeric RING E3s and multi-subunit E3s. See generally Li et al. (*PLOS One*, 2008, 3, 1487) titled "Genome-wide and functional annotation of human E3 ubiquitin ligases identifies MULAN, a mitochondrial E3 that regulates the organelle's dynamics and signaling."; Berndsen et al. (*Nat. Struct. Mol. Biol.*, 2014, 21, 301-307) titled "New insights into ubiquitin E3 ligase mechanism"; Deshaies et al. (*Ann. Rev. Biochem.*, 2009, 78, 399-434) titled "RING domain E3 ubiquitin ligases."; Spratt et al. (*Biochem.* 2014, 458, 421-437) titled "RBR E3 ubiquitin ligases: new structures, new insights, new questions."; and Wang et al. (*Nat. Rev. Cancer*, 2014, 14, 233-347) titled "Roles of F-box proteins in cancer."

Cereblon is a protein that in humans is encoded by the CRBN gene. CRBN orthologs are highly conserved from plants to humans, which underscores its physiological importance. Cereblon forms part of an E3 ubiquitin ligase protein complex which interacts with damaged DNA binding protein 1 (DDB1), forming an E3 ubiquitin ligase complex with Cullin 4 (CUL4A) and the E2-binding protein ROC1 (also known as RBX1) where it functions as a substrate receptor to select proteins for ubiquitination. Through a mechanism that has not been completely elucidated, cereblon ubiquitination of target proteins results in increased levels of fibroblast growth factor 8 (FGF8) and fibroblast growth factor 10 (FGF10). FGF8 in turn regulates a number of developmental processes, such as limb and auditory vesicle formation. The net result is that this E3 ubiquitin ligase complex is important for limb outgrowth in embryos. In the absence of cereblon, DDB1 forms a complex with DDB2 that functions as a DNA damage-binding protein.

In unrelated parallel research, Ito et al. (*Science* 2010, 327, 1345-1350) titled "Identification of a Primary Target of Thalidomide Teratogenicity", described that cereblon is a thalidomide binding protein. The study revealed that thalidomide-cereblon binding in vivo may be responsible for thalidomide teratogenicity. After the discovery that thalidomide causes teratogenicity in the mid-1960's, the compound and related structures were notwithstanding found to be useful as anti-inflammatory, anti-angiogenic and anti-cancer agents (see Bartlett et al. (*Nat. Rev. Cancer* 2004, 4, 314-322) titled "The Evolution of Thalidomide and Its Imid Derivatives as Anticancer Agents"). Thalidomide has been approved for the treatment of certain neoplastic diseases, including multiple myeloma, and is currently under investigation for use in treating a variety of other types of cancer along with the structural derivatives lenalidomide and pomalidomide (see Martiniani, R. et al. "Biological activity of lenalidomide and its underlying therapeutic effects in multiple myeloma" Adv Hematol, 2012, 2012:842945; and Terpos, E. et al. "Pomalidomide: a novel drug to treat relapsed and refractory multiple myeloma" Oncotargets and Therapy, 2013, 6:531).

The disclosure that thalidomide binds to the cereblon E3 ubiquitin ligase led to research to investigate incorporating thalidomide and certain derivatives into compounds for the targeted destruction of proteins. Celgene has disclosed imids for similar uses, including those in U.S. Pat. Nos. 6,045,501; 6,315,720; 6,395,754; 6,561,976; 6,561,977; 6,755,784; 6,869,399; 6,908,432; 7,141,018; 7,230,012; 7,820,697; 7,874,984; 7,959,566; 8,204,763; 8,315,886; 8,589,188; 8,626,531; 8,673,939; 8,735,428; 8,741,929; 8,828,427; 9,056,120; 9,101,621; and 9,101,622.

Patent applications filed by C4 Therapeutics, Inc., that describe compounds capable of binding to an E3 ubiquitin ligase and a target protein for degradation include: WO 2017/197051 titled "Amine-Linked C3-Glutarimide Degronimers for Target Protein Degradation"; WO 2017/197055 titled "Heterocyclic Degronimers for Target Protein Degradation"; WO 2017/197036 titled "Spirocyclic Degronimers for Target Protein Degradation"; WO 2017/197046 titled "C3-Carbon Linked Glutarimide Degronimers for Target Protein Degradation"; WO 2017/197056 titled "Bromodomain Targeting Degronimers for Target Protein Degradation."; and WO 2018/237026 titled "N/O-Linked Degrons and Degronimers for Protein Degradation."

Other patent applications that describe protein degrading compounds include: WO 2015/160845; WO 2016/105518; WO 2016/118666; WO 2016/149668; WO 2016/197032; WO 2016/197114; WO 2017/007612; WO 2017/011371; WO 2017/011590; WO 2017/030814; WO 25 2017/046036; WO 2017/176708; WO 2017/176957; WO 2017/180417; WO 2018/052945; WO 2018/052949; WO 2018/053354; WO 2018/071606; WO 2018/102067; WO 2018/102725; WO 2018/118598; WO 2018/119357; WO 2018/119441; WO 2018/119448; WO 2018/140809; WO 2018/144649; and WO 2018/226542. Other relevant patent applications include: WO 2013/020557; WO 2013/063560; WO 2013/106643; WO 2016/011906; WO 2017/024318; and WO 2017/117473.

Additional compound publications include: US 2012/071459; WO 2003/020721; WO 2011/025690; WO 2012/176123; WO 2013/020557; WO 2013/063560; WO 2013/106643; WO 2013/124026; WO 2015/031036; WO 2015/160845; WO 2016/011906; WO 2016/022644; WO 2016/105518; WO 2017/007612; WO 2017/024318; WO 2017/117473; WO 2017/189386; WO 2018/005591; U.S. Pat. No. 9,206,142;

There is a need for new compounds and methods of treatment that bind to the E3 ligase protein cereblon for use in the treatment of various medical conditions, notably abnormal cellular proliferation. There is also a need for new compounds that may be used in the preparation of bifunctional molecules that are used in the degradation of proteins that are involved in disease processes.

SUMMARY OF THE INVENTION

In a first aspect, compounds and their uses and manufacture are provided that bind to cereblon and enhance the ubiquitination of proteins by a cereblon-containing E3 ubiquitin ligase complex, which results in protein degradation and thus is useful for the treatment of abnormal cellular proliferation and other disorders as described herein. In a second aspect, compounds are provided that contain a chemical moiety capable of binding to cereblon, which can be used as synthetic intermediates in the preparation of bifunctional compounds that cause degradation of a selected protein via the ubiquitin proteasome pathway (UPP).

The compounds described herein can be administered to a host, for example, a human, in need thereof, in an effective amount, optionally as a pharmaceutically acceptable salt, and optionally in a pharmaceutically acceptable composition. The compounds can be administered for any therapeutic indication which can be treated by modulating the function or activity of the cereblon-containing E3 Ubiquitin Ligase Protein Complex, including but not limited to the treatment of abnormal cell proliferation, such as cancer or a tumor. In certain embodiments, the compounds as described herein can modulate the natural activity of cereblon.

The invention includes new compounds of Formula Ia, Formula Ib, Formula II, Formula IIIa, Formula IIIb, Formula IV, Formula V, Formula VI, Formula VIII, Formula IX, Formula X, Formula XI, and Formula XII. In addition, the invention includes the use of compounds generally in Formula VII and Formula XIII for the treatment of a therapeutic condition that can be treated by modulating the function or activity of the cereblon-containing E3 Ubiquitin Ligase Protein Complex. The invention also includes the use of compounds generally in Formula XIV and Formula XV in the preparation of bifunctional compounds that degrade a target protein by the ubiquitin proteasome pathway (UPP). The invention also includes compounds of Formula XIV-a, Formula XIV-b, Formula XIV-c, Formula XIV-d, Formula XIV-e, Formula XIV-f, Formula XIV-g, Formula XIV-h, Formula XIV-i, Formula XIV-j, Formula XIV-k, Formula XIV-l, Formula XIV-m, Formula XIV-n, Formula XIV-o, Formula XIV-p, Formula XIV-q, Formula XIV-r, Formula XIV-s, Formula XIV-t, Formula XIV-u, Formula XIV-v, Formula XIV-w, Formula XIV-x, Formula XV-a, Formula XV-b, Formula XV-c, Formula XV-d, Formula XV-e, Formula XV-f, Formula XV-g, Formula XV-h, Formula XV-i, Formula XV-j, Formula XV-k, Formula XV-m, Formula XV-n, Formula XV-o, Formula XV-p, Formula XV-q, Formula XV-r, Formula XV-s, and Formula XV-t.

In one aspect, a compound is provided of Formula Ia or Formula Ib:

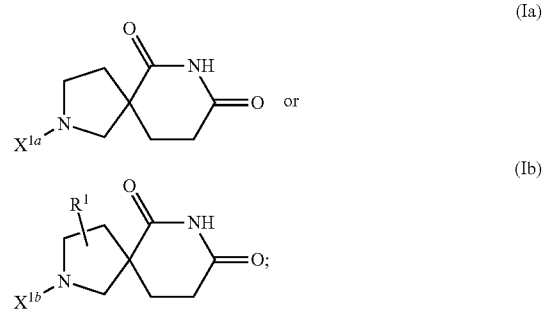

or a pharmaceutically acceptable salt thereof;
wherein:
$X^{1a}$ is selected from aryl and aryl substituted by $R^{2a}$;
$X^{1b}$ is selected from aryl and aryl substituted by $R^{2b}$;
$R^1$ is absent or =O;
$R^{2a}$ is selected from the group consisting of: —C(=O)—O—$C_{1-6}$-alkyl; —NH—C(=O)—$C_{1-6}$-alkyl; —NH$_2$; —OH; and —NO$_2$; and
$R^{2b}$ is selected from the group consisting of: —C(=O)—O—$C_{1-6}$-alkyl; —NH—C(=O)—$C_{1-6}$-alkyl; —NH$_2$; and —NO$_2$.

In another aspect, a compound is provided of Formula II:

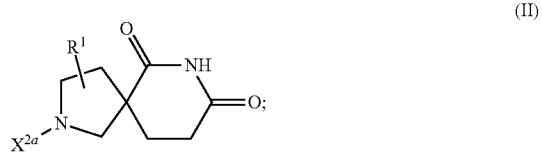

or a pharmaceutically acceptable salt thereof;
wherein:
$X^{2a}$ is selected from the group consisting of heterocyclyl, heterocyclyl substituted by $R^3$, heteroaryl, heteroaryl substituted by $R^4$, and $C_{1-6}$-alkyl;
$R^3$ is selected from the group consisting of —C(=O)—$C_{1-6}$-alkyl and =O;
$R^4$ is selected from the group consisting of —C(=O)—O—$C_{1-6}$-alkyl; $C_{1-6}$alkyl; —NH$_2$; —NH—C(=O)—$C_{1-6}$-alkyl; and —NO$_2$;
and all other variables are as defined herein.

In another aspect, a compound is provided of Formula IIIa or Formula IIIb:

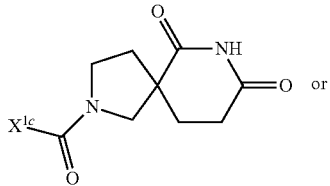
(IIIa)

or

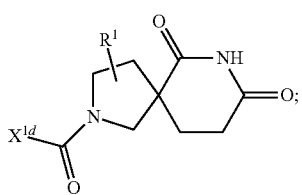
(IIIb)

or a pharmaceutically acceptable salt thereof;
wherein:

$X^1$ is selected from the group consisting of aryl and aryl substituted with $R^{2c}$;

$X^{1d}$ is selected from the group consisting of aryl and aryl substituted with $R^{2d}$;

$R^{2c}$ is selected from the group consisting of: —C(=O)—O—$C_{1-6}$-alkyl; —NH—C(=O)—$C_{1-6}$-alkyl; and —NO$_2$;

$R^{2d}$ is selected from the group consisting of: —C(=O)—O—$C_{1-6}$-alkyl; —NH—C(=O)—$C_{1-6}$-alkyl; —NH$_2$; and —NO$_2$;

and all other variables are as defined herein.

In another embodiment, a compound of Formula IV is provided:

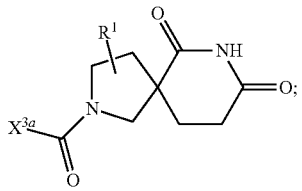
(IV)

or a pharmaceutically acceptable salt thereof;
wherein:

$X^{3a}$ is selected from the group consisting of hydrogen, heterocyclyl, heterocyclyl substituted by $R^3$, heteroaryl, heteroaryl substituted by $R^4$, and $C_{1-6}$-alkyl;

and all other variables are as defined herein.

In another embodiment, a compound of Formula V or VI is provided:

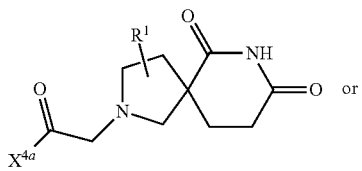
(V)

or

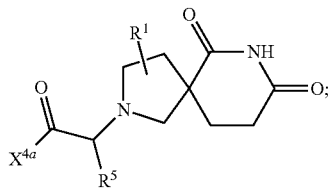
(VI)

or a pharmaceutically acceptable salt thereof;
wherein:

$X^{4a}$ is selected from the group consisting of hydrogen, aryl, aryl substituted by $R^2$, heterocyclyl, heterocyclyl substituted by $R^3$, heteroaryl, heteroaryl substituted by $R^4$, and $C_{1-6}$-alkyl;

$R^2$ is selected from the group consisting of: —C(=O)—O—$C_{1-6}$-alkyl; —NH—C(=O)—$C_{1-6}$-alkyl; —NH$_2$; —OH; and —NO$_2$;

$R^5$ is $C_{1-6}$-alkyl;

and all other variables are as defined herein.

In another aspect, the use of a compound for the treatment of a therapeutic condition which can be treated by modulating the function or activity of the cereblon containing E3 Ubiquitin Ligase Protein Complex is provided of Formula VII:

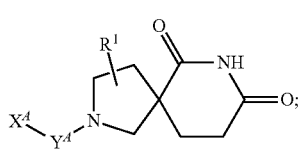
(VII)

or a pharmaceutically acceptable salt thereof;
wherein:

$Y^A$ is absent or selected from the group consisting of: —C(=O)—; —C(=O)—C(H,$C_{1-6}$-alkyl)-; and —C(=O)—CH$_2$—;

$X^A$ is selected from the group consisting of: hydrogen; aryl; aryl substituted by $R^2$; heterocyclyl; heterocyclyl substituted by $R^3$; heteroaryl; heteroaryl substituted by $R^4$; and $C_{1-6}$-alkyl;

wherein if $Y^A$ is absent, then $X^A$ cannot be hydrogen;
and all other variables are as defined herein.

In another aspect, a compound is provided of Formula VIII:

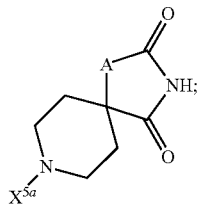
(VIII)

or a pharmaceutically acceptable salt thereof;
wherein:

A is selected from the group consisting of CH$_2$ and NH;

$X^{5a}$ is aryl substituted by $R^{6a}$; and $R^{6a}$ is selected from the group consisting of: —C(=O)—OH; —NH—C(=O)—$C_{1-6}$-alkyl; and —NO$_2$.

In another aspect, a compound is provided of Formula IX:

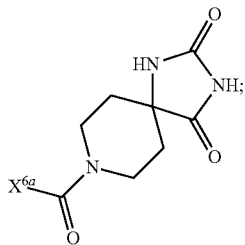

(IX)

or a pharmaceutically acceptable salt thereof;
wherein $X^{6a}$ is aryl substituted with —C(=O)—OH.

In another aspect, a compound is provided of Formula X:

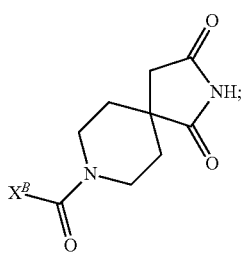

(X)

or a pharmaceutically acceptable salt thereof;
wherein:

$X^B$ is selected from the group consisting of: aryl; aryl substituted by $R^6$; heteroaryl; and heteroaryl substituted by $R^7$;

$R^6$ is selected from the group consisting of: —C(=O)—OH; —NH—C(=O)—$C_{1-6}$-alkyl; —NH$_2$; and —NO$_2$; and $R^7$ is selected from the group consisting of: —C(=O)—OH; —C(=O)—O—$C_{1-6}$-alkyl; —NH$_2$; and —NO$_2$.

In another aspect, a compound is provided of Formula XI:

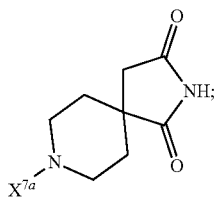

(XI)

or a pharmaceutically acceptable salt thereof;
wherein $X^{7a}$ is selected from the group consisting of heteroaryl and heteroaryl substituted by $R^7$.

In another aspect, a compound is provided of Formula XII:

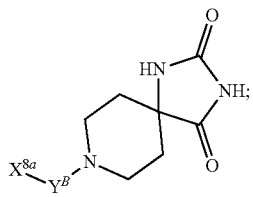

(XII)

or a pharmaceutically acceptable salt thereof;
wherein:
$Y^B$ is absent or —C(=O)—;
$X^{8a}$ heteroaryl substituted by $R^{7a}$; and
$R^{7a}$ is selected from the group consisting of —C(=O)—OH and —C(=O)—O—$C_{1-6}$-alkyl.

In another aspect, the use of a compound for the treatment of a therapeutic condition which can be treated by modulating the function or activity of the cereblon containing E3 Ubiquitin Ligase Protein Complex is provided of Formula XIII:

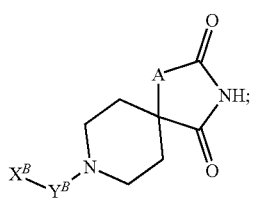

(XIII)

or a pharmaceutically acceptable salt thereof;
wherein all variables are as defined herein.

The compounds of Formula Ia, Formula Ib, Formula II, Formula IIIa, Formula IIIb, Formula IV, Formula V, Formula VI, Formula VIII, Formula IX, Formula X, Formula XI, and Formula XII are useful as therapeutic agents when administered in an effective amount to a host, typically a human, for the treatment of a medical disorder including, but not limited to, abnormal cellular proliferation, including a tumor or cancer, or a myelo- or lymphoproliferative disorder such as B- or T-cell lymphomas, multiple myeloma, Waldenstrom's macroglobulinemia, Wiskott-Aldrich syndrome, or a post-transplant lymphoproliferative disorder; an immune disorder, including autoimmune disorder such as Addison disease, Celiac disease, Dermatomyositis, Graves disease, thyroiditis, multiple sclerosis, pernicious anemia, reactive arthritis, lupus, or type I diabetes; a disease of cardiologic malfunction including hypercholesterolemia; an infectious disease including viral or bacterial infections; inflammatory conditions including asthma, chronic peptic ulcers, tuberculosis, rheumatoid arthritis, periodontitis, ulcerative colitis, Crohn's disease, or hepatitis.

In certain embodiments, the present invention provides the administration of an effective amount of a compound of Formula Ia, Formula Ib, Formula II, Formula IIIa, Formula IIIb, Formula IV, Formula V, Formula VI, Formula VIII, Formula IX, Formula X, Formula XI, and Formula XII to treat a patient, for example a human, having an infectious disease, wherein the therapy acts via binding to cereblon or its E3 Ubiquitin Ligase or acts through an independent mechanism, optionally in combination with another bioactive agent. The disease state or condition may be caused by a microbial agent or other exogenous agent such as a virus (as non-limiting examples, HIV, HBV, HCV, HSV, HPV, RSV, CMV, Ebola, Flavivirus, Pestivirus, Rotavirus, Influenza, Coronavirus, EBV, viral pneumonia, drug-resistant viruses, Bird Flu, RNA virus, DNA virus, adenovirus, poxvirus, Picornavirus, Togavirus, Orthomyxovirus, Retrovirus, or Hepadovirus), bacterial (including but not limited to Gram-negative, Gram-positive, Atypical, *Staphylococcus, Streptococcus, E. Coli, Salmonella, Helicobacter pylori*, meningitis, gonorrhea, Chlamydiaceae, Mycoplasmataceae, etc.), fungus, protozoa, helminth, worm, prion, parasite, or other microbe.

In another aspect, the compounds disclosed can be used as synthetic intermediates in the preparation of bifunctional compounds that cause degradation of a selected protein via the ubiquitin proteosome pathway (UPP) is provided. These compounds contain a functional group that can react with a second compound, wherein the second compound is capable of binding to a selected protein of interest, to create a bifunctional compound as described above that can cause the degradation of the selected protein via the UPP.

Thus, compounds of Formula XIV or XV, or a pharmaceutically acceptable salt thereof, which can be used in the preparation of compounds that cause degradation of a selected protein via the UPP are provided:

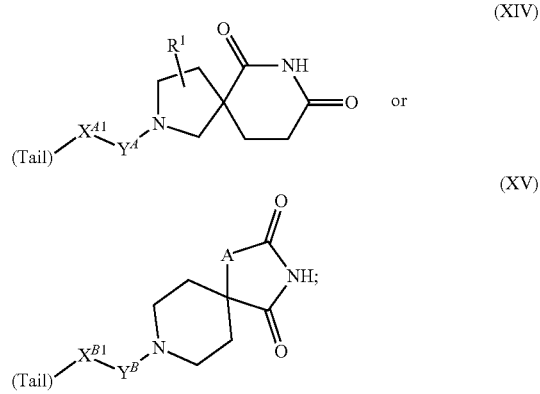

wherein:

$X^{A1}$ is selected from the group consisting of arylene, heterocyclylene, heteroarylene, and $C_{1-6}$-alkylene;

$X^{B1}$ is selected from the group consisting of arylene and heteroarylene; and "Tail" is a chemical moiety that contains a reactive functional group that can covalently bind to a protein binding moiety to produce a targeted protein degrader, or "Tail is a chemical moiety that can be used to modify the properties of the compound such as hydrophobicity, hydrophilicity, solubility, drug deliver, pharmacokinetic, or other properties such as charge, polarity, or fit within the active pocket;

in one embodiment, "Tail" is "T",
wherein "T" is

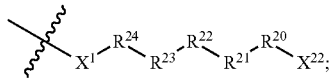

$X^1$ is selected from bond, $NR^{34}$, $CH_2$, $CHR^{34}$, $C(R^{34})_2$, O, and S;

$X^{22}$ is a functional group that can be used as a linking group to a protein binding moiety; or $X^{22}$ is a group that caps the valence and is not typically a linking group; representative examples of $X^{22}$ include, but are not limited to, halo, —$NH_2$, —$NHR^{34}$, —$N(R^{34})_2$, hydroxyl, thiol, —$B(OH)_2$, —$Sn(R^{36})_3$, —$Si(R^{36})_3$, —$OS(O)_2$alkyl, —$OS(O)_2$haloalkyl, alkenyl, alkynyl, ethynyl, ethenyl, —C(O)H, —$NR^{34}$C(O)alkene, —$NR^{34}$C(O)alkyne, cyano, —SC(O)alkyl, OC(O)alkyl, heterocycle, —C(O)OH, hydrogen, alkyl, aryl, heteroaryl, aliphatic, heteroaliphatic, and carbocyclic;

$R^{34}$ and $R^{34'}$ are independently selected at each occurrence from hydrogen, $C_1$-$C_6$alkyl (for example methyl, ethyl, cyclopropyl, or $C_1$-$C_3$alkyl), $C_1$-$C_6$haloalkyl, $C_2$-$C_6$alkenyl, $C_2$-$C_6$alkynyl, $C_3$-$C_6$cycloalkyl, $C_3$-$C_6$heterocycle, aryl, heteroaryl, —(CO)$R^{36}$, —(CS)$R^{36}$, —(C=NH)$R^{36}$, —(SO)$R^{36}$, and —(SO$_2$)$R^{36}$;

$R^{36}$ is independently selected at each occurrence from hydrogen, $C_1$-$C_6$alkyl, $C_1$-$C_6$haloalkyl, $C_2$-$C_6$alkenyl, $C_2$-$C_6$alkynyl, $C_3$-$C_6$cycloalkyl, $C_3$-$C_6$heterocycle, aryl, heteroaryl, hydroxyl, $C_1$-$C_6$alkoxy, thio, $C_1$-$C_6$thioalkyl, —$NH_2$, —NH($C_1$-$C_6$alkyl, $C_3$-$C_7$cycloalkyl, $C_3$-$C_7$heterocycle, aryl, or heteroaryl), and —N(independently $C_1$-$C_6$alkyl, $C_3$-$C_7$cycloalkyl, $C_3$-$C_7$heterocycle, aryl, or heteroaryl)$_2$;

$R^{20}$, $R^{21}$, $R^{22}$, $R^{23}$ and $R^{24}$ are independently a divalent or multivalent linking group, including but not limited to a covalent bond, alkyl, —C(O)—, —C(O)O—, —OC(O)—, —C(O)alkyl, —C(O)Oalkyl, —C(S)—, —SO$_2$—, —S(O)—, —C(S)—, —C(O)NH—, —NHC(O)—, —N(alkyl)C(O)—, —C(O)N(alkyl)-, —O—, —S—, —NH—, —N(alkyl)-, —CH(—O—$R^{26}$)—, —CH(—$NR^{34}R^{34'}$)—, —C(—O—$R^{26}$)alkyl-, —C(—$NR^{34}R^{34'}$)alkyl-, —C($R^{40}R^{40}$)—, -alkyl($R^{27}$)-alkyl($R^{28}$)—, —C($R^{27}R^{28}$)—, —P(O)(O$R^{26}$)O—, —P(O)(O$R^{26}$)—, —$NR^{34}$C(O)$NR^{34'}$—, alkene, haloalkyl, alkoxy, alkyneheteroarylalkyl, aryl, arylalkyl, heterocycle, aliphatic, heteroaliphatic, heteroaryl, lactic acid, glycolic acid, carbocycle, -(ethylene glycol)$_{1-6}$-, -(lactic-co-glycolic acid)$_{1-6}$-, -(propylene glycol)$_{1-6}$-, —O—(CH$_2$)$_{1-12}$—O—, —NH—(CH$_2$)$_{1-12}$—NH—, —NH—(CH$_2$)$_{1-12}$—O—, —O—(CH$_2$)$_{1-12}$—NH—, —S—(CH$_2$)$_{1-12}$—O—, —O—(CH$_2$)$_{1-12}$—S—, —S—(CH$_2$)$_{1-12}$—S—, —S—(CH$_2$)$_{1-12}$—NH—, and —NH—(CH$_2$)$_{1-12}$—S—, wherein the 1-6 can be independently 1, 2, 3, 4, 5, or 6, wherein the 1-12 can be independently 1, 2, 3, 4, 5, 6, 7, 8, 9, 10, 11 or 12, and wherein one or more of the CH$_2$ or NH groups can be modified by substitution of a H for a methyl, ethyl, cyclopropyl, F (if on carbon), etc, as described herein, and optionally, a heteroatom, heteroalkyl, aryl, heteroaryl or cycloaliphatic group is interspersed in the chain. Certain non-limiting examples include —O—CH(CH$_3$)—CH(CH$_3$)CH—O—, —O—CH$_2$—CH(CH$_3$)CH—O—, —O—CH(CH$_3$)—CH$_2$CH—O—, etc., each of which $R^{20}$, $R^{21}$, $R^{22}$, $R^{23}$, and $R^{24}$ is optionally substituted with one or more substituents selected from $R^{101}$ or alternatively as described in the Definitions section; wherein at least one of $R^{20}$, $R^{21}$, $R^{22}$, $R^{23}$, and $R^{24}$ is not a bond;

$R^{101}$ is independently selected at each occurrence from hydrogen, alkyl, alkene, alkyne, haloalkyl, alkoxy, hydroxyl, aryl, heteroaryl, heterocycle, arylalkyl, heteroarylalkyl, heterocycloalkyl, aryloxy, heteroaryloxy, CN, —COOalkyl, COOH, NO$_2$, F, Cl, Br, I, CF$_3$, NH$_2$, NHalkyl, N(alkyl)$_2$, aliphatic, and heteroaliphatic;

$R^{26}$ is selected from hydrogen, alkyl, silane, arylalkyl, heteroarylalkyl, alkene, alkyne, aryl, heteroaryl, heterocyclic, aliphatic and heteroaliphatic;

$R^{27}$ and $R^{28}$ are independently selected from hydrogen, alkyl, and amine, or together with the carbon atom to which they are attached, form C(O), C(S), C=CH$_2$, a C$_3$-C$_6$ spirocarbocycle, or a 4-, 5-, or 6-membered spiroheterocycle comprising 1 or 2 heteroatoms selected from N and O, or form a 1 or 2 carbon bridged ring;

$R^{40}$ is selected at each instance from: hydrogen, alkyl, alkene, alkyne, halogen, hydroxyl, alkoxy, azide, amino, cyano, —NH(aliphatic, including alkyl), —N(aliphatic, including alkyl)$_2$, —NHSO$_2$(aliphatic, including alkyl), —N(aliphatic, including alkyl)SO$_2$alkyl, —NHSO$_2$(aryl, heteroaryl or heterocyclic), —N(alkyl)SO$_2$(aryl, heteroaryl or heterocyclic) —NHSO$_2$alkenyl, —N(alkyl)SO$_2$alkenyl, —NHSO$_2$alkynyl, —N(alkyl)SO$_2$alkynyl, haloalkyl, aliphatic, heteroaliphatic, aryl, heteroaryl, heteroalkyl, heterocyclic, and carbocyclic; and all other variables are as defined herein.

In one aspect, a compound is provided of one of the following formulas:

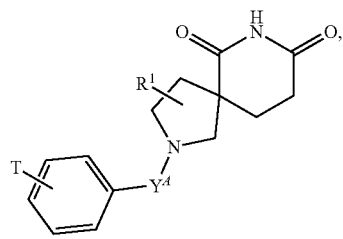
(XIV-a)

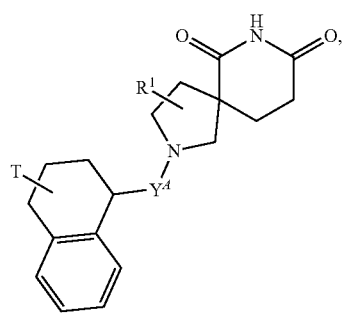
(XVI-b)

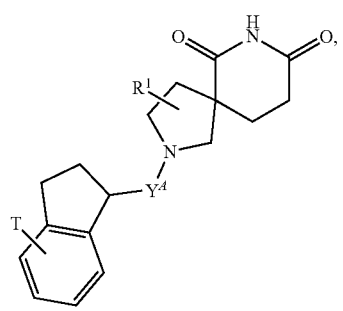
(XIV-c)

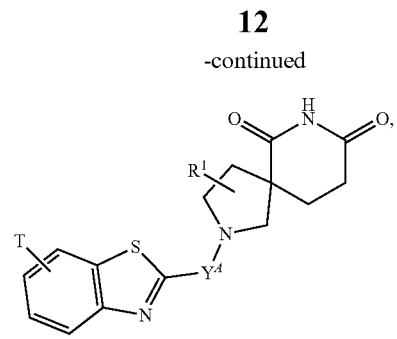
(XIV-d)

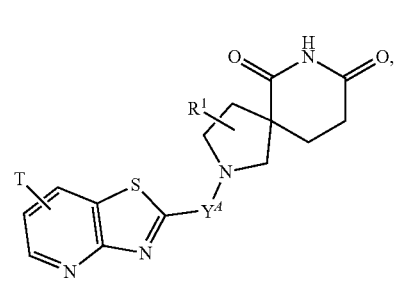
(XIV-e)

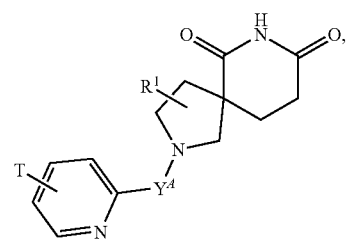
(XIV-f)

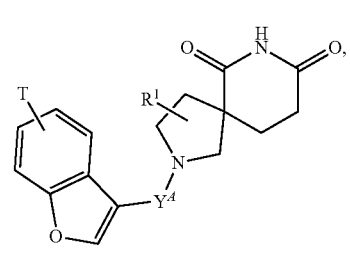
(XIV-g)

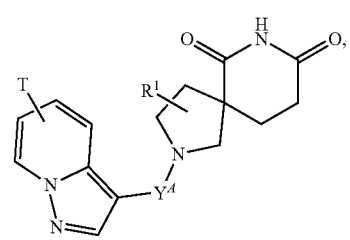
(XIV-h)

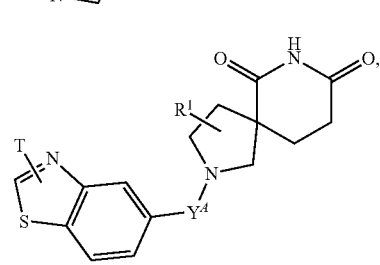
(XIV-i)

(XIV-j)
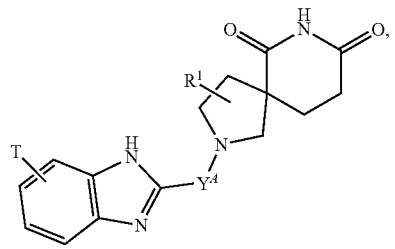
(XIV-k)
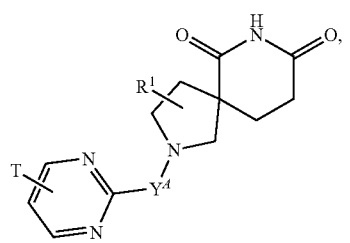
(XIV-l)
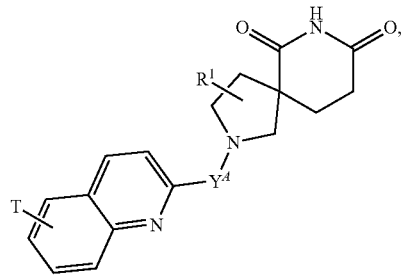
(XVI-m)
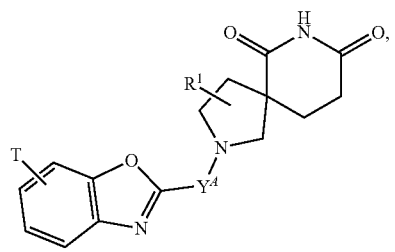
(XVI-n)
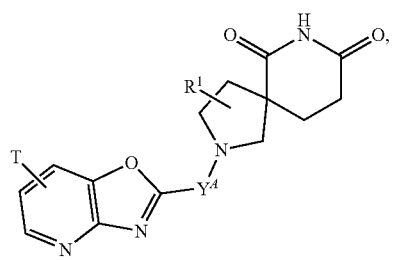
(XVI-o)
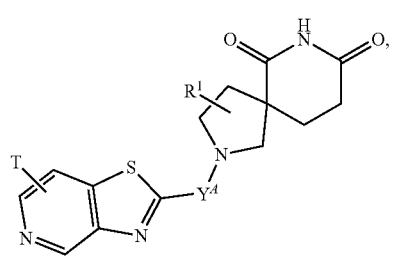
(XVI-p)
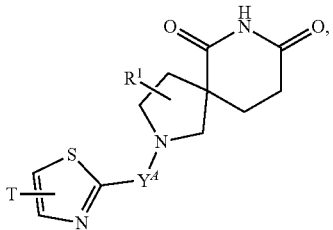
(XVI-q)
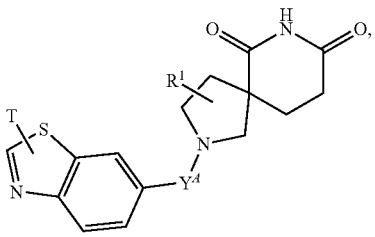
(XVI-r)
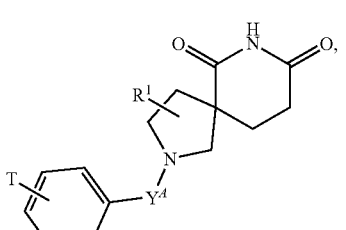
(XIV-s)
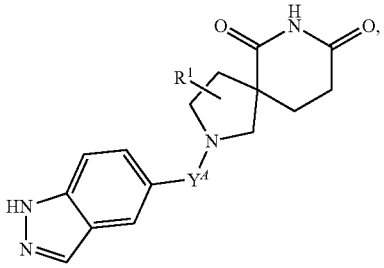
(XIV-t)
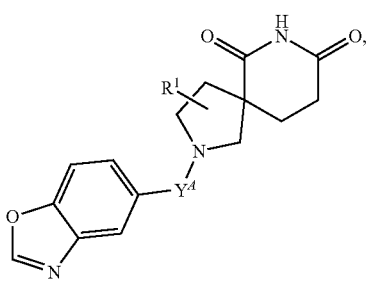
(XIV-u)
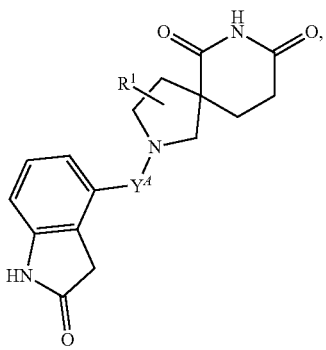

(XIV-v)
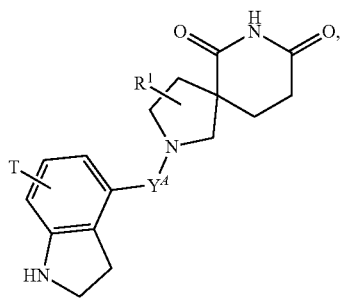
(XIV-w)
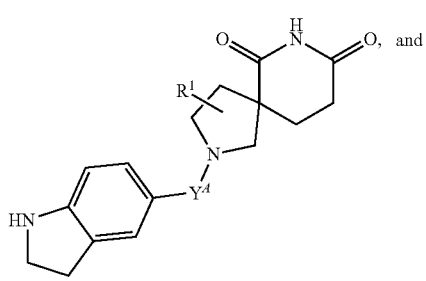
and
(XIV-x)
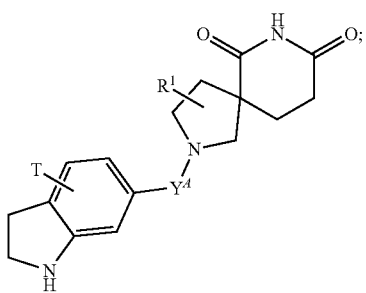
or a pharmaceutically acceptable salt thereof; wherein T is
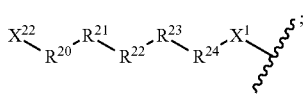
and all other variables are as defined herein.
In another aspect, a compound is provided of one of the following formulas:
(XV-a)
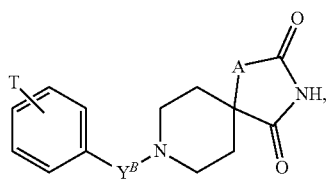
(XV-b)
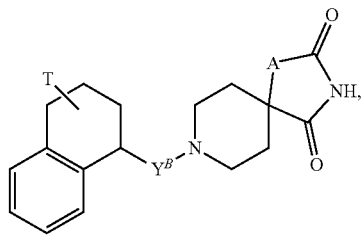
(XV-c)
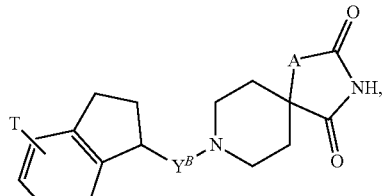
(XV-d)
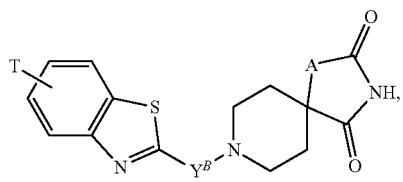
(XV-e)
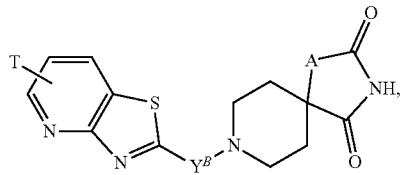
(XV-f)
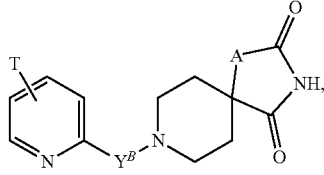
(XV-g)
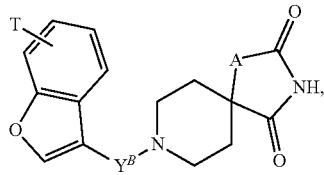
(XV-h)
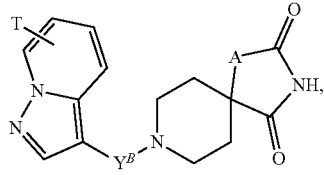
(XV-i)
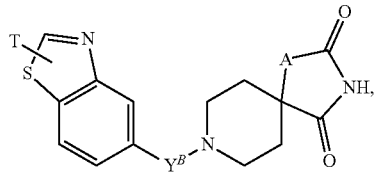

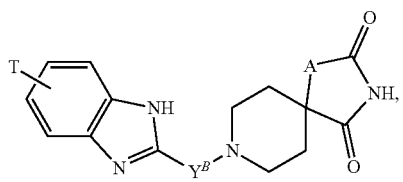
(XV-j)

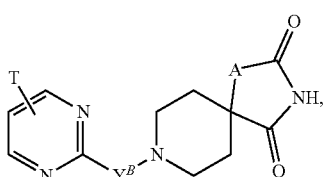
(XV-k)

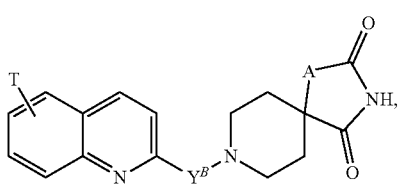
(XV-l)

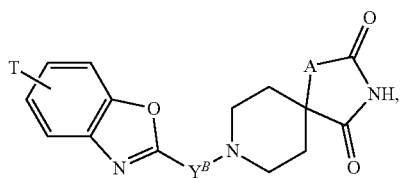
(XV-m)

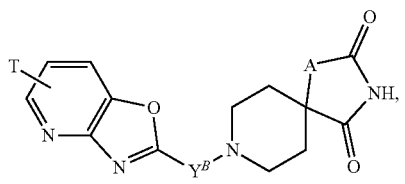
(XV-n)

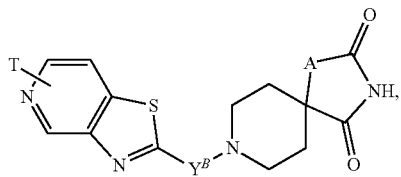
(XV-o)

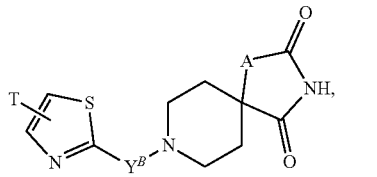
(XV-p)

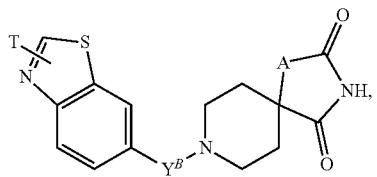
(XV-q)

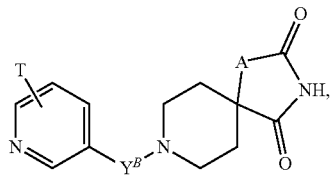
(XV-r)

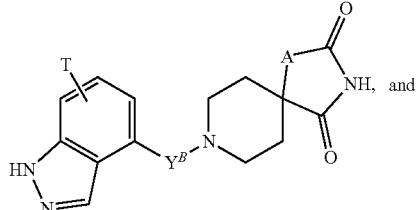
(XV-s)

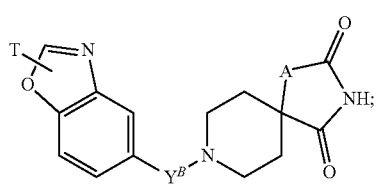
(XV-t)

or a pharmaceutically acceptable salt thereof;
wherein all variables are as defined herein.

In a first aspect, the present invention provides compounds of Formula Ia, Formula Ib, Formula II, Formula IIIa, Formula IIIb, Formula IV, Formula V, Formula VI, Formula VII, Formula VIII, Formula IX, Formula X, Formula XI, Formula XII, Formula XIII, Formula XIV, Formula XV, Formula XIV-a to XIV-x, and Formula XV-a to XV-t as defined herein for use as a therapeutically active substance.

In a further aspect, the present invention provides pharmaceutical compositions comprising a compound of Formula Ia, Formula Ib, Formula II, Formula IIIa, Formula IIIb, Formula IV, Formula V, Formula VI, Formula VII, Formula VIII, Formula IX, Formula X, Formula XI, Formula XII, Formula XIII, Formula XIV, Formula XV, Formula XIV-a to XIV-x, and Formula XV-a to XV-t as defined herein and a therapeutically inert carrier.

In certain embodiments, the compound of Formula Ia, Formula Ib, Formula II, Formula IIIa, Formula IIIb, Formula IV, Formula V, Formula VI, Formula VII, Formula VIII, Formula IX, Formula X, Formula XI, Formula XII, Formula XIII, Formula XIV, Formula XV, Formula XIV-a to XIV-x, and Formula XV-a to XV-t has at least one desired isotopic substitution of an atom, at an amount above the natural abundance of the isotope, i.e., enriched. In one embodiment, the compound of Formula Ia, Formula Ib, Formula II, Formula IIIa, Formula IIIb, Formula IV, Formula V, Formula VI, Formula VII, Formula VIII, Formula IX, Formula X, Formula XI, Formula XII, Formula XIII, Formula XIV, Formula XV, Formula XIV-a to XIV-x, and Formula XV-a to XV-t includes a deuterium or multiple deuterium atoms.

The present compounds are useful for the therapeutic and/or prophylactic treatment of cancer.

The compounds of the present invention can further be used as part of bifunctional compounds that comprise the compounds of present invention as E3 Ubiquitin Ligase moiety that is linked to a moiety that binds to a target protein where the target protein is proximate to the ubiquitin ligase to effect degradation of said protein.

Other features and advantages of the present application will be apparent from the following detailed description and claims.

The present invention therefore includes at least the following features:

a) a compound of Formula Ia, Formula Ib, Formula II, Formula IIIa, Formula IIIb, Formula IV, Formula V, Formula VI, Formula VIII, Formula IX, Formula X, Formula XI, Formula XII, Formula XIV, Formula XV, Formula XIV-a to XIV-x, or Formula XV-a to XV-t or a pharmaceutically acceptable salt thereof;

b) use of a compound of Formula Ia, Formula Ib, Formula II, Formula IIIa, Formula IIIb, Formula IV, Formula V, Formula VI, Formula VII, Formula VIII, Formula IX, Formula X, Formula XI, Formula XII, Formula XIII, Formula XIV, Formula XV, Formula XIV-a to XIV-x, or Formula XV-a to XV-t or a pharmaceutically acceptable salt thereof, in an effective amount in the treatment of a patient, typically a human, with a disorder that responds to such treatment, including by modulating the cereblon-based ubiquitination of a protein, such as for example, abnormal cellular proliferation such as a tumor or cancer, an immune or autoimmune or inflammatory disorder, a cardiologic disorder, an infectious disease, or other disorder that responds to such treatment;

c) use of a compound of Formula Ia, Formula Ib, Formula II, Formula IIIa, Formula IIIb, Formula IV, Formula V, Formula VI, Formula VII, Formula VIII, Formula IX, Formula X, Formula XI, Formula XII, Formula XIII, Formula XIV, Formula XV, Formula XIV-a to XIV-x, or Formula XV-a to XV-t or a pharmaceutically acceptable salt thereof, in the manufacture of a medicament for the treatment of a medical disorder, as further described herein;

d) a method for manufacturing a medicament intended for the therapeutic treatment of a disorder in a host, characterized in that a compound of Formula Ia, Formula Ib, Formula II, Formula IIIa, Formula IIIb, Formula IV, Formula V, Formula VI, Formula VII, Formula VIII, Formula IX, Formula X, Formula XI, Formula XII, Formula XIII, Formula XIV, Formula XV, Formula XIV-a to XIV-x, or Formula XV-a to XV-t is used in the manufacture;

e) a compound of Formula Ia, Formula Ib, Formula II, Formula IIIa, Formula IIIb, Formula IV, Formula V, Formula VI, Formula VII, Formula VIII, Formula IX, Formula X, Formula XI, Formula XII, Formula XIII, Formula XIV, Formula XV, Formula XIV-a to XIV-x, or Formula XV-a to XV-t or a pharmaceutically acceptable salt thereof, that are useful in the treatment of an abnormal cellular proliferation such as cancer in a host, including any of the cancers described herein;

f) use of a compound of Formula Ia, Formula Ib, Formula II, Formula IIIa, Formula IIIb, Formula IV, Formula V, Formula VI, Formula VII, Formula VIII, Formula IX, Formula X, Formula XI, Formula XII, Formula XIII, Formula XIV, Formula XV, Formula XIV-a to XIV-x, and Formula XV-a to XV-t, or a pharmaceutically acceptable salt thereof, in the manufacture of a medicament for the treatment of an abnormal cellular proliferation such as cancer, including any of the cancers described herein;

g) a method for manufacturing a medicament intended for the therapeutic use of treating an abnormal cellular proliferation such as cancer in a host, including any of the cancers described herein, characterized in that a compound of Formula Ia, Formula Ib, Formula II, Formula IIIa, Formula IIIb, Formula IV, Formula V, Formula VI, Formula VII, Formula VIII, Formula IX, Formula X, Formula XI, Formula XII, Formula XIII, Formula XIV, Formula XV, Formula XIV-a to XIV-x, or Formula XV-a to XV-t is used in the manufacture;

h) a compound of Formula Ia, Formula Ib, Formula II, Formula IIIa, Formula IIIb, Formula IV, Formula V, Formula VI, Formula VII, Formula VIII, Formula IX, Formula X, Formula XI, Formula XII, Formula XIII, Formula XIV, Formula XV, Formula XIV-a to XIV-x, or Formula XV-a to XV-t or a pharmaceutically acceptable salt thereof, that is useful in the treatment of a tumor in a host, including any of the tumors described herein;

i) use of a compound of Formula Ia, Formula Ib, Formula II, Formula IIIa, Formula IIIb, Formula IV, Formula V, Formula VI, Formula VII, Formula VIII, Formula IX, Formula X, Formula XI, Formula XII, Formula XIII, Formula XIV, Formula XV, Formula XIV-a to XIV-x, or Formula XV-a to XV-t or a pharmaceutically acceptable salt thereof, in the manufacture of a medicament for the treatment of a tumor in a host, including any of the tumors described herein;

j) a method for manufacturing a medicament intended for the therapeutic use of treating a tumor in a host, including any of the tumors described herein, characterized in that a compound of Formula Ia, Formula Ib, Formula II, Formula IIIa, Formula IIIb, Formula IV, Formula V, Formula VI, Formula VII, Formula VIII, Formula IX, Formula X, Formula XI, Formula XII, Formula XIII, Formula XIV, Formula XV, Formula XIV-a to XIV-x, or Formula XV-a to XV-t is used in the manufacture;

k) a compound of Formula Ia, Formula Ib, Formula II, Formula IIIa, Formula IIIb, Formula IV, Formula V, Formula VI, Formula VII, Formula VIII, Formula IX, Formula X, Formula XI, Formula XII, Formula XIII, Formula XIV, Formula XV, Formula XIV-a to XIV-x, or Formula XV-a to XV-t or a pharmaceutically acceptable salt thereof, that is useful in the treatment of an immune, autoimmune, or inflammatory disorder in a host;

l) use of a compound of Formula Ia, Formula Ib, Formula II, Formula IIIa, Formula IIIb, Formula IV, Formula V, Formula VI, Formula VII, Formula VIII, Formula IX, Formula X, Formula XI, Formula XII, Formula XIII, Formula XIV, Formula XV, Formula XIV-a to XIV-x, or Formula XV-a to XV-t or a pharmaceutically acceptable salt thereof, in the manufacture of a medicament for the treatment of an immune, autoimmune, or inflammatory disorder in a host;

m) a method for manufacturing a medicament intended for the therapeutic use of treating an immune, autoimmune, or inflammatory disorder in a host, characterized in that a compound of Formula Ia, Formula Ib, Formula II, Formula IIIa, Formula IIIb, Formula IV, Formula V, Formula VI, Formula VII, Formula VIII, Formula IX, Formula X, Formula XI, Formula XII, Formula XIII, Formula XIV, Formula XV, Formula XIV-a to XIV-x, or Formula XV-a to XV-t is used in the manufacture;

n) a pharmaceutical formulation comprising an effective host-treating amount of a compound of a compound of Formula Ia, Formula Ib, Formula II, Formula IIIa, Formula IIIb, Formula IV, Formula V, Formula VI, Formula VII, Formula VIII, Formula IX, Formula X, Formula XI, Formula XII, Formula XIII, Formula XIV, Formula XV, Formula XIV-a to XIV-x, or Formula XV-a to XV-t or a pharmaceutically acceptable salt thereof, with a pharmaceutically acceptable carrier or diluent;

o) a compound of Formula Ia, Formula Ib, Formula II, Formula IIIa, Formula IIIb, Formula IV, Formula V, Formula VI, Formula VII, Formula VIII, Formula IX, Formula X, Formula XI, Formula XII, Formula XIII, Formula XIV, Formula XV, Formula XIV-a to XIV-x, or Formula XV-a to XV-t as described herein in enantiomerically or diastereomerically (as relevant) enriched form, including an isolated enantiomer or diastereomer (i.e., greater than 85, 90, 95, 97, or 99% pure);

p) a process for the preparation of therapeutic products that contain an effective amount of a compound of Formula Ia, Formula Ib, Formula II, Formula IIIa, Formula IIIb, Formula IV, Formula V, Formula VI, Formula VII, Formula VIII, Formula IX, Formula X, Formula XI, Formula XII, Formula XIII, Formula XIV, Formula XV, Formula XIV-a to XIV-x, or Formula XV-a to XV-t or a pharmaceutically acceptable salt thereof; and q) a process for the preparation of a bifunctional compound that causes degradation of a selected protein via the ubiquitin proteasome pathway, characterized in that a compound of Formula XIV, Formula XV, Formula XIV-a to XIV-x, or Formula XV-a to XV-t is used in the preparation of the bifunctional compound.

DETAILED DESCRIPTION OF THE INVENTION

I. Definitions

Unless otherwise defined, all technical and scientific terms used herein have the same meaning as commonly understood by one of ordinary skill in the art to which this application belongs. In the specification, singular forms also include the plural unless the context clearly dictates otherwise. Although methods and materials similar or equivalent to those described herein can be used in the practice or testing of the present application, suitable methods and materials are described below. All publications, patent applications, patents, and other references mentioned herein are incorporated by reference. The references cited herein are not admitted to be prior art to the claimed application. In the case of conflict, the present specification, including definitions, will control. In addition, the materials, methods, and examples are illustrative only and are not intended to be limiting.

The following definitions of the general terms used in the present description apply irrespectively of whether the terms in question appear alone or in combination with other groups.

Unless otherwise stated, the following terms used in this application, including the specification and claims, have the definitions given below. It must be noted that, as used in the specification and the appended claims, the singular forms "a", "an," and "the" include plural referents unless the context clearly dictates otherwise.

Compounds are described using standard nomenclature. Unless defined otherwise, all technical and scientific terms used herein have the same meaning as is commonly understood by one of skill in the art to which this invention belongs.

The compounds in any of the Formulas described herein may be in the form of a racemate, enantiomer, mixture of enantiomers, diastereomer, mixture of diastereomers, tautomer, N-oxide, isomer, such as rotamer, as if each is specifically described unless specifically excluded by context.

The compounds of the present invention may form a solvate with a solvent (including water). Therefore, in one non-limiting embodiment, the invention includes a solvated form of the compound. The term "solvate" refers to a molecular complex of a compound of the present invention (including a salt thereof) with one or more solvent molecules. Non-limiting examples of solvents are water, ethanol, isopropanol, dimethyl sulfoxide, acetone and other common organic solvents. The term "hydrate" refers to a molecular complex comprising a compound of the invention and water. Pharmaceutically acceptable solvates in accordance with the invention include those wherein the solvent may be isotopically substituted, e.g. $D_2O$, d6-acetone, $d_6$-DMSO. A solvate can be in a liquid or solid form.

The term "$C_{1-6}$-alkyl", alone or in combination with other groups, stands for a hydrocarbon radical which may be linear or branched, with single or multiple branching, wherein the alkyl group in general comprises 1 to 6 carbon atoms, for example, methyl (Me), ethyl (Et), propyl, isopropyl (i-propyl), n-butyl, i-butyl (isobutyl), 2-butyl (sec-butyl), t-butyl (tent-butyl), isopentyl, 2-ethyl-propyl (2-methyl-propyl), 1,2-dimethyl-propyl and the like. A specific group is methyl.

The term "heteroaryl" denotes a monovalent heterocyclic mono- or bicyclic ring system of 5 to 12 ring atoms, comprising 1, 2, 3 or 4 heteroatoms selected from N, O and S, the remaining ring atoms being carbon and in which all rings are aromatic. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolinyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, dihydroquinolyl, dihydropyrrolopyridinyl, dihydronaphthyridinyl, chromanyl, tetrahydroquinolinyl, dihydrocyclopentapyridinyl quinazolinyl, or quinoxalinyl. Particular examples are pyridinyl, benzimidazolyl, pyrimidyl, benzothiazolyl, thiazolyl thiazolo[4,5-b]pyridinyl, benzothiazolyl, quinolinyl, oxazolo[4,5-b]pyridinyl, benzoxazolyl, thiazolo[4,5-c]pyridinyl, indazolyl, benzofuranyl or pyrazolo[1,5-a]pyridinyl.

In one embodiment "heteroaryl" is a 5 membered aromatic group containing 1, 2, 3, or 4 nitrogen atoms.

Non-limiting examples of 5 membered "heteroaryl" groups include pyrrole, furan, thiophene, pyrazole, imidazole, triazole, tetrazole, isoxazole, oxazole, oxadiazole, oxatriazole, isothiazole, thiazole, thiadiazole, and thiatriazole.

Additional non-limiting examples of 5 membered "heteroaryl" groups include:

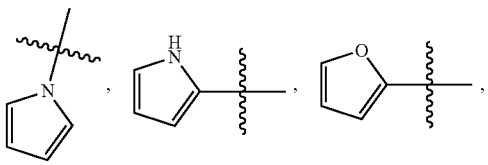

-continued

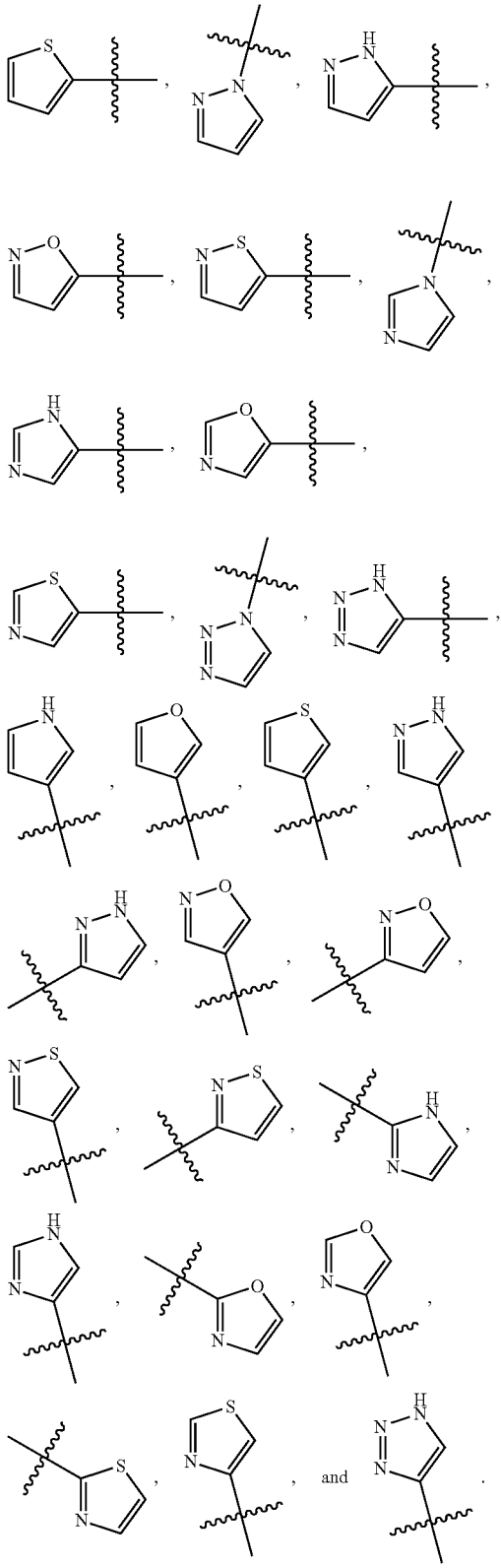

In one embodiment "heteroaryl" is a 6 membered aromatic group containing 1, 2, or 3 nitrogen atoms (i.e. pyridinyl, pyridazinyl, triazinyl, pyrimidinyl, and pyrazinyl).

Non-limiting examples of 6 membered "heteroaryl" groups with 1 or 2 nitrogen atoms include:

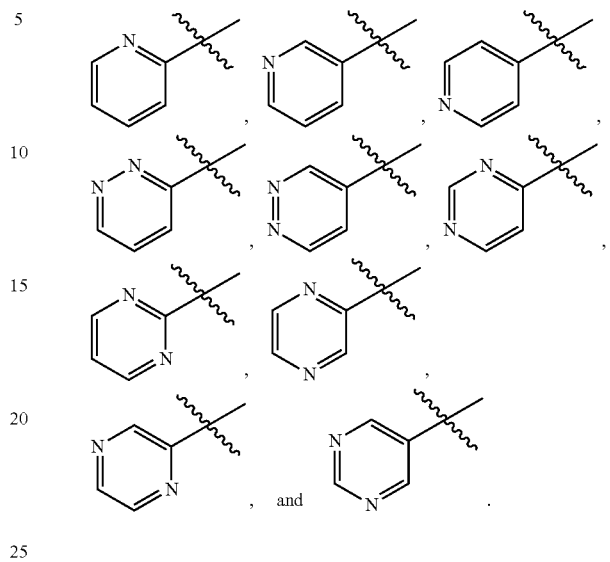

In one embodiment "heteroaryl" is a 9 membered bicyclic aromatic group containing 1 or 2 atoms selected from nitrogen, oxygen, and sulfur.

Non-limiting examples of "heteroaryl" groups that are bicyclic include indole, benzofuran, isoindole, indazole, benzimidazole, azaindole, azaindazole, purine, isobenzofuran, benzothiophene, benzoisoxazole, benzoisothiazole, benzooxazole, and benzothiazole.

Additional non-limiting examples of "heteroaryl" groups that are bicyclic include:

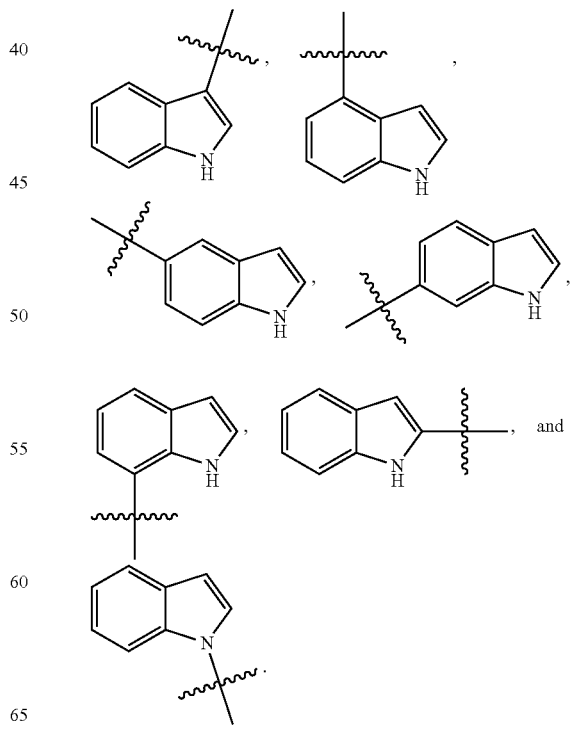

Additional non-limiting examples of "heteroaryl" groups that are bicyclic include:

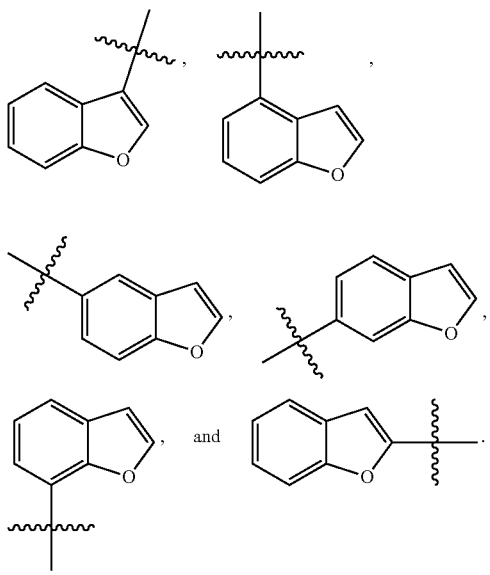

Additional non-limiting examples of "heteroaryl" groups that are bicyclic include:

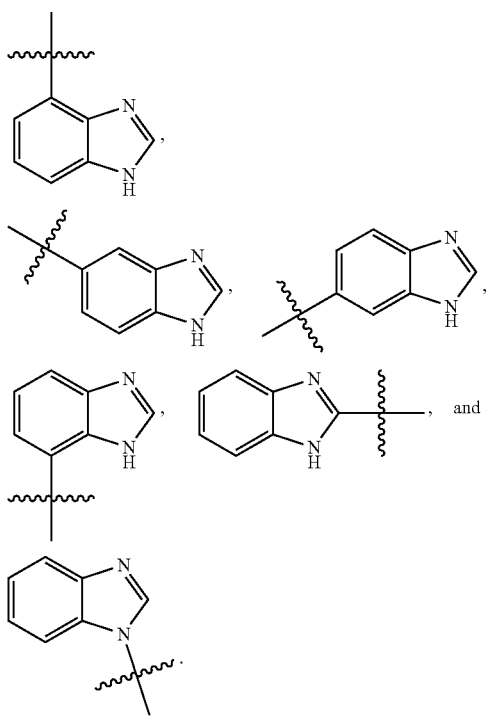

In one embodiment "heteroaryl" is a 10 membered bicyclic aromatic group containing 1 or 2 atoms selected from nitrogen, oxygen, and sulfur.

Non-limiting examples of "heteroaryl" groups that are bicyclic include quinoline, isoquinoline, quinoxaline, phthalazine, quinazoline, cinnoline, and naphthyridine.

Additional non-limiting examples of "heteroaryl" groups that are bicyclic include:

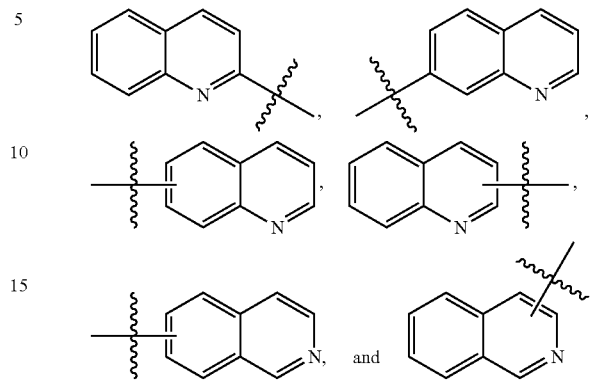

In another embodiment "heteroaryl" is "optionally substituted" with 1, 2, 3, or 4 subsituents.

The term "heterocycloalkyl" or "heterocyclyl" denotes a monovalent saturated or partly unsaturated mono- or bicyclic ring system of 4 to 9 ring atoms, comprising 1, 2, or 3 ring heteroatoms selected from N, O and S, the remaining ring atoms being carbon. Examples for monocyclic saturated heterocycloalkyl are azetidinyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, or dihydropyranyl. A particular example is indolinyl.

In one embodiment "heterocyclyl" refers to a cyclic ring with one nitrogen and 3, 4, 5, 6, 7, or 8 carbon atoms.

In one embodiment "heterocyclyl" refers to a cyclic ring with one nitrogen and one oxygen and 3, 4, 5, 6, 7, or 8 carbon atoms.

In one embodiment "heterocyclyl" refers to a cyclic ring with two nitrogens and 3, 4, 5, 6, 7, or 8 carbon atoms.

In one embodiment "heterocyclyl" refers to a cyclic ring with one oxygen and 3, 4, 5, 6, 7, or 8 carbon atoms.

In one embodiment "heterocyclyl" refers to a cyclic ring with one sulfur and 3, 4, 5, 6, 7, or 8 carbon atoms.

Non-limiting examples of "heterocyclyl" include aziridine, oxirane, thiirane, azetidine, 1,3-diazetidine, oxetane, and thietane.

Additional non-limiting examples of "heterocyclyl" include pyrrolidine, 3-pyrroline, 2-pyrroline, pyrazolidine, and imidazolidine.

Additional non-limiting examples of "heterocyclyl" include tetrahydrofuran, 1,3-dioxolane, tetrahydrothiophene, 1,2-oxathiolane, and 1,3-oxathiolane.

Additional non-limiting examples of "heterocyclyl" include piperidine, piperazine, tetrahydropyran, 1,4-dioxane, thiane, 1,3-dithiane, 1,4-dithiane, morpholine, and thiomorpholine.

Non-limiting examples of "heterocyclyl" also include:
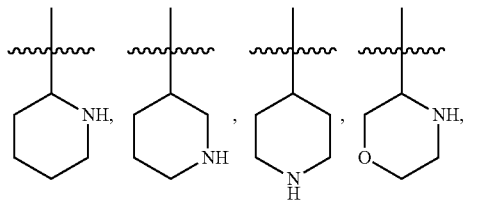
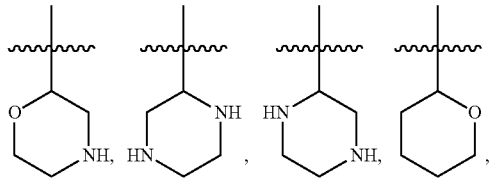
Additional non-limiting examples of "heterocyclyl" include:
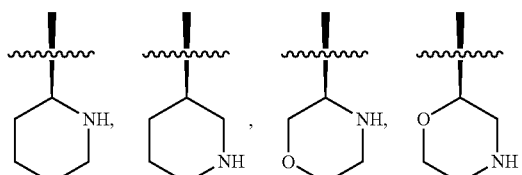
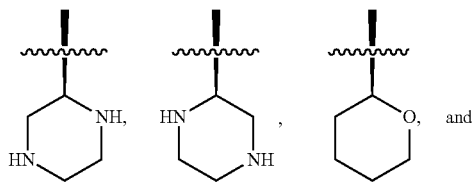
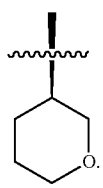
Additional non-limiting examples of "heterocyclyl" include:
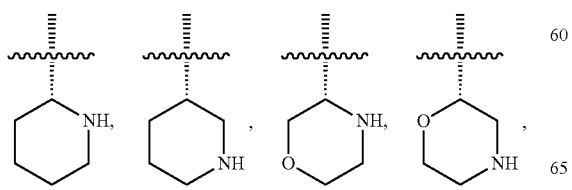
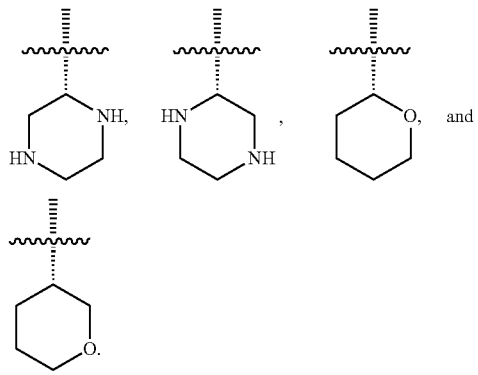
Non-limiting examples of "heterocyclyl" also include:
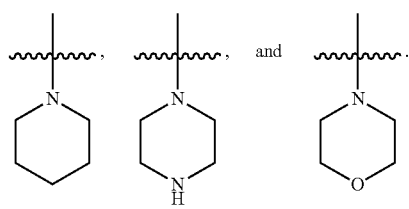
Non-limiting examples of "heterocyclyl" also include:
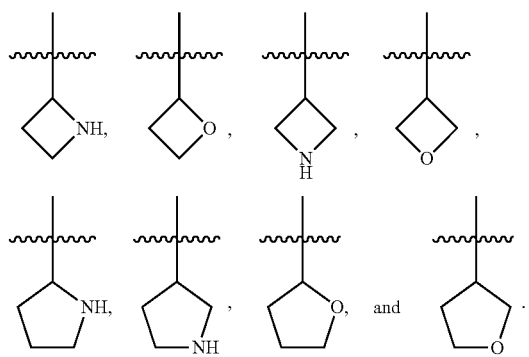
Additional non-limiting examples of "heterocyclyl" include:
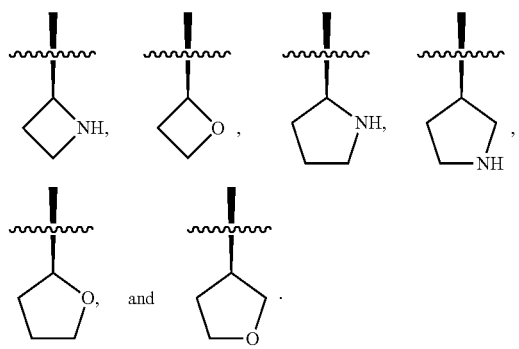

Additional non-limiting examples of "heterocyclyl" include:

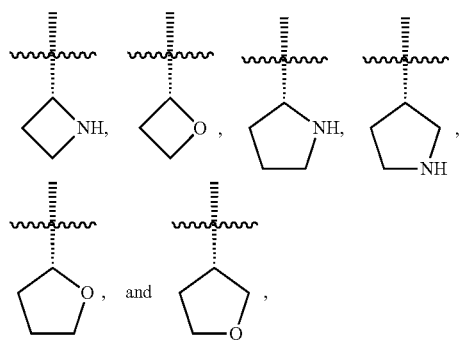

In another embodiment "heterocyclyl" is "optionally substituted" with 1, 2, 3, or 4 substituents.

The term "aryl" denotes a monovalent aromatic carbocyclic mono- or bicyclic ring system comprising 6 to 10 carbon ring atoms and in which at least one ring is aromatic. Examples of aryl moieties include phenyl (Ph), indanyl, 1,2,3,4-tetrahydronaphthalenyl and naphthyl. Particular examples are phenyl, indanyl and 1,2,3,4-tetrahydronaphthalenyl.

In one embodiment "aryl" is a 6 carbon aromatic group (phenyl).

In one embodiment "aryl" is a 10 carbon aromatic group (napthyl).

In another embodiment "aryl" is "optionally substituted" with 1, 2, 3, or 4 substituents.

The term "optionally substituted" denotes the substitution of a group herein by a moiety including, but not limited to, $C_1$-$C_{10}$ alkyl, $C_2$-$C_{10}$ alkenyl, $C_2$-$C_{10}$ alkynyl, $C_3$-$C_{12}$ cycloalkyl, $C_3$-$C_{12}$ cycloalkenyl, $C_1$-$C_{12}$ heterocycloalkyl, $C_3$-$C_{12}$ heterocycloalkenyl, alkoxy, aryl, aryloxy, heteroaryl, heteroaryloxy, amino, $C_1$-$C_{10}$ alkylamino, dialkylamino, arylamino, diarylamino, $C_1$-$C_{10}$ alkylsulfonamino, arylsulfonamino, $C_1$-$C_{10}$ alkylimino, arylimino, alkylsulfonimino, arylsulfonimino, hydroxyl, halo, thio, $C_1$-$C_{10}$ alkylthio, arylthio, alkylsulfonyl, arylsulfonyl, acylamino, aminoacyl, aminothioacyl, amidino, guanidine, ureido, cyano, nitro, azido, acyl, thioacyl, acyloxy, carboxyl, and carboxylic ester.

In another embodiment any suitable group may be present on a "substituted" or "optionally substituted" position if indicated that forms a stable molecule and meets the desired purpose of the invention and includes, but is not limited to, e.g., halogen (which can independently be F, Cl, Br or I); cyano; hydroxyl; nitro; azido; alkanoyl (such as a $C_2$-$C_6$ alkanoyl group); carboxamide; alkyl, cycloalkyl, alkenyl, alkynyl, alkoxy, aryloxy such as phenoxy; thioalkyl including those having one or more thioether linkages; alkylsulfinyl; alkylsulfonyl groups including those having one or more sulfonyl linkages; aminoalkyl groups including groups having more than one N atoms; aryl (e.g., phenyl, biphenyl, naphthyl, or the like, each ring either substituted or unsubstituted); arylalkyl having for example, 1 to 3 separate or fused rings and from 6 to about 14 or 18 ring carbon atoms, with benzyl being an exemplary arylalkyl group; arylalkoxy, for example, having 1 to 3 separate or fused rings with benzyloxy being an exemplary arylalkoxy group; or a saturated or partially unsaturated heterocycle having 1 to 3 separate or fused rings with one or more N, O or S atoms, or a heteroaryl having 1 to 3 separate or fused rings with one or more N, O or S atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such groups may be further substituted, e.g. with hydroxy, alkyl, alkoxy, halogen and amino. In certain embodiments "optionally substituted" includes one or more substituents independently selected from halogen, hydroxyl, amino, cyano, —CHO, —COOH, —CONH$_2$, alkyl including $C_1$-$C_6$alkyl, alkenyl including $C_2$-$C_6$alkenyl, alkynyl including $C_2$-$C_6$alkynyl, —$C_1$-$C_6$alkoxy, alkanoyl including $C_2$-$C_6$alkanoyl, $C_1$-$C_6$alkylester, (mono- and di-$C_1$-$C_6$alkylamino)$C_0$-$C_2$alkyl, haloalkyl including $C_1$-$C_6$haloalkyl, hydoxy$C_1$-$C_6$alkyl, ester, carbamate, urea, sulfonamide, —$C_1$-$C_6$alkyl(heterocyclo), $C_1$-$C_6$alkyl(heteroaryl), —$C_1$-$C_6$alkyl($C_3$-$C_7$cycloalkyl), O—$C_1$-$C_6$alkyl($C_3$-$C_7$cycloalkyl), B(OH)$_2$, phosphate, phosphonate and haloalkoxy including $C_1$-$C_6$haloalkoxy. In some embodiments, the suitable group present on a "substituted" or "optionally substituted" is divalent including, but not limited to, oxo (=O), =S, =CH$_2$, etc. The suitable group on a "substituted" or "optional substituted" position may be monovalent, divalent, or trivalent such that it forms a stable molecule and meets the desired purpose of the invention.

In one embodiment a group described herein that can be substituted with 1, 2, 3, or 4 substituents is substituted with one substituent.

In one embodiment a group described herein that can be substituted with 1, 2, 3, or 4 sub stituents is substituted with two sub stituents.

In one embodiment a group described herein that can be substituted with 1, 2, 3, or 4 sub stituents is substituted with three sub stituents.

In one embodiment a group described herein that can be substituted with 1, 2, 3, or 4 sub stituents is substituted with four sub stituents.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The term "a pharmaceutically acceptable salt" refers to a salt that is suitable for use in contact with the tissues of humans and animals. Examples of suitable salts with inorganic and organic acids are, but are not limited to, acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid (sulphuric acid), tartaric acid, trifluoroacetic acid and the like. Particular acids are formic acid, trifluoroacetic acid and hydrochloric acid. Specific acids are hydrochloric acid, trifluoroacetic acid and fumaric acid.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like, or using a different acid that produces the same counterion. Lists of additional suitable salts may be found, e.g., in *Remington's Pharmaceutical Sciences,* 17th ed., Mack Publishing Company, Easton, Pa., p. 1418 (1985).

The terms "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. Particularly it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as particularly, more particularly and most particularly definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The term "aromatic" denotes the conventional idea of aromaticity as defined in the literature, in particular in IUPAC—Compendium of Chemical Terminology, $2^{nd}$ Edition, A. D. McNaught & A. Wilkinson (Eds). Blackwell Scientific Publications, Oxford (1997).

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

Whenever a chiral carbon is present in a chemical structure, it is intended that all stereoisomers associated with that chiral carbon are encompassed by the structure as pure stereoisomers as well as mixtures thereof.

Furthermore, the invention includes all optical isomers, i.e. diastereoisomers, diastereomeric mixtures, racemic mixtures, all their corresponding enantiomers and/or tautomers as well as their solvates of the compounds described herein.

The compounds may contain one or more asymmetric centers and can therefore occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

In the embodiments, where optically pure enantiomers are provided, optically pure enantiomer means that the compound contains >90% of the desired isomer by weight, particularly >95% of the desired isomer by weight, or more particularly >99% of the desired isomer by weight, said weight percent based upon the total weight of the isomer(s) of the compound. Chirally pure or chirally enriched compounds may be prepared by chirally selective synthesis or by separation of enantiomers. The separation of enantiomers may be carried out on the final product or alternatively on a suitable intermediate.

All separate embodiments may be combined.

The term "treatment" as used herein includes: (1) inhibiting the state, disorder or condition (e.g. arresting, reducing or delaying the development of the disease, or a relapse thereof in case of maintenance treatment, of at least one clinical or subclinical symptom thereof); and/or (2) relieving the condition (i.e., causing regression of the state, disorder or condition or at least one of its clinical or subclinical symptoms). However, it will be appreciated that when a medicament is administered to a patient to treat a disease, the outcome may not always be effective treatment.

The term "prophylaxis" as used herein includes: preventing or delaying the appearance of clinical symptoms of the state, disorder or condition developing in a mammal and especially a human that may be afflicted with or predisposed to the state, disorder or condition but does not yet experience or display clinical or subclinical symptoms of the state, disorder or condition.

Isotopic Substitution

The present invention includes compounds of Formula Ia, Formula Ib, Formula II, Formula III a, Formula IIIb, Formula IV, Formula V, Formula VI, Formula VII, Formula VIII, Formula IX, Formula X, Formula XI, Formula XII, Formula XIII, Formula XIV, Formula XV, Formula XIV-a to XIV-x, and Formula XV-a to XV-t with at least one desired isotopic substitution of an atom, at an amount above the natural abundance of the isotope, i.e., enriched. Isotopes are atoms having the same atomic number but different mass numbers, i.e., the same number of protons but a different number of neutrons.

Examples of isotopes that can be incorporated into compound of the invention include isotopes of hydrogen, carbon, nitrogen, and oxygen such as $^2H$, $^3H$, $^{11}C$, $^{13}C$, $^{14}C$, $^{15}N$ and $^{17}O$, $^{18}O$ respectively. In one non-limiting embodiment, isotopically labelled compounds can be used in metabolic studies (with, for example $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Isotopic substitutions, for example deuterium substitutions, can be partial or complete. Partial deuterium substitution means that at least one hydrogen is substituted with deuterium. In certain embodiments, the isotope is 90, 95, or 99% or more enriched in an isotope at any location of interest. In one non-limiting embodiment, deuterium is 90, 95, or 99% enriched at a desired location.

In one non-limiting embodiment, the substitution of a hydrogen atom for a deuterium atom can be provided in any compound of Formula Ia, Formula Ib, Formula II, Formula IIIa, Formula IIIb, Formula IV, Formula V, Formula VI, Formula VII, Formula VIII, Formula IX, Formula X, Formula XI, Formula XII, Formula XIII, Formula XIV, Formula XV, Formula XIV-a to XIV-x, and Formula XV-a to XV-t. In one non-limiting embodiment, the substitution of a hydrogen atom for a deuterium atom occurs within one or more groups selected from the variables described herein. For example, when any of the groups are, or contain for example through substitution, methyl, ethyl, or methoxy, the alkyl residue may be deuterated (in non-limiting embodiments, $CDH_2$, $CD_2H$, $CD_3$, $CH_2CD_3$, $CD_2CD_3$, $CHDCH_2D$, $CHDCHD_2$, $OCDH_2$, $OCD_2H$, or $OCD_3$, etc.). In certain other embodiments, when two substitutions are combined to form a cycle, the unsubstituted carbons may be deuterated.

II. Compounds of the Present Invention

The present invention provides compounds of Formula Ia, Formula Ib, Formula II, Formula IIIa, Formula IIIb, Formula IV, Formula V, Formula VI, Formula VIII, Formula IX, Formula X, Formula XI, Formula XII, Formula XIV, Formula XV, Formula XIV-a to XIV-x, and Formula XV-a to XV-t, and pharmaceutically acceptable salts thereof. The invention also provides the use of compounds of Formula VII and Formula XIII as further described herein.

Compounds of Formula Ia to Formula VI

In one aspect, a compound is provided of Formula Ia or Formula Ib:

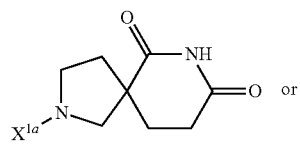
(Ia)

or

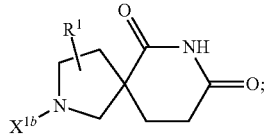
(Ib)

or a pharmaceutically acceptable salt thereof; wherein all variables are as defined herein.

In one embodiment of Formula Ia, a compound is provided of the formula:

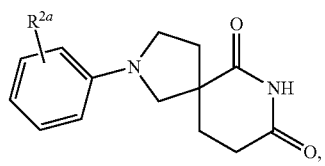

In one embodiment of Formula Ia, a compound is provided selected from:

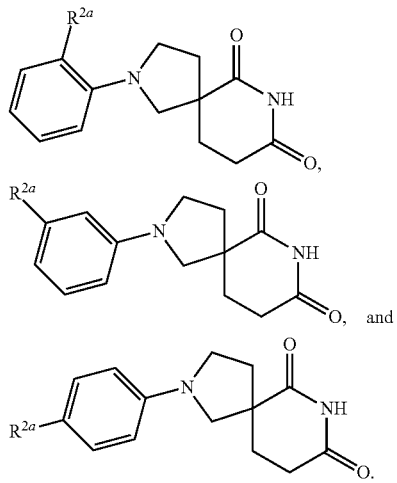

In one embodiment of Formula Ib, a compound is provided selected from:

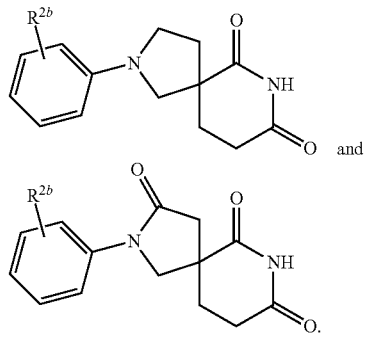

In one embodiment of Formula Ib, a compound is provided selected from:
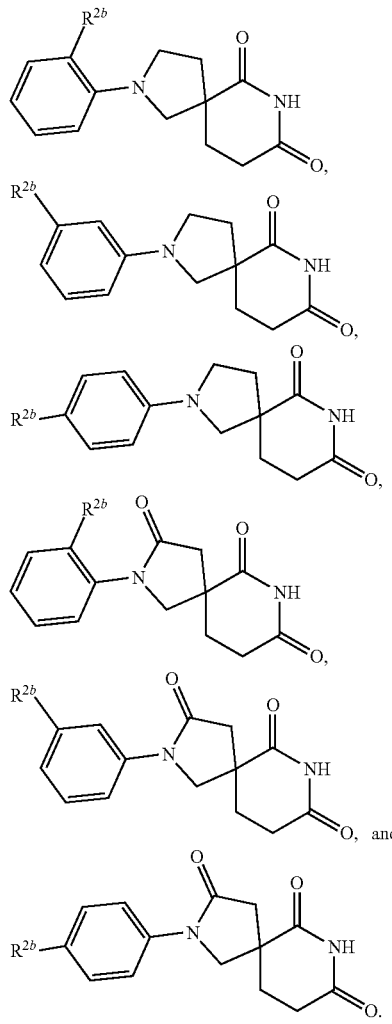
In another aspect, a compound is provided of Formula II:
$$(II)$$
or a pharmaceutically acceptable salt thereof;
wherein all variables are as defined herein.
In one embodiment of Formula II, a compound is provided selected from:
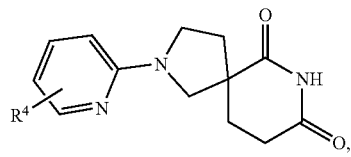
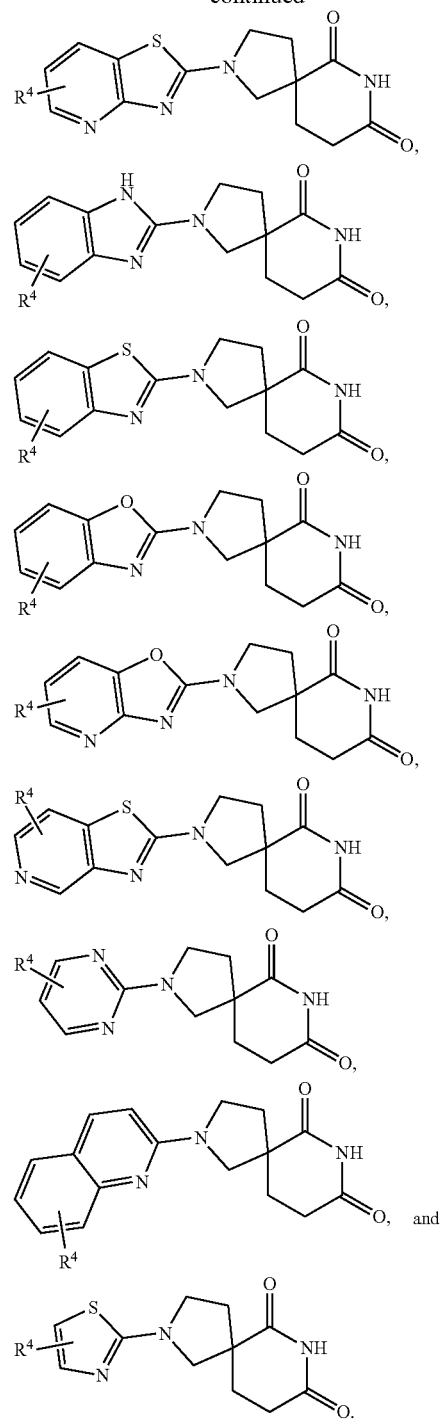
In one embodiment of Formula II, a compound is provided selected from:
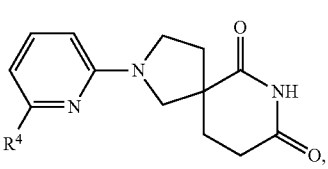

-continued
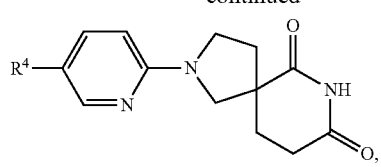
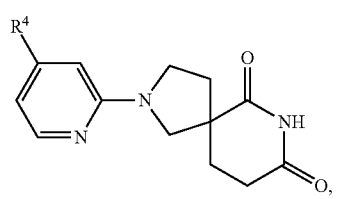
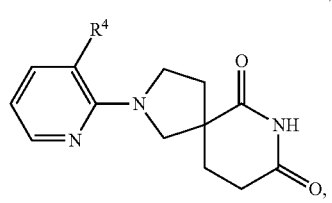
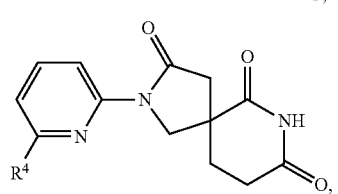
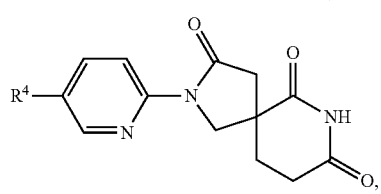
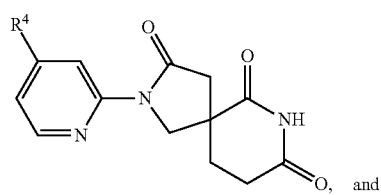
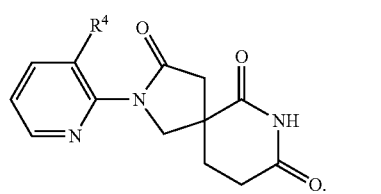
In one embodiment of Formula II, a compound is provided selected from:
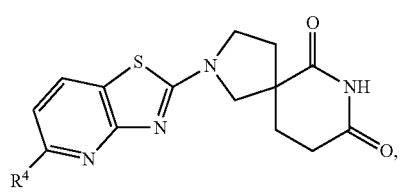
-continued
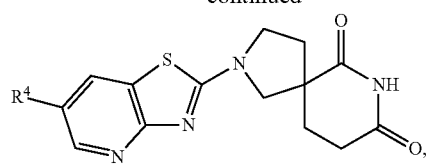
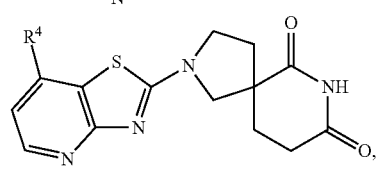
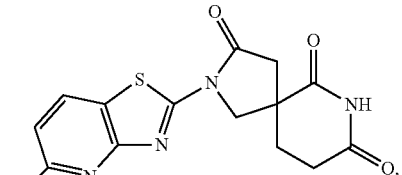
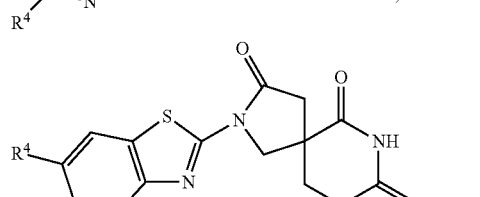
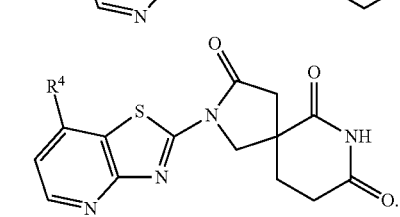, and
In one embodiment of Formula II, a compound is provided from:
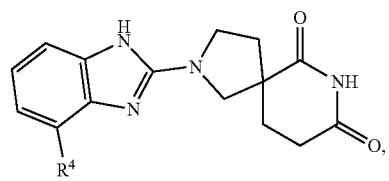
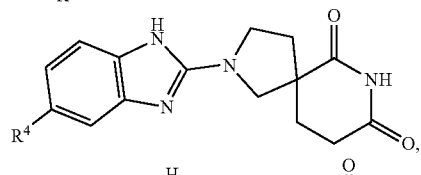
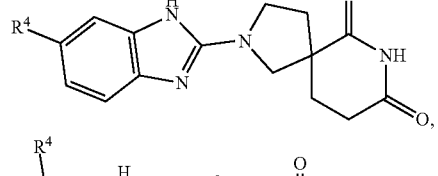
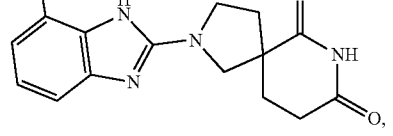

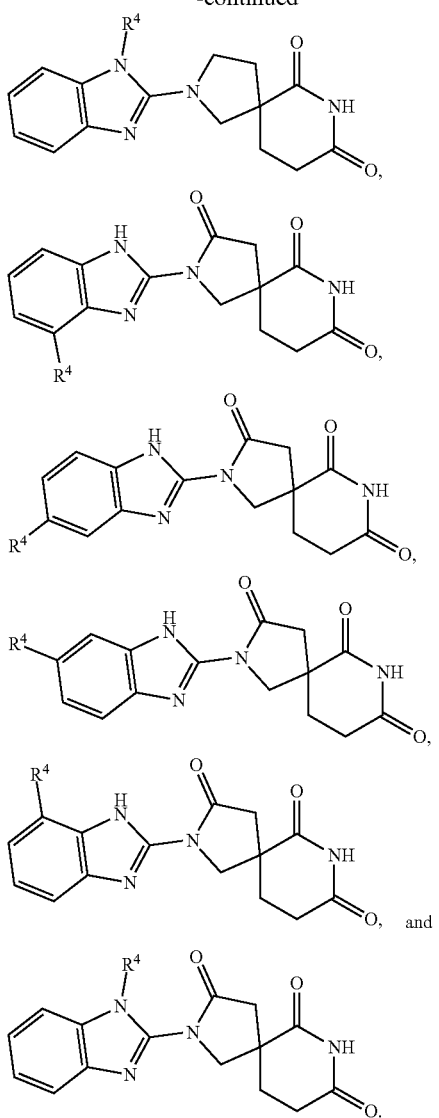
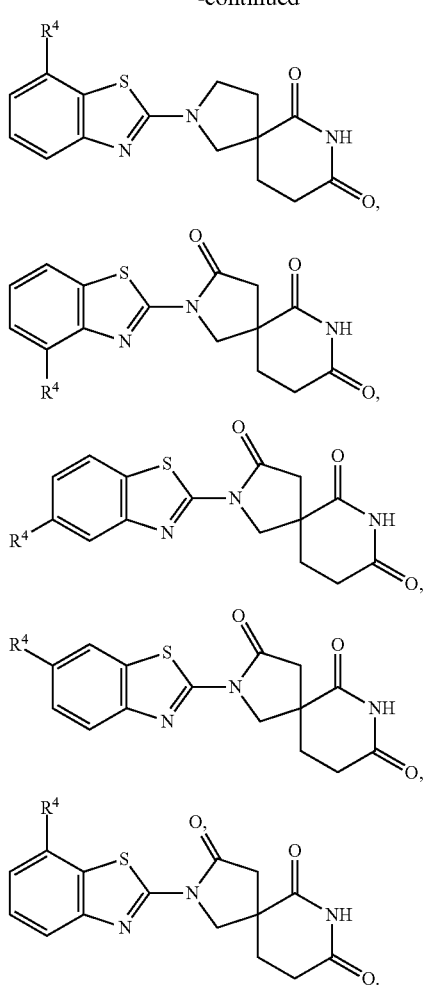
In one embodiment of Formula II, a compound is provided selected from:
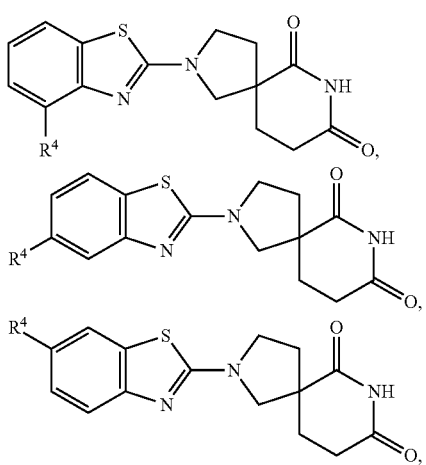
In one embodiment of Formula II, a compound is provided selected from:
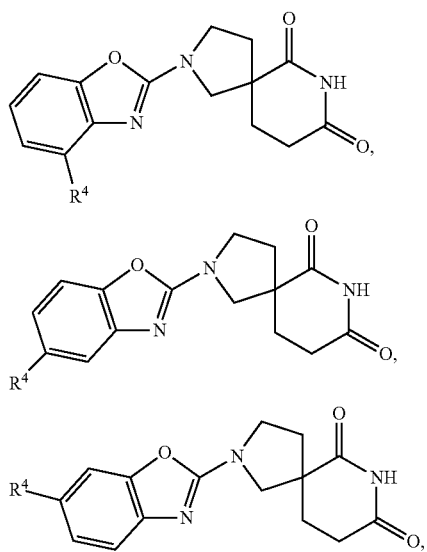

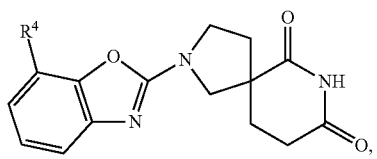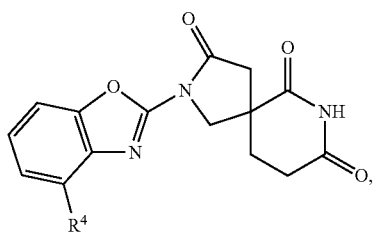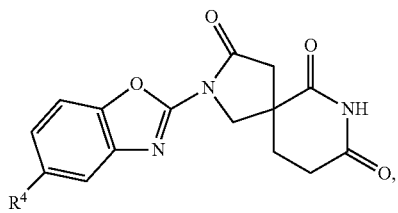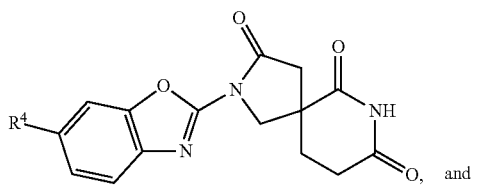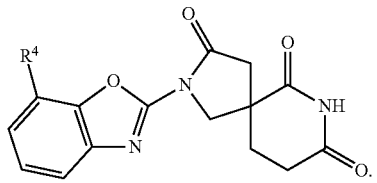
In one embodiment of Formula II, a compound is provided selected from:
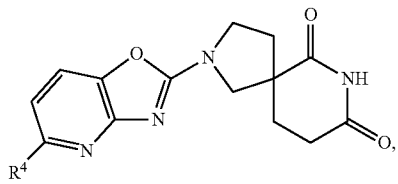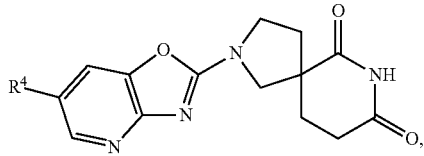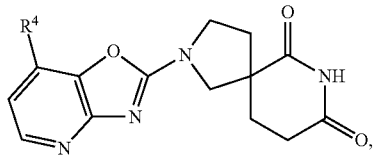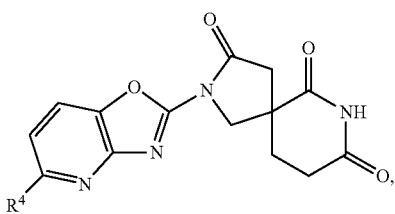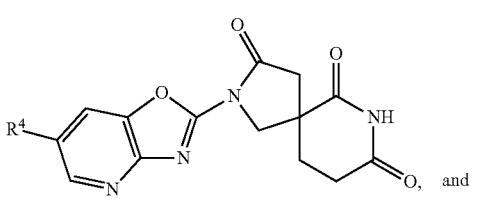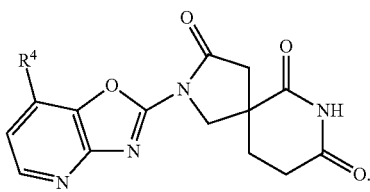
In one embodiment of Formula II, a compound is provided selected from:
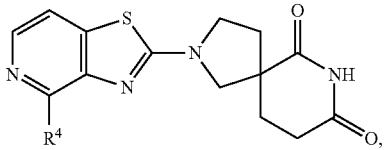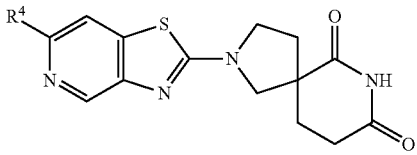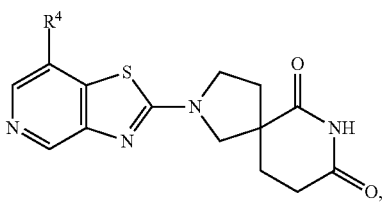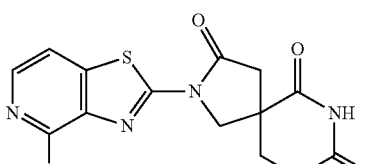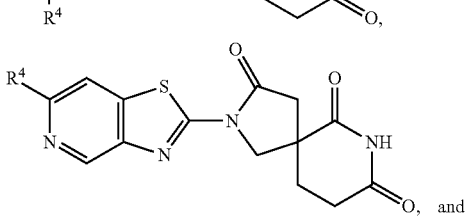

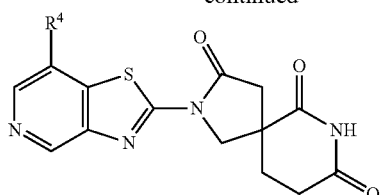
In one embodiment of Formula II, a compound is provided selected from:
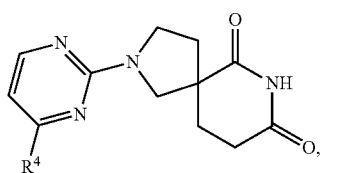
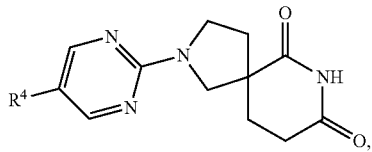
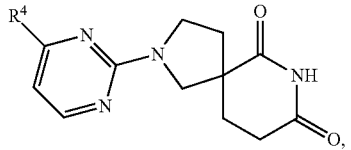
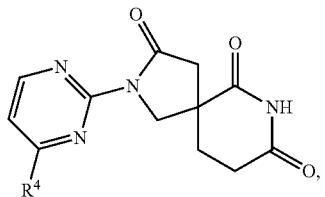
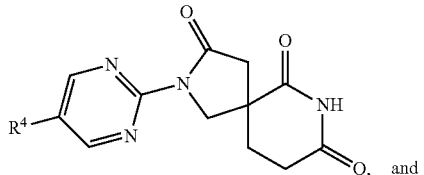
and
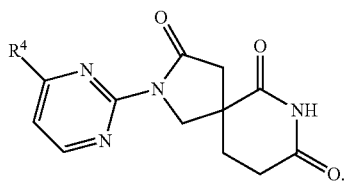
In one embodiment of Formula II, a compound is provided selected from:
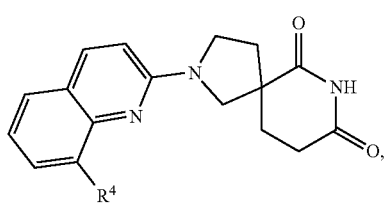
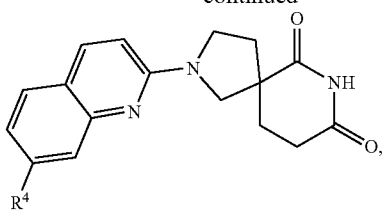
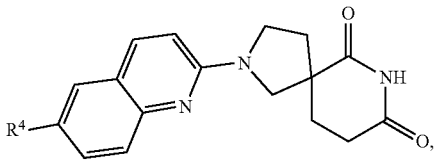
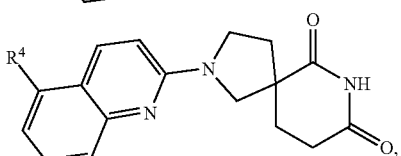
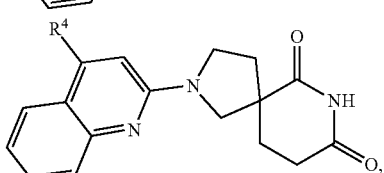
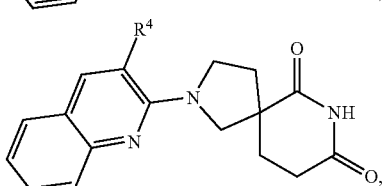
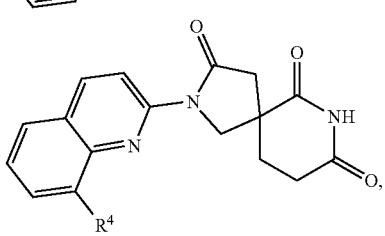
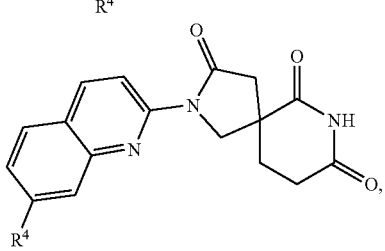
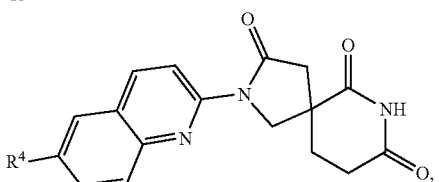
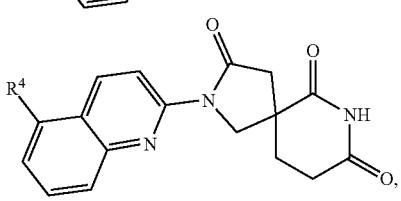

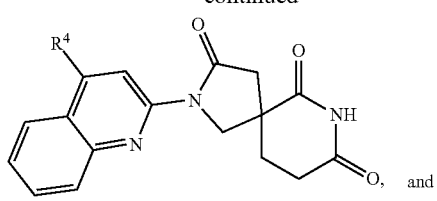

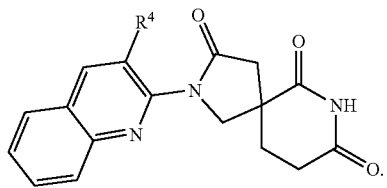

In one embodiment of Formula II, a compound is provided selected from:

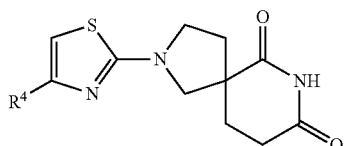

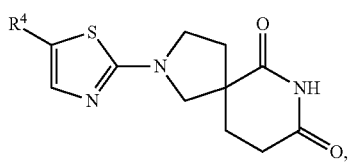

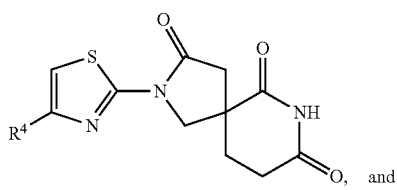

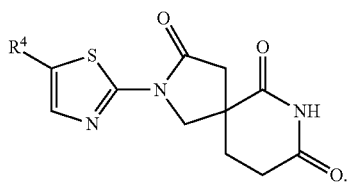

In another aspect, a compound is provided of Formula IIIa or Formula IIIb:

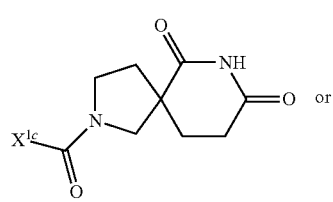

(IIIa)

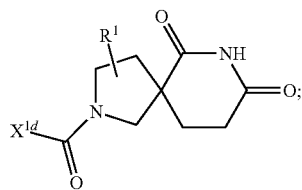

(IIIb)

or a pharmaceutically acceptable salt thereof;
wherein all variables are as defined herein.

In one embodiment of Formula IIIa, a compound is provided of the formula:

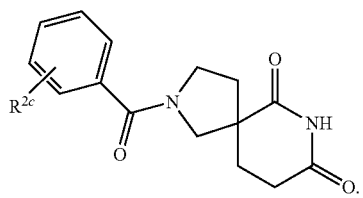

In one embodiment of Formula IIIa, a compound is provided selected from:

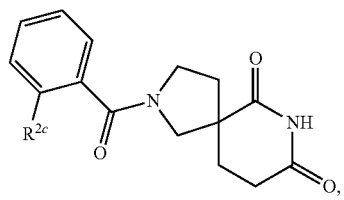

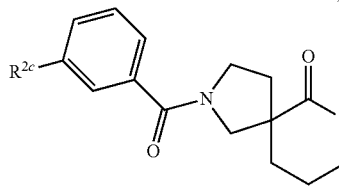

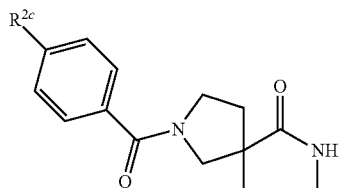

In one embodiment of Formula IIIb, a compound is provided of the formula:

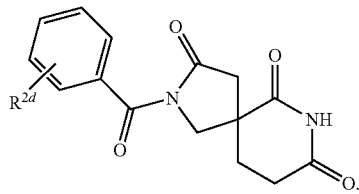

In one embodiment of Formula IIIb, a compound is provided selected from:
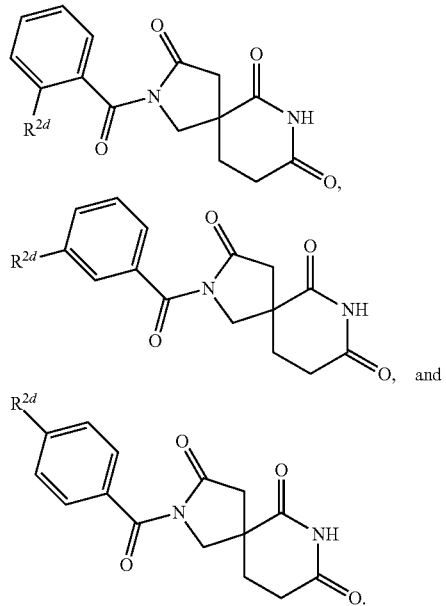
In another embodiment, a compound of Formula IV is provided:
(IV)
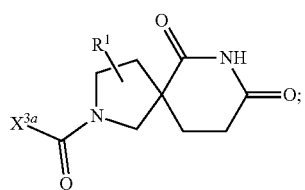
or a pharmaceutically acceptable salt thereof;
wherein all variables are as defined herein.
In one embodiment of Formula IV, a compound is provided selected from:
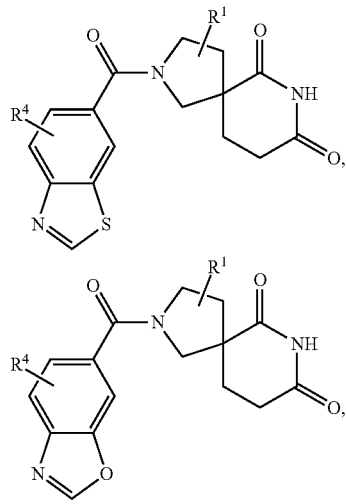
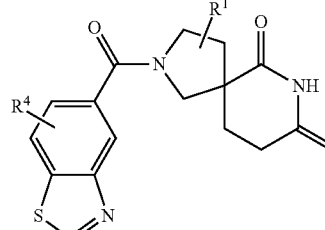
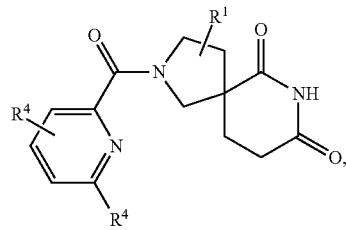
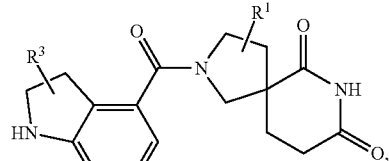
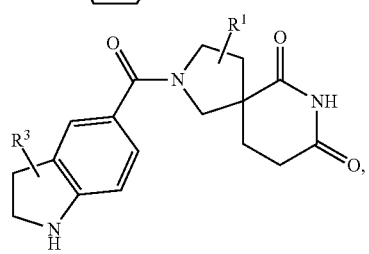
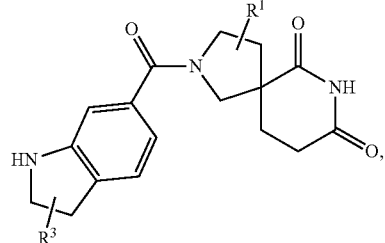
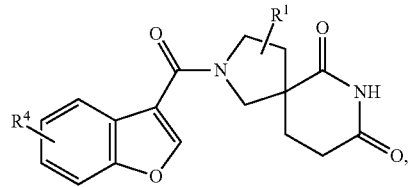
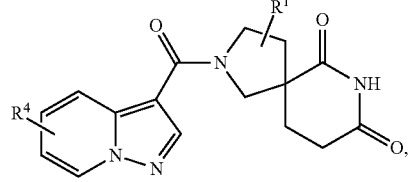
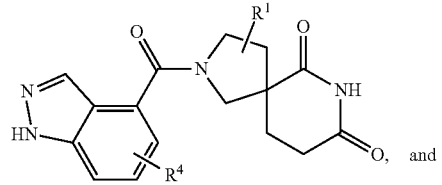

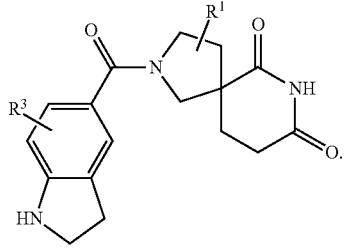
In one embodiment of Formula IV, a compound is provided selected from:
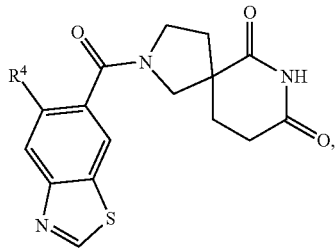
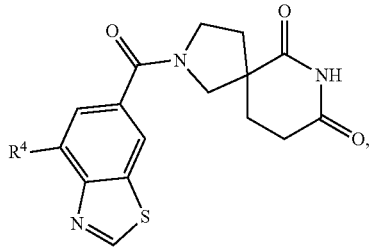
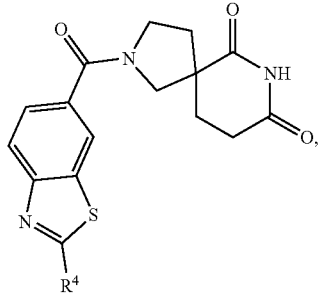
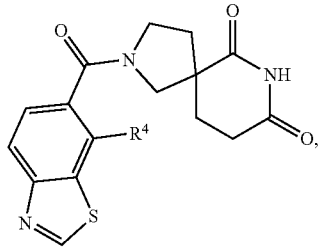
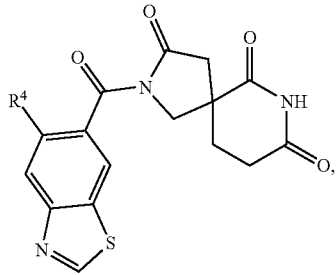
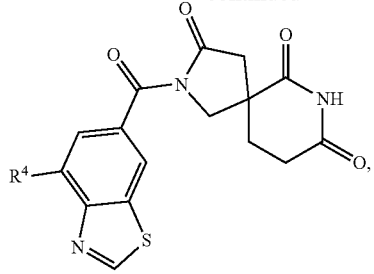
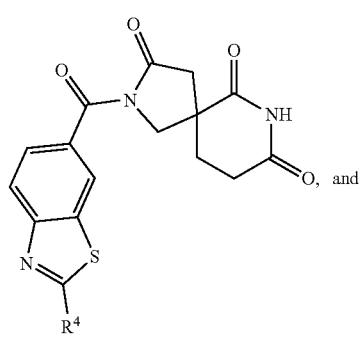
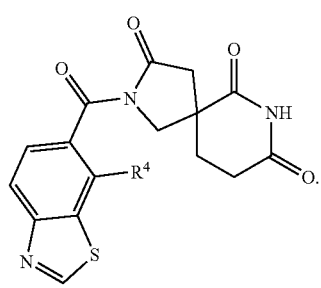
In one embodiment of Formula IV, a compound is provided selected from:
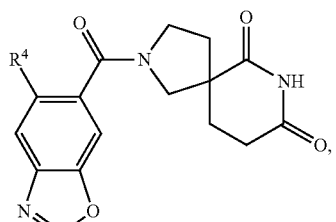
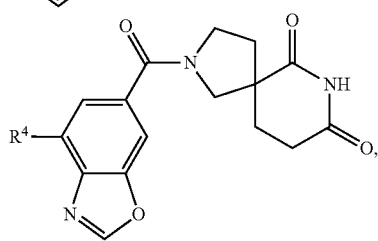

-continued
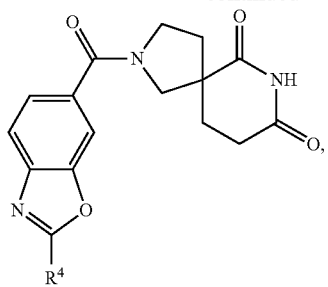
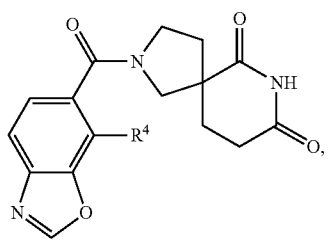
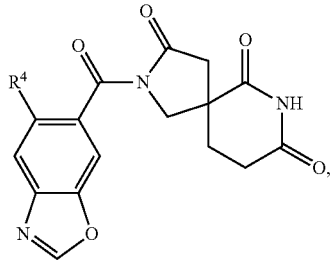
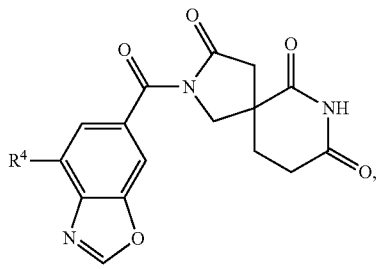
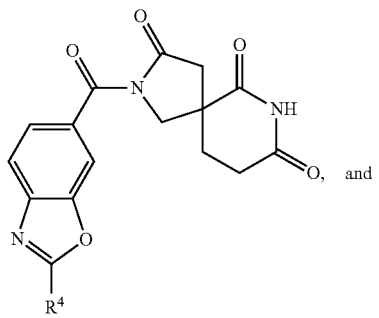, and
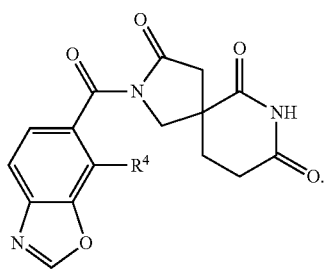.
In one embodiment of Formula IV, a compound is provided selected from:
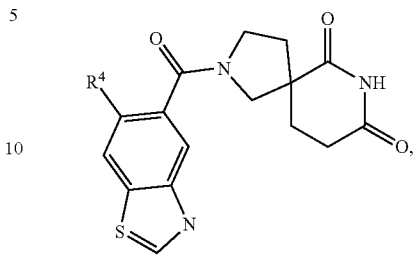
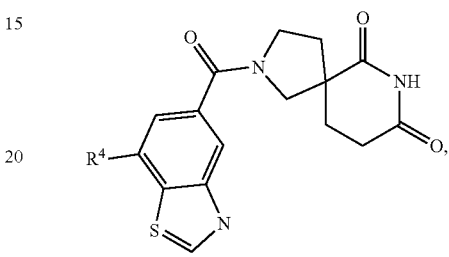
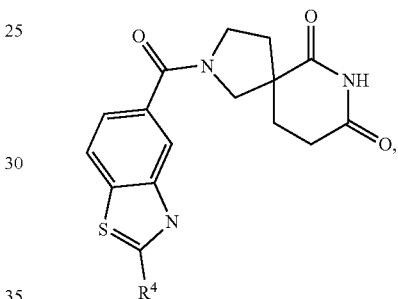
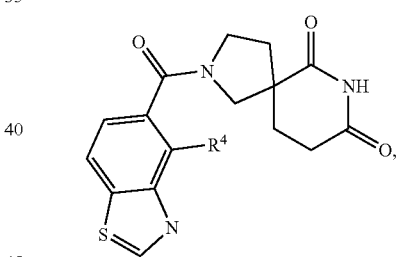
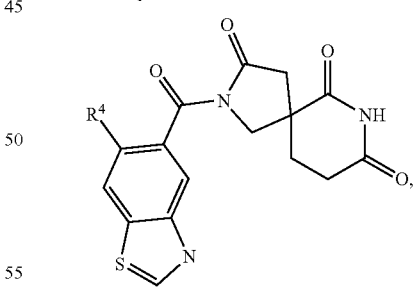
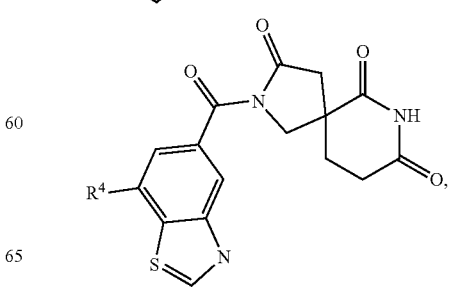

53
-continued
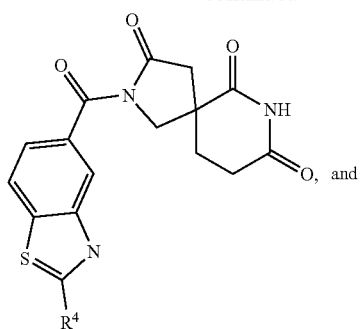
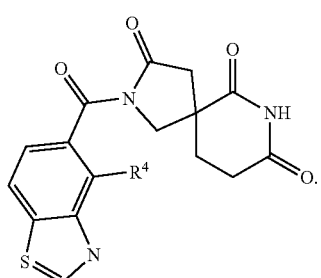
In one embodiment of Formula IV, a compound is provided selected from:
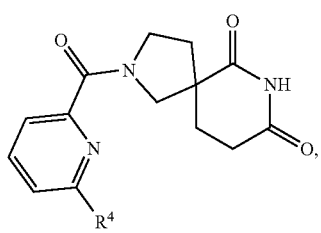
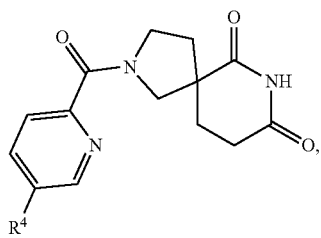
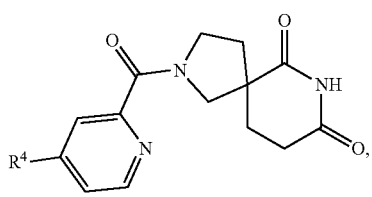
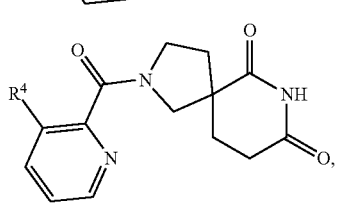
54
-continued
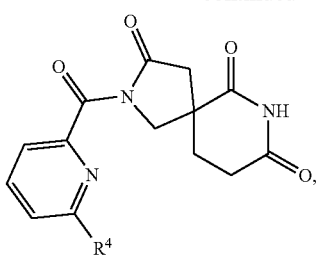
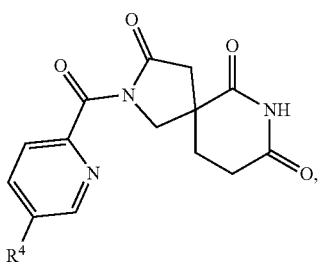
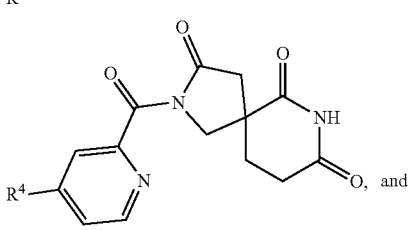
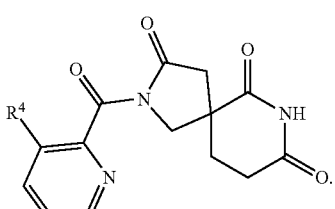
In one embodiment of Formula IV, a compound is provided selected from:
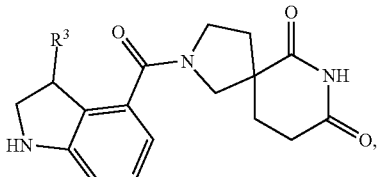
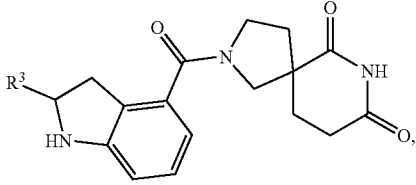
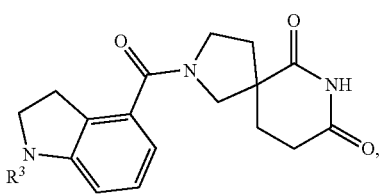

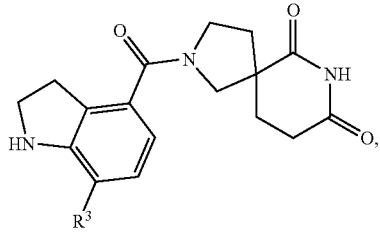
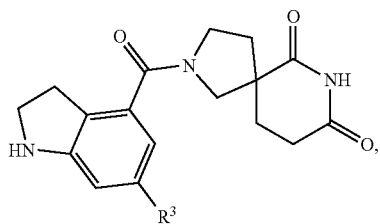
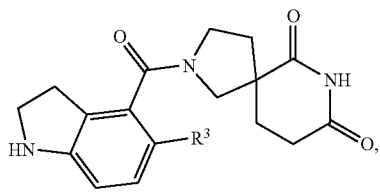
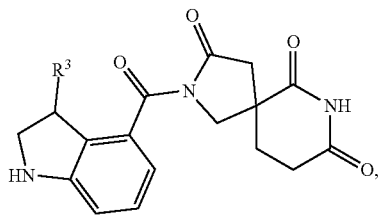
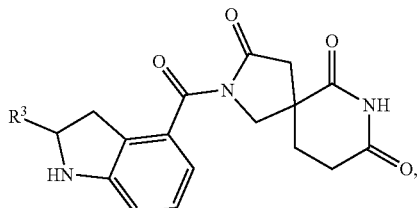
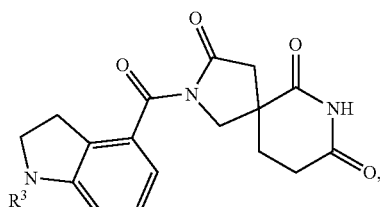
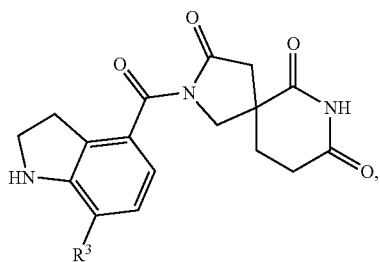
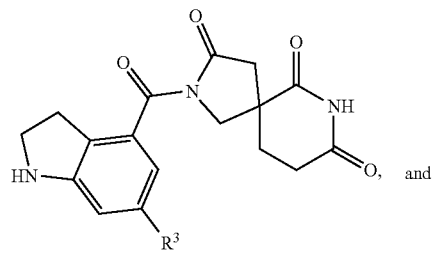
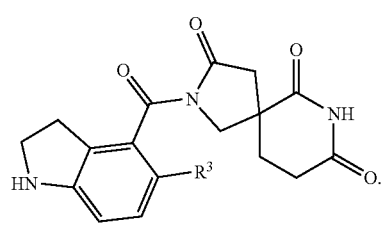
In one embodiment of Formula IV, a compound is provided selected from:
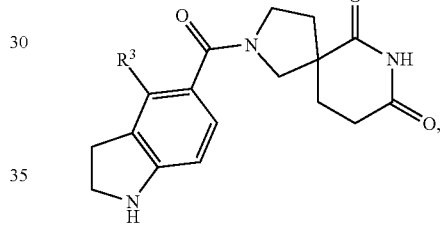
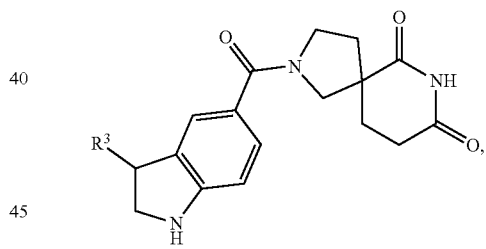
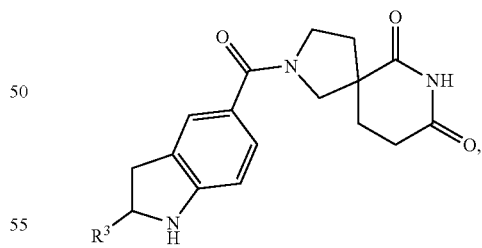
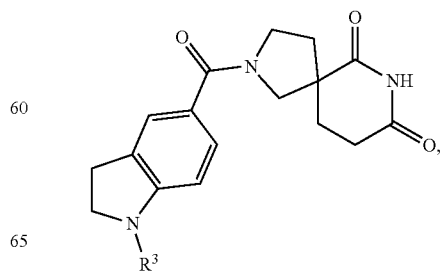

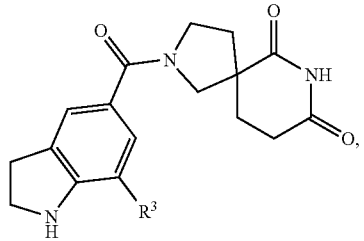
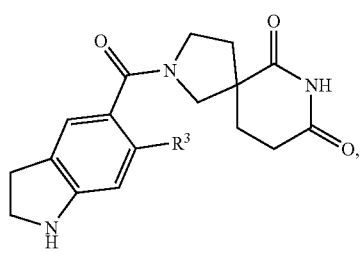
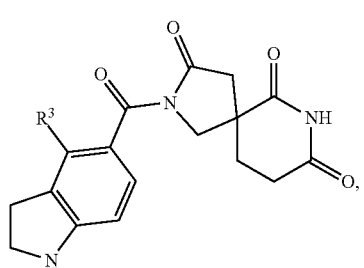
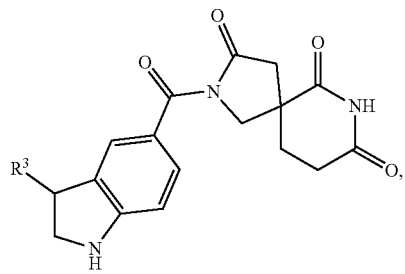
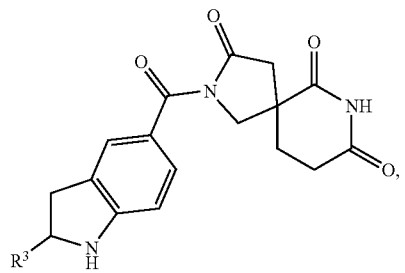
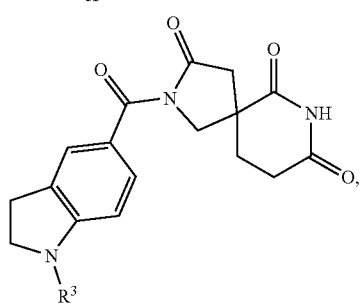
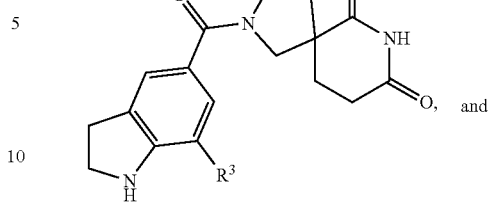
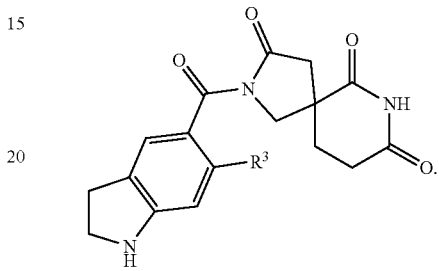
In one embodiment of Formula IV, a compound is provided selected from:
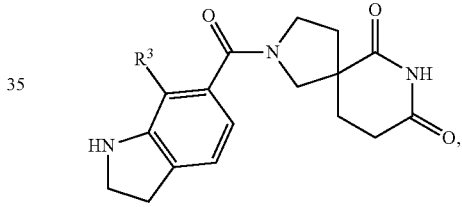
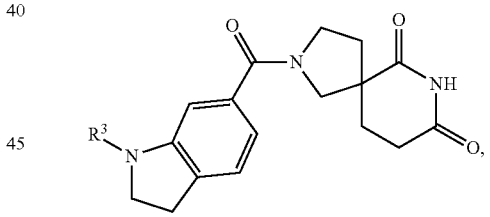
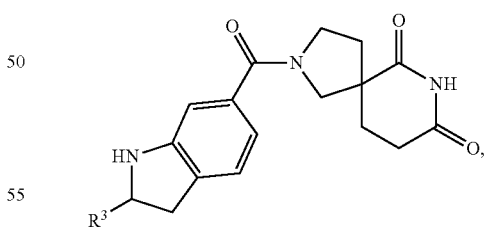
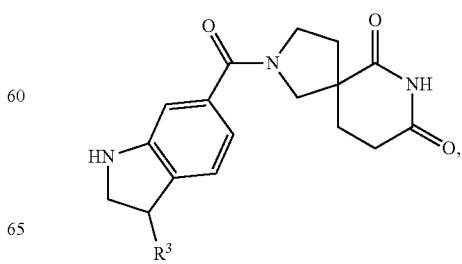

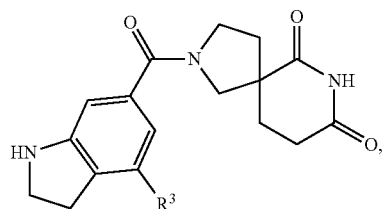
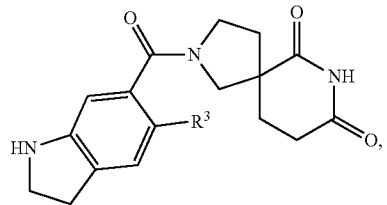
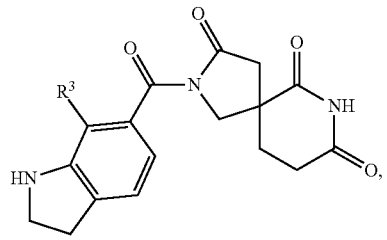
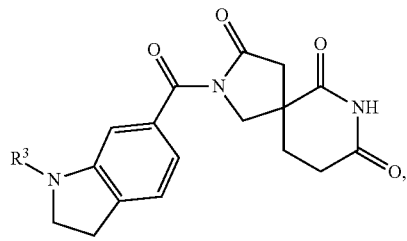
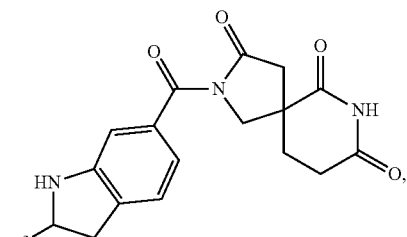
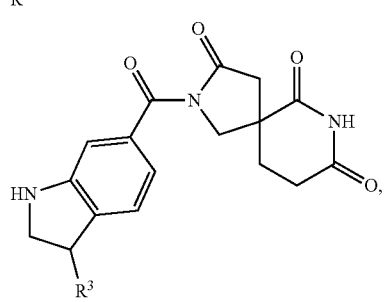
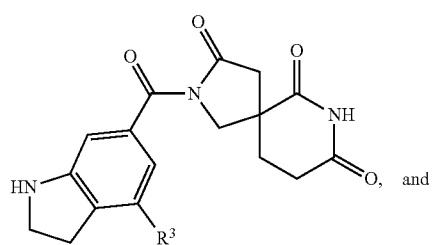
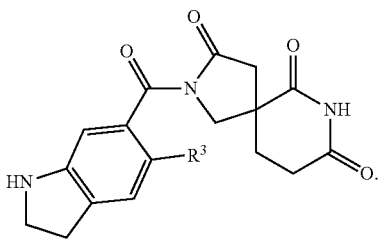
In one embodiment of Formula IV, a compound is provided selected from:
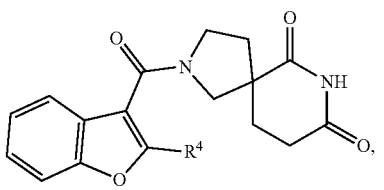
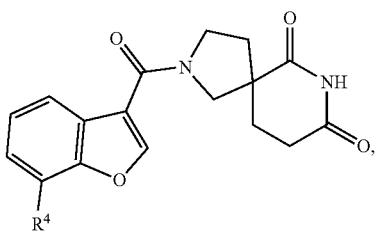
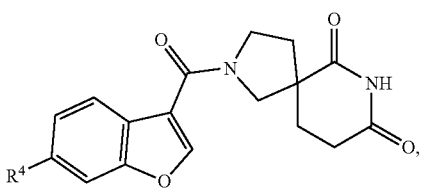
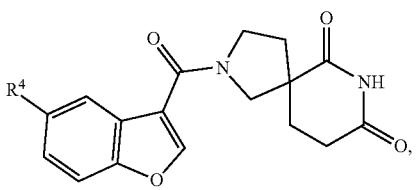
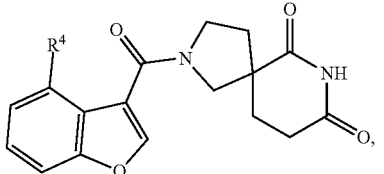
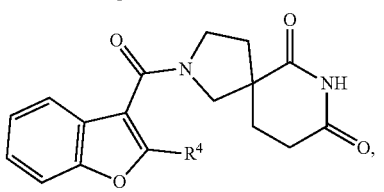

61
-continued
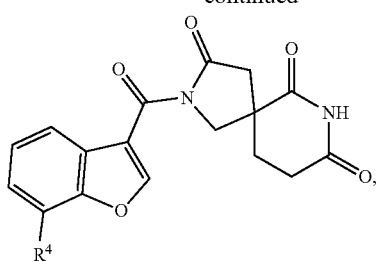
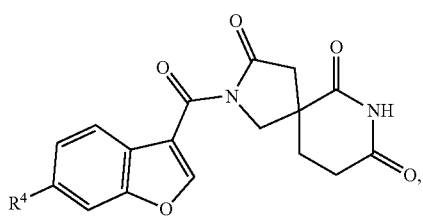
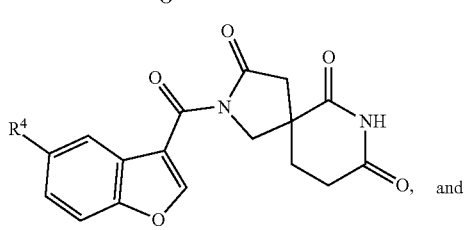
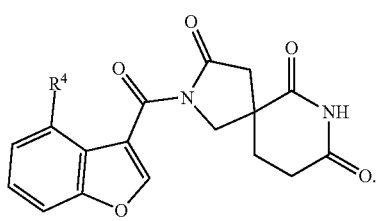
In one embodiment of Formula IV, a compound is provided selected from:
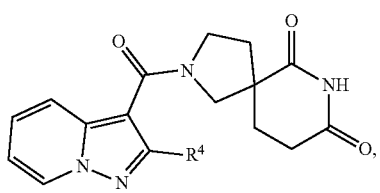
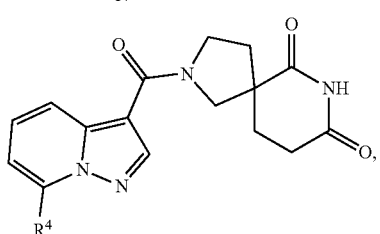
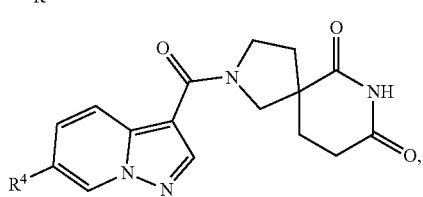
62
-continued
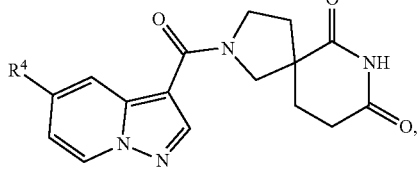
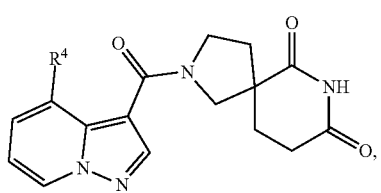
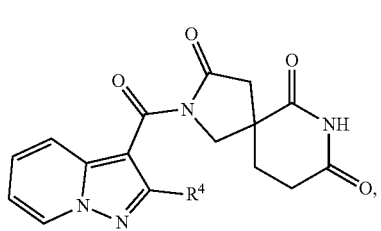
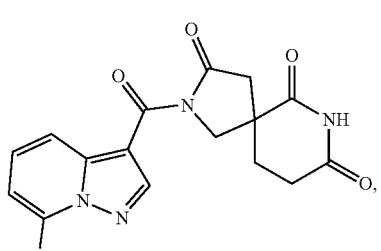
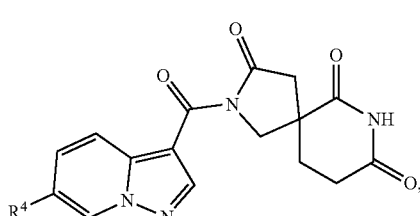
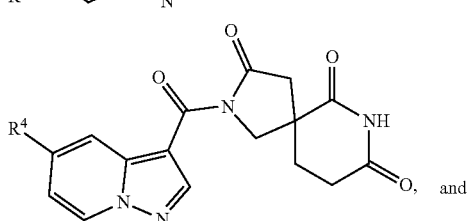
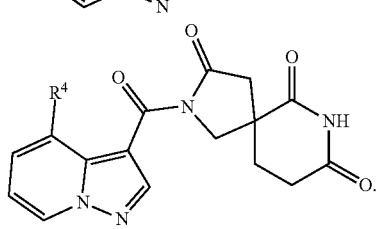

In one embodiment of Formula IV, a compound is provided selected from:
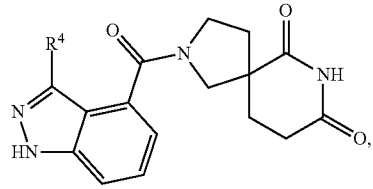
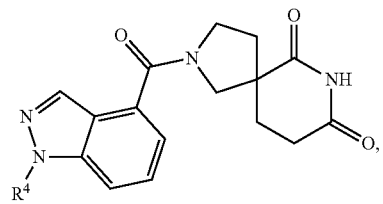
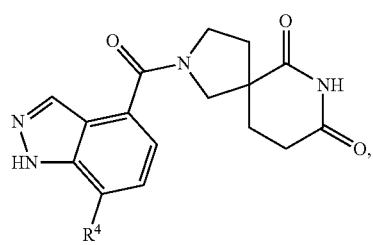
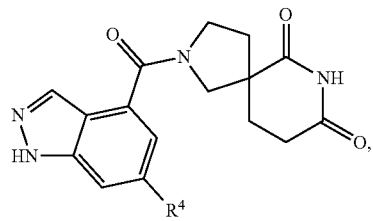
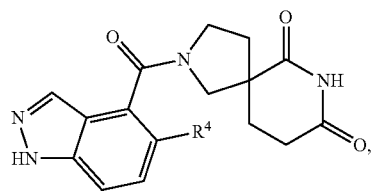
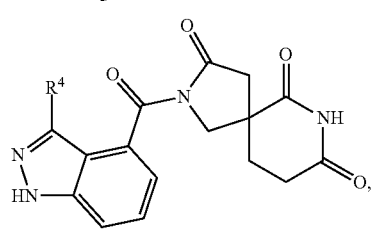
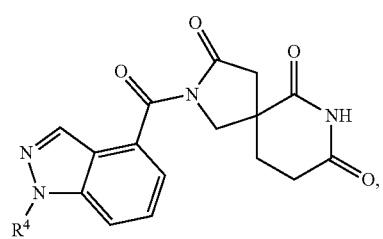
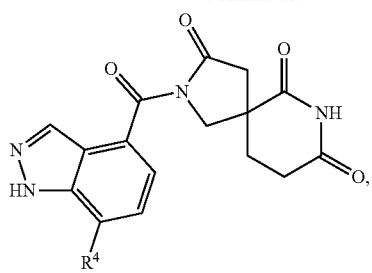
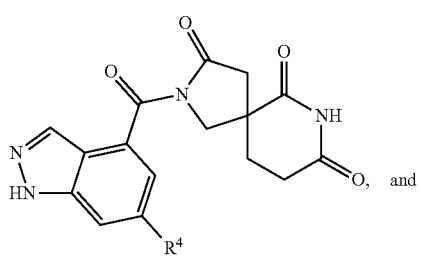
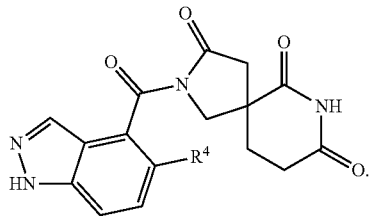, and
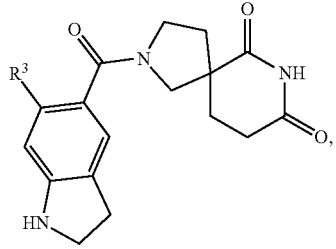.
In one embodiment of Formula IV, a compound is provided selected from:
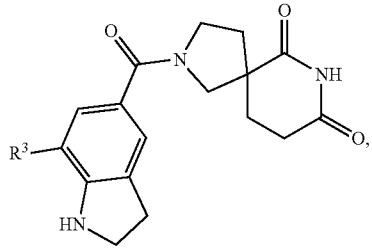
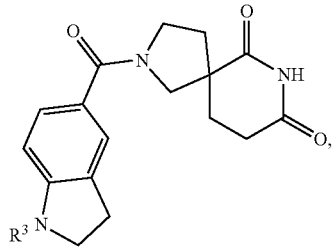

-continued
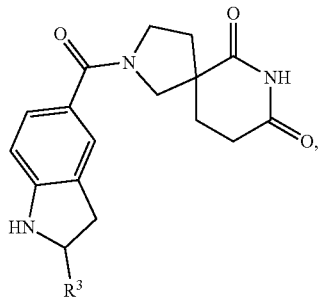
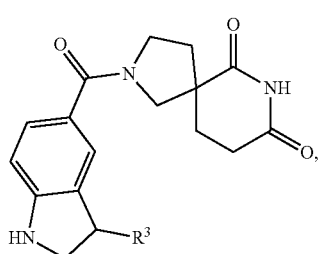
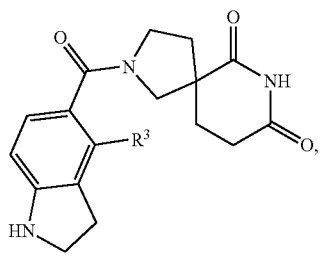
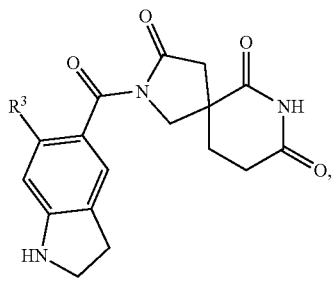
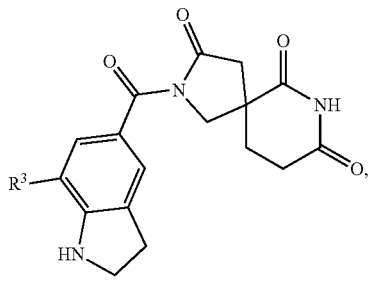
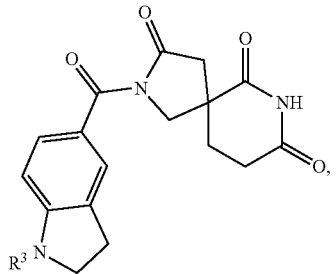
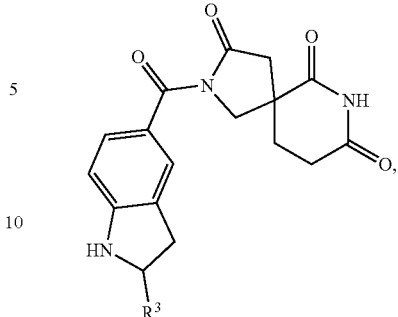
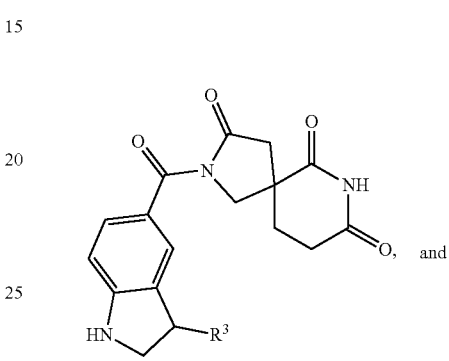, and
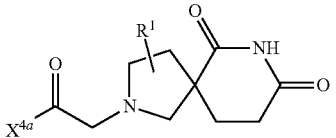
In another embodiment, a compound of Formula V or VI is provided:
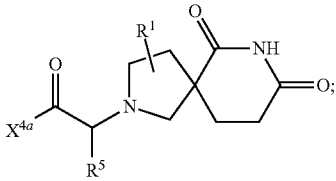
(V)
(VI)
or a pharmaceutically acceptable salt thereof;
wherein all variables are as defined herein.

In one embodiment of Formula V, a compound is provided selected from:
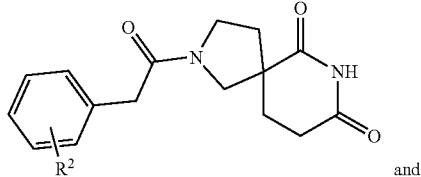
and
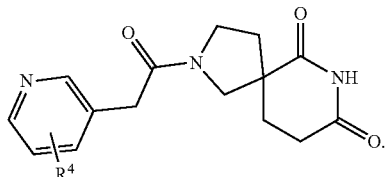
In one embodiment of Formula V, a compound is provided selected from:
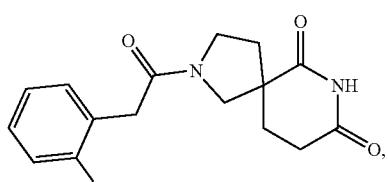
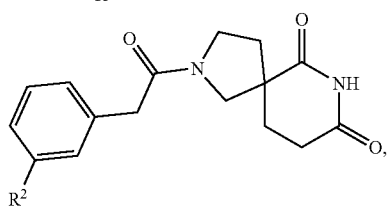
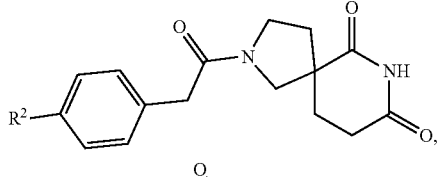
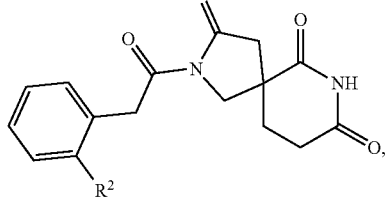
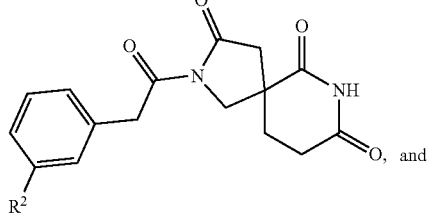, and
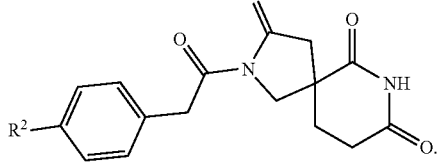
In one embodiment of Formula V, a compound is provided selected from:
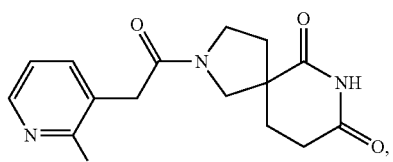
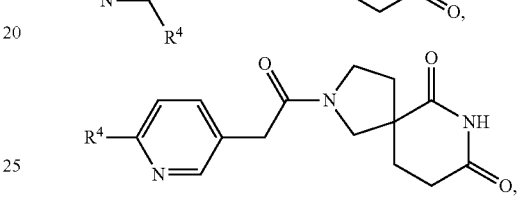
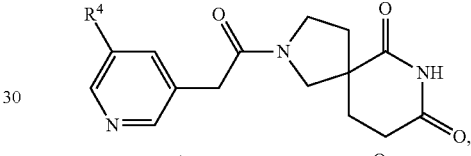
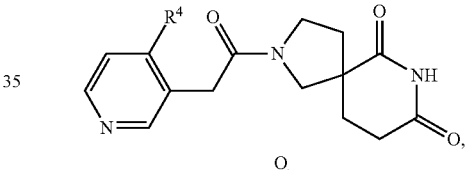
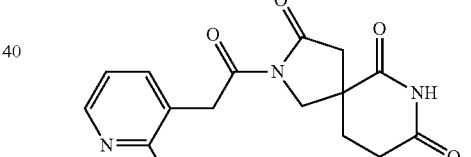
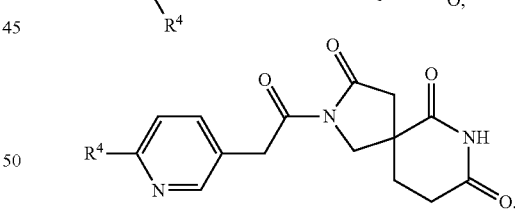
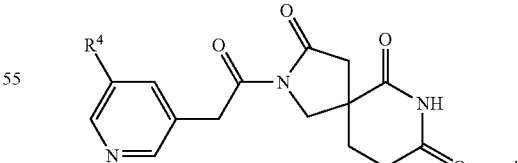, and
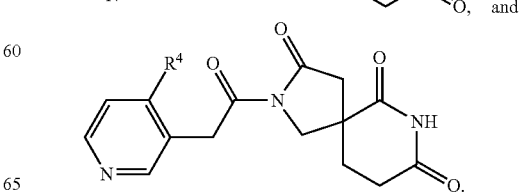

In one embodiment of Formula VI, a compound is provided selected from:
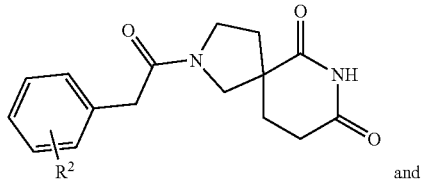
and
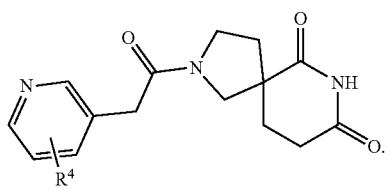
In one embodiment of Formula VI, a compound is provided selected from:
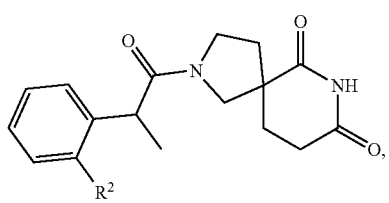
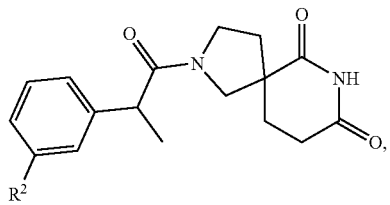
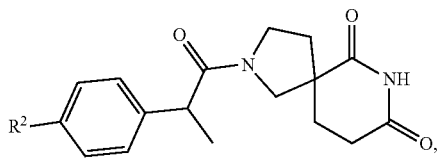
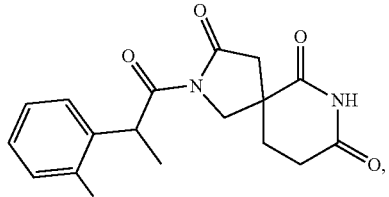
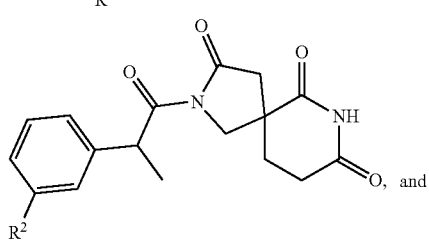
-continued
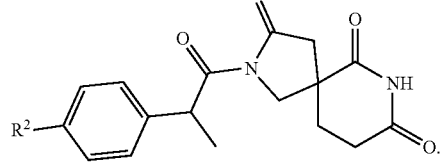
In one embodiment of Formula VI, a compound is provided selected from:
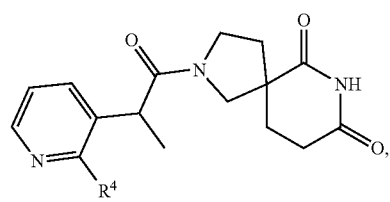
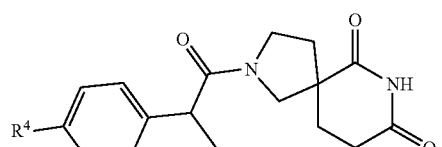
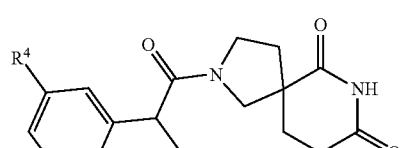
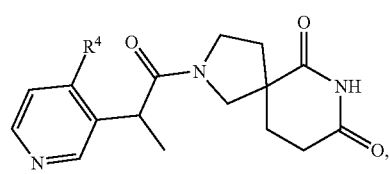
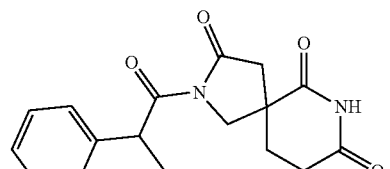
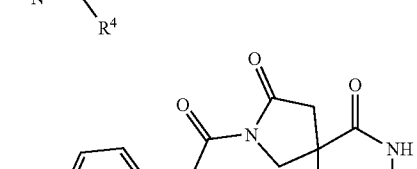
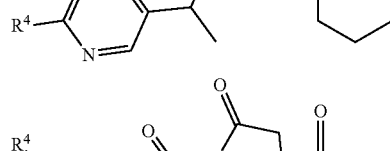
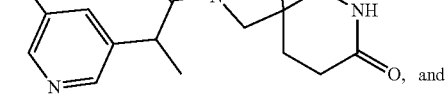
and

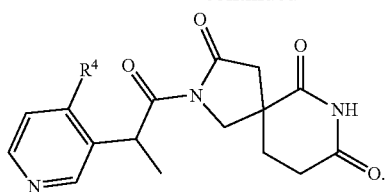
In one embodiment, a compound is provided selected from:
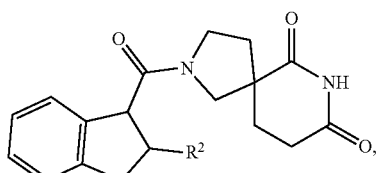
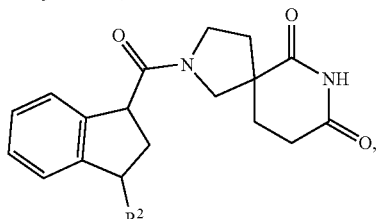
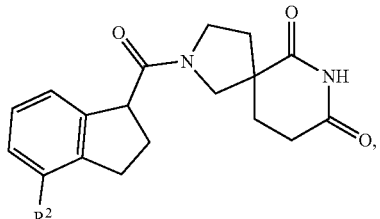
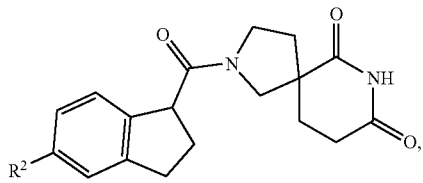
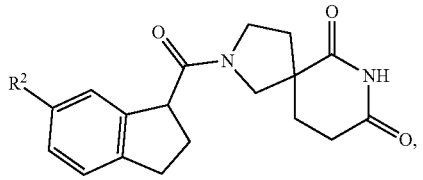
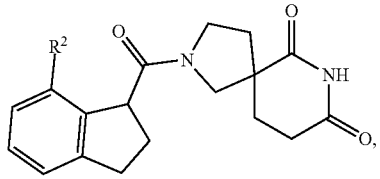
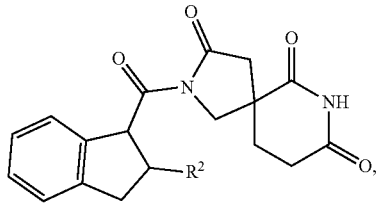
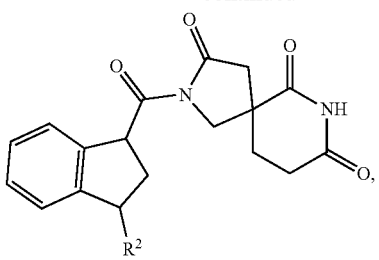
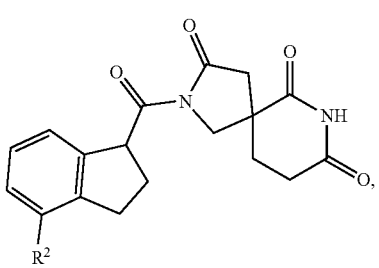
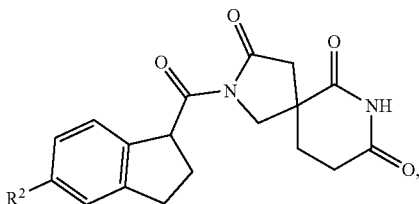
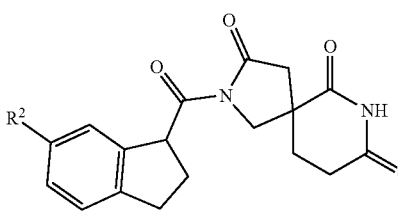
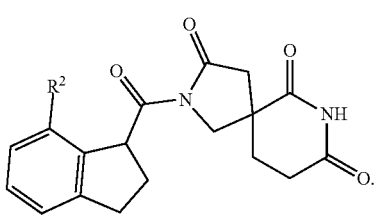
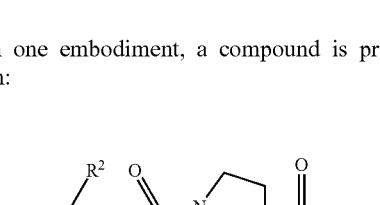, and
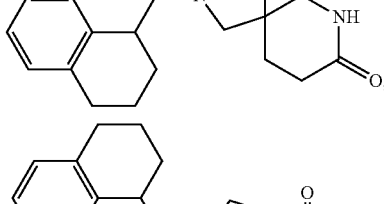
In one embodiment, a compound is provided selected from:
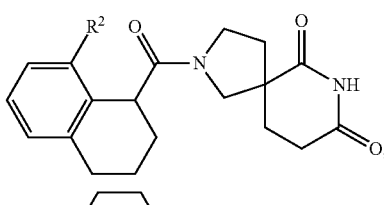
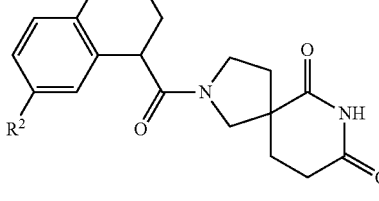

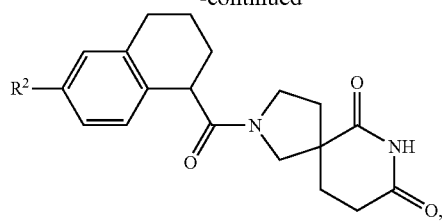
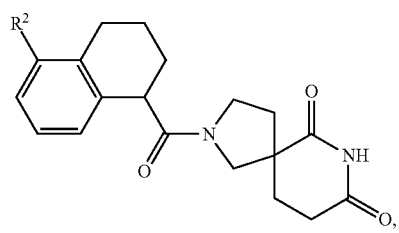
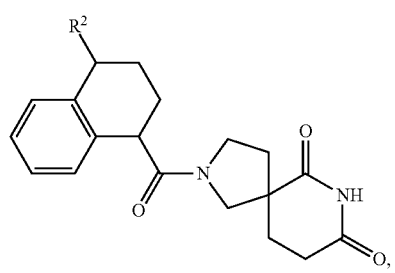
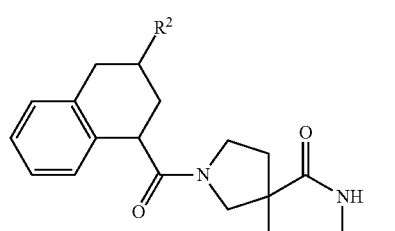
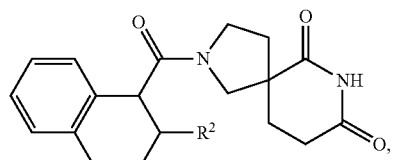
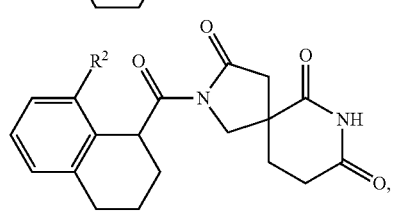
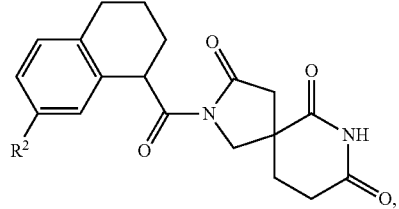
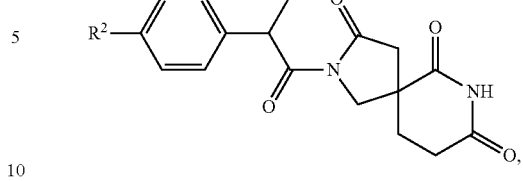
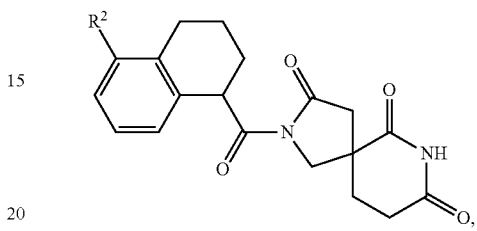
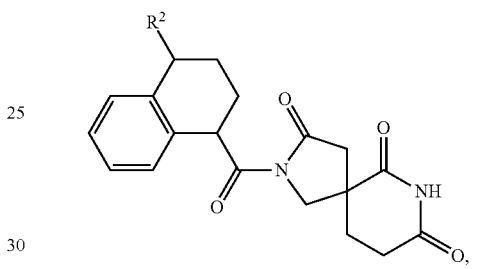
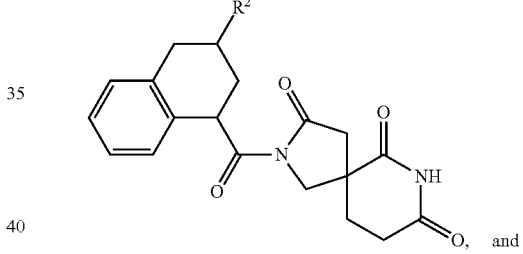
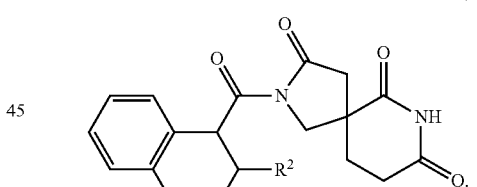
In one embodiment, a compound is provided selected from:
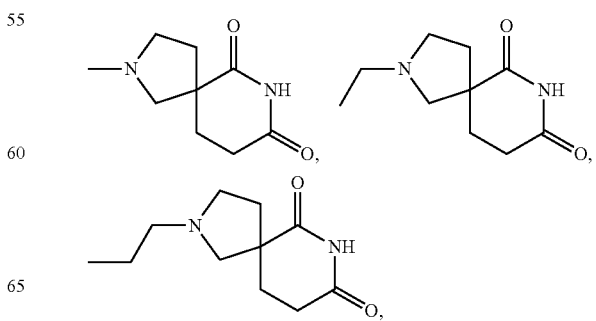

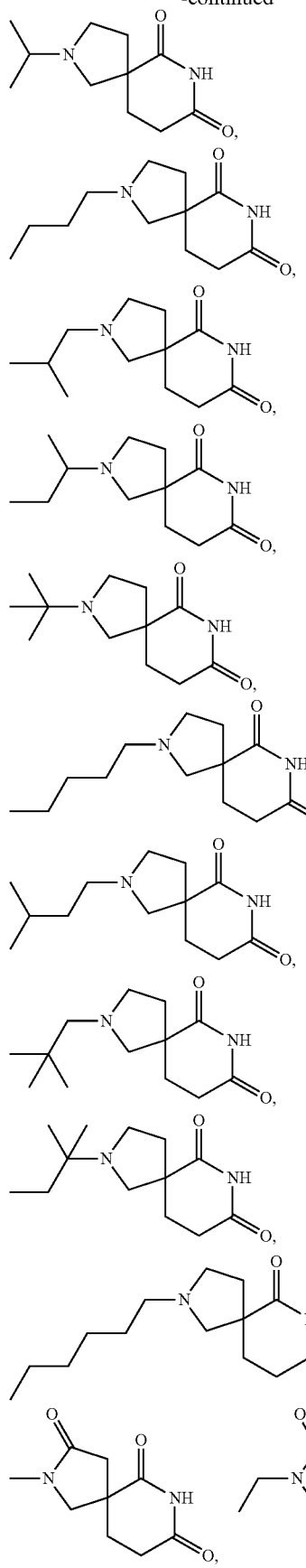
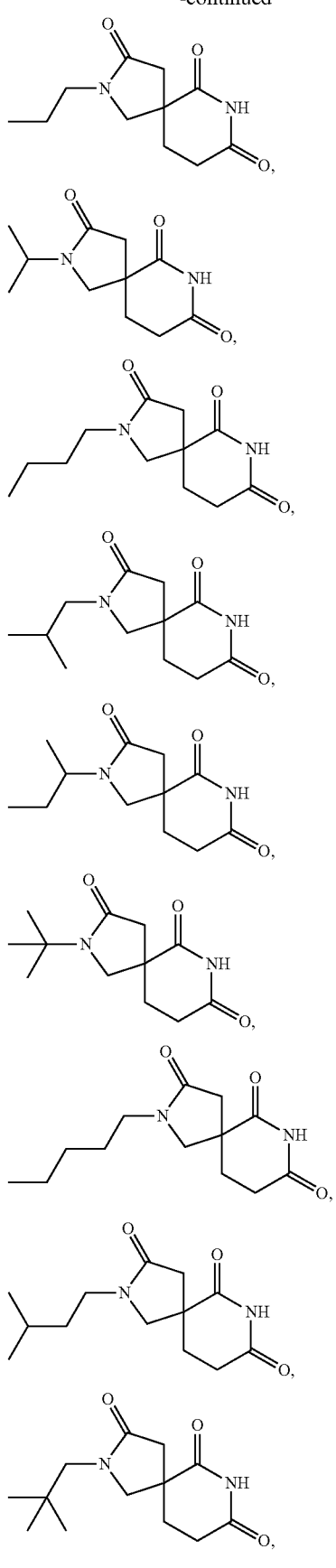

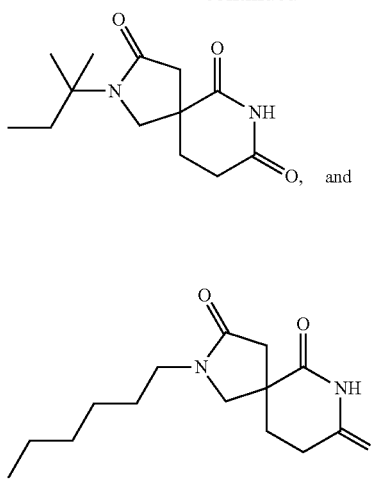

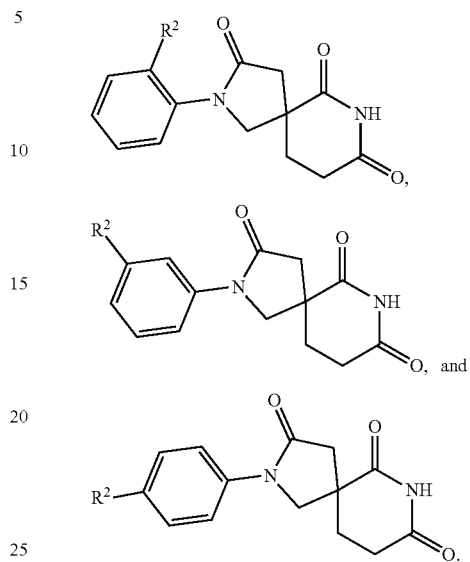

In one embodiment, the compound of Formula VII for use in the methods described herein is selected from:

Compounds of Formula VII

In another aspect, the use of a compound for the treatment of a therapeutic condition which can be treated by modulating the function or activity of the cereblon containing E3 Ubiquitin Ligase Protein Complex is provided of Formula VII:

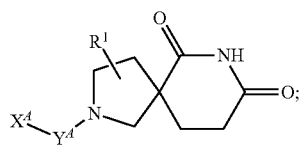

(VII)

or a pharmaceutically acceptable salt thereof;

wherein all variables are as defined herein.

In one embodiment, the compound of Formula VII for use in the methods described herein is selected from:

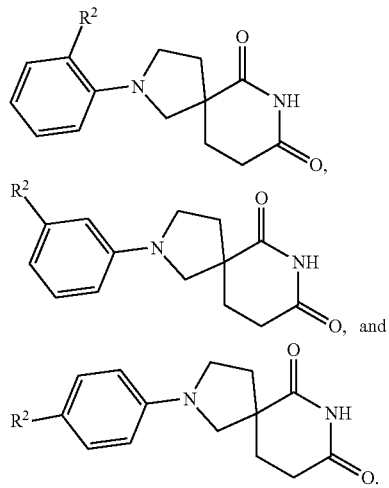

In one embodiment, the compound of Formula VII for use in the methods described herein is selected from:

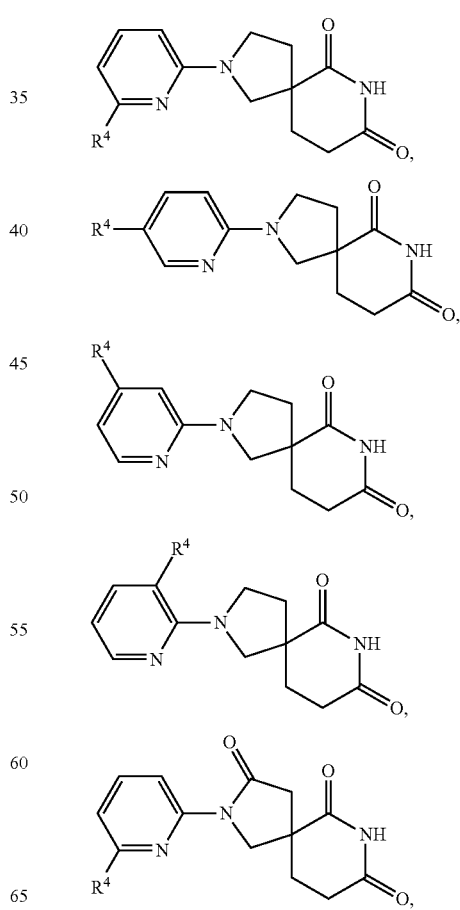

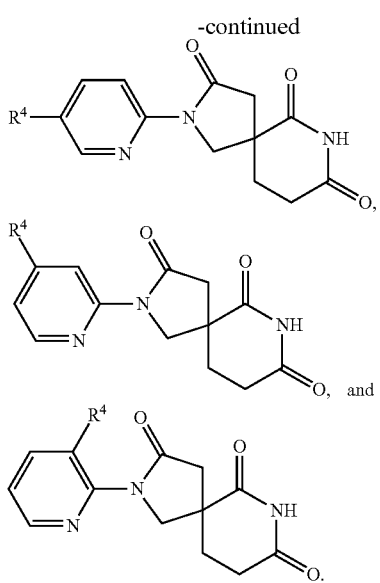
In one embodiment, the compound of Formula VII for use in the methods described herein is selected from:
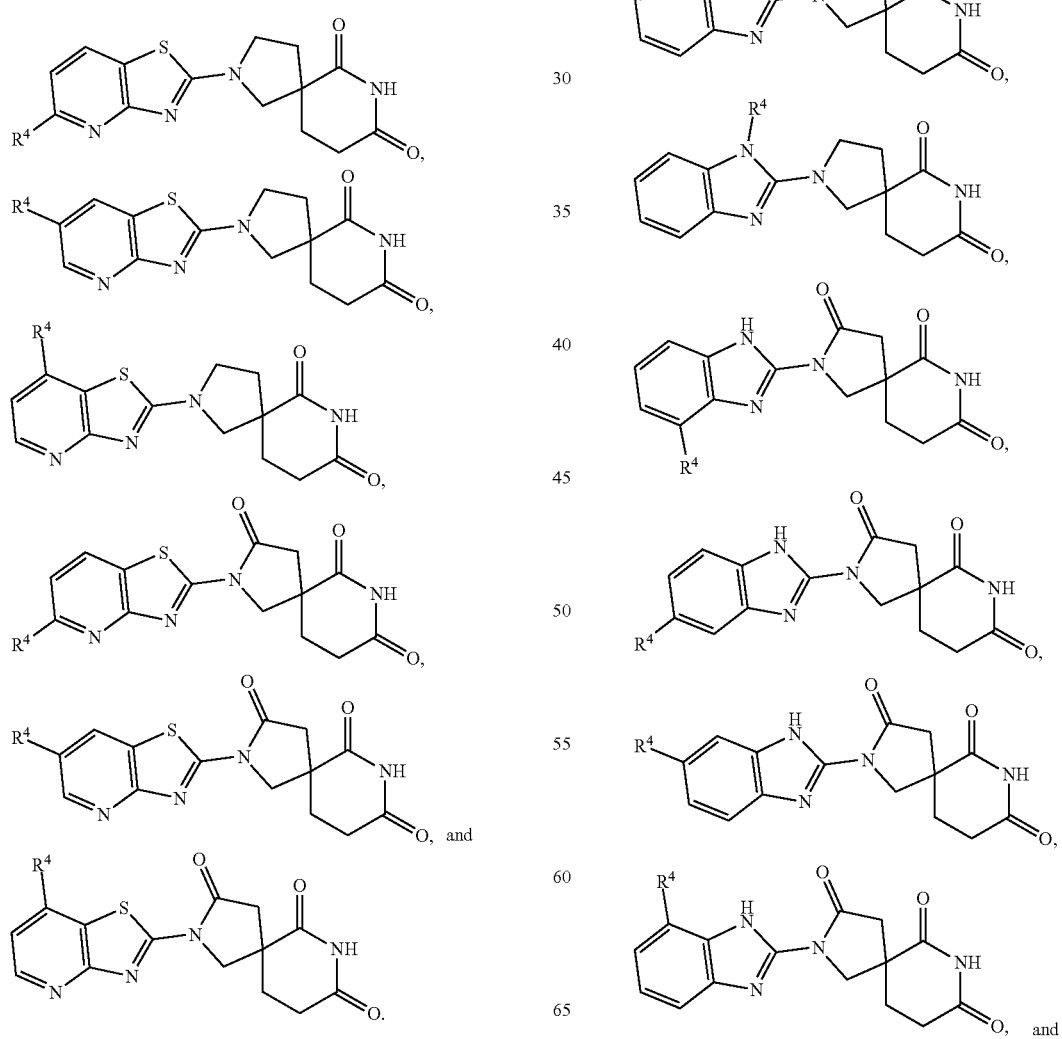

-continued
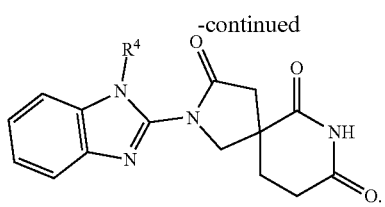
In one embodiment, the compound of Formula VII for use in the methods described herein is selected from:
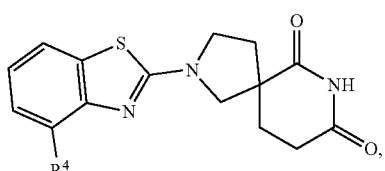
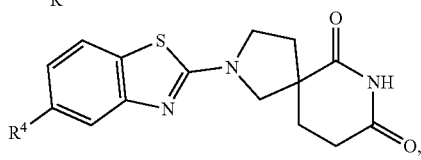
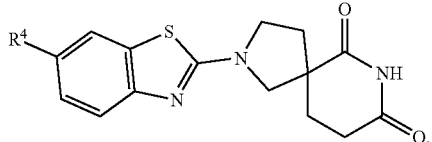
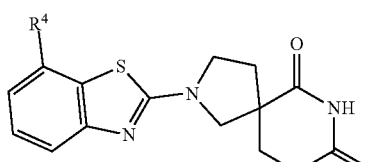
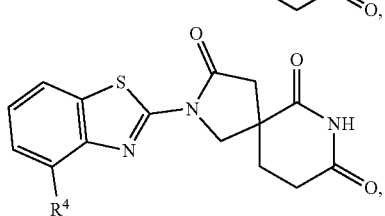
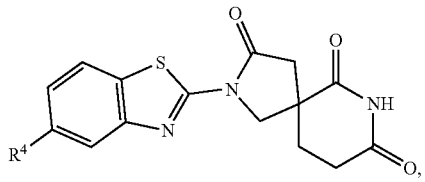
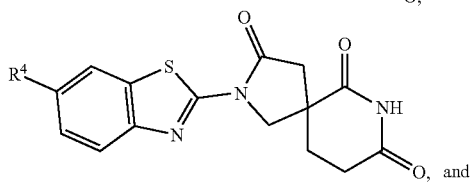, and
In one embodiment, the compound of Formula VII for use in the methods described herein is selected from:
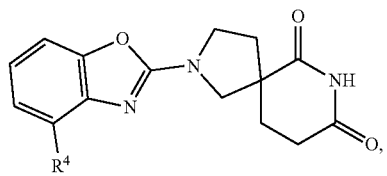
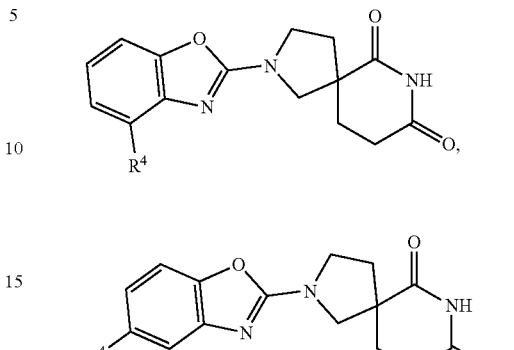
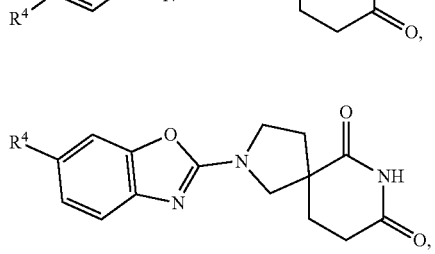
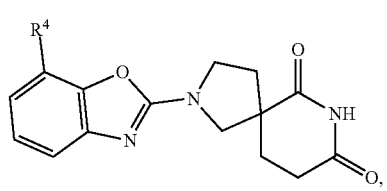
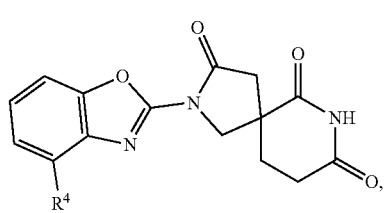
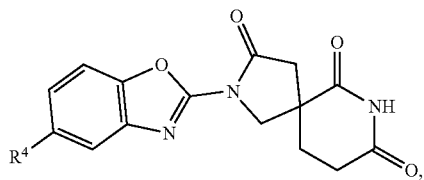
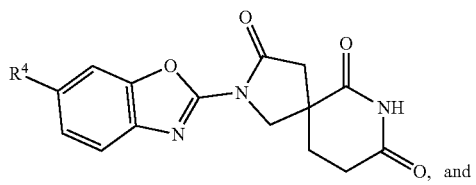, and
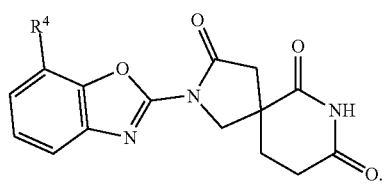

In one embodiment, the compound of Formula VII for use in the methods described herein is selected from:
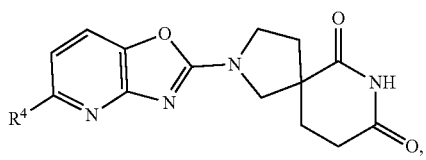
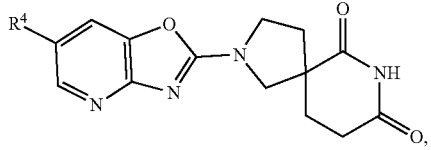
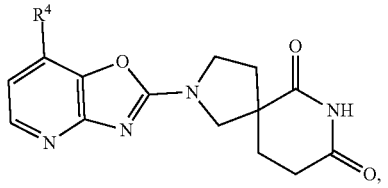
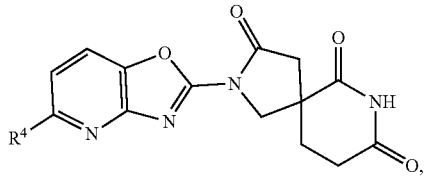
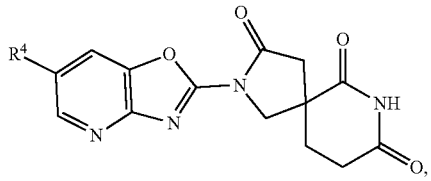 and
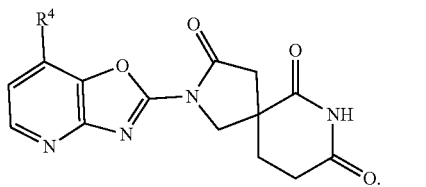
In one embodiment, the compound of Formula VII for use in the methods described herein is selected from:
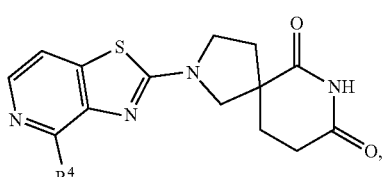
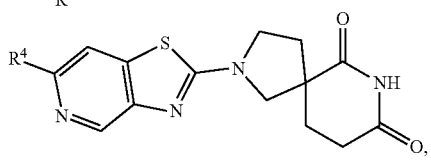
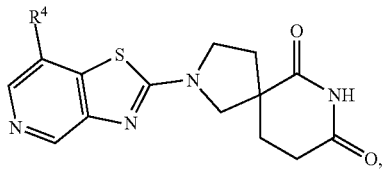
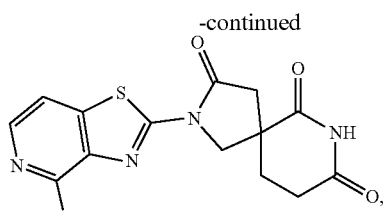
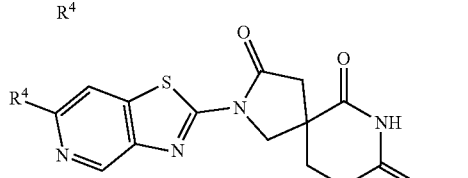
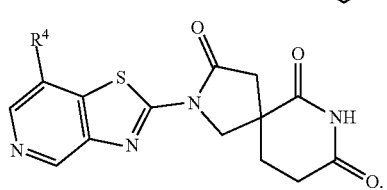 and
In one embodiment, the compound of Formula VII for use in the methods described herein is selected from:
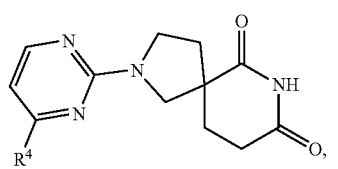
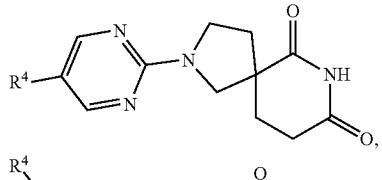
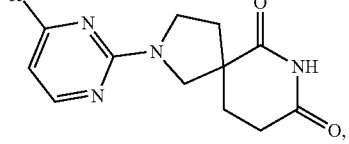
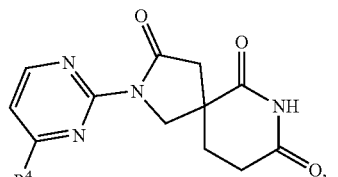
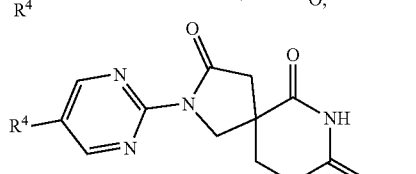 and
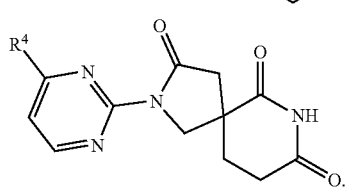

In one embodiment, the compound of Formula VII for use in the methods described herein is selected from:
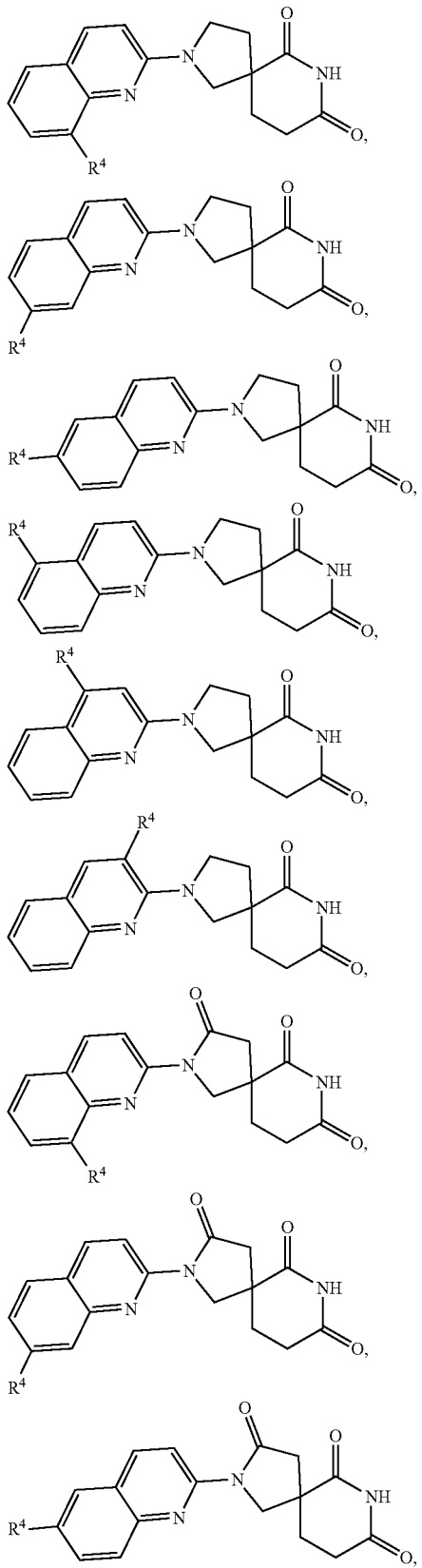
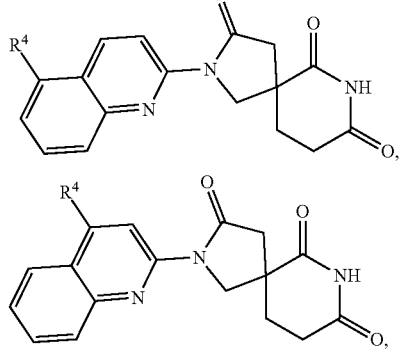
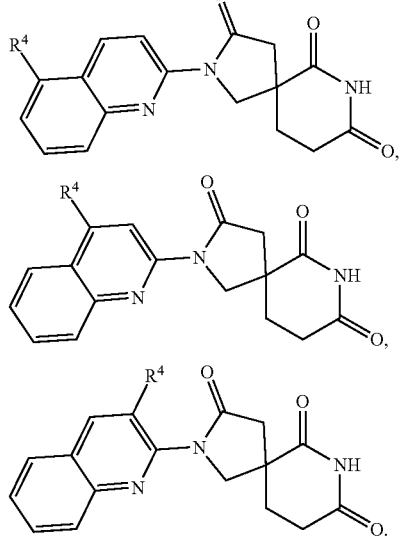
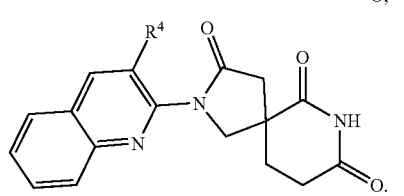 and
In one embodiment, the compound of Formula VII for use in the methods described herein is selected from:
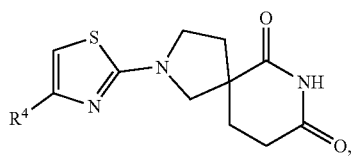
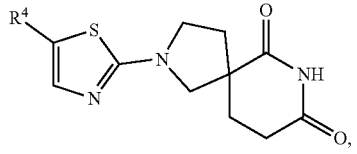
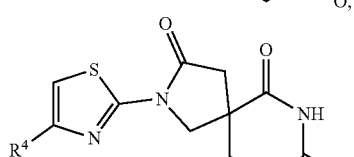 and
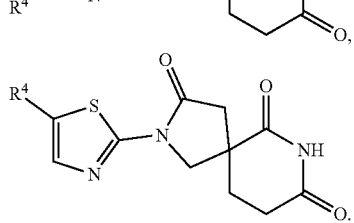
In one embodiment, the compound of Formula VII for use in the methods described herein is selected from:
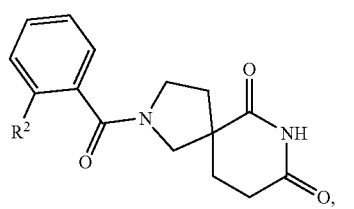

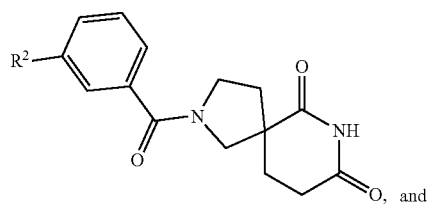
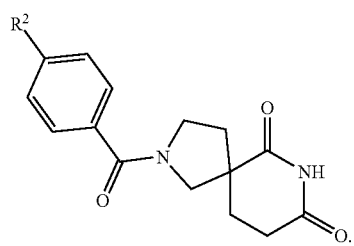
In one embodiment, the compound of Formula VII for use in the methods described herein is selected from:
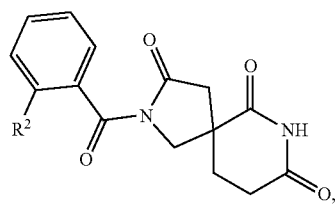
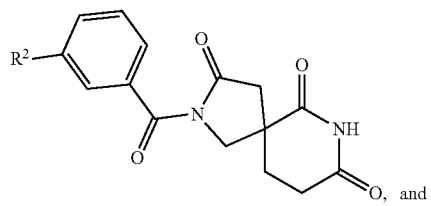
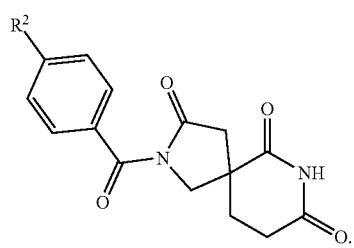
In one embodiment, the compound of Formula VII for use in the methods described herein is selected from:
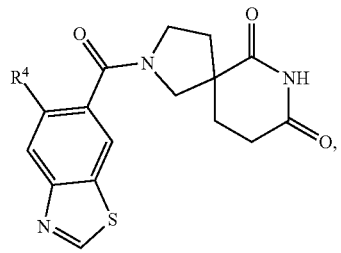
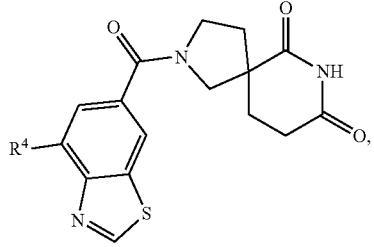
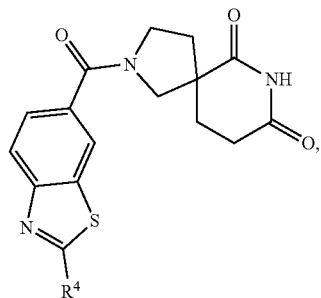
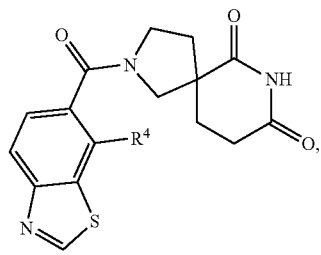
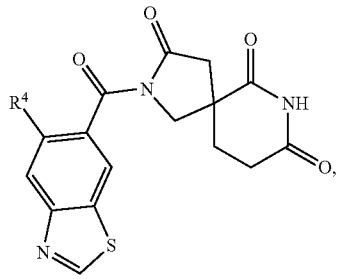
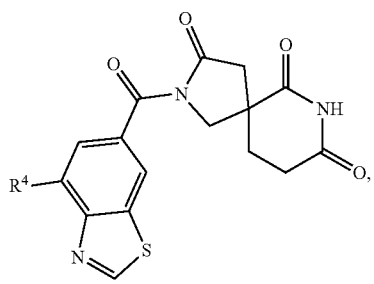
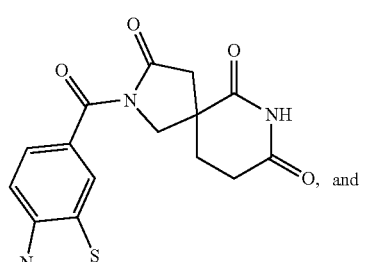

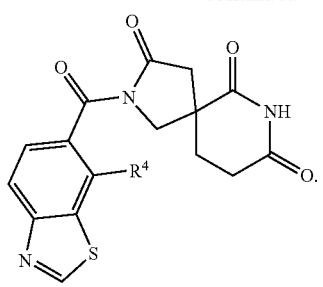
In one embodiment, the compound of Formula VII for use in the methods described herein is selected from:
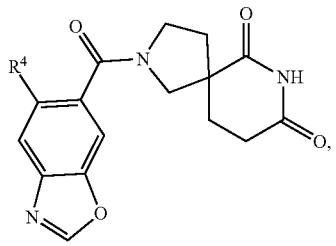
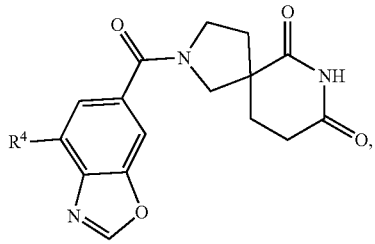
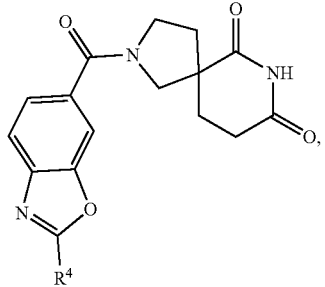
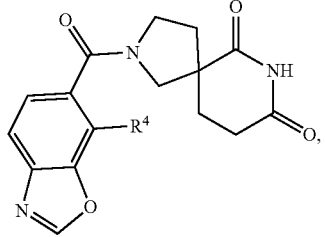
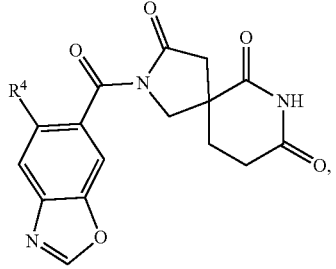
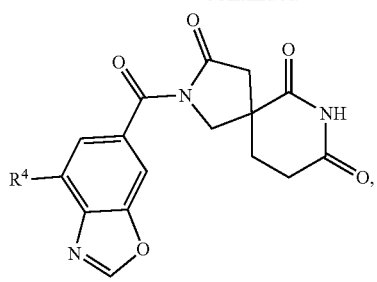
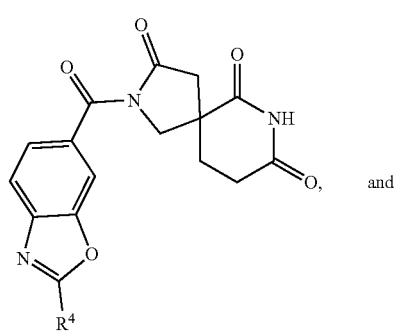, and
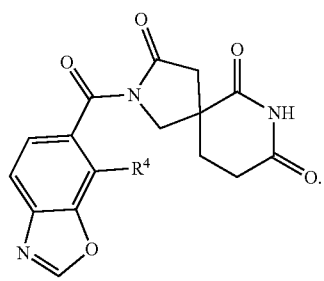
In one embodiment, the compound of Formula VII for use in the methods described herein is selected from:
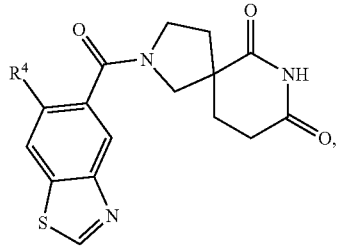
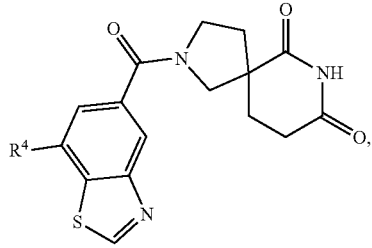

-continued
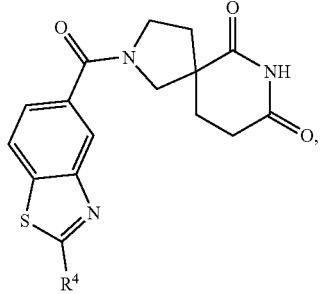
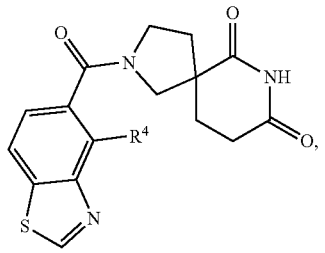
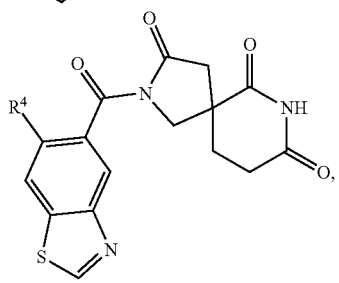
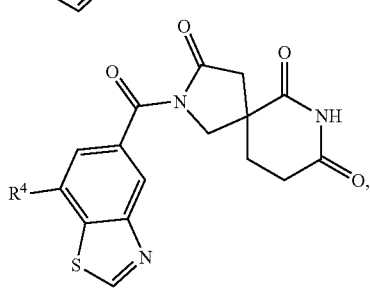
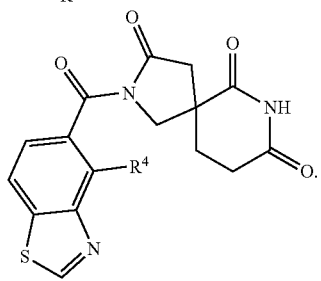
, and
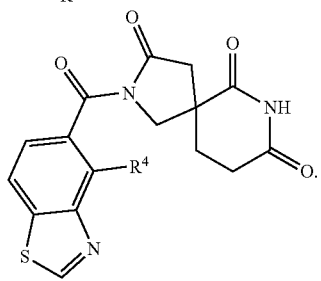
.
In one embodiment, the compound of Formula VII for use in the methods described herein is selected from:
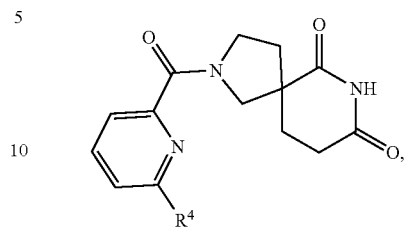
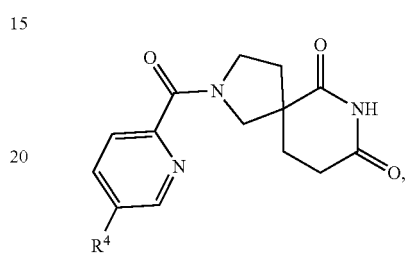
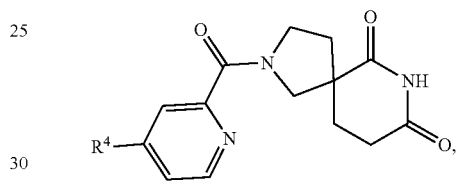
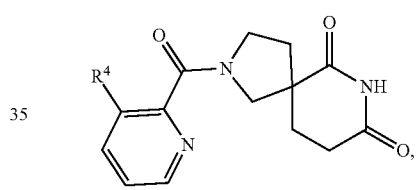
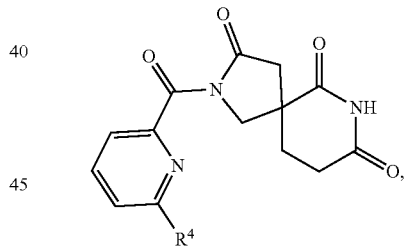
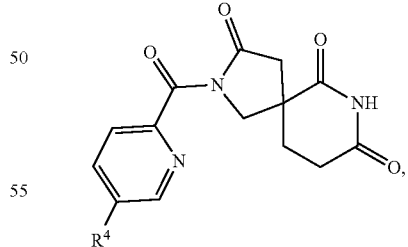
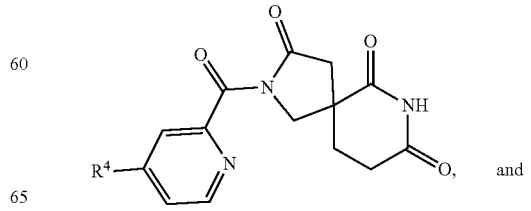
and

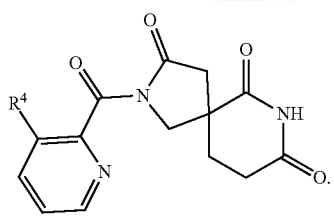
In one embodiment, the compound of Formula VII for use in the methods described herein is selected from:
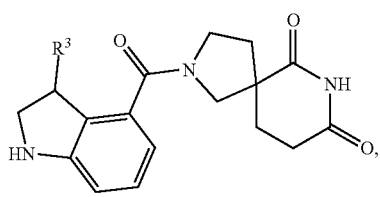
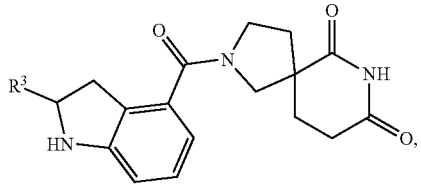
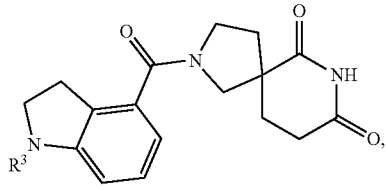
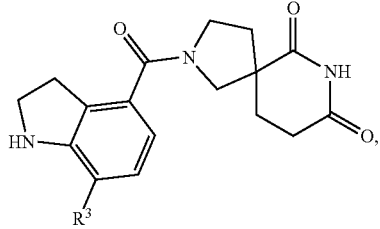
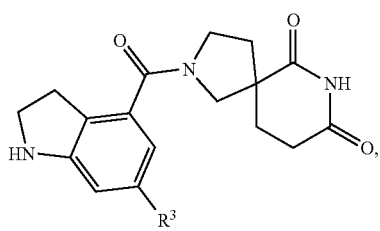
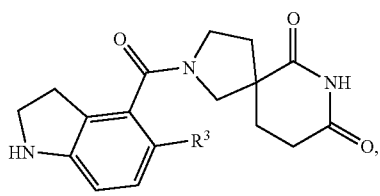
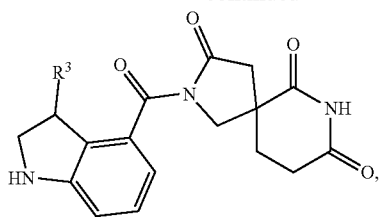
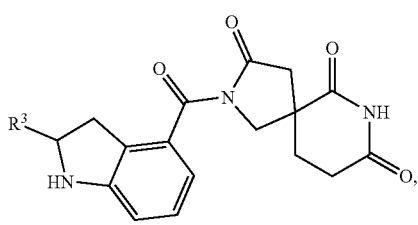
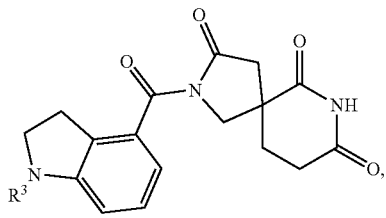
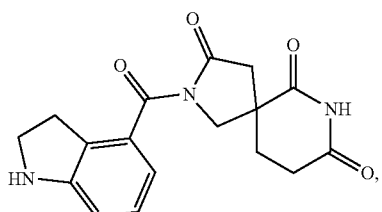
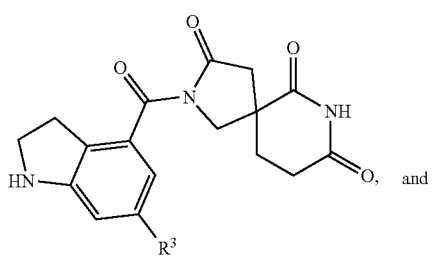
and
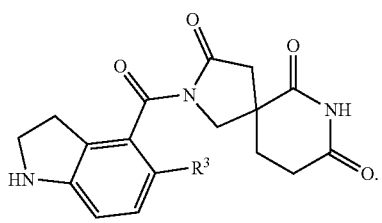

In one embodiment, the compound of Formula VII for use in the methods described herein is selected from:
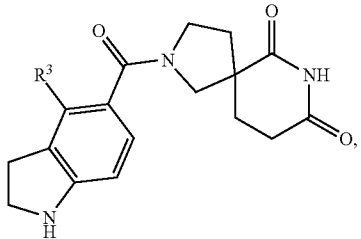
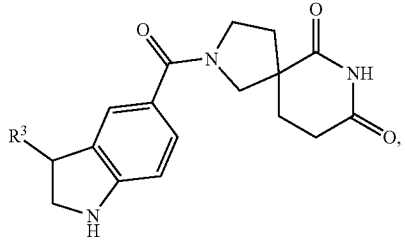
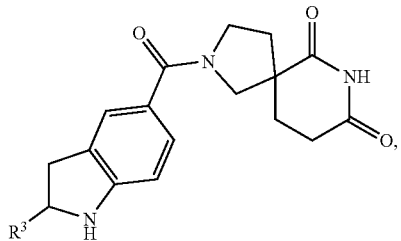
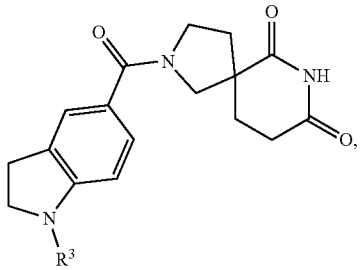
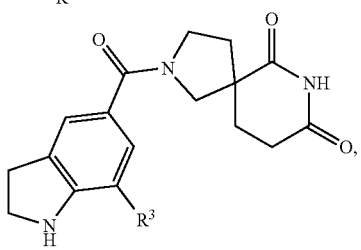
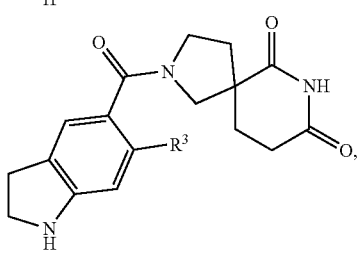
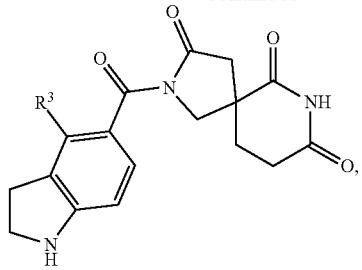
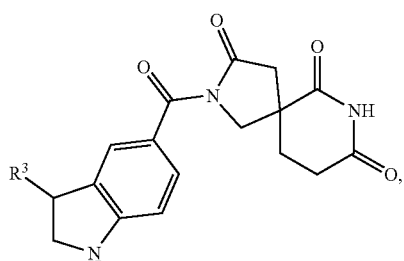
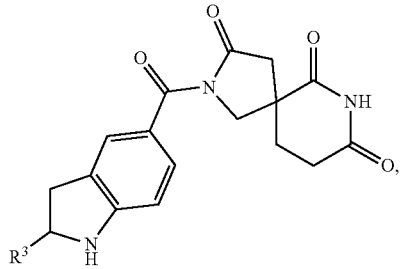
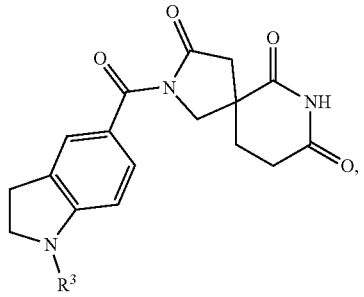
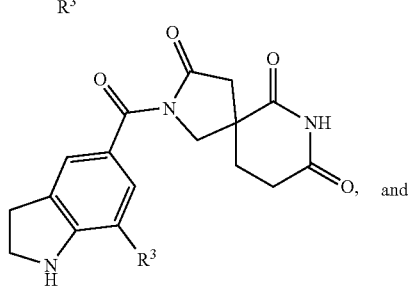
and
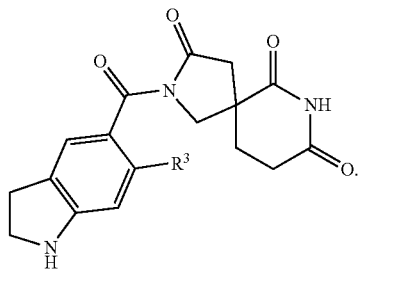

In one embodiment, the compound of Formula VII for use in the methods described herein is selected from:
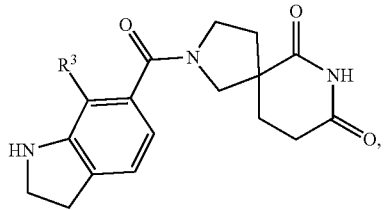,
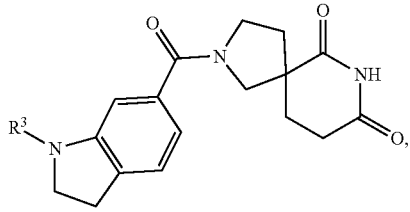,
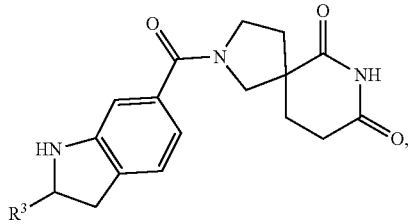,
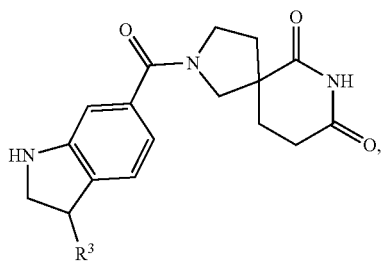,
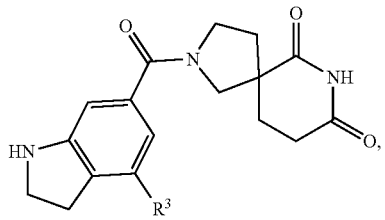,
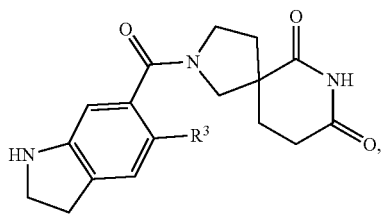,
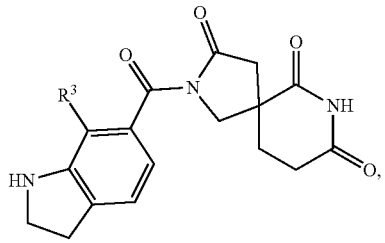,
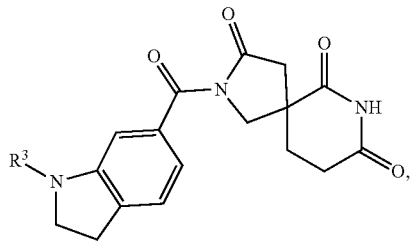,
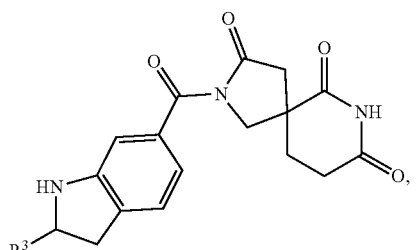,
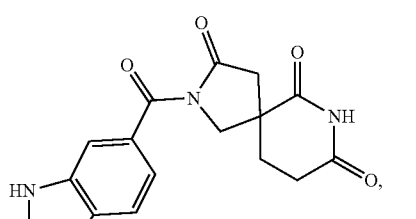,
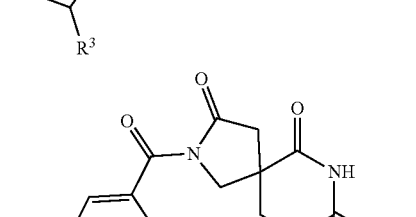,
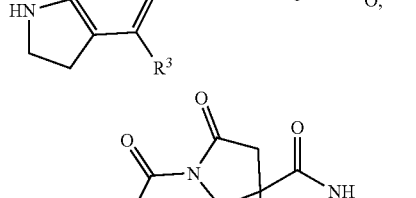, and
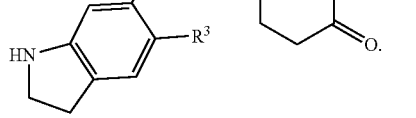.
In one embodiment, the compound of Formula VII for use in the methods described herein is selected from:
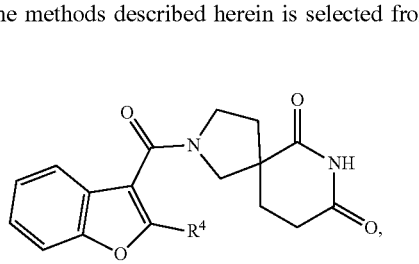, 99
-continued
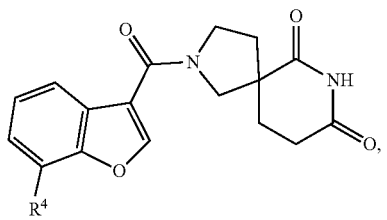
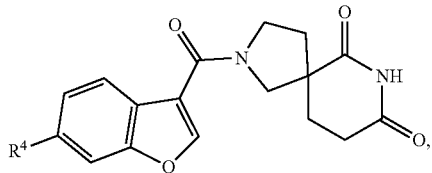
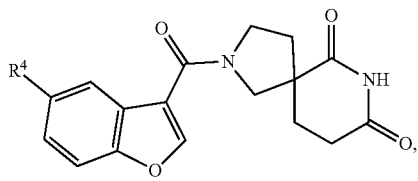
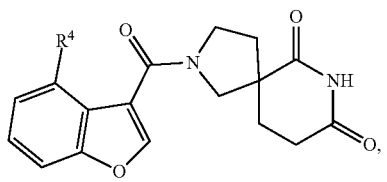
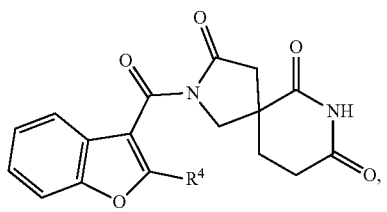
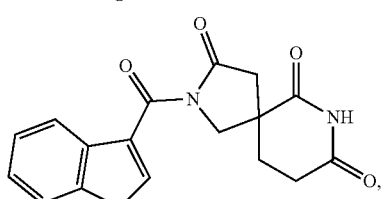
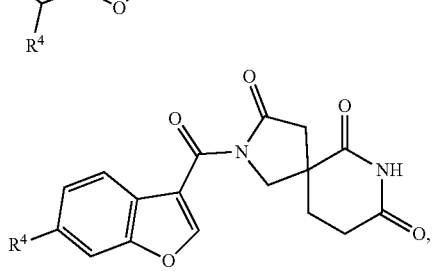
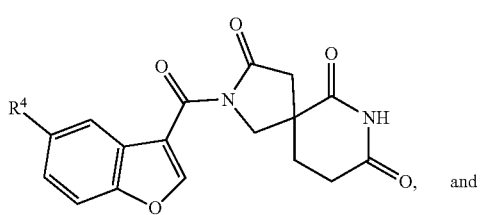, and
100
-continued
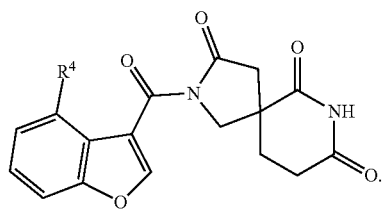.
In one embodiment, the compound of Formula VII for use in the methods described herein is selected from:
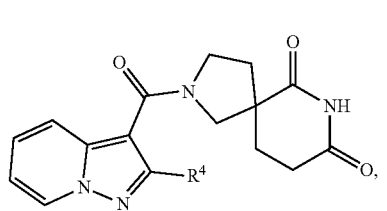
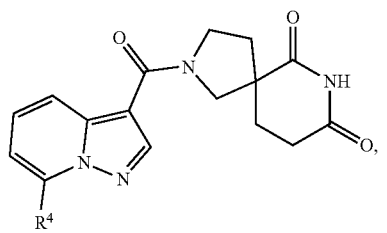
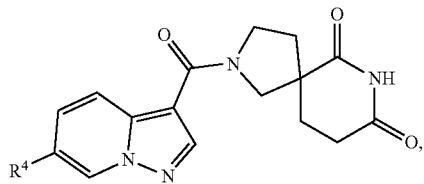
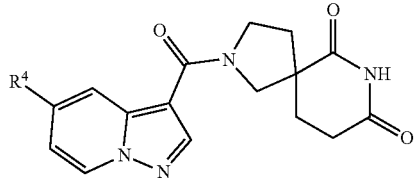
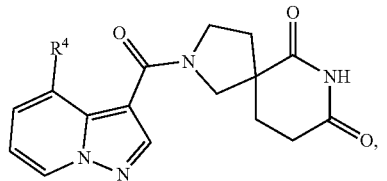
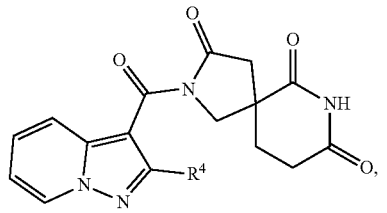

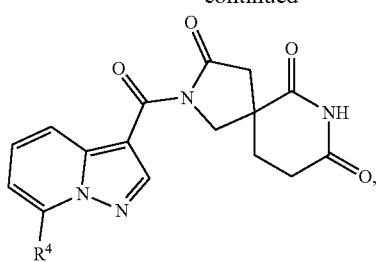
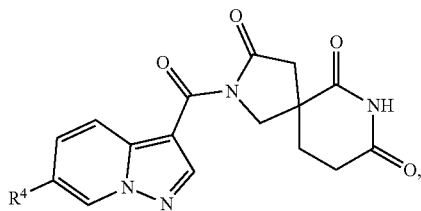
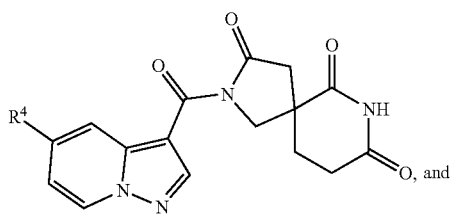
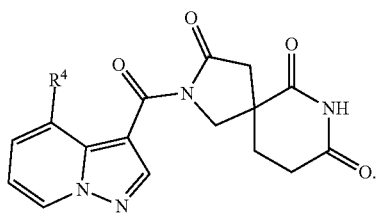
In one embodiment, the compound of Formula VII for use in the methods described herein is selected from:
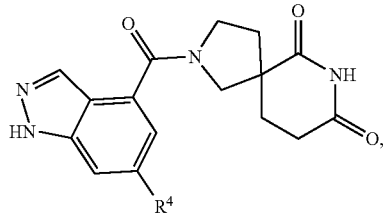
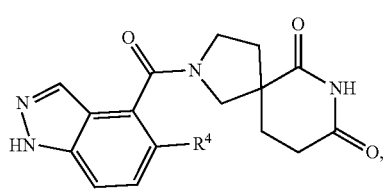
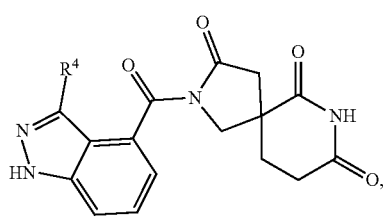
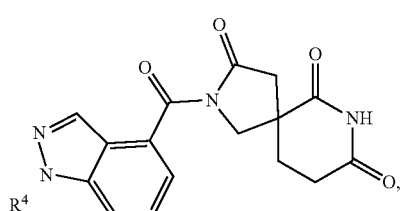
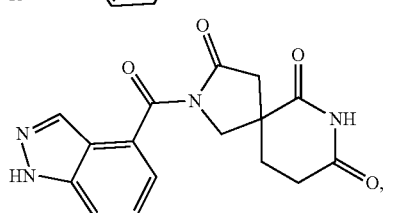
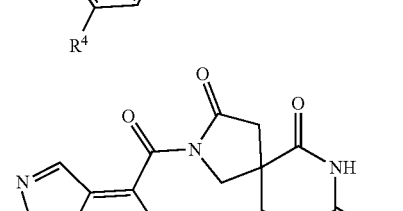
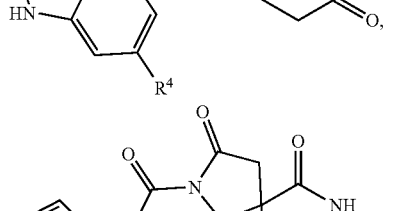

In one embodiment, the compound of Formula VII for use in the methods described herein is selected from:
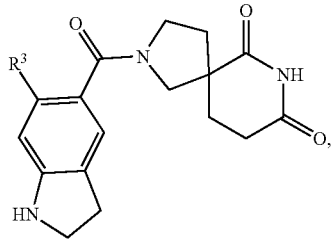
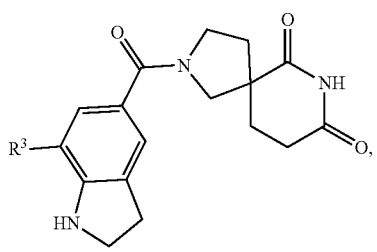
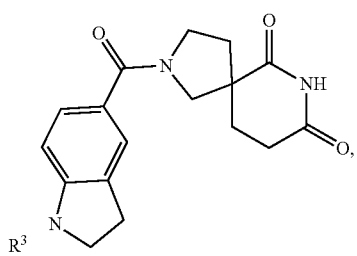
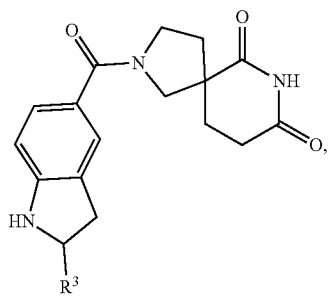
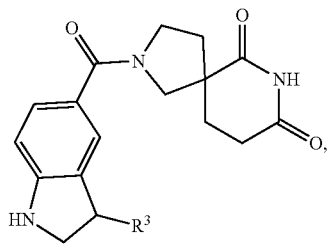
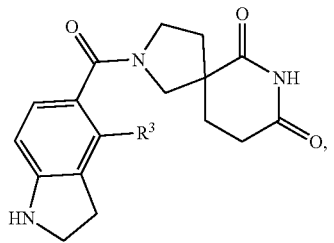
-continued
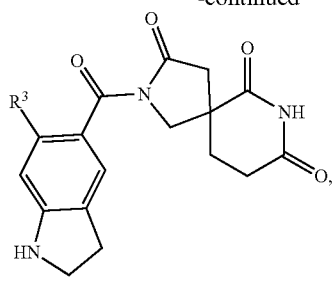
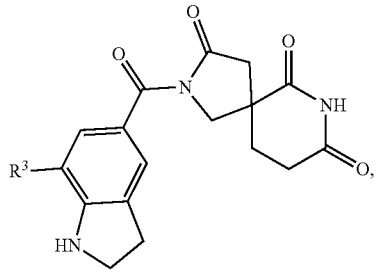
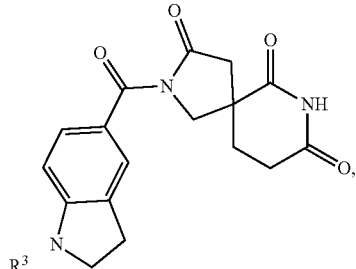
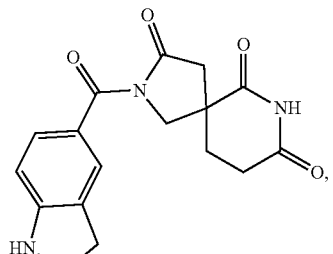
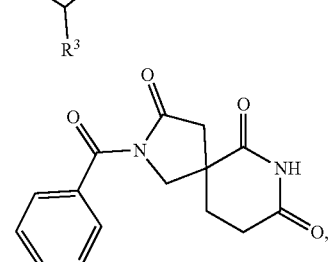
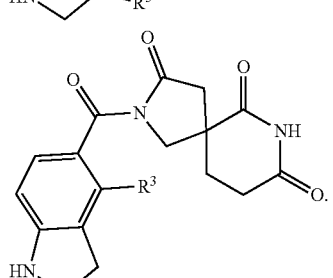 and

In one embodiment, the compound of Formula VII for use in the methods described herein is selected from:
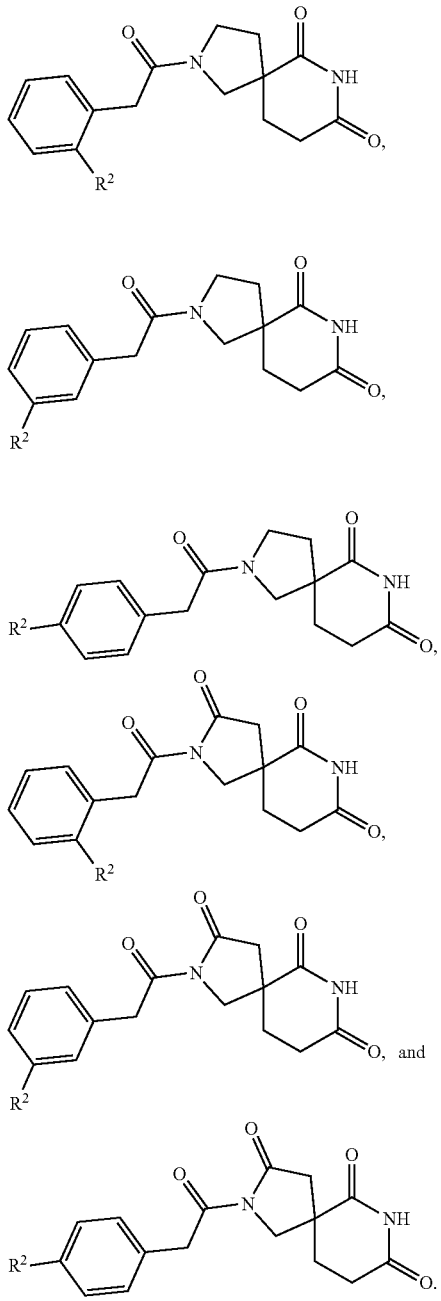
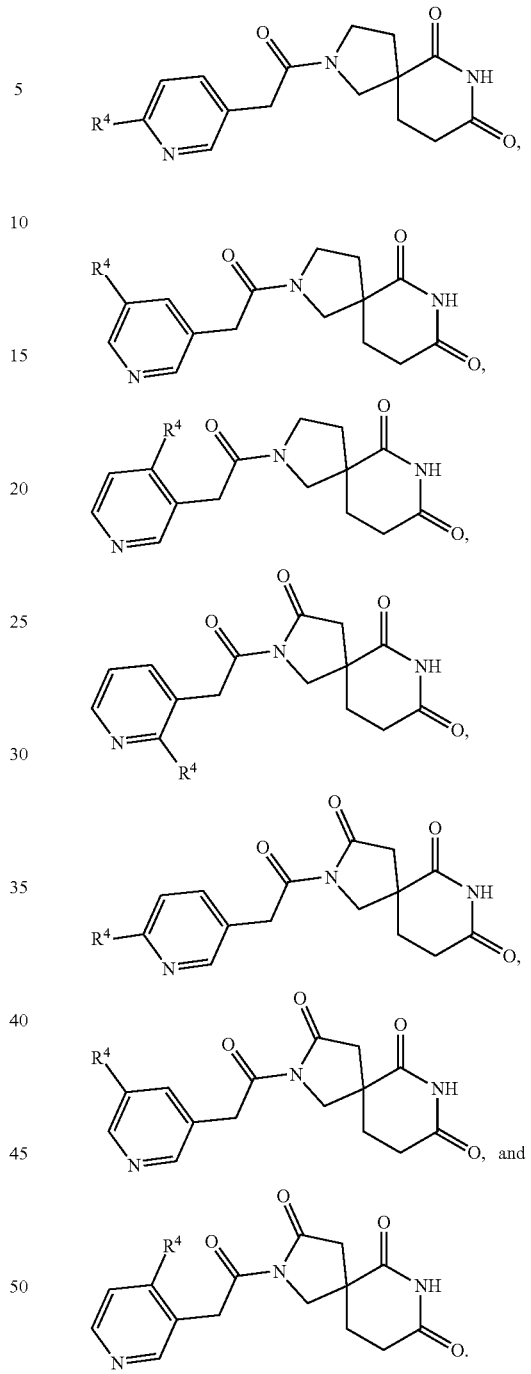
In one embodiment, the compound of Formula VII for use in the methods described herein is selected from:
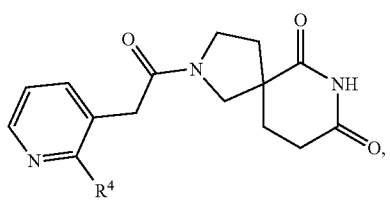
In one embodiment, the compound of Formula VII for use in the methods described herein is selected from:
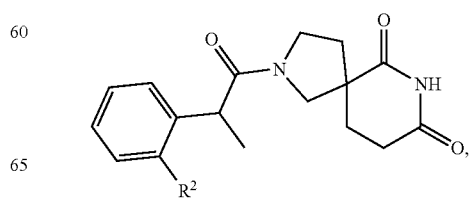

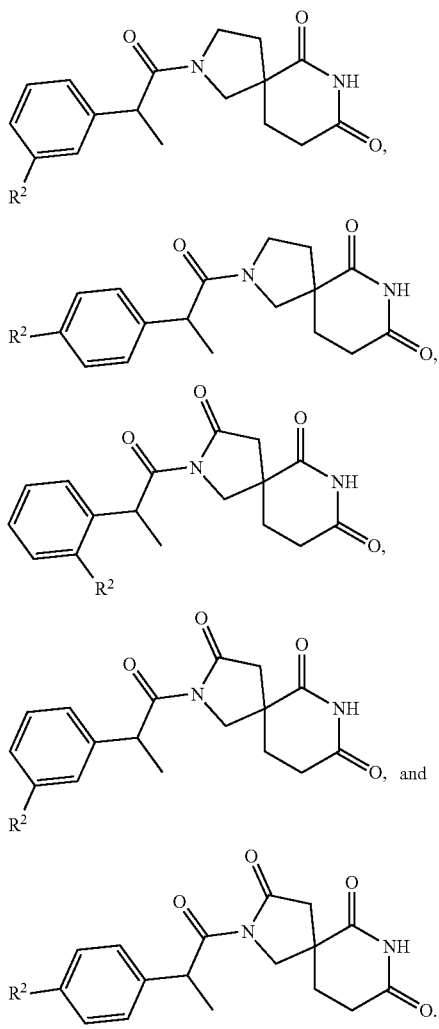
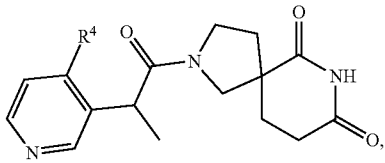
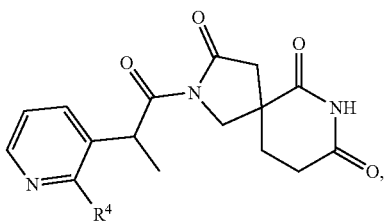
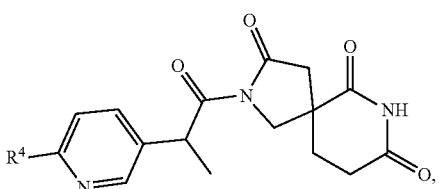
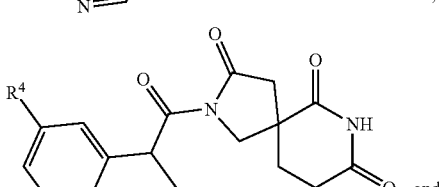
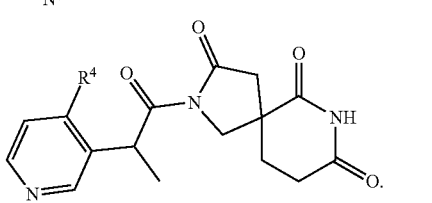
In one embodiment, the compound of Formula VII for use in the methods described herein is selected from:
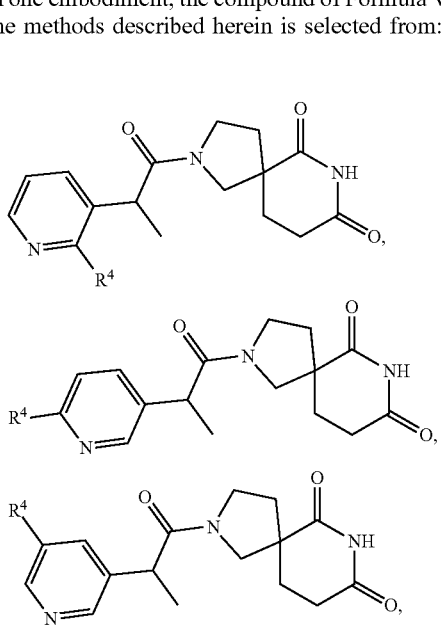
In one embodiment, the compound of Formula VII for use in the methods described herein is selected from:
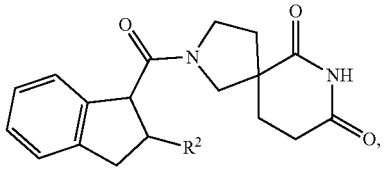
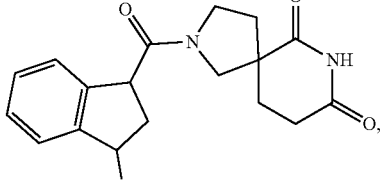
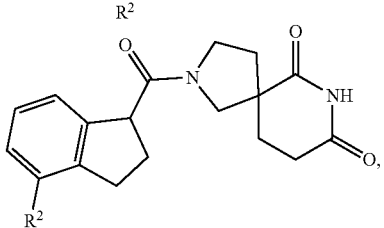

-continued
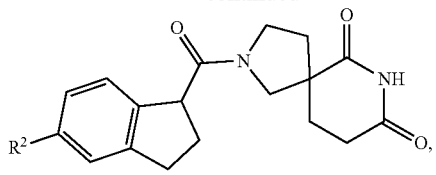
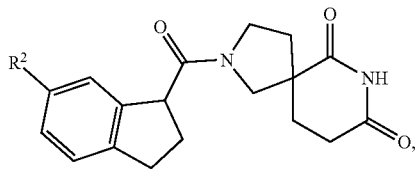
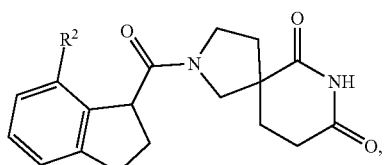
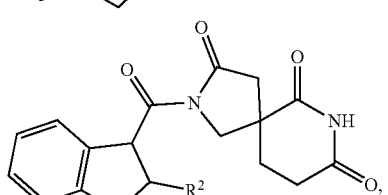
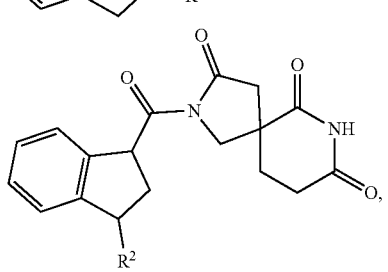
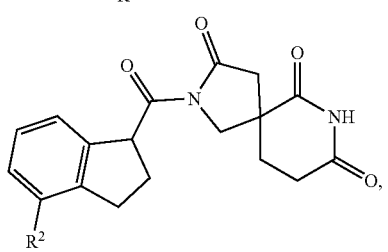
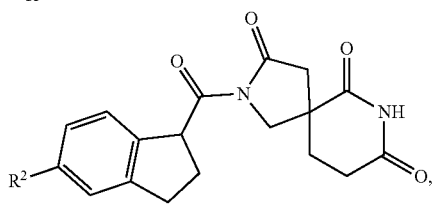
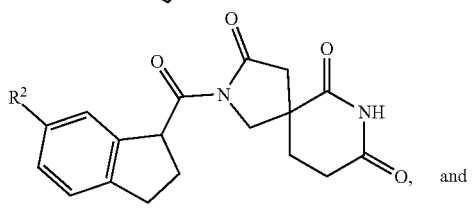 and
-continued
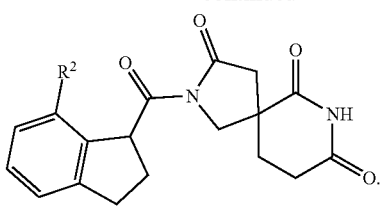.
In one embodiment, the compound of Formula VII for use in the methods described herein is selected from:
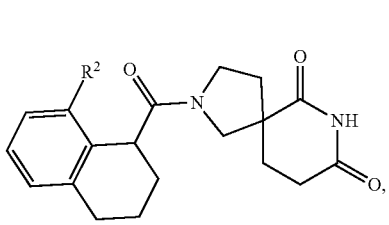
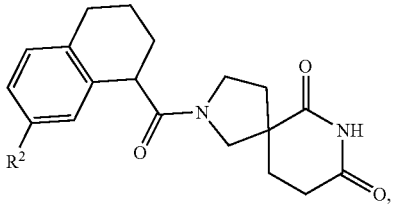
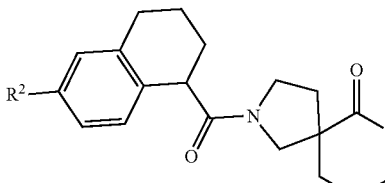
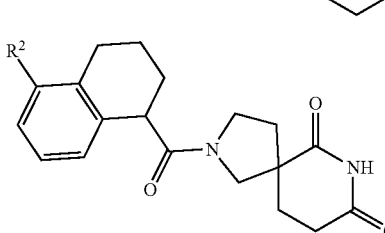
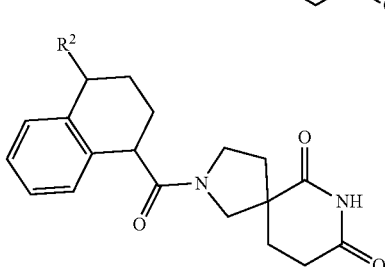
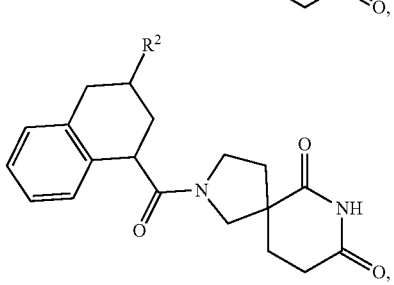

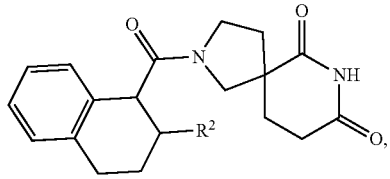
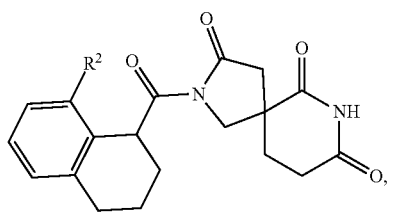
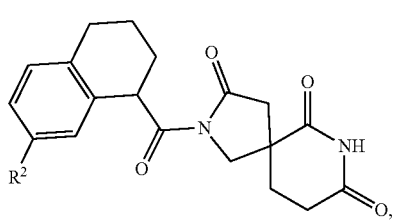
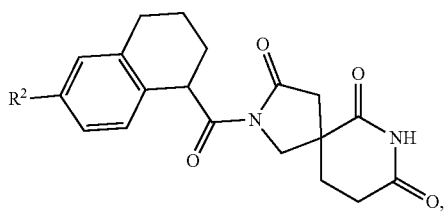
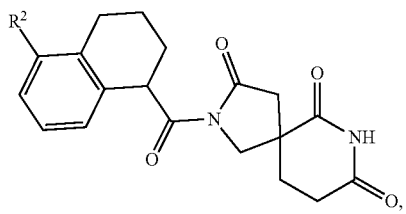
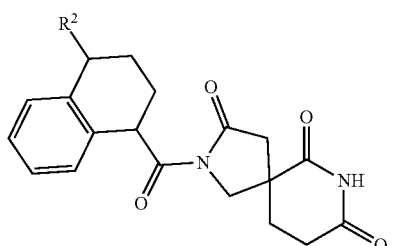
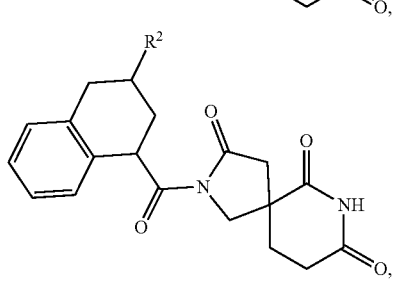
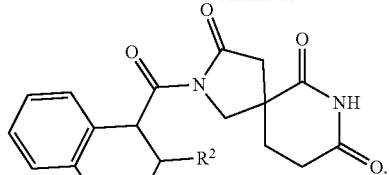
In one embodiment, the compound of Formula VII for use in the methods described herein is selected from:
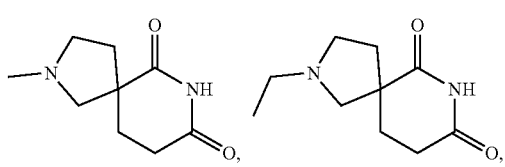
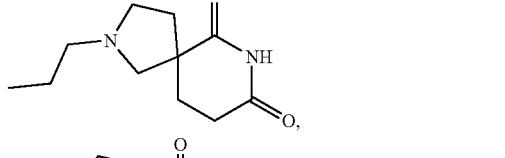
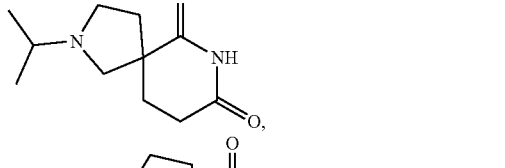
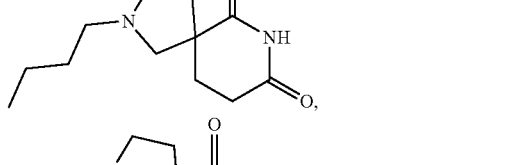
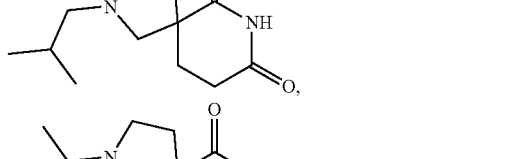
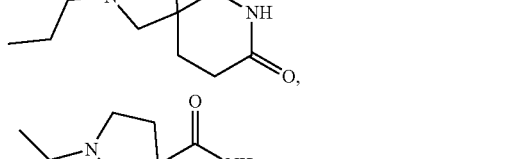
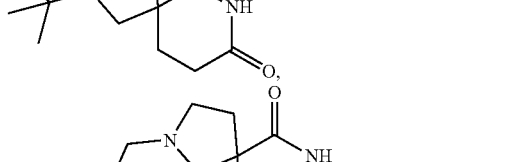
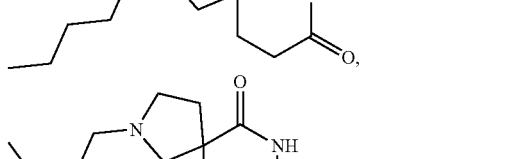
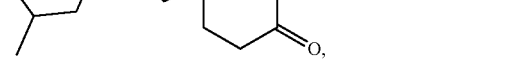

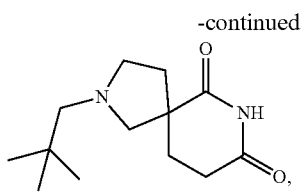
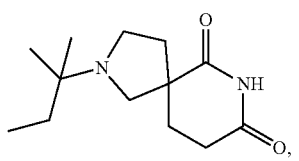
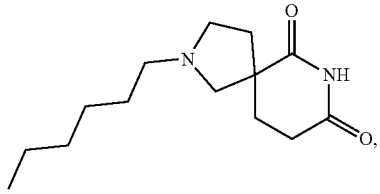
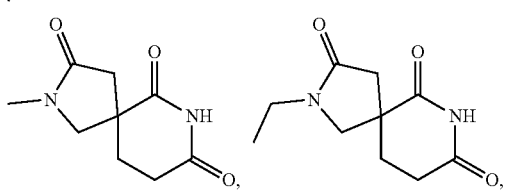
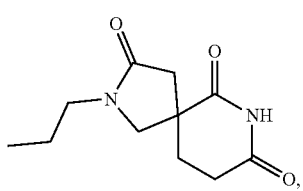
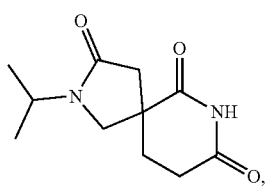
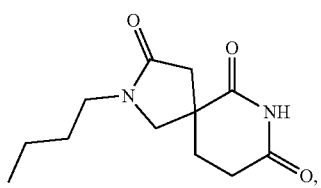
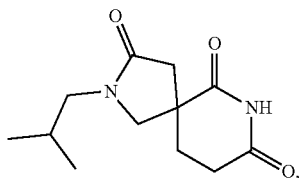
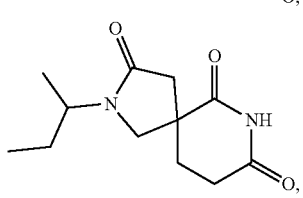

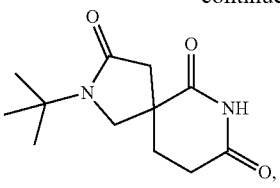
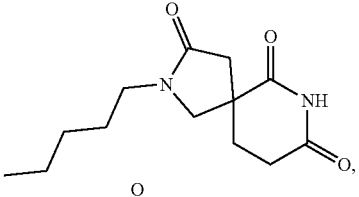
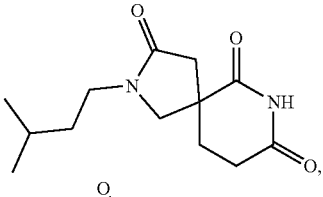
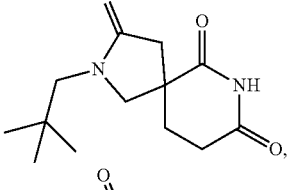
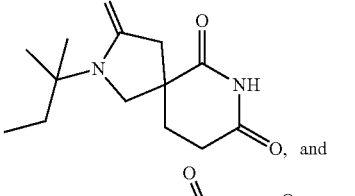
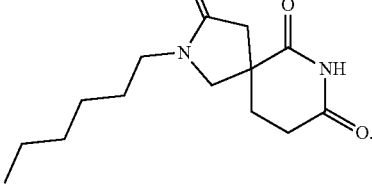

A compound of Formula VII for use in the methods described herein is also provided in the following enumerated embodiments, all of which may be separately combined.

E1: A compound of formula VII, or a pharmaceutically acceptable salt thereof, as described herein, wherein
$X^A$ is selected from the group consisting of
  i.) heteroaryl, in particular pyridinyl, benzimidazolyl, pyrimidyl, benzothiazolyl or thiazolyl, each individually substituted by $R^4$;
  ii.) heteroaryl, in particular thiazolo[4,5-b]pyridinyl, benzothiazolyl, quinolinyl, oxazolo[4,5-b]pyridinyl, benzoxazolyl, thiazolo[4,5-c]pyridinyl, indazolyl, benzofuranyl or pyrazolo[1,5-a]pyridinyl,
  iii.) heterocyclyl, in particular indolinyl,
  iv.) heterocyclyl, in particular indolinyl, substituted by $R^3$,
  v.) phenyl, indanyl or 1,2,3,4-tetrahydronaphthalenyl, and
  vi.) phenyl, substituted by $NO_2$, —COOCH$_3$ or —NH—C(=O)—CH$_3$;
$Y^A$ is absent or selected from the group consisting of
  i.) —C(=O)—;
  ii.) —C(=O)—C(H,C$_{1-6}$-alkyl)-, and iii.) —C(=O)—CH$_2$—;
R$^1$ is absent or =O;
R$^2$ is selected from the group consisting of
  i.) —C(=O)—O—C$_{1-6}$-alkyl, in particular —C(=O)—O—CH$_3$,
  ii.) —NH—C(=O)—C$_{1-6}$-alkyl, in particular —NH—C(=O)—CH$_3$, and
  iii.) —NO$_2$;
R$^3$ is selected from the group consisting of
  i.) —C(=O)—C$_{1-6}$-alkyl, in particular —C(=O)—CH$_3$; and
  ii.) =O;
R$^4$ is selected from the group consisting of
  i.) —C$_{1-6}$-alkyl, in particular CH$_3$,
  ii.) —COOC$_{1-6}$-alkyl, in particular —COOCH$_3$ or —COOC(CH$_3$)$_3$,
  iii.) —NH$_2$,
  iv.) —NH—C(=O)—C$_{1-6}$-alkyl, in particular —NH—C(=O)—CH$_3$, and
  v.) —NO$_2$.
E2: A compound of formula VII, or a pharmaceutically acceptable salt thereof, as described herein, wherein
a) X$^A$ is unsubstituted phenyl or phenyl substituted by R$^2$ and R$^2$ is selected from the group consisting of
  i.) —C(=O)—O—CH$_3$,
  ii.) —NH—C(=O)—CH$_3$, and
  iii.) —NO$_2$,
b) X$^A$ is indanyl or 1,2,3,4-tetrahydronaphthalenyl,
c) X$^A$ is thiazolo[4,5-b]pyridinyl, benzothiazolyl, quinolinyl, oxazolo[4,5-b]pyridinyl, benzoxazolyl, thiazolo[4,5-c]pyridinyl, indazolyl, benzofuranyl or pyrazolo[1,5-a]pyridinyl,
d) X$^A$ is pyridinyl, benzimidazolyl, pyrimidyl, benzothiazolyl or thiazolyl, each individually substituted by R$^4$; and R$^4$ is selected from the group consisting of
  i.) —CH$_3$,
  ii.) —COOCH$_3$ or —COOC(CH$_3$)$_3$,
  iii.) —NH$_2$,
  iv.) —NH—C(=O)—CH$_3$, and
  v.) —NO$_2$; or
e) X$^A$ is unsubstituted indolinyl or indolinyl substituted by R$^3$, and
R$^3$ is selected from the group consisting of
  i.) —C(=O)—CH$_3$; and
  ii.) =O.
E3: The compound of formula VII, or pharmaceutically acceptable salts thereof, as described herein, selected from the group consisting of
2-((R)-1,2,3,4-tetrahydronaphthalene-1-carbonyl)-2,7-diazaspiro[4.5]decane-6,8-dione,
2-((S)-1,2,3,4-tetrahydronaphthalene-1-carbonyl)-2,7-diazaspiro[4.5]decane-6,8-dione,
2-methyl-2,7-diazaspiro[4.5]decane-3,6,8-trione,
2-(2,3-dihydro-1H-indene-1-carbonyl)-2,7-diazaspiro[4.5]decane-6,8-dione,
methyl 6-(6,8-dioxo-2,7-diazaspiro[4.5]decan-2-yl)nicotinate,
2-(5-nitro-1H-benzo[d]imidazol-2-yl)-2,7-diazaspiro[4.5]decane-6,8-dione,
methyl 2-(6,8-dioxo-2,7-diazaspiro[4.5]decan-2-yl)-1H-benzo[d]imidazole-7-carboxylate,
methyl 2-(6,8-dioxo-2,7-diazaspiro[4.5]decan-2-yl)pyrimidine-4-carboxylate,
2-(1-methyl-1H-benzo[d]imidazol-2-yl)-2,7-diazaspiro[4.5]decane-6,8-dione,
methyl 2-(6,8-dioxo-2,7-diazaspiro[4.5]decan-2-yl)benzo[d]thiazole-6-carboxylate,
methyl 2-(6,8-dioxo-2,7-diazaspiro[4.5]decan-2-yl)thiazole-4-carboxylate,
methyl 2-(6,8-dioxo-2,7-diazaspiro[4.5]decan-2-yl)thiazole-5-carboxylate,
tert-butyl 6-(6,8-dioxo-2,7-diazaspiro[4.5]decan-2-yl)nicotinate,
methyl 4-(6,8-dioxo-2,7-diazaspiro[4.5]decane-2-carbonyl)benzoate,
methyl 6-(6,8-dioxo-2,7-diazaspiro[4.5]decan-2-yl)picolinate,
2-(5-nitro-1H-benzo[d]imidazol-2-yl)-2,7-diazaspiro[4.5]decane-6,8-dione,
N-(3-(6,8-dioxo-2,7-diazaspiro[4.5]decane-2-carbonyl)phenyl)acetamide,
N-(6-(6,8-dioxo-2,7-diazaspiro[4.5]decan-2-yl)pyridin-3-yl)acetamide,
2-(pyrazolo[1,5-a]pyridine-3-carbonyl)-2,7-diazaspiro[4.5]decane-6,8-dione,
2,7-diazaspiro[4.5]decane-6,8-dione,
2-(2-phenylacetyl)-2,7-diazaspiro[4.5]decane-6,8-dione,
2-(3-nitrobenzoyl)-2,7-diazaspiro[4.5]decane-6,8-dione,
2-(thiazolo[4,5-b]pyridin-2-yl)-2,7-diazaspiro[4.5]decane-6,8-dione,
2-(4-nitrophenyl)-2,7-diazaspiro[4.5]decane-6,8-dione,
2-(benzo[d]thiazol-2-yl)-2,7-diazaspiro[4.5]decane-6,8-dione,
2-(quinolin-2-yl)-2,7-diazaspiro[4.5]decane-6,8-dione,
2-(6-aminobenzo[d]thiazol-2-yl)-2,7-diazaspiro[4.5]decane-6,8-dione,
2-(oxazolo[4,5-b]pyridin-2-yl)-2,7-diazaspiro[4.5]decane-6,8-dione,
2-(benzo[d]oxazol-2-yl)-2,7-diazaspiro[4.5]decane-6,8-dione,
2-(thiazolo[4,5-c]pyridin-2-yl)-2,7-diazaspiro[4.5]decane-6,8-dione,
2-(benzo[d]thiazole-6-carbonyl)-2,7-diazaspiro[4.5]decane-6,8-dione,
2-(4-nitropicolinoyl)-2,7-diazaspiro[4.5]decane-6,8-dione,
2-(2-oxoindoline-4-carbonyl)-2,7-diazaspiro[4.5]decane-6,8-dione,
2-(benzo[d]thiazole-5-carbonyl)-2,7-diazaspiro[4.5]decane-6,8-dione,
2-(5-nitropyridin-2-yl)-2,7-diazaspiro[4.5]decane-6,8-dione,
2-(2-(pyridin-3-yl)propanoyl)-2,7-diazaspiro[4.5]decane-6,8-dione,
2-(1-acetylindoline-4-carbonyl)-2,7-diazaspiro[4.5]decane-6,8-dione,
2-benzoyl-2,7-diazaspiro[4.5]decane-6,8-dione,
2-(1H-indazole-4-carbonyl)-2,7-diazaspiro[4.5]decane-6,8-dione,
2-(5-aminopyridin-2-yl)-2,7-diazaspiro[4.5]decane-6,8-dione,
2-(indoline-4-carbonyl)-2,7-diazaspiro[4.5]decane-6,8-dione,
2-(indoline-6-carbonyl)-2,7-diazaspiro[4.5]decane-6,8-dione,
2-(1-acetylindoline-6-carbonyl)-2,7-diazaspiro[4.5]decane-6,8-dione,
2-(benzofuran-3-carbonyl)-2,7-diazaspiro[4.5]decane-6,8-dione,
2-(benzo[d]oxazole-6-carbonyl)-2,7-diazaspiro[4.5]decane-6,8-dione, and
2-(indoline-5-carbonyl)-2,7-diazaspiro[4.5]decane-6,8-dione.

E4: The compound of formula VII, or pharmaceutically acceptable salts thereof, as described herein, selected from the group consisting of
2-((R)-1,2,3,4-tetrahydronaphthalene-1-carbonyl)-2,7-diazaspiro[4.5]decane-6,8-dione,
2-((S)-1,2,3,4-tetrahydronaphthalene-1-carbonyl)-2,7-diazaspiro[4.5]decane-6,8-dione,
2-(2,3-dihydro-1H-indene-1-carbonyl)-2,7-diazaspiro[4.5]decane-6,8-dione,
methyl 6-(6,8-dioxo-2,7-diazaspiro[4.5]decan-2-yl)nicotinate,
2-(5-nitro-1H-benzo[d]imidazol-2-yl)-2,7-diazaspiro[4.5]decane-6,8-dione,
methyl 2-(6,8-dioxo-2,7-diazaspiro[4.5]decan-2-yl)-1H-benzo[d]imidazole-7-carboxylate,
methyl 2-(6,8-dioxo-2,7-diazaspiro[4.5]decan-2-yl)pyrimidine-4-carboxylate,
2-(1-methyl-1H-benzo[d]imidazol-2-yl)-2,7-diazaspiro[4.5]decane-6,8-dione,
methyl 2-(6,8-dioxo-2,7-diazaspiro[4.5]decan-2-yl)benzo[d]thiazole-6-carboxylate,
methyl 2-(6,8-dioxo-2,7-diazaspiro[4.5]decan-2-yl)thiazole-4-carboxylate,
methyl 2-(6,8-dioxo-2,7-diazaspiro[4.5]decan-2-yl)thiazole-5-carboxylate,
tert-butyl 6-(6,8-dioxo-2,7-diazaspiro[4.5]decan-2-yl)nicotinate,
methyl 4-(6,8-dioxo-2,7-diazaspiro[4.5]decane-2-carbonyl)benzoate,
methyl 6-(6,8-dioxo-2,7-diazaspiro[4.5]decan-2-yl)picolinate,
2-(5-nitro-1H-benzo[d]imidazol-2-yl)-2,7-diazaspiro[4.5]decane-6,8-dione,
N-(3-(6,8-dioxo-2,7-diazaspiro[4.5]decane-2-carbonyl)phenyl)acetamide,
N-(6-(6,8-dioxo-2,7-diazaspiro[4.5]decan-2-yl)pyridin-3-yl)acetamide,
2-(pyrazolo[1,5-a]pyridine-3-carbonyl)-2,7-diazaspiro[4.5]decane-6,8-dione,
2-(2-phenylacetyl)-2,7-diazaspiro[4.5]decane-6,8-dione,
2-(3-nitrobenzoyl)-2,7-diazaspiro[4.5]decane-6,8-dione,
2-(thiazolo[4,5-b]pyridin-2-yl)-2,7-diazaspiro[4.5]decane-6,8-dione,
2-(4-nitrophenyl)-2,7-diazaspiro[4.5]decane-6,8-dione,
2-(benzo[d]thiazol-2-yl)-2,7-diazaspiro[4.5]decane-6,8-dione,
2-(quinolin-2-yl)-2,7-diazaspiro[4.5]decane-6,8-dione,
2-(6-aminobenzo[d]thiazol-2-yl)-2,7-diazaspiro[4.5]decane-6,8-dione,
2-(oxazolo[4,5-b]pyridin-2-yl)-2,7-diazaspiro[4.5]decane-6,8-dione,
2-(benzo[d]oxazol-2-yl)-2,7-diazaspiro[4.5]decane-6,8-dione,
2-(thiazolo[4,5-c]pyridin-2-yl)-2,7-diazaspiro[4.5]decane-6,8-dione,
2-(benzo[d]thiazole-6-carbonyl)-2,7-diazaspiro[4.5]decane-6,8-dione,
2-(4-nitropicolinoyl)-2,7-diazaspiro[4.5]decane-6,8-dione,
2-(2-oxoindoline-4-carbonyl)-2,7-diazaspiro[4.5]decane-6,8-dione,
2-(benzo[d]thiazole-5-carbonyl)-2,7-diazaspiro[4.5]decane-6,8-dione,
2-(5-nitropyridin-2-yl)-2,7-diazaspiro[4.5]decane-6,8-dione,
2-(2-(pyridin-3-yl)propanoyl)-2,7-diazaspiro[4.5]decane-6,8-dione,
2-(1-acetylindoline-4-carbonyl)-2,7-diazaspiro[4.5]decane-6,8-dione,
2-benzoyl-2,7-diazaspiro[4.5]decane-6,8-dione,
2-(1H-indazole-4-carbonyl)-2,7-diazaspiro[4.5]decane-6,8-dione,
2-(5-aminopyridin-2-yl)-2,7-diazaspiro[4.5]decane-6,8-dione,
2-(indoline-4-carbonyl)-2,7-diazaspiro[4.5]decane-6,8-dione,
2-(indoline-6-carbonyl)-2,7-diazaspiro[4.5]decane-6,8-dione,
2-(1-acetylindoline-6-carbonyl)-2,7-diazaspiro[4.5]decane-6,8-dione,
2-(benzofuran-3-carbonyl)-2,7-diazaspiro[4.5]decane-6,8-dione,
2-(benzo[d]oxazole-6-carbonyl)-2,7-diazaspiro[4.5]decane-6,8-dione, and
2-(indoline-5-carbonyl)-2,7-diazaspiro[4.5]decane-6,8-dione.

E5: The compound of formula VII, or pharmaceutically acceptable salts thereof, as described herein, wherein $X^4$ is selected from the group consisting of
  i.) H,
  ii.) aryl, in particular indanyl or 1,2,3,4-tetrahydronaphthalenyl,
  iii.) aryl, in particular phenyl, substituted by $R^2$,
  iv.) heterocyclyl, in particular indolinyl,
  v.) heterocyclyl, in particular indolinyl, substituted by $R^3$,
  vi.) heteroaryl, in particular thiazolo[4,5-b]pyridinyl, benzothiazolyl, quinolinyl, oxazolo[4,5-b]pyridinyl, benzoxazolyl, thiazolo[4,5-c]pyridinyl, indazolyl, benzofuranyl or pyrazolo[1,5-a]pyridinyl,
  vii.) heteroaryl, in particular pyridinyl, benzimidazolyl, pyrimidyl, benzothiazolyl or thiazolyl, each individually substituted by $R^4$, and
  viii.) $C_{1-6}$-alkyl, in particular methyl.

E6: The compound of formula VII, or pharmaceutically acceptable salts thereof, as described herein, wherein $X^4$ is selected from the group consisting of
  i.) H,
  ii.) phenyl, indanyl or 1,2,3,4-tetrahydronaphthalenyl,
  iii.) phenyl, substituted by $R^2$,
  iv.) indolinyl,
  v.) indolinyl, substituted by $R^3$,
  vi.) thiazolo[4,5-b]pyridinyl, benzothiazolyl, quinolinyl, oxazolo[4,5-b]pyridinyl, benzoxazolyl, thiazolo[4,5-c]pyridinyl, indazolyl, benzofuranyl or pyrazolo[1,5-a]pyridinyl,
  vii.) pyridinyl, benzimidazolyl, pyrimidyl, benzothiazolyl or thiazolyl, each individually substituted by $R^4$, and
  viii.) methyl.

E7: The compound of formula VII, or pharmaceutically acceptable salts thereof, as described herein, wherein $X^4$ is selected from the group consisting of
  i.) aryl, in particular phenyl, indanyl or 1,2,3,4-tetrahydronaphthalenyl,
  ii.) aryl, in particular phenyl, substituted by $R^2$,
  iii.) heterocyclyl, in particular indolinyl,
  iv.) heterocyclyl, in particular indolinyl, substituted by $R^3$,
  v.) heteroaryl, in particular thiazolo[4,5-b]pyridinyl, benzothiazolyl, quinolinyl, oxazolo[4,5-b]pyridinyl, benzoxazolyl, thiazolo[4,5-c]pyridinyl, indazolyl, benzofuranyl or pyrazolo[1,5-a]pyridinyl, and
  vi.) heteroaryl, in particular pyridinyl, benzimidazolyl, pyrimidyl, benzothiazolyl or thiazolyl, each individually substituted by $R^4$.

E8: The compound of formula VII, or pharmaceutically acceptable salts thereof, as described herein, wherein $X^A$ is selected from the group consisting of
  i.) phenyl, indanyl or 1,2,3,4-tetrahydronaphthalenyl,
  ii.) phenyl, substituted by $R^2$,
  iii.) indolinyl,
  iv.) indolinyl, substituted by $R^3$,
  v.) thiazolo[4,5-b]pyridinyl, benzothiazolyl, quinolinyl, oxazolo[4,5-b]pyridinyl, benzoxazolyl, thiazolo[4,5-c]pyridinyl, indazolyl, benzofuranyl or pyrazolo[1,5-a]pyridinyl, and
  vi.) pyridinyl, benzimidazolyl, pyrimidyl, benzothiazolyl or thiazolyl, each individually substituted by $R^4$.

E9: The compound of formula VII, or pharmaceutically acceptable salts thereof, as described herein, wherein $X^A$ is H.

E10: The compound of formula VII, or pharmaceutically acceptable salts thereof, as described herein, wherein $X^A$ is aryl.

E11: The compound of formula VII, or pharmaceutically acceptable salts thereof, as described herein, wherein $X^A$ is phenyl, indanyl or 1,2,3,4-tetrahydronaphthalenyl.

E12: The compound of formula VII, or pharmaceutically acceptable salts thereof, as described herein, wherein $X^A$ is phenyl.

E13: The compound of formula VII, or pharmaceutically acceptable salts thereof, as described herein, wherein $X^A$ is indanyl.

E14: The compound of formula VII, or pharmaceutically acceptable salts thereof, as described herein, wherein $X^A$ is 1,2,3,4-tetrahydronaphthalenyl.

E15: The compound of formula VII, or pharmaceutically acceptable salts thereof, as described herein, wherein $X^A$ is aryl substituted by $R^2$.

E16: The compound of formula VII, or pharmaceutically acceptable salts thereof, as described herein, wherein $X^A$ is phenyl substituted by $R^2$.

E17: The compound of formula VII, or pharmaceutically acceptable salts thereof, as described herein, wherein $X^A$ is heterocyclyl.

E18: The compound of formula VII, or pharmaceutically acceptable salts thereof, as described herein, wherein $X^A$ is indolinyl.

E19: The compound of formula VII, or pharmaceutically acceptable salts thereof, as described herein, wherein $X^A$ is heterocyclyl substituted by $R^3$.

E20: The compound of formula VII, or pharmaceutically acceptable salts thereof, as described herein, wherein $X^A$ is indolinyl, substituted by $R^3$.

E21: The compound of formula VII, or pharmaceutically acceptable salts thereof, as described herein, wherein $X^A$ is heteroaryl.

E21: The compound of formula VII, or pharmaceutically acceptable salts thereof, as described herein, wherein $X^A$ is thiazolo[4,5-b]pyridinyl, benzothiazolyl, quinolinyl, oxazolo[4,5-b]pyridinyl, benzoxazolyl, thiazolo[4,5-c]pyridinyl, indazolyl, benzofuranyl or pyrazolo[1,5-a]pyridinyl E23: The compound of formula VII, or pharmaceutically acceptable salts thereof, as described herein, wherein $X^A$ is heteroaryl substituted by $R^4$.

E24: The compound of formula VII, or pharmaceutically acceptable salts thereof, as described herein, wherein $X^A$ is pyridinyl, benzimidazolyl, pyrimidyl, benzothiazolyl or thiazolyl, each individually substituted by $R^4$ E25: The compound of formula VII, or pharmaceutically acceptable salts thereof, as described herein, wherein $X^A$ is $C_{1-6}$-alkyl.

E26: The compound of formula VII, or pharmaceutically acceptable salts thereof, as described herein, wherein $X^A$ is methyl.

E27: The compound of formula VII, or pharmaceutically acceptable salts thereof, as described herein, wherein $Y^A$ is selected from the group consisting of
  i.) —C(=O)—;
  ii.) —C(=O)—C(H,$C_{1-6}$-alkyl)-, in particular —C(=O)—C(H,$CH_3$)—, and
  iii.) —C(=O)—$CH_2$—.

E28: The compound of formula VII, or pharmaceutically acceptable salts thereof, as described herein, wherein $Y^A$ is selected from the group consisting of
  i.) —C(=O)—;
  ii.) —C(=O)—C(H,$CH_3$)—, and
  iii.) —C(=O)—$CH_2$—.

E29: The compound of formula VII, or pharmaceutically acceptable salts thereof, as described herein, wherein $Y^A$ is —C(=O)—.

E30: The compound of formula VII, or pharmaceutically acceptable salts thereof, as described herein, wherein $Y^A$ is —C(=O)—C(H,$C_{1-6}$-alkyl)-.

E31: The compound of formula VII, or pharmaceutically acceptable salts thereof, as described herein, wherein $Y^A$ is —C(=O)—C(H,$CH_3$)—.

E32: The compound of formula VII, or pharmaceutically acceptable salts thereof, as described herein, wherein $Y^A$ is —C(=O)—$CH_2$—.

E33: The compound of formula VII, or pharmaceutically acceptable salts thereof, as described herein, wherein $R^1$ is absent.

E34: The compound of formula VII, or pharmaceutically acceptable salts thereof, as described herein, wherein $R^1$ is =O.

E35: The compound of formula VII, or pharmaceutically acceptable salts thereof, as described herein, wherein $R^2$ is selected from the group consisting of
  i.) —C(=O)—O—$C_{1-6}$-alkyl, in particular —C(=O)—O—$CH_3$,
  ii.) —NH—C(=O)—$C_{1-6}$-alkyl, in particular —NH—C(=O)—$CH_3$,
  iii.) —$NH_2$,
  iv.) —OH, and
  v.) —$NO_2$.

E36: The compound of formula VII, or pharmaceutically acceptable salts thereof, as described herein, wherein $R^2$ is selected from the group consisting of
  i.) —C(=O)—O—$C_{1-6}$-alkyl, in particular —C(=O)—O—$CH_3$,
  ii.) —NH—C(=O)—$C_{1-6}$-alkyl, in particular —NH—C(=O)—$CH_3$, and
  iii.) —$NO_2$.

E37: The compound of formula VII, or pharmaceutically acceptable salts thereof, as described herein, wherein $R^2$ is selected from the group consisting of
  i.) —C(=O)—O—$CH_3$,
  ii.) —NH—C(=O)—$CH_3$, and
  iii.) —$NO_2$.

E38: The compound of formula VII, or pharmaceutically acceptable salts thereof, as described herein, wherein $R^2$ is —C(=O)—O—$C_{1-6}$-alkyl.

E39: The compound of formula VII, or pharmaceutically acceptable salts thereof, as described herein, wherein $R^2$ is —C(=O)—O—$CH_3$.

E40: The compound of formula VII, or pharmaceutically acceptable salts thereof, as described herein, wherein $R^2$ is —NH—C(=O)—$C_{1-6}$-alkyl.

E41: The compound of formula VII, or pharmaceutically acceptable salts thereof, as described herein, wherein $R^2$ is —NH—C(=O)—$CH_3$.

E42: The compound of formula VII, or pharmaceutically acceptable salts thereof, as described herein, wherein $R^2$ is —$NO_2$.

E43: The compound of formula VII, or pharmaceutically acceptable salts thereof, as described herein, wherein $R^3$ is selected from the group consisting of
i.) —C(=O)—$C_{1-6}$-alkyl, in particular —C(=O)—$CH_3$, and
ii.) =O.

E44: The compound of formula VII, or pharmaceutically acceptable salts thereof, as described herein, wherein $R^3$ is selected from the group consisting of
i.) —C(=O)—$CH_3$, and
ii.) =O.

E45: The compound of formula VII, or pharmaceutically acceptable salts thereof, as described herein, wherein $R^3$ is —C(=O)—$C_{1-6}$-alkyl.

E46: The compound of formula VII, or pharmaceutically acceptable salts thereof, as described herein, wherein $R^3$ is —C(=O)—$CH_3$.

E47: The compound of formula VII, or pharmaceutically acceptable salts thereof, as described herein, wherein $R^3$ is =O.

E48: The compound of formula VII, or pharmaceutically acceptable salts thereof, as described herein, wherein $R^4$ is selected from the group consisting of
i.) —C(=O)—O—$C_{1-6}$-alkyl, in particular —C(=O)—O—$CH_3$ or —C(=O)—O—$C(CH_3)_3$,
ii.) $C_{1-6}$-alkyl, in particular methyl,
iii.) —$NH_2$,
iv.) —NH—C(=O)—$C_{1-6}$-alkyl, in particular —NH—C(=O)—$CH_3$, and
v.) —$NO_2$.

E49: The compound of formula VII, or pharmaceutically acceptable salts thereof, as described herein, wherein $R^4$ is selected from the group consisting of
i.) —C(=O)—O—$CH_3$ or —C(=O)—O—$C(CH_3)_3$,
ii.) methyl,
iii.) —$NH_2$,
iv.) —NH—C(=O)—$CH_3$, and
v.) —$NO_2$.

E50: The compound of formula VII, or pharmaceutically acceptable salts thereof, as described herein, wherein $R^4$ is —C(=O)—O—$C_{1-6}$-alkyl.

E51: The compound of formula VII, or pharmaceutically acceptable salts thereof, as described herein, wherein $R^4$ is —C(=O)—O—$CH_3$.

E52: The compound of formula VII, or pharmaceutically acceptable salts thereof, as described herein, wherein $R^4$ is —C(=O)—O—$C(CH_3)_3$.

E53: The compound of formula VII, or pharmaceutically acceptable salts thereof, as described herein, wherein $R^4$ is $C_{1-6}$-alkyl.

E54: The compound of formula VII, or pharmaceutically acceptable salts thereof, as described herein, wherein $R^4$ is methyl.

E55: The compound of formula VII, or pharmaceutically acceptable salts thereof, as described herein, wherein $R^4$ is —NH—C(=O)—$C_{1-6}$-alkyl.

E56: The compound of formula VII, or pharmaceutically acceptable salts thereof, as described herein, wherein $R^4$ is —NH—C(=O)—$CH_3$.

E57: The compound of formula VII, or pharmaceutically acceptable salts thereof, as described herein, wherein $R^4$ is —$NO_2$.

E58: A certain embodiment of the invention relates to the compound of formula VII as described herein, or a pharmaceutically acceptable salt thereof, for use as therapeutically active substance.

E59: A certain embodiment of the invention relates to the compound of formula VII as described herein, or a pharmaceutically acceptable salt thereof, for the use in the therapeutic and/or prophylactic treatment of cancer.

E60: A certain embodiment of the invention relates to the compound of formula VII as described herein, or a pharmaceutically acceptable salt thereof, for the manufacture of a medicament for the therapeutic and/or prophylactic treatment of cancer.

E61: A certain embodiment of the invention relates to a pharmaceutical composition comprising the compound of formula VII as described herein, or a pharmaceutically acceptable salt thereof, and a pharmaceutically acceptable auxiliary substance.

E62: A certain embodiment of the invention relates to a method for the therapeutic and/or prophylactic treatment of cancer, by administering the compound of formula VII as described herein, or a pharmaceutically acceptable salt thereof, to a patient.

Compounds of Formula VIII to Formula XII

In another aspect, a compound is provided of Formula VIII:

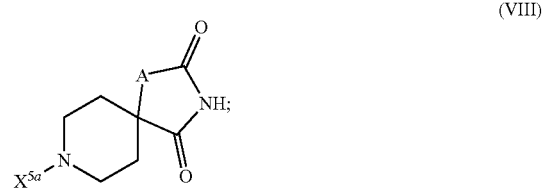

(VIII)

or a pharmaceutically acceptable salt thereof;
wherein all variables are as defined herein.

In one embodiment, a compound of Formula VIII is provided selected from:

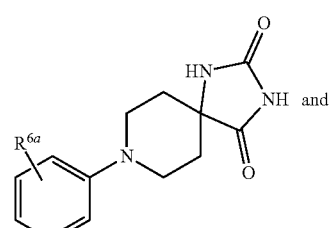

and

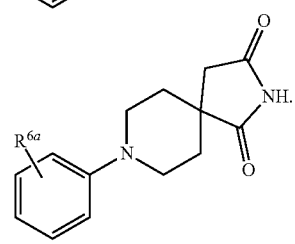

In one embodiment, a compound of Formula VIII is provided selected from:
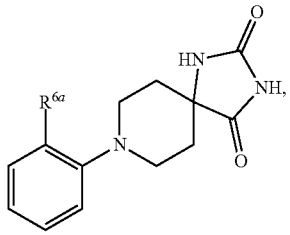
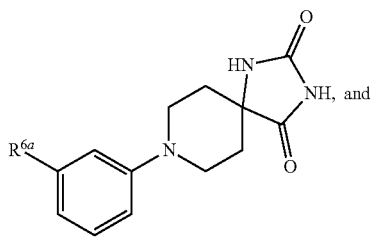
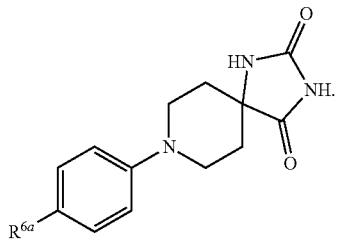
In one embodiment, a compound of Formula VIII is provided selected from:
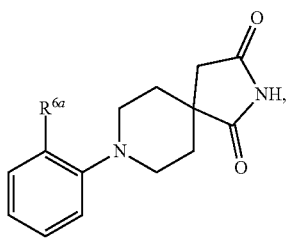
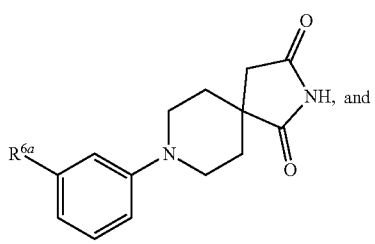
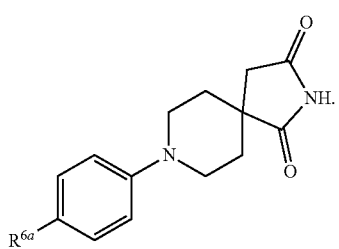
In another aspect, a compound is provided of Formula IX:
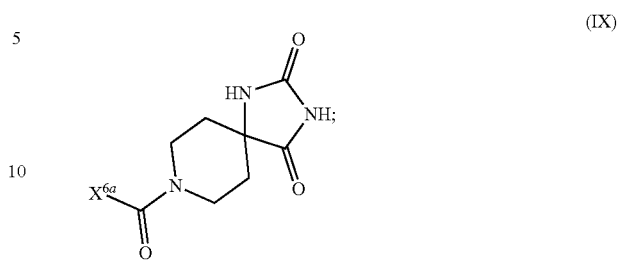
(IX)
or a pharmaceutically acceptable salt thereof;
wherein all variables are as defined herein.
In one embodiment, a compound of Formula IX is provided selected from:
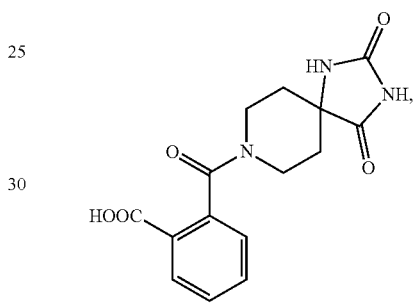
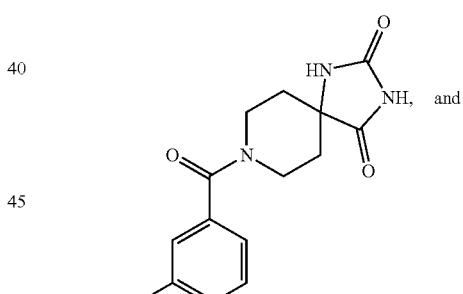
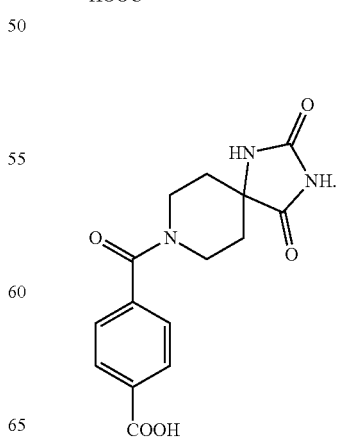

In another aspect, a compound is provided of Formula X:
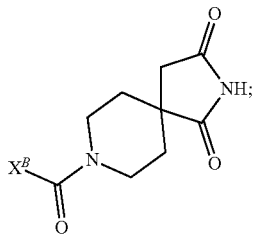
(X)
or a pharmaceutically acceptable salt thereof;
wherein all variables are as defined herein.
In one embodiment, a compound of Formula X is provided selected from:
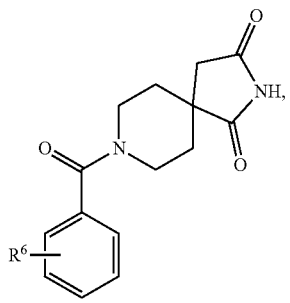
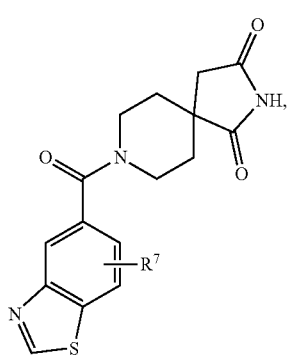
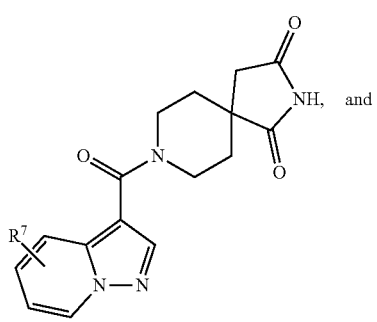
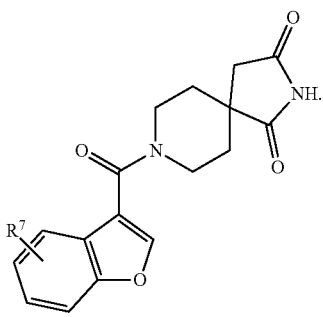
In one embodiment, a compound of Formula X is provided selected from:
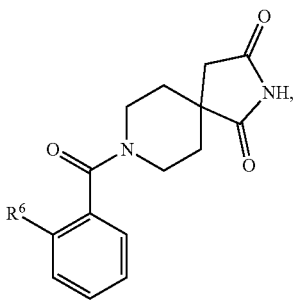
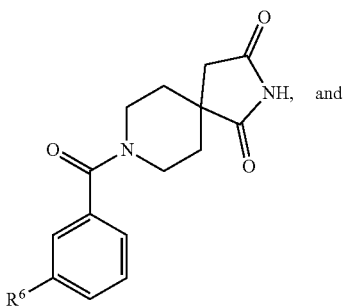
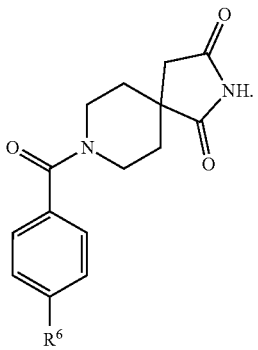

In one embodiment, a compound of Formula X is provided selected from:
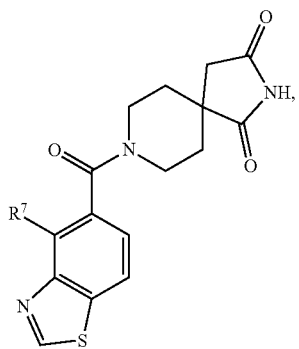
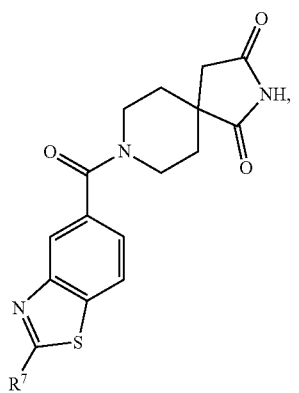
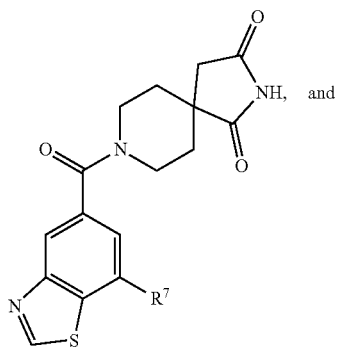
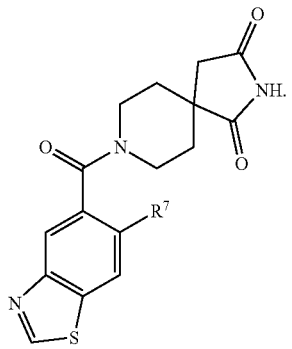
In one embodiment, a compound of Formula X is provided selected from:
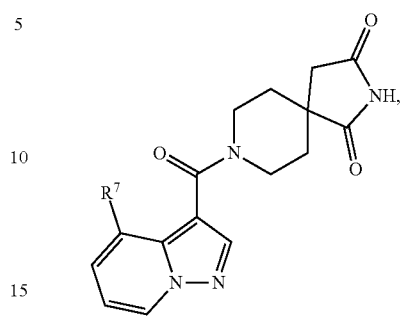
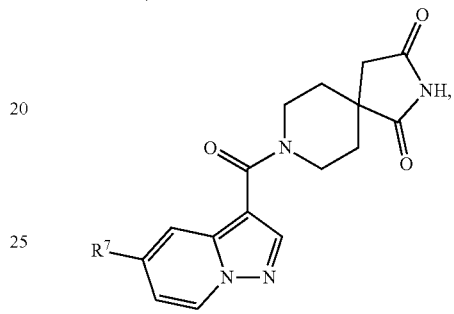
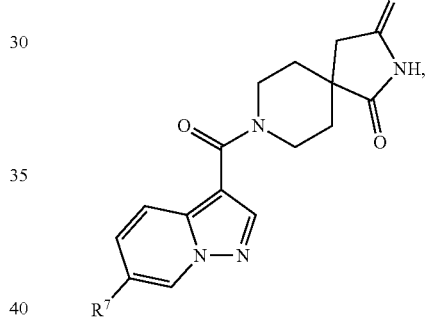
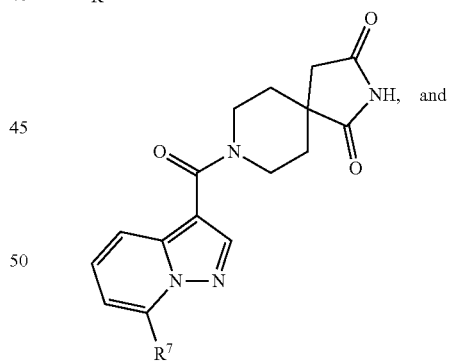
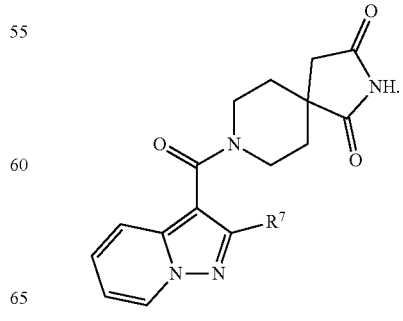

In one embodiment, a compound of Formula X is provided selected from:
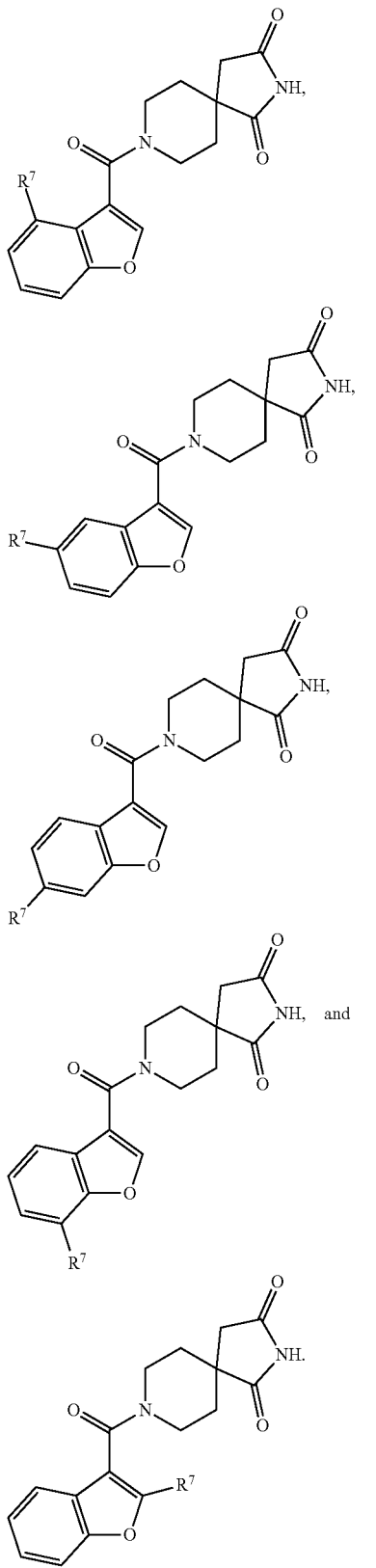
In another aspect, a compound is provided of Formula XI:
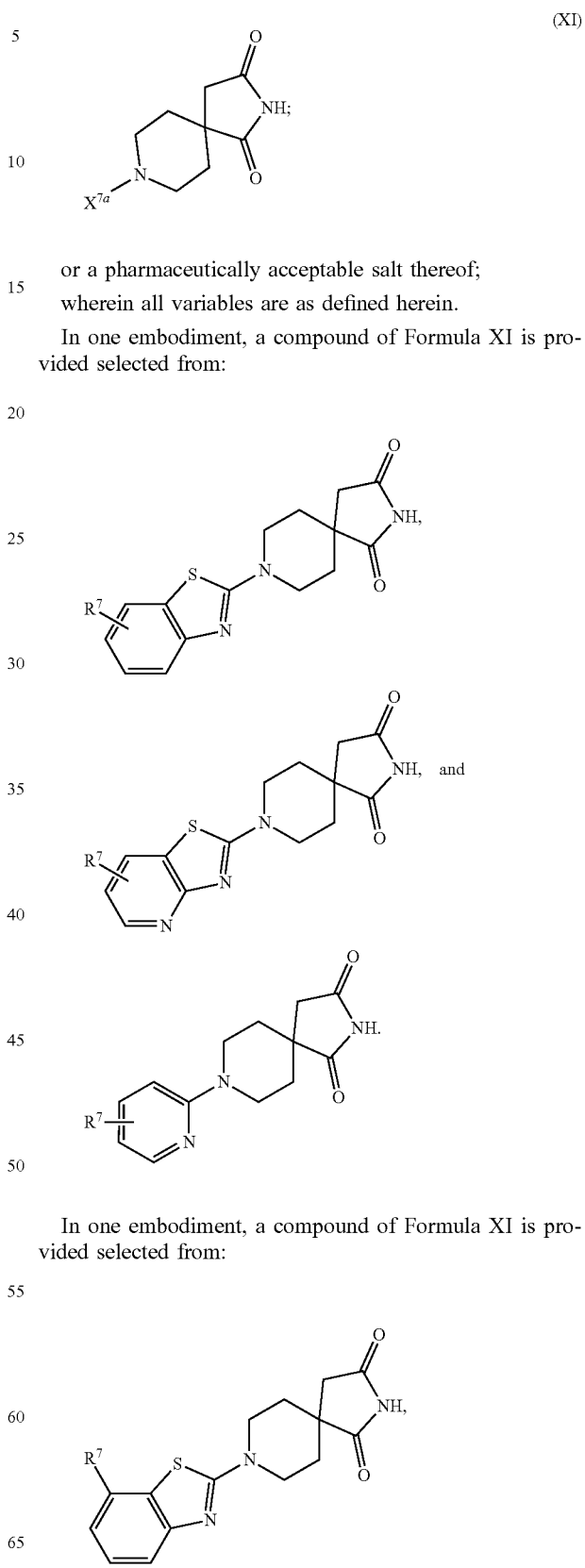
(XI)
or a pharmaceutically acceptable salt thereof;
wherein all variables are as defined herein.
In one embodiment, a compound of Formula XI is provided selected from:
In one embodiment, a compound of Formula XI is provided selected from:

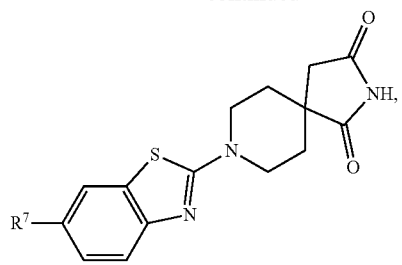
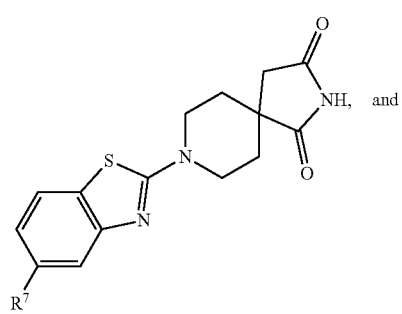
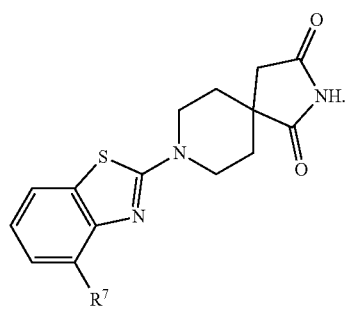
In one embodiment, a compound of Formula XI is provided selected from:
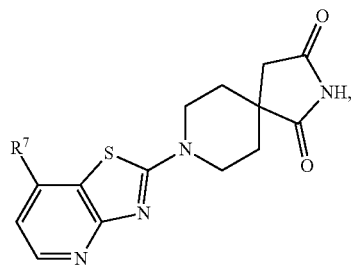
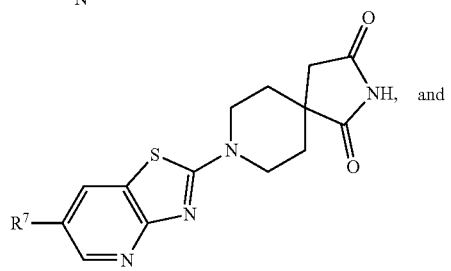
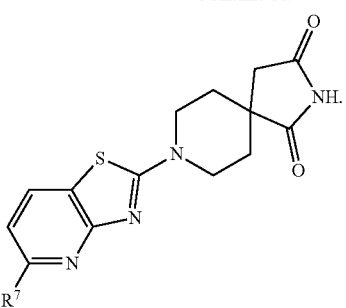
In one embodiment, a compound of Formula XI is provided selected from:
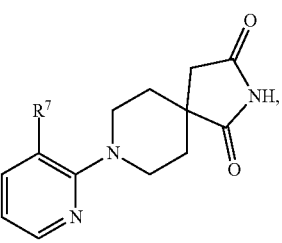
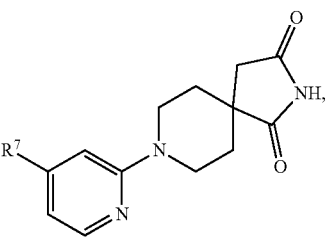
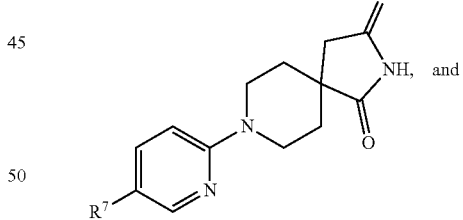
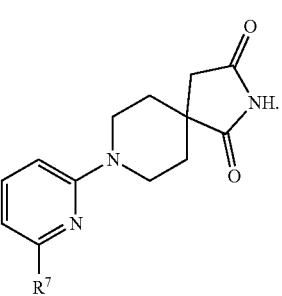

In another aspect, a compound is provided of Formula XII:

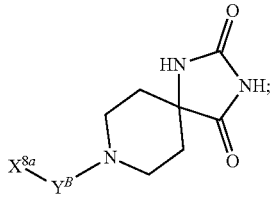

(XII)

or a pharmaceutically acceptable salt thereof;
wherein all variables are as defined herein.

In one embodiment, a compound of Formula XII is of the formula:

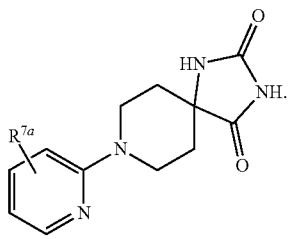

In one embodiment, a compound of Formula XII is provided selected from:

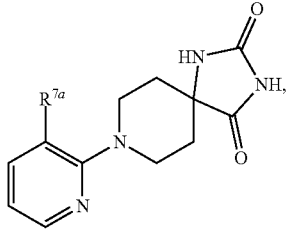

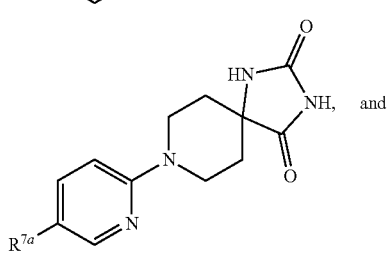

and

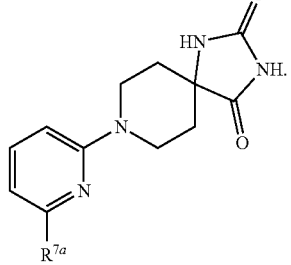

In one embodiment, a compound is provided of the formula

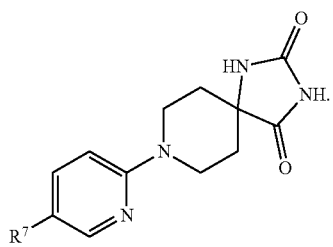

In one embodiment, a compound is provided selected from:

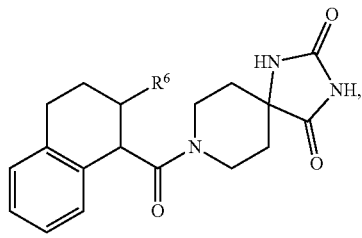

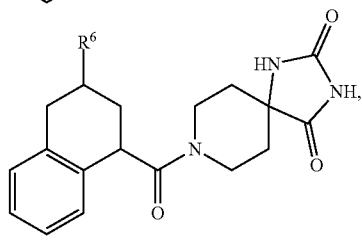

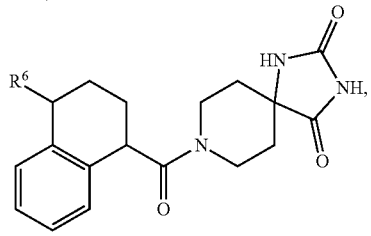

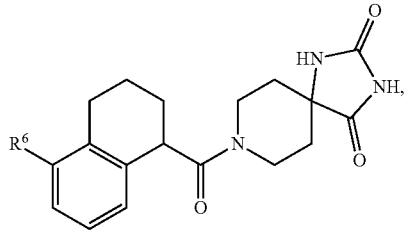

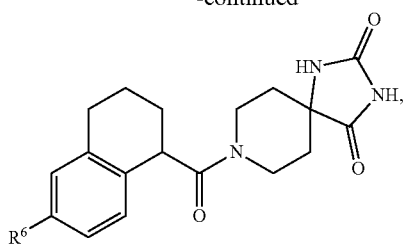
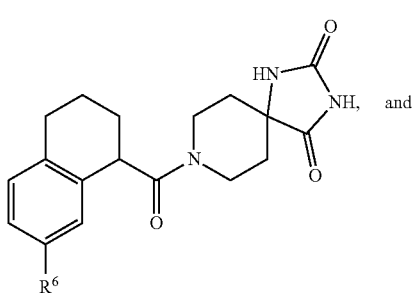
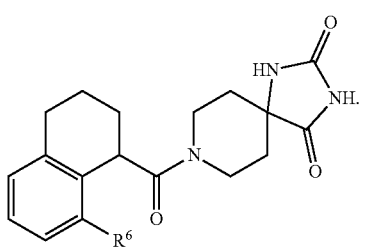
In one embodiment, a compound is provided selected from:
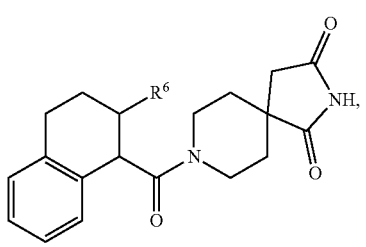
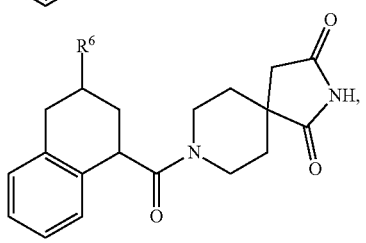
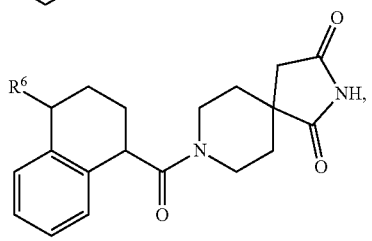
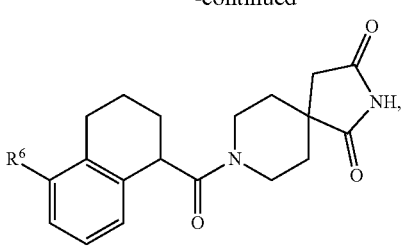
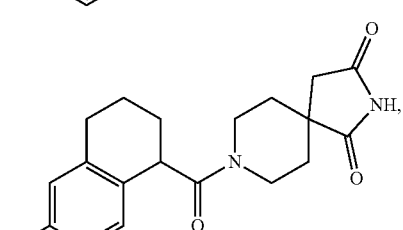
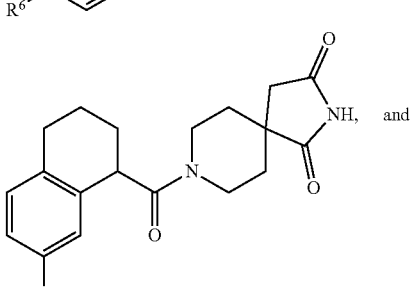
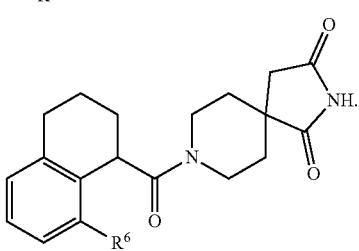
In one embodiment, a compound is provided selected from:
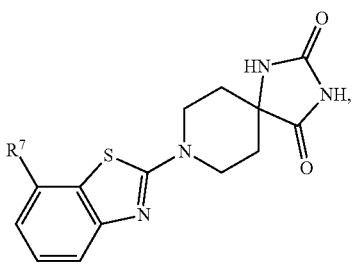
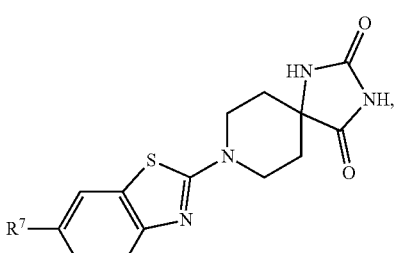

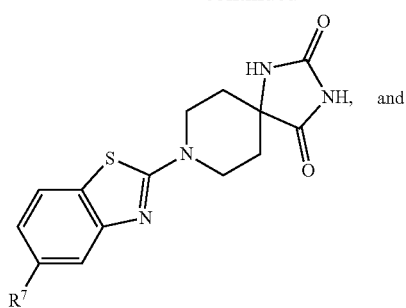 and
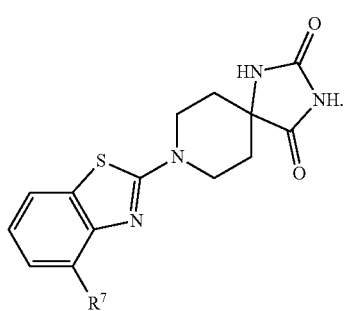
In one embodiment, a compound is provided selected from:
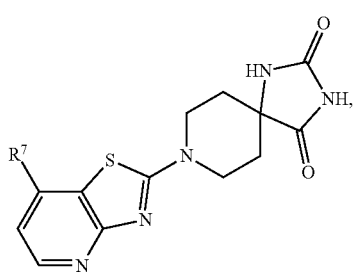
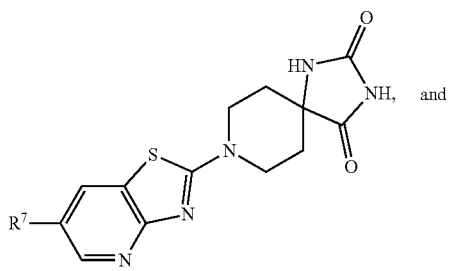 and
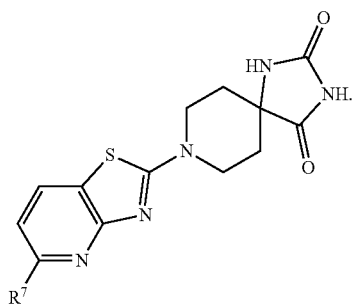
In one embodiment, a compound is provided selected from:
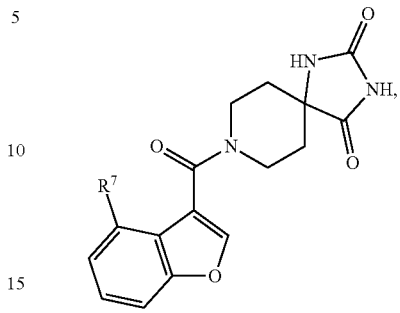
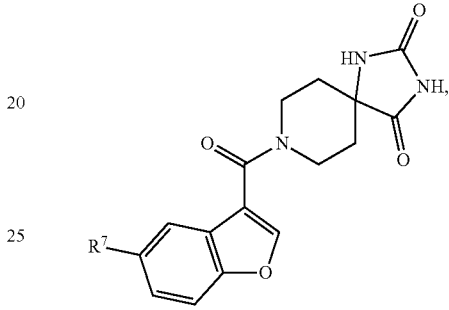
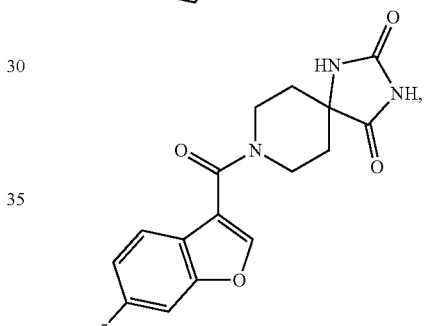
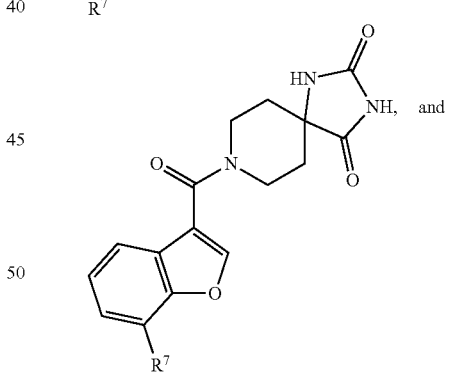 and
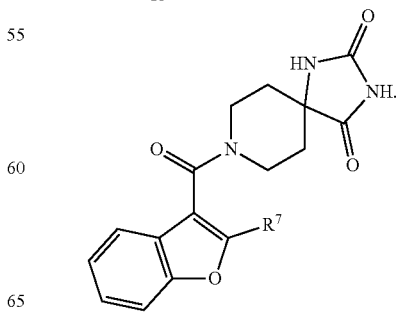

In one embodiment, a compound is provided selected from:

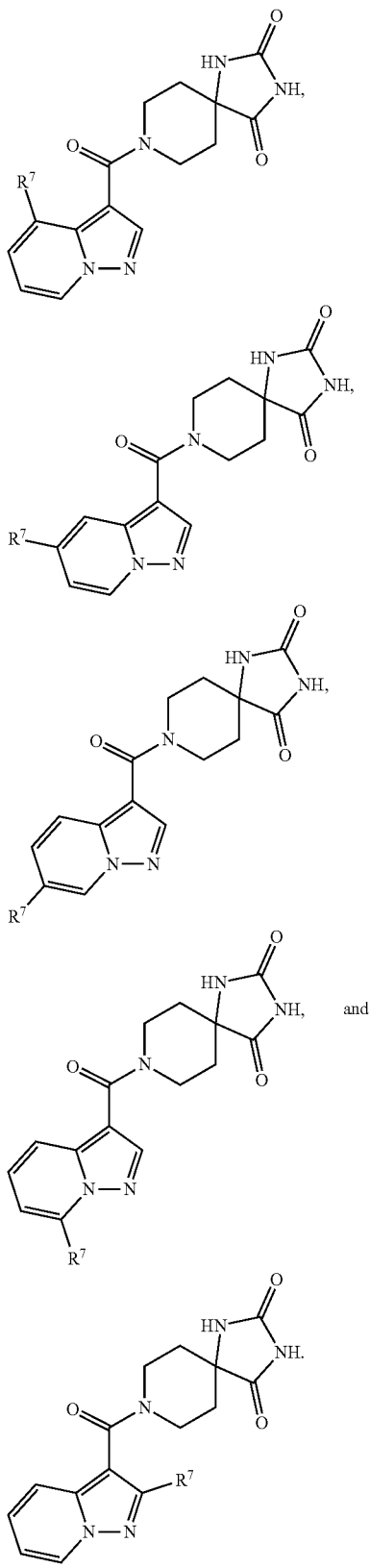

In one embodiment, a compound is provided selected from:

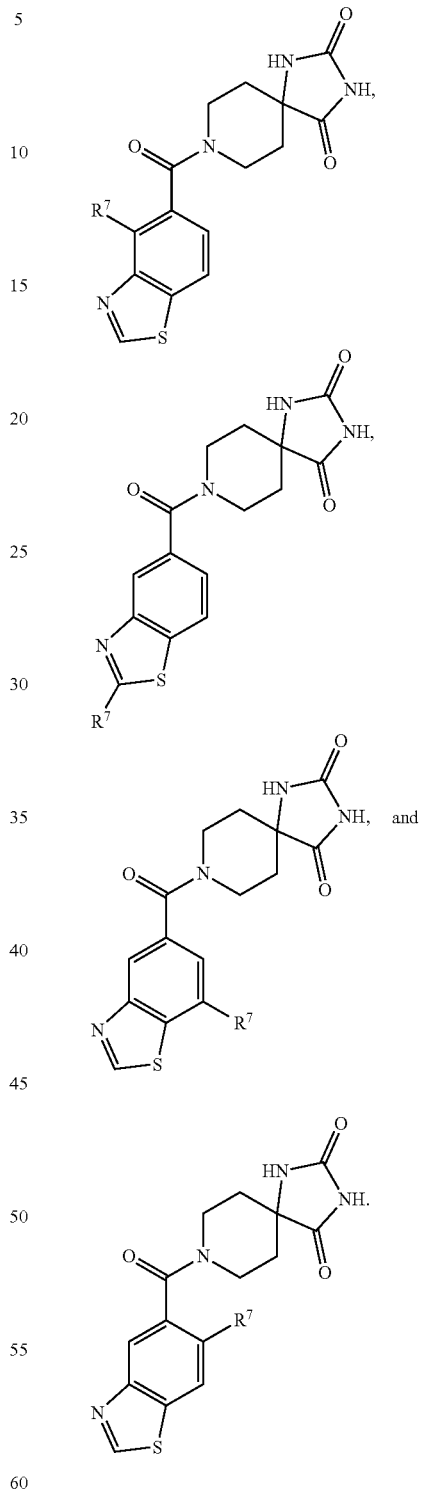

Compounds of Formula XIII

In another aspect, the use of a compound for the treatment of a therapeutic condition which can be treated by modulating the function or activity of the cereblon containing E3 Ubiquitin Ligase Protein Complex is provided of Formula XIII:

(XIII)

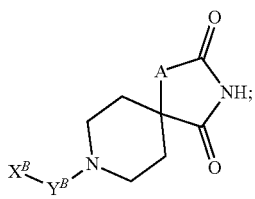

or a pharmaceutically acceptable salt thereof;
wherein all variables are as defined herein.

In one embodiment, a compound of Formula XIII for use in the methods provided herein is selected from:

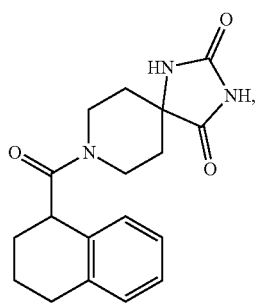

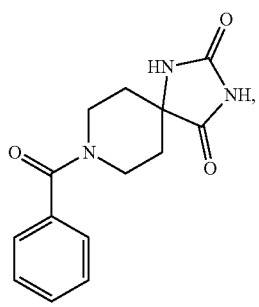

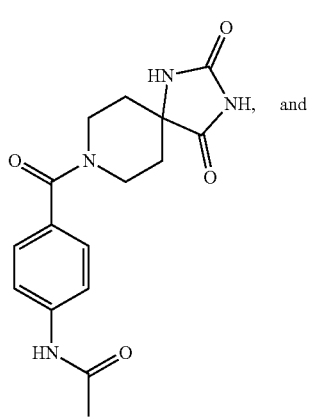

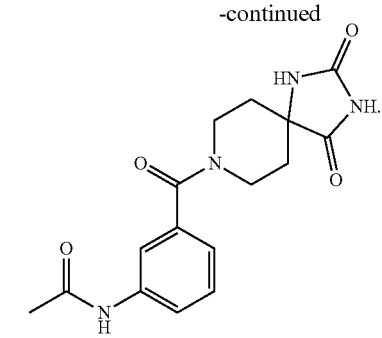

In one embodiment, a compound of Formula XIII for use in the methods provided herein is selected from:

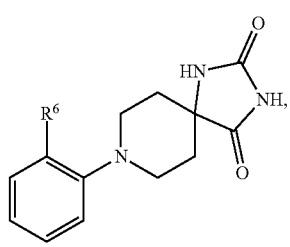

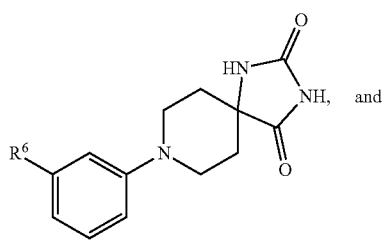

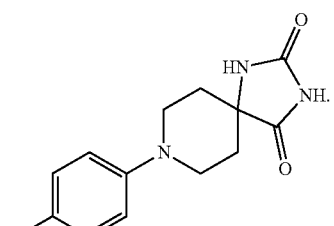

In one embodiment, a compound of Formula XIII for use in the methods provided herein is selected from:

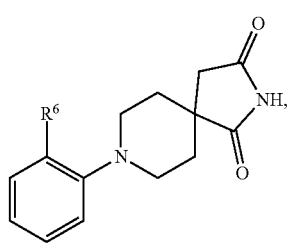

143
-continued
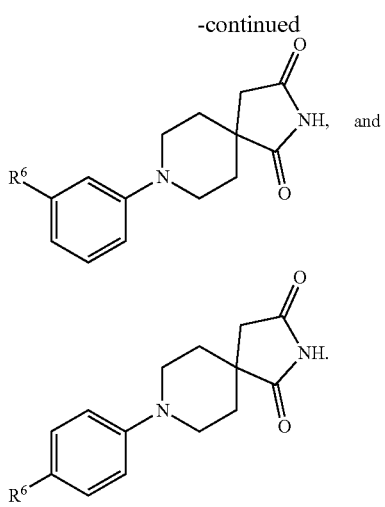
In one embodiment, a compound of Formula XIII for use in the methods provided herein is selected from:
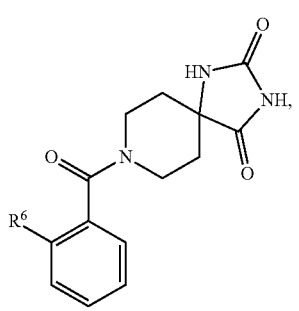
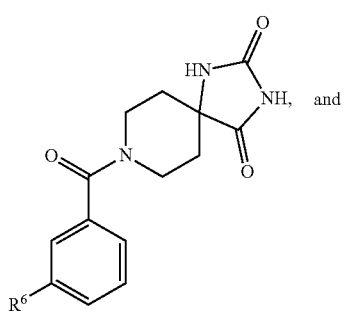
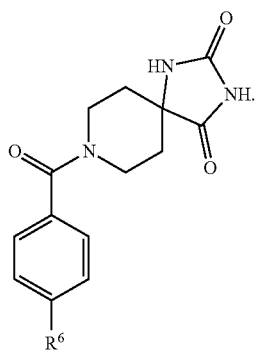
144
In one embodiment, a compound of Formula XIII for use in the methods provided herein is selected from:
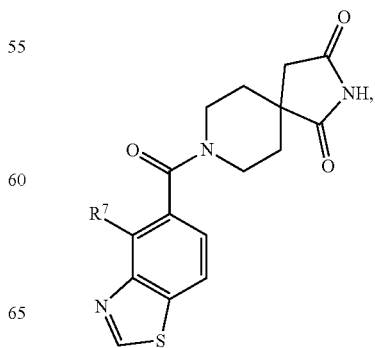
In one embodiment, a compound of Formula XIII for use in the methods provided herein is selected from:

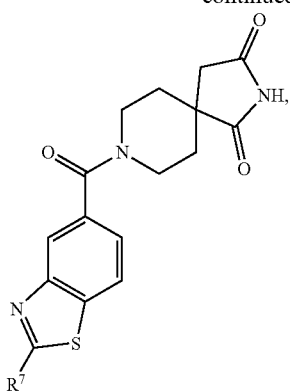
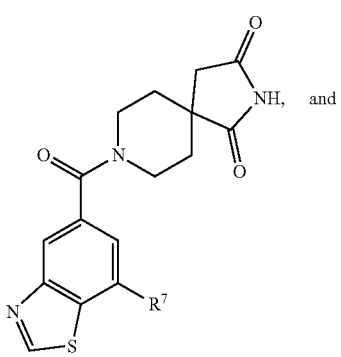
and
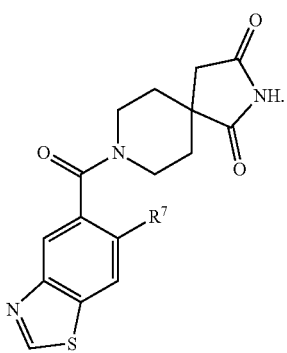
In one embodiment, a compound of Formula XIII for use in the methods provided herein is selected from:
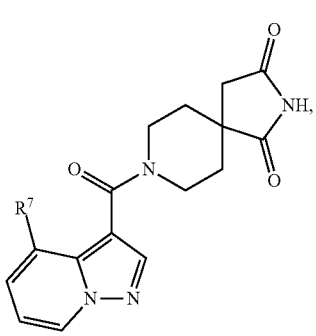
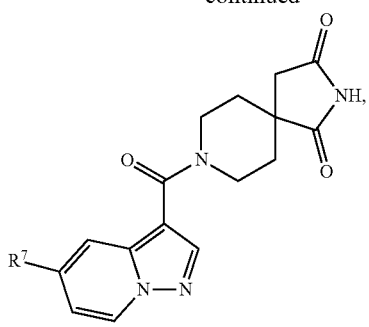
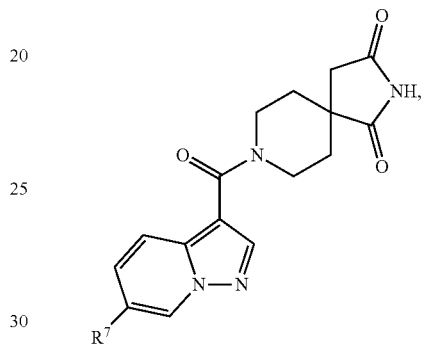
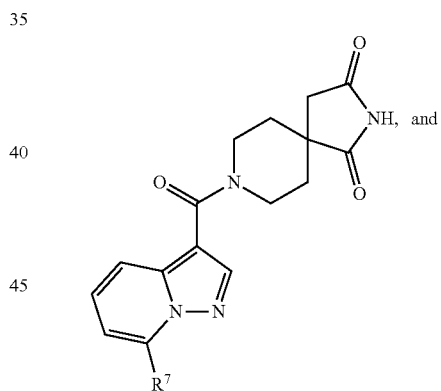
and
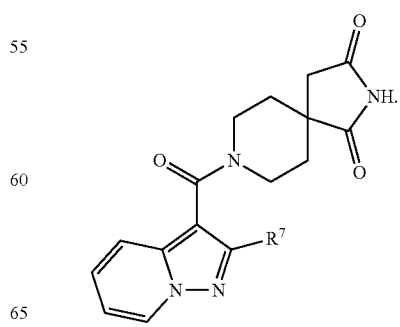

In one embodiment, a compound of Formula XIII for use in the methods provided herein is selected from:
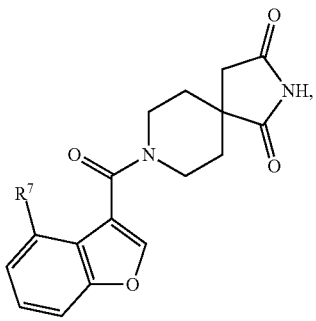
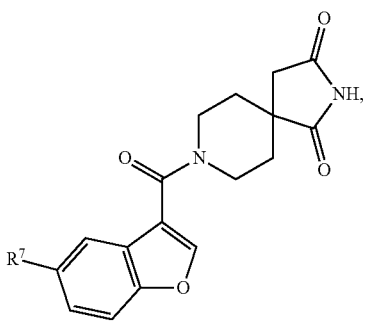
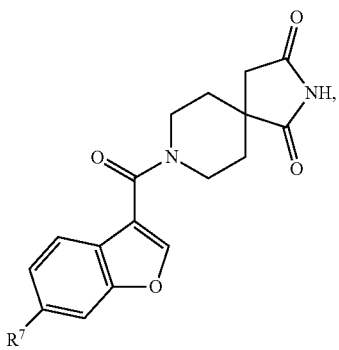
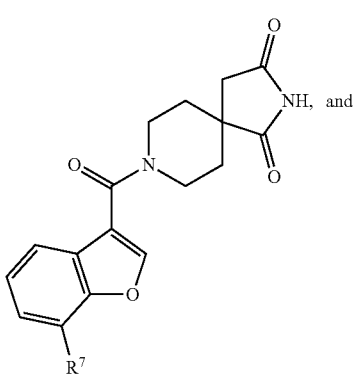
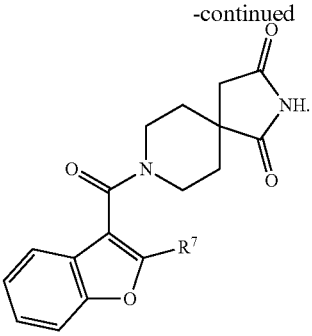
In one embodiment, a compound of Formula XIII for use in the methods provided herein is selected from:
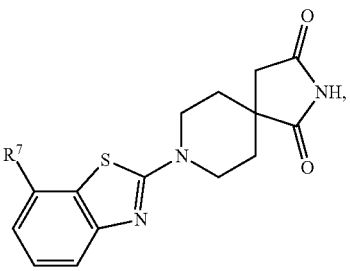
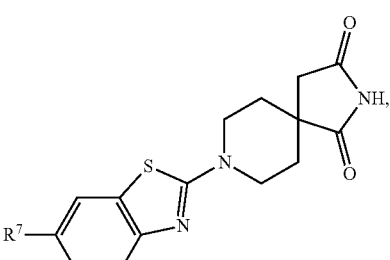
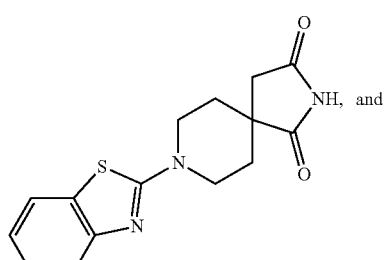
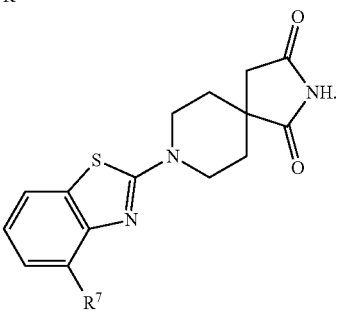

In one embodiment, a compound of Formula XIII for use in the methods provided herein is selected from:
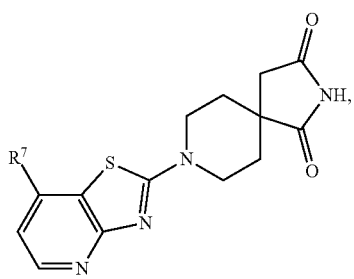
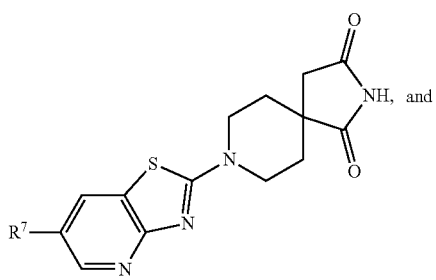
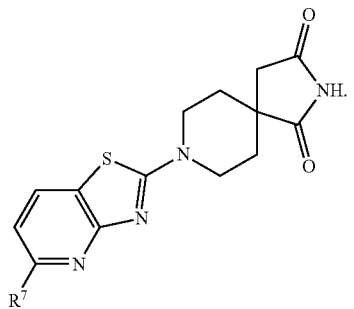
In one embodiment, a compound of Formula XIII for use in the methods provided herein is selected from:
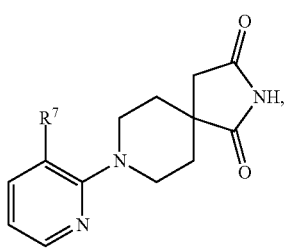
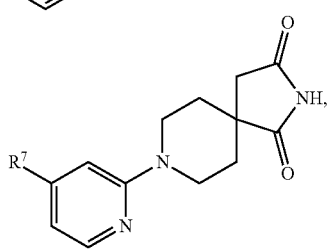
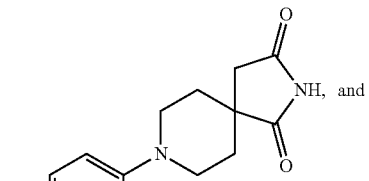
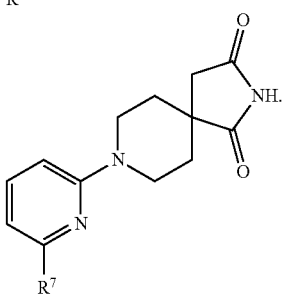
In one embodiment, a compound of Formula XIII for use in the methods provided herein is selected from:
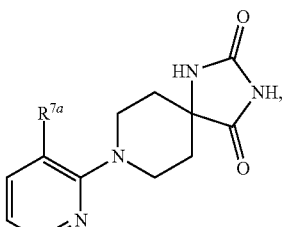
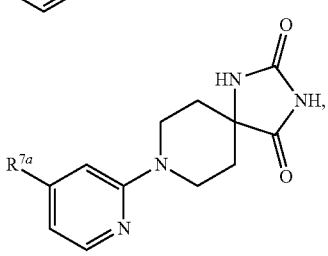
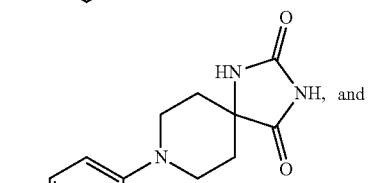
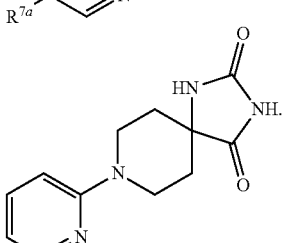

In one embodiment, a compound of Formula XIII for use in the methods provided herein is selected from:
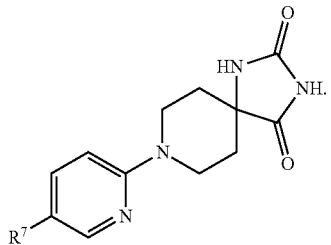
In one embodiment, a compound of Formula XIII for use in the methods provided herein is selected from:
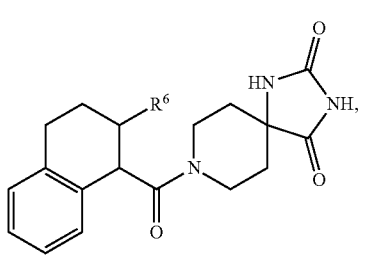
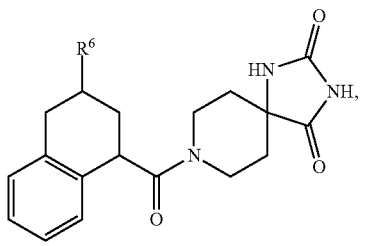
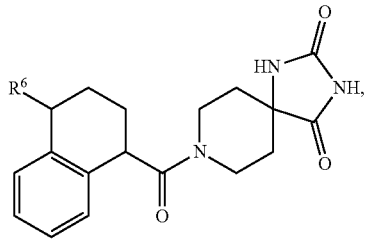
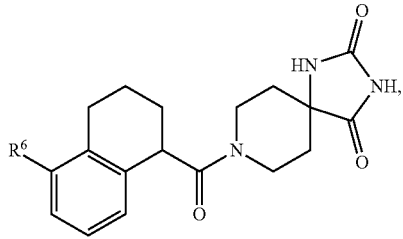
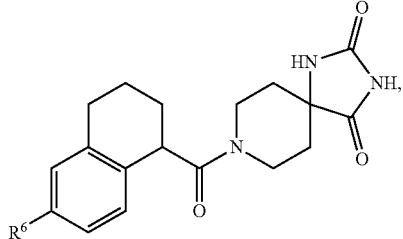
-continued
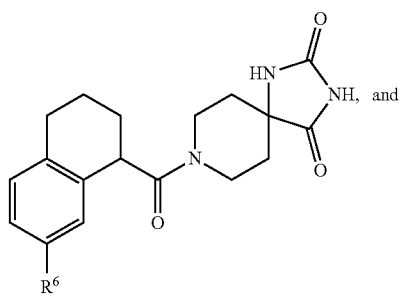
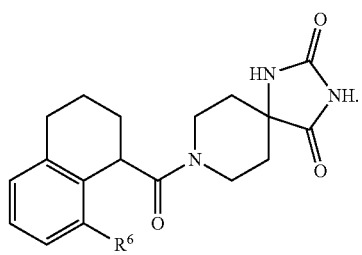
In one embodiment, a compound of Formula XIII for use in the methods provided herein is selected from:
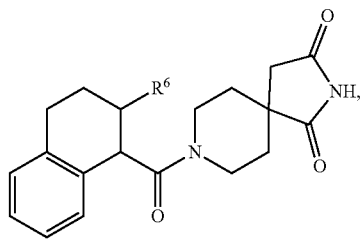
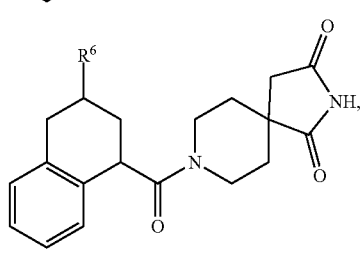
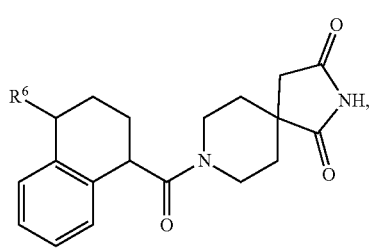
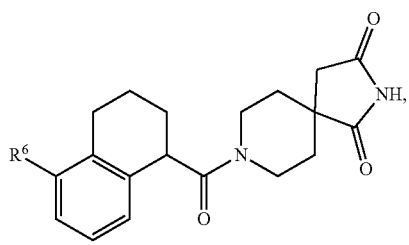

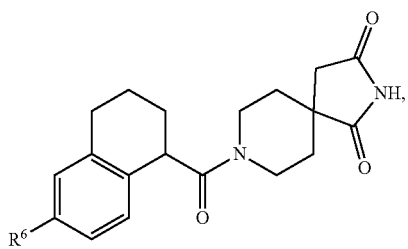
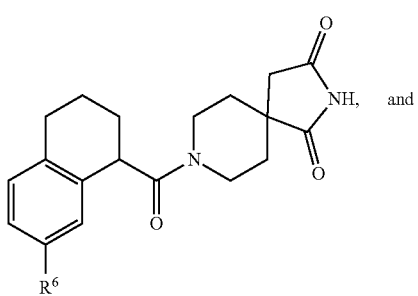
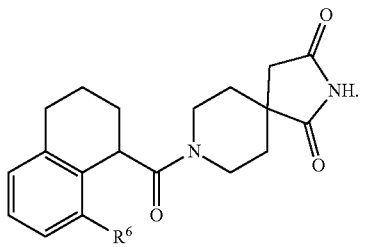
In one embodiment, a compound of Formula XIII for use in the methods provided herein is selected from:
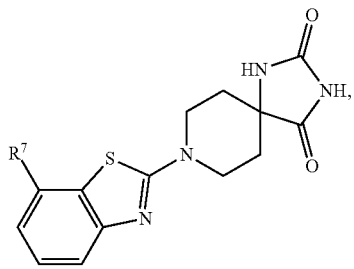
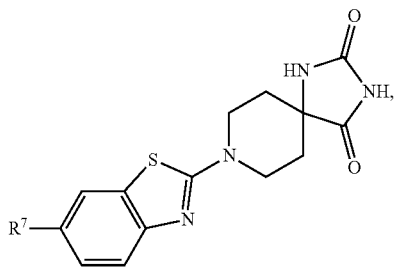
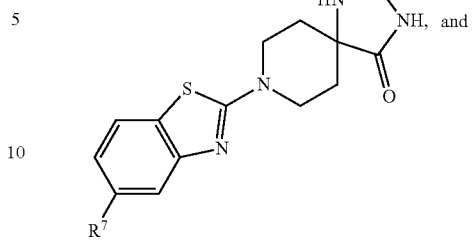
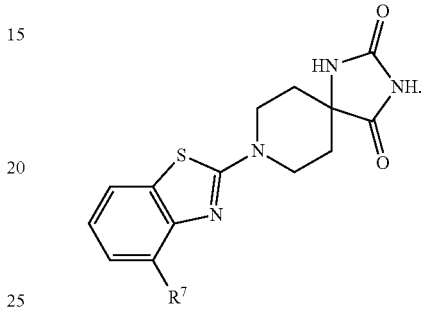
In one embodiment, a compound of Formula XIII for use in the methods provided herein is selected from:
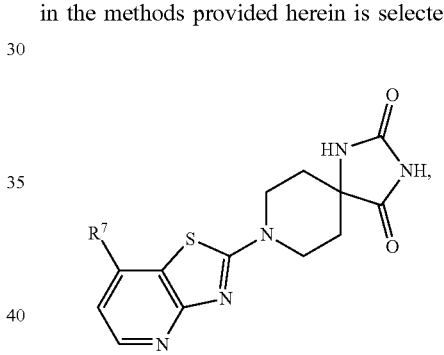
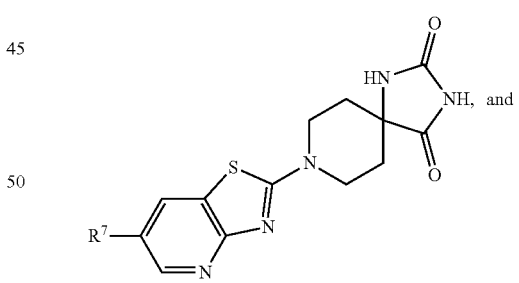
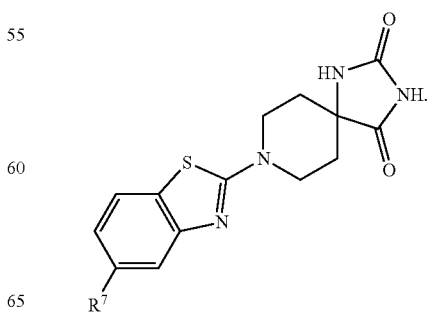

In one embodiment, a compound of Formula XIII for use in the methods provided herein is selected from:
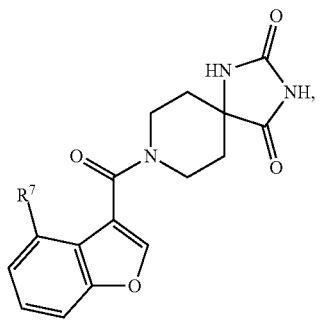
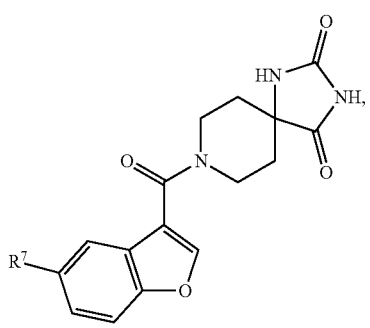
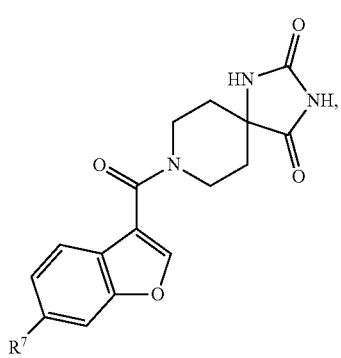
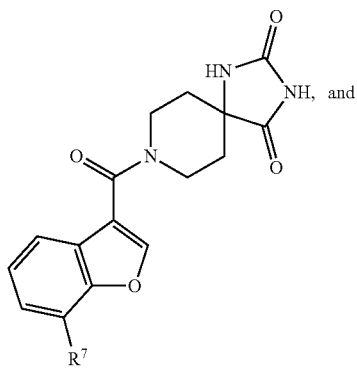
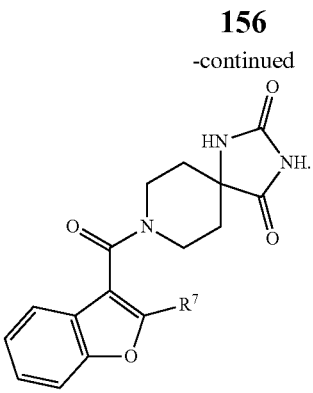
In one embodiment, a compound of Formula XIII for use in the methods provided herein is selected from:
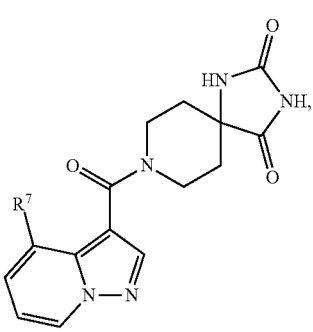
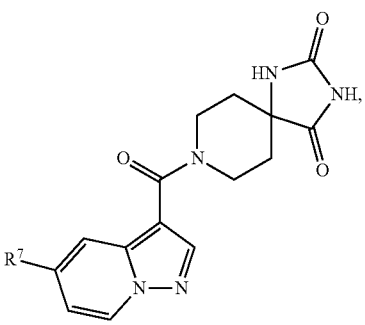
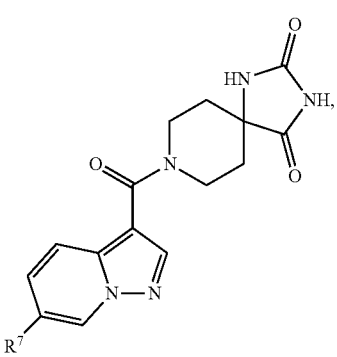

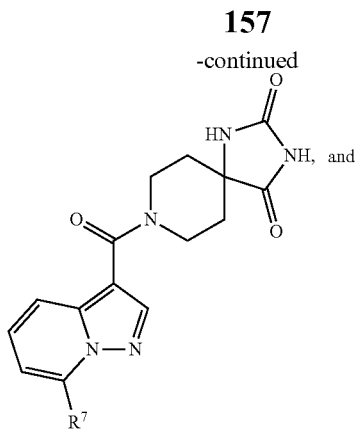

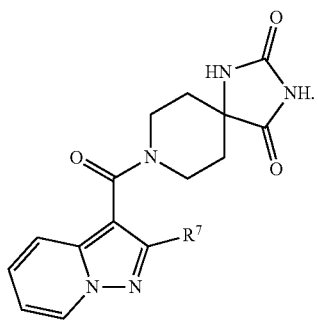

In one embodiment, a compound of Formula XIII for use in the methods provided herein is selected from:

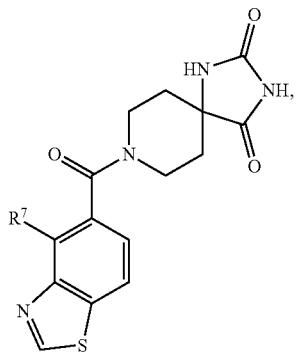

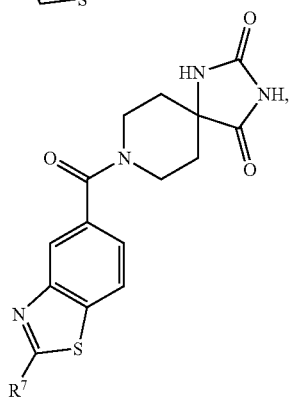

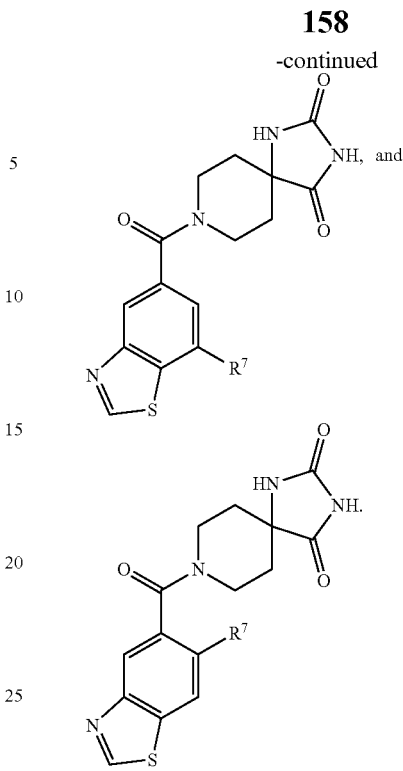

A compound of Formula XIII for use in the methods described herein is also provided in the following enumerated embodiments, all of which may be separately combined.

E1: A compound of formula XIII, or a pharmaceutically acceptable salt thereof, as described herein, wherein
$X^B$ is selected from the group consisting of
i.) aryl, in particular 1,2,3,4-tetrahydronaphthalenyl or phenyl,
ii.) phenyl substituted by $R^6$,
iii.) heteroaryl, in particular benzo[d]thiazolyl, thiazolo[4,5-b]pyridinyl, benzofuranyl or pyrazolo[1,5-a]pyridinyl,
iv.) pyridinyl substituted by $R^7$;
$R^6$ is selected from the group consisting of
i.) —NH—C(=O)—$C_{1-6}$-alkyl, in particular —NH—C(=O)—$CH_3$, and
ii.) —$NO_2$;
$R^7$ is selected from the group consisting of
i.) —C(=O)—O—$C_{1-6}$-alkyl, in particular —C(=O)—O—$CH_3$, and
ii.) —$NO_2$.

E2: A compound of formula XIII, or a pharmaceutically acceptable salt thereof, as described herein, wherein A is NH.

E3: A compound of formula XIII, or a pharmaceutically acceptable salt thereof, as described herein, wherein A is $CH_2$.

E4: A compound of formula XIII, or a pharmaceutically acceptable salt thereof, as described herein, wherein $Y^B$ is absent.

E5: A compound of formula XIII, or a pharmaceutically acceptable salt thereof, as described herein, wherein $Y^B$ is —C(=O)—.

E6: The compound of formula XIII, or pharmaceutically acceptable salts thereof, as described herein, selected from the group consisting of
(S)-8-(1,2,3,4-tetrahydronaphthalene-1-carbonyl)-2,8-diazaspiro[4.5]decane-1,3-dione, (R)-8-(1,2,3,4-tetrahydronaphthalene-1-carbonyl)-2,8-diazaspiro[4.5]decane-1,3-dione,
(S)-8-(1,2,3,4-tetrahydronaphthalene-1-carbonyl)-1,3,8-triazaspiro[4.5]decane-2,4-dione,
(R)-8-(1,2,3,4-tetrahydronaphthalene-1-carbonyl)-1,3,8-triazaspiro[4.5]decane-2,4-dione,
8-benzoyl-1,3,8-triazaspiro[4.5]decane-2,4-dione,
8-(benzo[d]thiazol-2-yl)-1,3,8-triazaspiro[4.5]decane-2,4-dione,
8-(thiazolo[4,5-b]pyridin-2-yl)-1,3,8-triazaspiro[4.5]decane-2,4-dione,
methyl 6-(2,4-dioxo-1,3,8-triazaspiro[4.5]decan-8-yl)nicotinate,
N-(4-(2,4-dioxo-1,3,8-triazaspiro[4.5]decane-8-carbonyl)phenyl)acetamide,
N-(3-(2,4-dioxo-1,3,8-triazaspiro[4.5]decane-8-carbonyl)phenyl)acetamide,
8-(benzofuran-3-carbonyl)-1,3,8-triazaspiro[4.5]decane-2,4-dione,
8-(pyrazolo[1,5-a]pyridine-3-carbonyl)-1,3,8-triazaspiro[4.5]decane-2,4-dione,
8-(5-nitropyridin-2-yl)-1,3,8-triazaspiro[4.5]decane-2,4-dione,
8-(4-nitrophenyl)-1,3,8-triazaspiro[4.5]decane-2,4-dione,
8-(benzo[d]thiazole-5-carbonyl)-1,3,8-triazaspiro[4.5]decane-2,4-dione,
8-(thiazolo[4,5-b]pyridin-2-yl)-2,8-diazaspiro[4.5]decane-1,3-dione,
8-(5-nitropyridin-2-yl)-2,8-diazaspiro[4.5]decane-1,3-dione,
8-(benzo[d]thiazol-2-yl)-2,8-diazaspiro[4.5]decane-1,3-dione,
8-(4-nitrophenyl)-2,8-diazaspiro[4.5]decane-1,3-dione,
8-benzoyl-2,8-diazaspiro[4.5]decane-1,3-dione,
8-(benzo[d]thiazole-5-carbonyl)-2,8-diazaspiro[4.5]decane-1,3-dione,
8-(benzofuran-3-carbonyl)-2,8-diazaspiro[4.5]decane-1,3-dione,
methyl 6-(1,3-dioxo-2,8-diazaspiro[4.5]decan-8-yl)nicotinate, and
8-(pyrazolo[1,5-a]pyridine-3-carbonyl)-2,8-diazaspiro[4.5]decane-1,3-dione.

E7: The compound of formula XIII, or pharmaceutically acceptable salts thereof, as described herein, wherein $X^B$ is selected from the group consisting of
ix.) 1,2,3,4-tetrahydronaphthalenyl or phenyl,
x.) phenyl substituted by $R^6$, wherein $R^6$ is —NH—C(=O)—CH$_3$ or —NO$_2$,
xi.) benzo[d]thiazolyl, thiazolo[4,5-b]pyridinyl, benzofuranyl or pyrazolo[1,5-a]pyridinyl, and
xii.) pyridinyl substituted by $R^7$, wherein $R^7$ is —C(=O)—O—CH$_3$ or —NO$_2$.

E8: The compound of formula XIII, or pharmaceutically acceptable salts thereof, as described herein, wherein $X^B$ is aryl.

E9: The compound of formula XIII, or pharmaceutically acceptable salts thereof, as described herein, wherein $X^B$ is phenyl.

E10: The compound of formula XIII, or pharmaceutically acceptable salts thereof, as described herein, wherein $X^B$ is 1,2,3,4-tetrahydronaphthalenyl.

E11: The compound of formula XIII, or pharmaceutically acceptable salts thereof, as described herein, wherein $X^B$ is aryl substituted by $R^6$.

E12: The compound of formula XIII, or pharmaceutically acceptable salts thereof, as described herein, wherein $X^B$ is phenyl substituted by —NH—C(=O)—CH$_3$ or —NO$_2$.

E13: The compound of formula XIII, or pharmaceutically acceptable salts thereof, as described herein, wherein $X^B$ is phenyl substituted by —NH—C(=O)—CH$_3$.

E14: The compound of formula XIII, or pharmaceutically acceptable salts thereof, as described herein, wherein $X^B$ is phenyl substituted by —NO$_2$.

E15: The compound of formula XIII, or pharmaceutically acceptable salts thereof, as described herein, wherein $X^B$ is heteroaryl.

E16: The compound of formula XIII, or pharmaceutically acceptable salts thereof, as described herein, wherein $X^B$ is benzo[d]thiazolyl, thiazolo[4,5-b]pyridinyl, benzofuranyl or pyrazolo[1,5-a]pyridinyl E17: The compound of formula XIII, or pharmaceutically acceptable salts thereof, as described herein, wherein $X^B$ is benzo[d]thiazolyl.

E18: The compound of formula XIII, or pharmaceutically acceptable salts thereof, as described herein, wherein $X^B$ is thiazolo[4,5-b]pyridinyl.

E19: The compound of formula XIII, or pharmaceutically acceptable salts thereof, as described herein, wherein $X^B$ is benzofuranyl.

E20: The compound of formula XIII, or pharmaceutically acceptable salts thereof, as described herein, wherein $X^B$ is pyrazolo[1,5-a]pyridinyl.

E21: The compound of formula XIII, or pharmaceutically acceptable salts thereof, as described herein, wherein $X^B$ is heteroaryl substituted by $R^7$.

E22: The compound of formula XIII, or pharmaceutically acceptable salts thereof, as described herein, wherein $X^B$ is pyridinyl substituted by —C(=O)—O—CH$_3$ or —NO$_2$.

E23: The compound of formula XIII, or pharmaceutically acceptable salts thereof, as described herein, wherein $X^B$ is pyridinyl substituted by —C(=O)—O—CH$_3$.

E25: The compound of formula XIII, or pharmaceutically acceptable salts thereof, as described herein, wherein $X^B$ is pyridinyl substituted by —NO$_2$.

E26: A certain embodiment of the invention relates to the compound of formula XIII as described herein, or a pharmaceutically acceptable salt thereof, for use as therapeutically active sub stance.

E27: A certain embodiment of the invention relates to the compound of formula XIII as described herein, or a pharmaceutically acceptable salt thereof, for the use in the therapeutic and/or prophylactic treatment of cancer.

E28: A certain embodiment of the invention relates to the compound of formula XIII as described herein, or a pharmaceutically acceptable salt thereof, for the manufacture of a medicament for the therapeutic and/or prophylactic treatment of cancer.

E29: A certain embodiment of the invention relates to a pharmaceutical composition comprising the compound of formula XIII as described herein, or a pharmaceutically acceptable salt thereof, and a pharmaceutically acceptable auxiliary substance.

E30: A certain embodiment of the invention relates to a method for the therapeutic and/or prophylactic treatment of cancer, by administering the compound of formula XIII as described herein, or a pharmaceutically acceptable salt thereof, to a patient.

Compounds of Formula XIV or XV
In one aspect, compounds of Formula XIV or XV, or a pharmaceutically acceptable salt thereof, are provided:
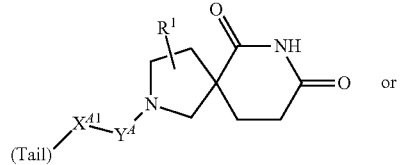
(XIV)
or
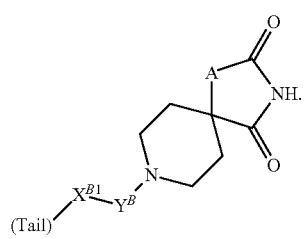
(XV)
In one embodiment, a compound of Formula XIV is provided selected from:
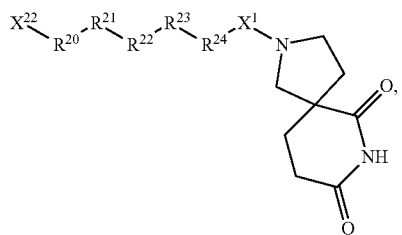
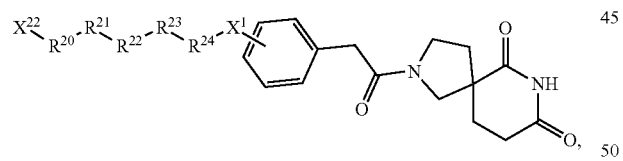
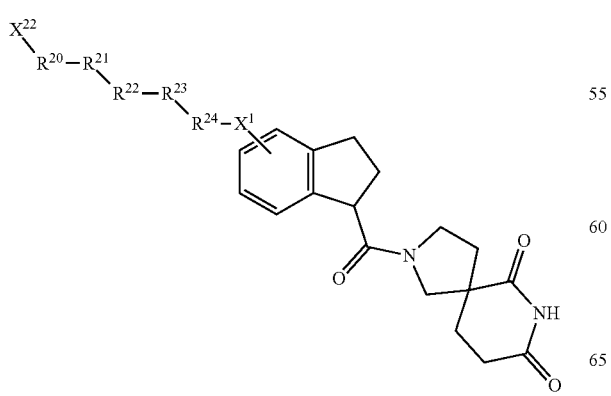
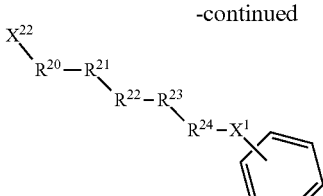
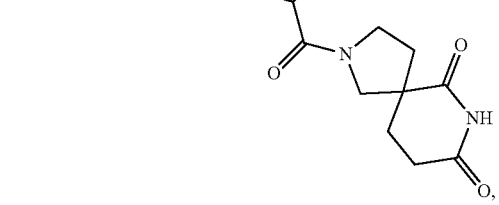
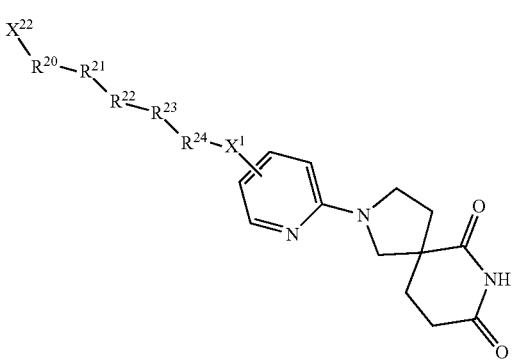
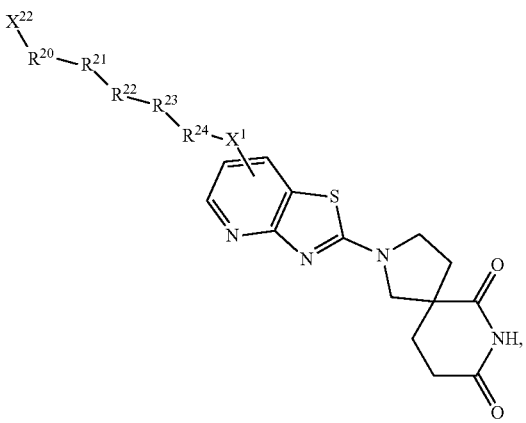
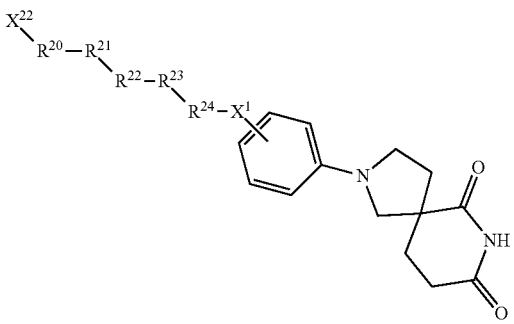

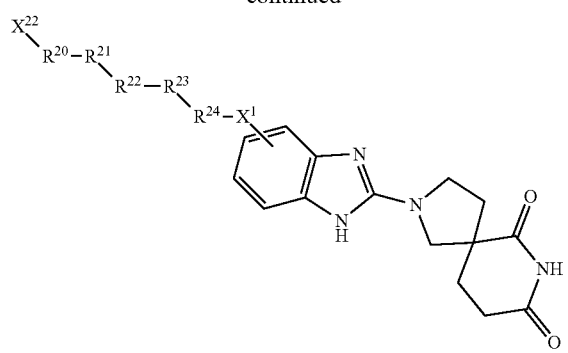
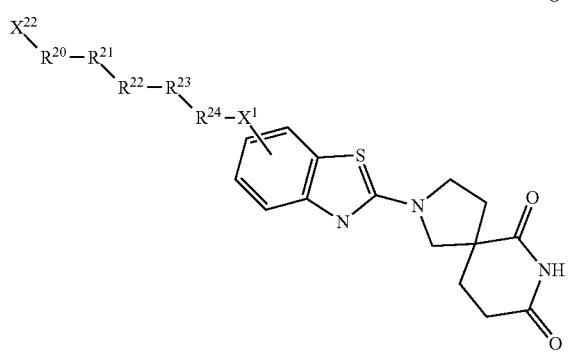
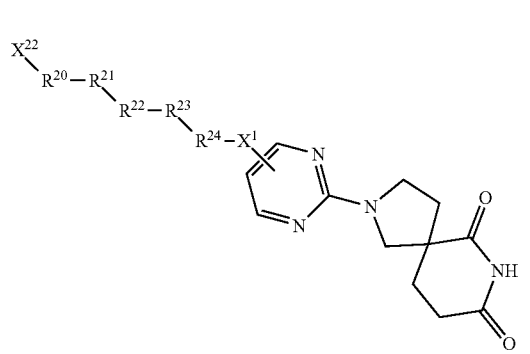
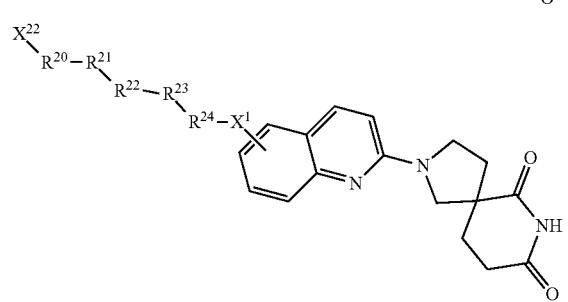
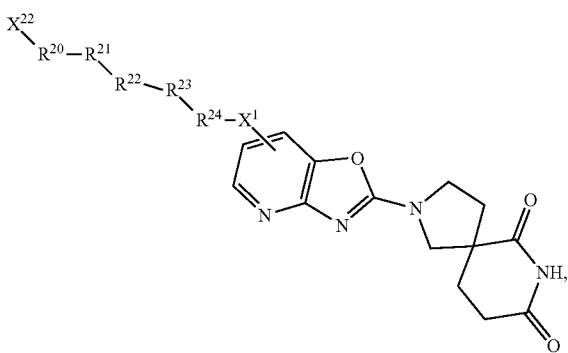
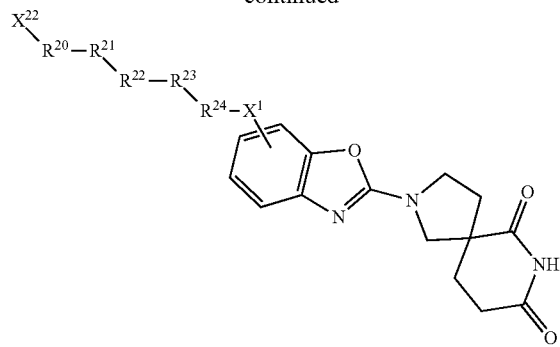
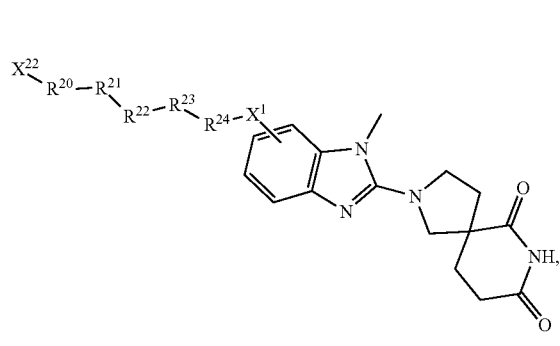
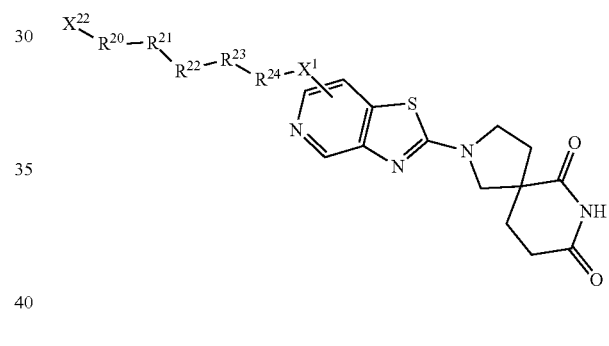
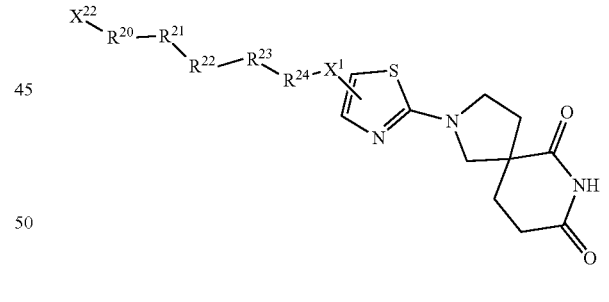
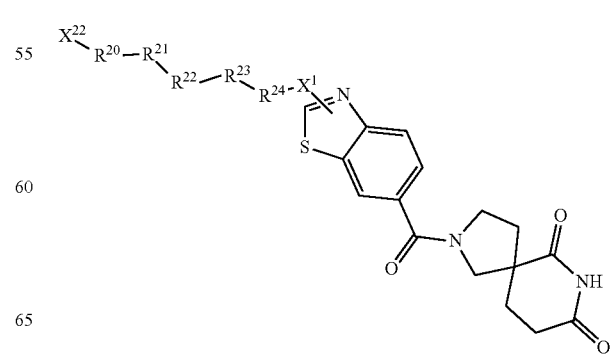

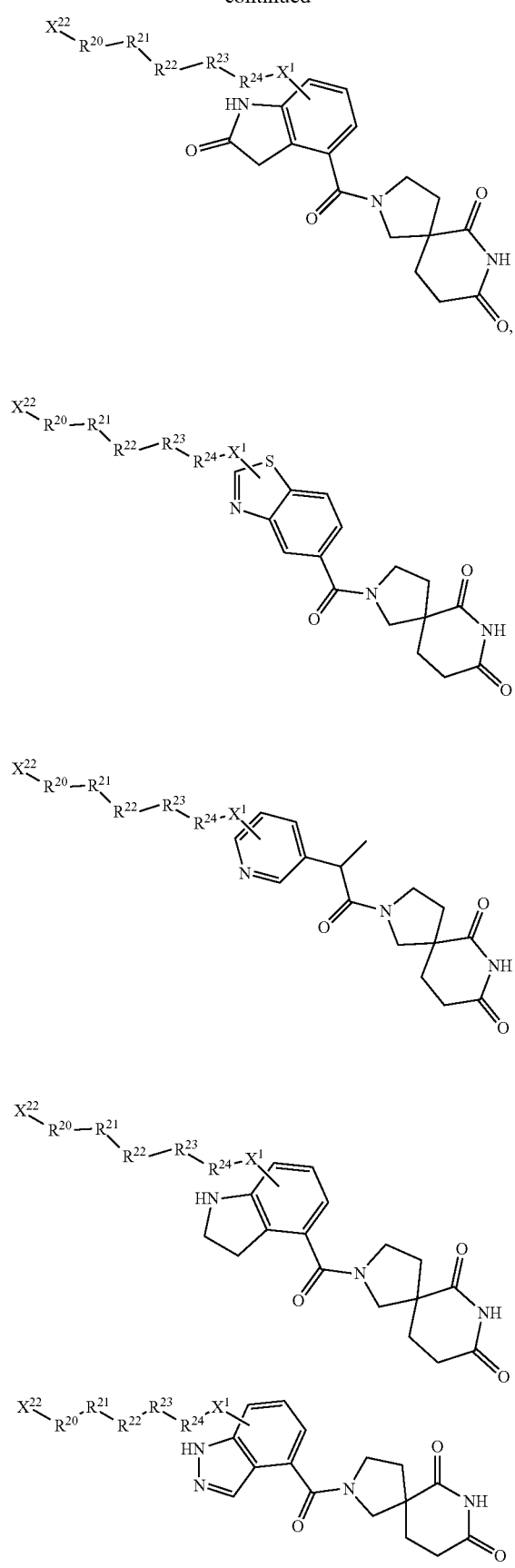
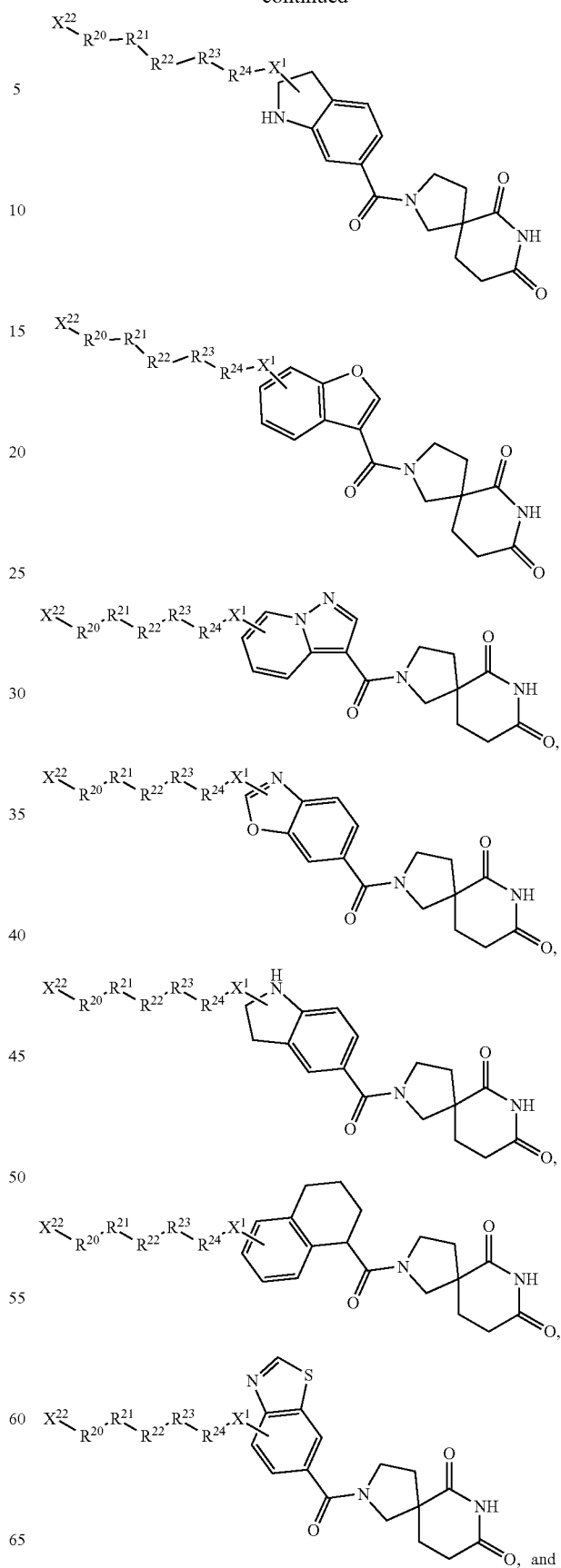

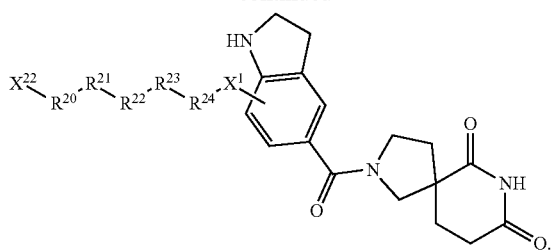
In one embodiment, a compound of Formula XV is provided selected from:
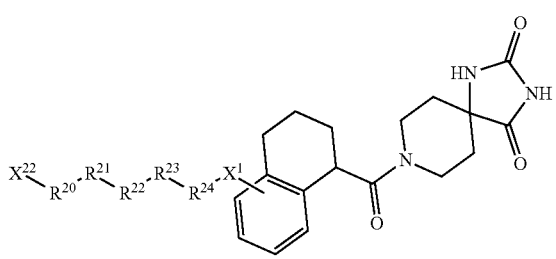
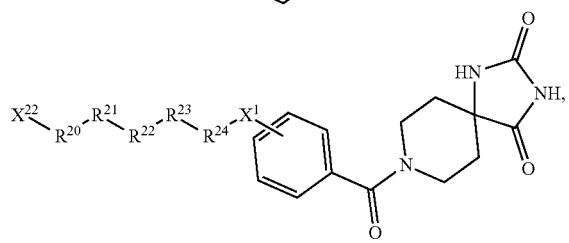
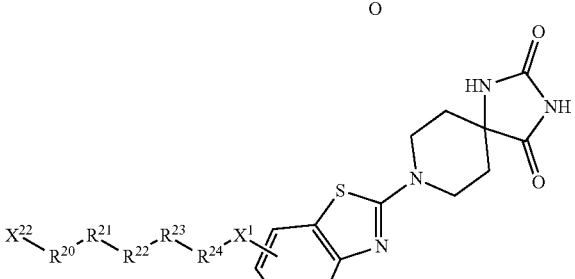
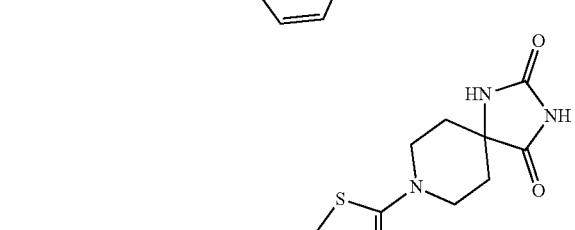
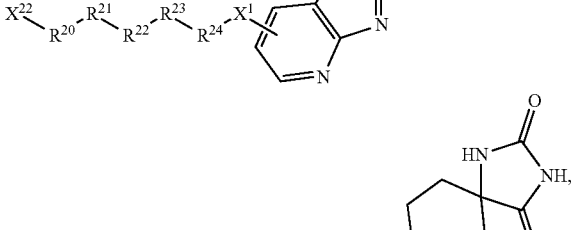
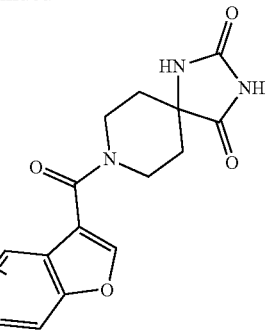
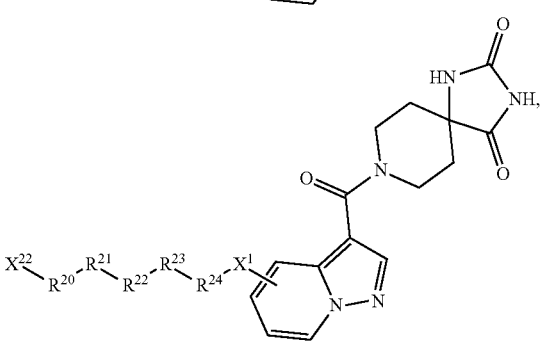
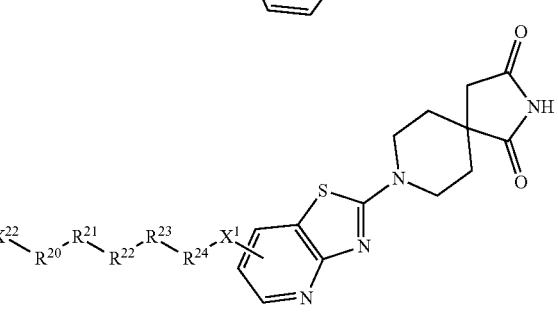
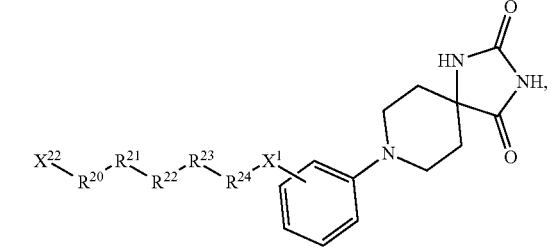
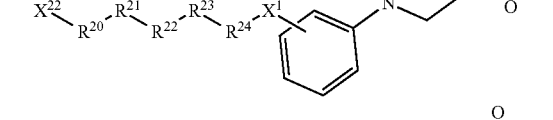
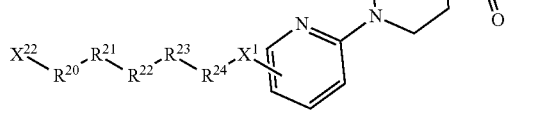

-continued
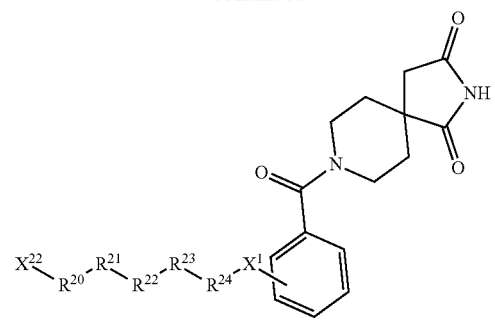
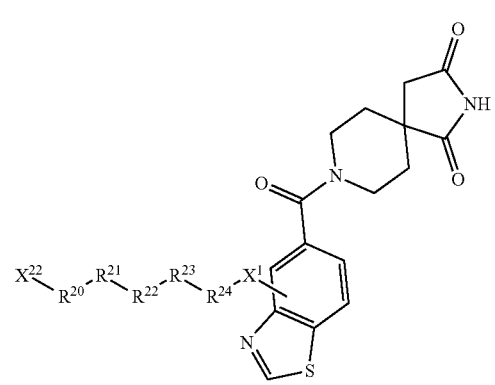
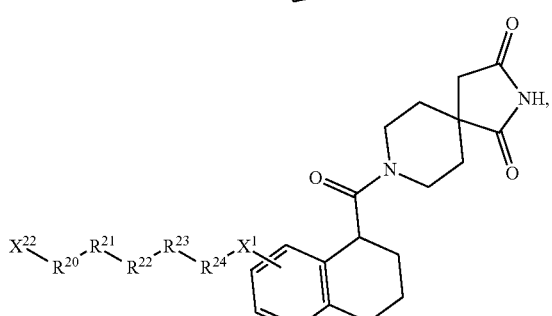
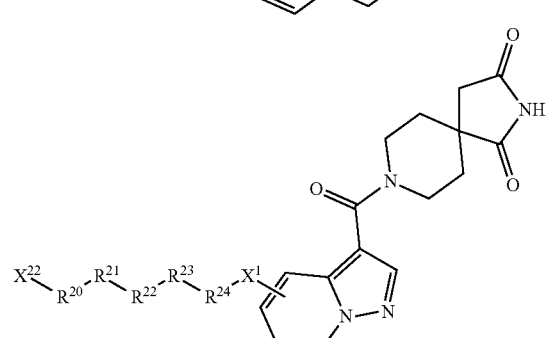
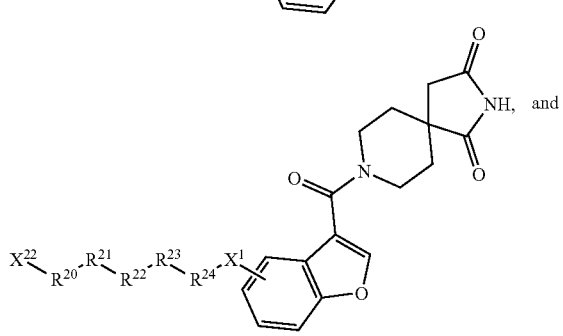
-continued
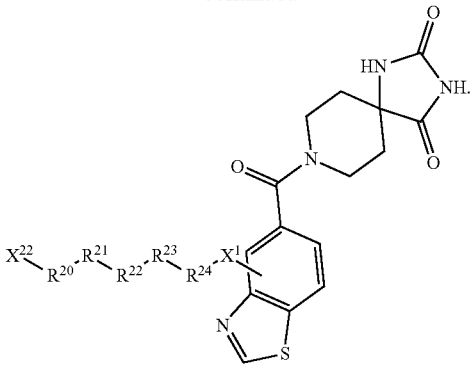
In one embodiment, a compound is provided of Formula XIV-a:
(XIV-a)
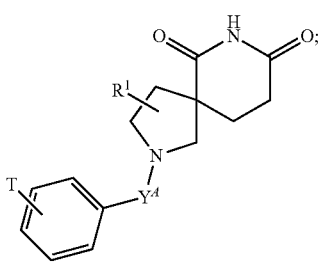
wherein all variables are as defined herein.
In one embodiment, a compound is provided of Formula XV-a:
(XV-a)
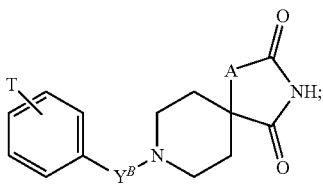
wherein all variables are as defined herein.
In some embodiments of Formula XIV-a or XV-a,
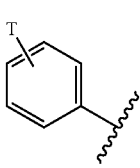
is selected from:
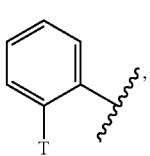 , 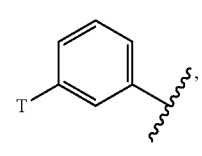 and

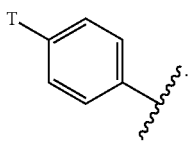

In one embodiment, a compound is provided of Formula XIV-b:

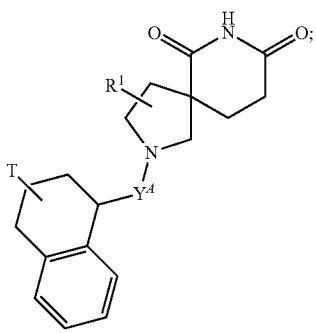
(XIV-b)

wherein all variables are as defined herein.

In one embodiment, a compound is provided of Formula XV-b:

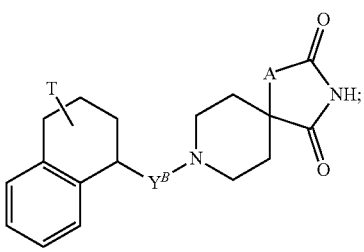
(XV-b)

wherein all variables are as defined herein.

In some embodiments of Formula XIV-b or XV-b,

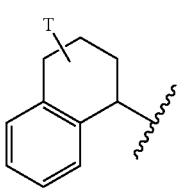

is selected from:

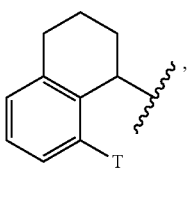

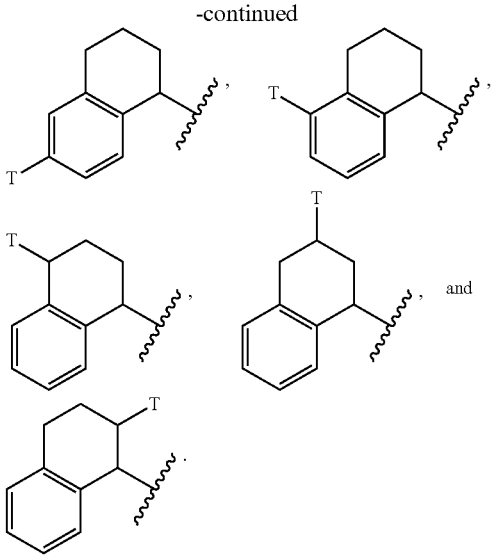

In one embodiment, a compound is provided of Formula XIV-c:

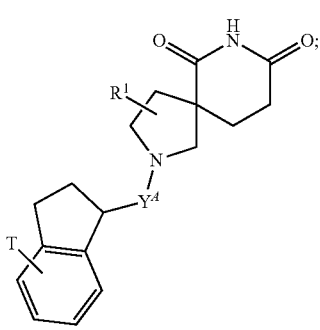
(XIV-c)

wherein all variables are as defined herein.

In one embodiment, a compound is provided of Formula XV-c:

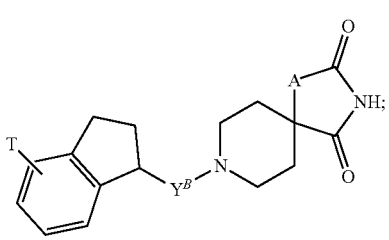
(XV-c)

wherein all variables are as defined herein.

In some embodiments of Formula XIV-c or XV-c,

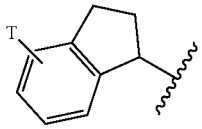

is selected from:

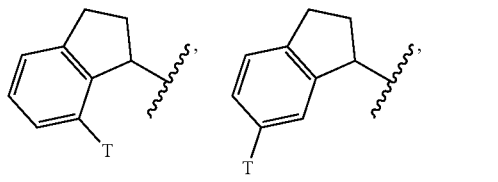

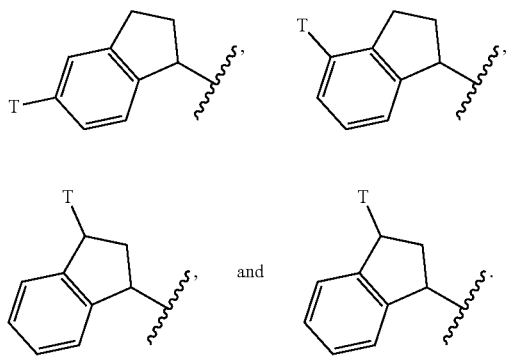

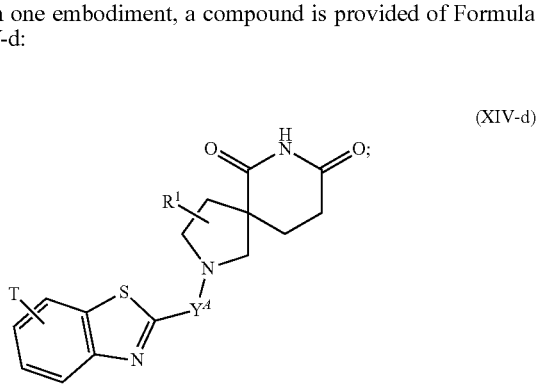

and

In one embodiment, a compound is provided of Formula XIV-d:

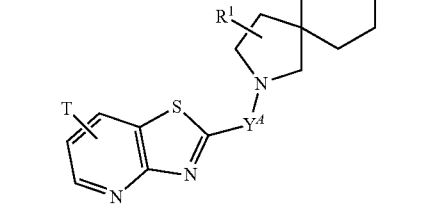
(XIV-d)

wherein all variables are as defined herein.
In one embodiment, a compound is provided of Formula XV-d:

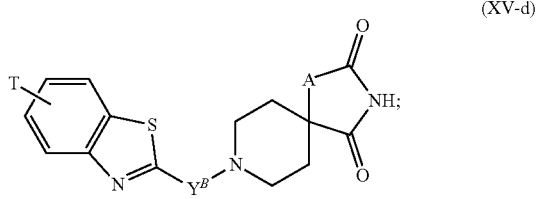
(XV-d)

wherein all variables are as defined herein.
In some embodiments of Formula XIV-d or XV-d,

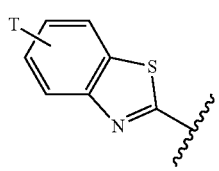

is selected from:

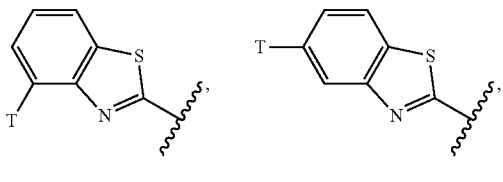

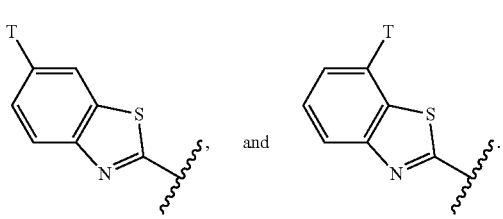

and

In one embodiment, a compound is provided of Formula XIV-e:

(XIV-e)

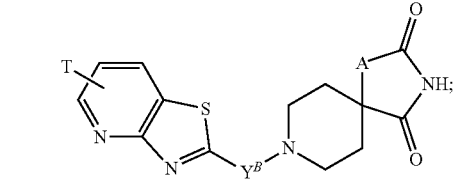

wherein all variables are as defined herein.
In one embodiment, a compound is provided of Formula XV-e:

(XV-e)

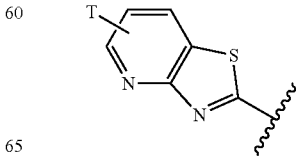

wherein all variables are as defined herein.
In some embodiments of Formula XIV-e or XV-e, is selected from:

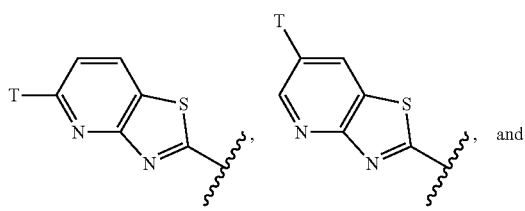

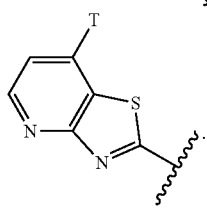

In one embodiment, a compound is provided of Formula XIV-f:

(XIV-f)

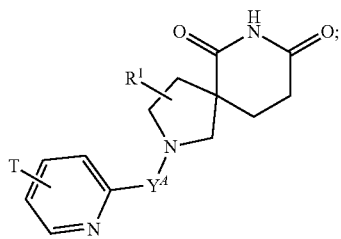

wherein all variables are as defined herein.
In one embodiment, a compound is provided of Formula XV-f:

(XV-f)

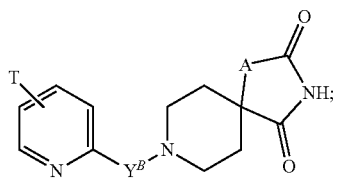

wherein all variables are as defined herein.
In some embodiments or XIV-f or XV-f,

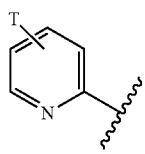

is selected from:

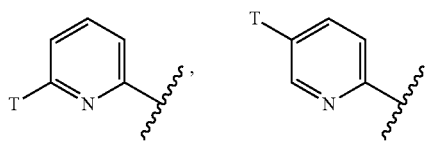 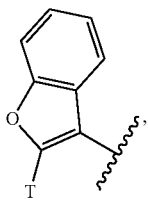

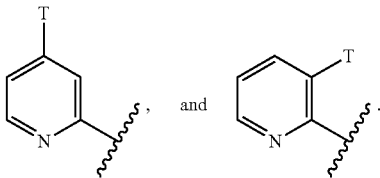

In one embodiment, a compound is provided of Formula XIV-g:

(XIV-g)

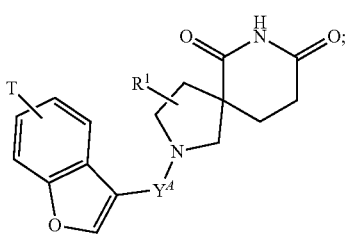

wherein all variables are as defined herein.
In one embodiment, a compound is provided of Formula XV-g:

(XV-g)

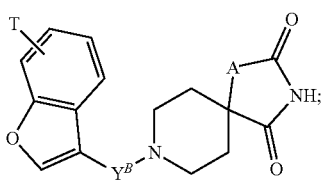

wherein all variables are as defined herein.
In some embodiments of Formula XIV-g or XV-g,

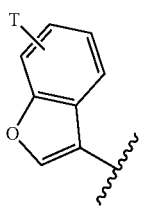

is selected from:

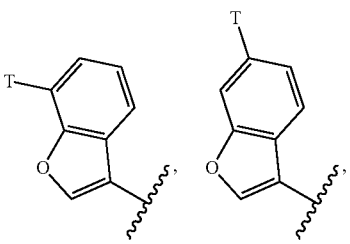

-continued

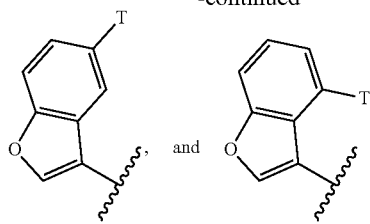 and 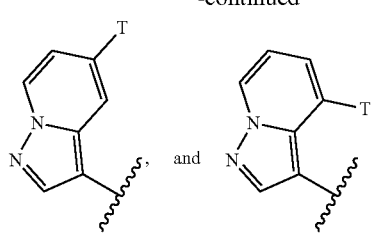

In one embodiment, a compound is provided of Formula XIV-h:

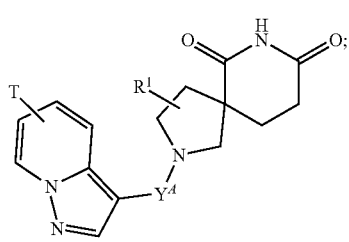
(XIV-h)

wherein all variables are as defined herein.

In one embodiment, a compound is provided of Formula XV-h:

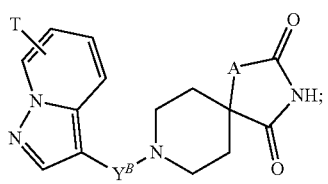
(XV-h)

wherein all variables are as defined herein.

In some embodiments of Formula XIV-h or XV-h,

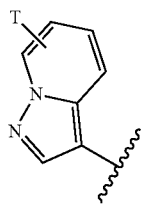

is selected from:

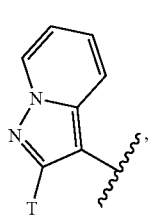, 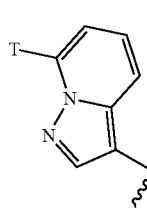, 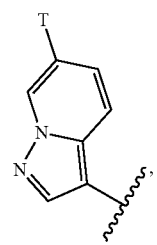,

In one embodiment, a compound is provided of Formula XIV-i:

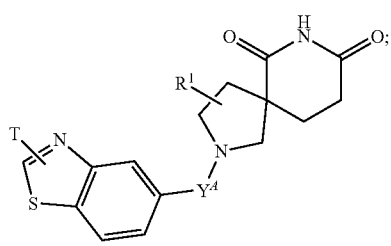
(XIV-i)

wherein all variables are as defined herein.

In one embodiment, a compound is provided of Formula XV-i:

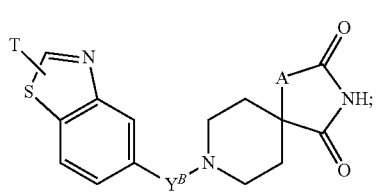
(XV-i)

wherein all variables are as defined herein.

In some embodiments of Formula XIV-i or XV-i, is selected from:

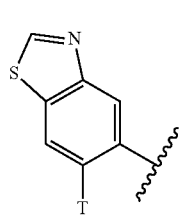, 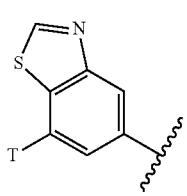,

-continued

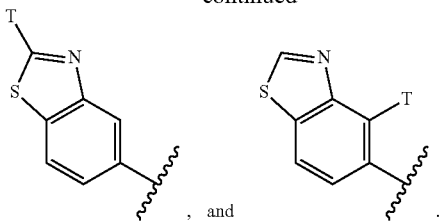, and

In one embodiment, a compound is provided of Formula XIV-j:

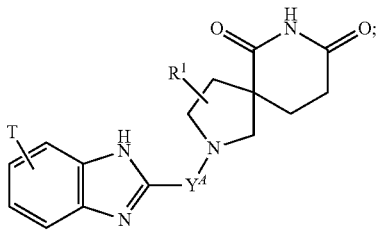

(XIV-j)

wherein all variables are as defined herein.

In one embodiment, a compound is provided of Formula XV-j:

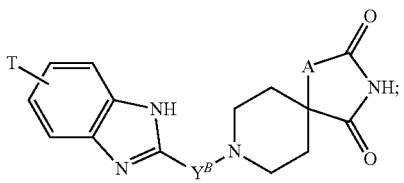

(XV-j)

wherein all variables are as defined herein.

In some embodiments of Formula XIV-j or XVj,

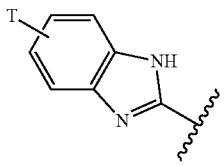

is selected from:

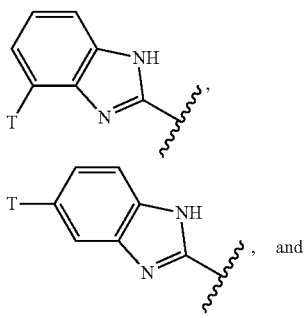, and

-continued

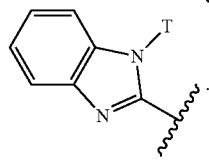

In one embodiment, a compound is provided of Formula XIV-k:

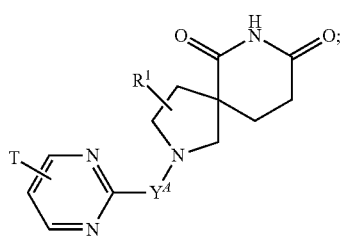

(XIV-k)

wherein all variables are as defined herein.

In one embodiment, a compound is provided of Formula XV-k:

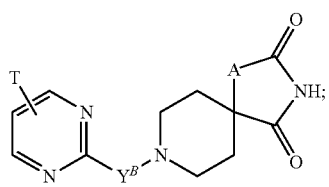

(XV-k)

wherein all variables are as defined herein.

In some embodiments of Formula XIV-k or XV-k,

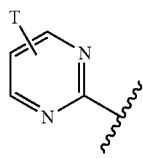

is selected from:

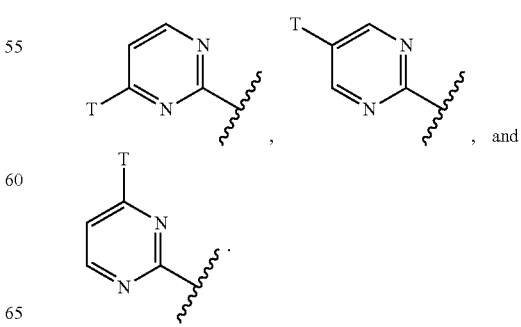

In one embodiment, a compound is provided of Formula XIV-l:

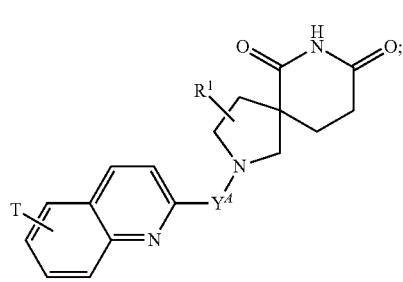

(XIV-l)

wherein all variables are as defined herein.

In one embodiment, a compound is provided of Formula XV-l:

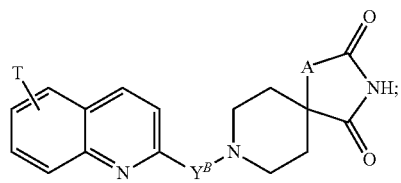

(XV-l)

wherein all variables are as defined herein.

In some embodiments of Formula XIV-l or XV-l,

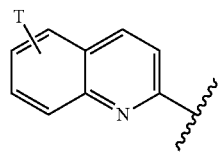

is selected from:

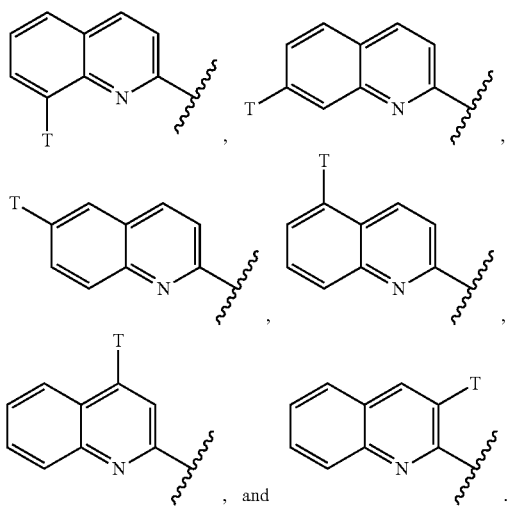

, and

In one embodiment, a compound is provided of Formula XIV-m:

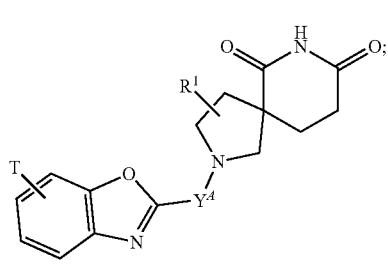

(XIV-m)

wherein all variables are as defined herein.

In one embodiment, a compound is provided of Formula XV-m:

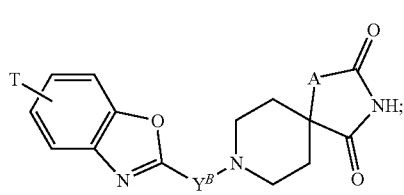

(XV-m)

wherein all variables are as defined herein.

In some embodiments of Formula XIV-m or XV-m,

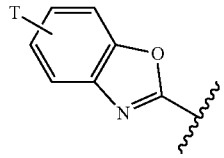

is selected from:

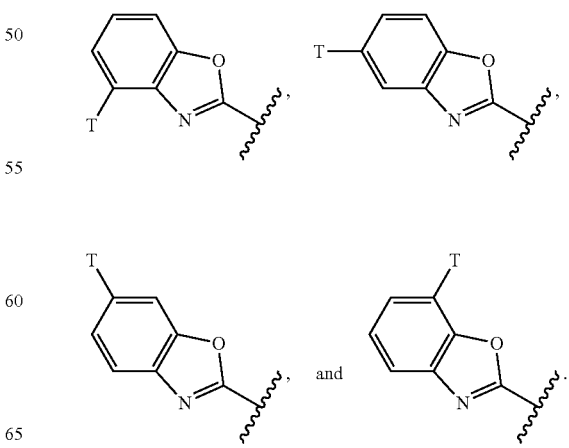

, and .

In one embodiment, a compound is provided of Formula XIV-n:

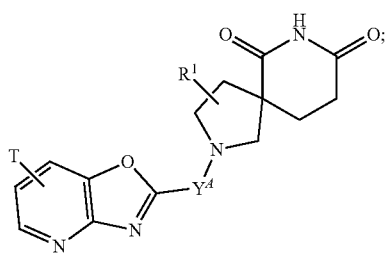

(XIV-n)

wherein all variables are as defined herein.

In one embodiment, a compound is provided of Formula XV-n:

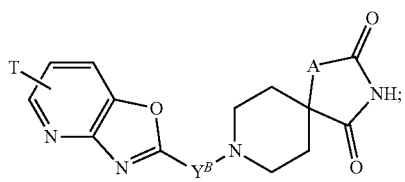

(XV-n)

wherein all variables are as defined herein.

In some embodiments of Formula XIV-n or XV-n,

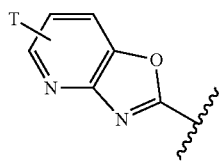

is selected from:

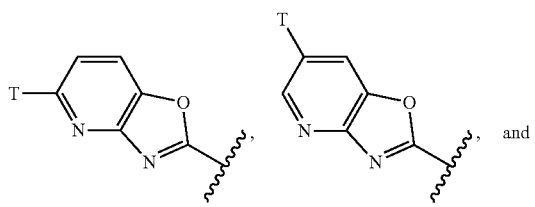, and

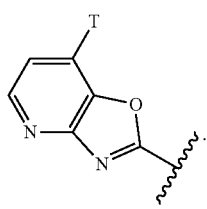.

In one embodiment, a compound is provided of Formula XIV-o:

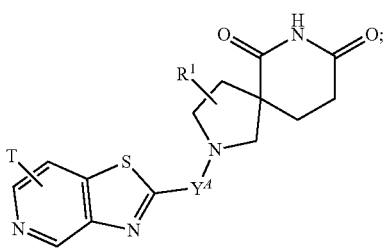

(XIV-o)

wherein all variables are as defined herein.

In one embodiment, a compound is provided of Formula XV-o:

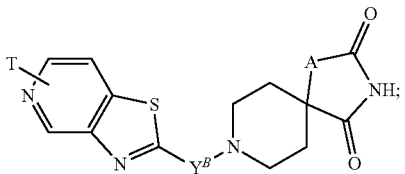

(XV-o)

wherein all variables are as defined herein.

In some embodiments of XIV-o or XV-o,

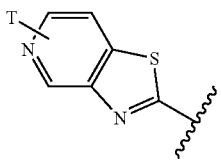

is selected from:

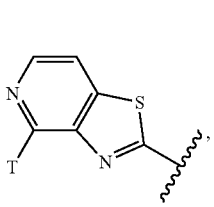, 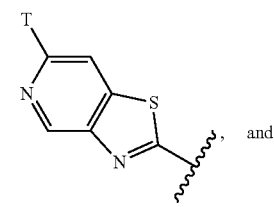, and

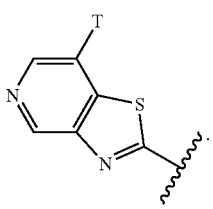.

In one embodiment, a compound is provided of Formula XIV-p:

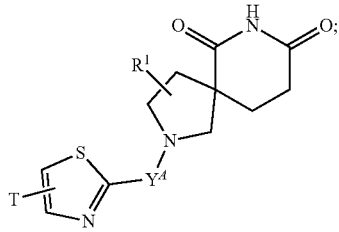

(XIV-p)

wherein all variables are as defined herein.

In one embodiment, a compound is provided of Formula XV-p:

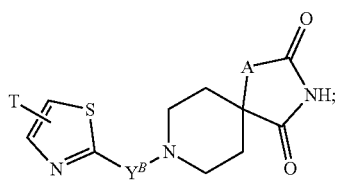

(XV-p)

wherein all variables are as defined herein.

In some embodiments of Formula XIV-p or XV-p,

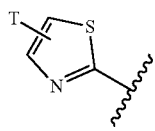

is selected from:

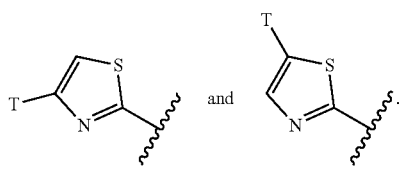

In one embodiment, a compound is provided of Formula XIV-q:

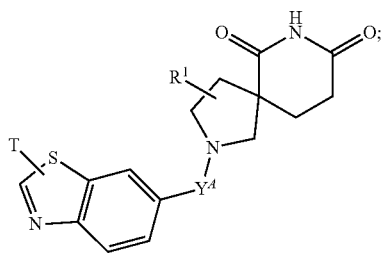

(XIV-q)

wherein all variables are as defined herein.

In one embodiment, a compound is provided of Formula XV-q:

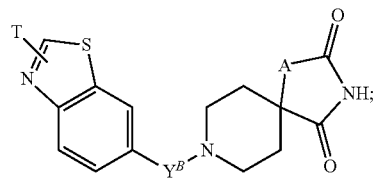

(XV-q)

wherein all variables are as defined herein.

In some embodiments of Formula XIV-q or XV-q,

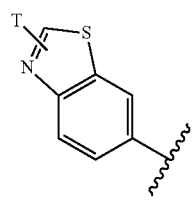

is selected from:

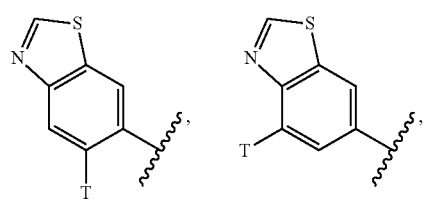

In one embodiment, a compound is provided of Formula XIV-r:

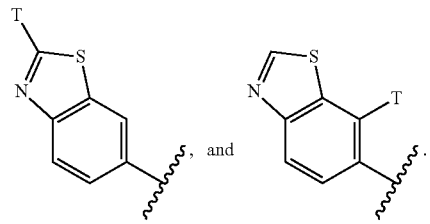

(XIV-r)

wherein all variables are as defined herein.

In one embodiment, a compound is provided of Formula XV-r:

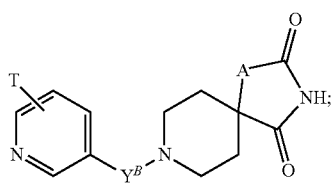

(XV-r)

wherein all variables are as defined herein.

In some embodiments of Formula XIV-r or XV-r,

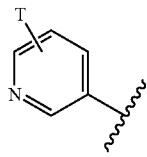

is selected from:

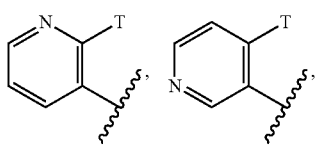

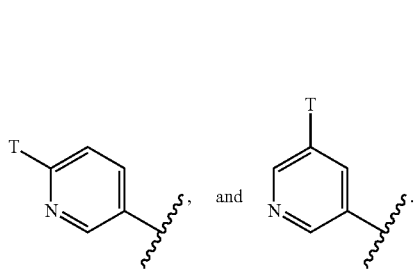

In one embodiment, a compound is provided of Formula XIV-s:

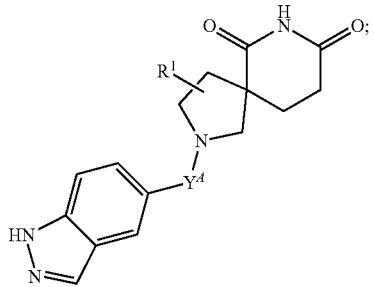

(XIV-s)

Wherein all variables are as defined herein.

In one embodiment, a compound is provided of Formula XV-s:

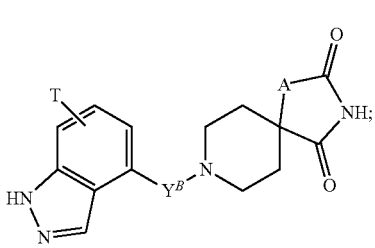

(XV-s)

wherein all variables are as defined herein.

In some embodiments of Formula XIV-s or XV-s,

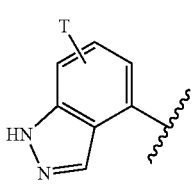

is selected from:

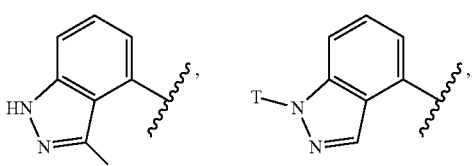

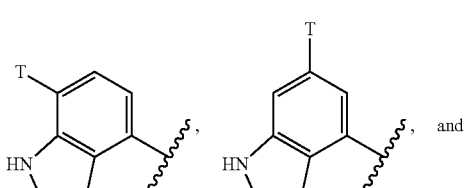

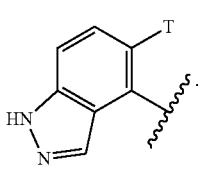

In one embodiment, a compound is provided of Formula XIV-t:

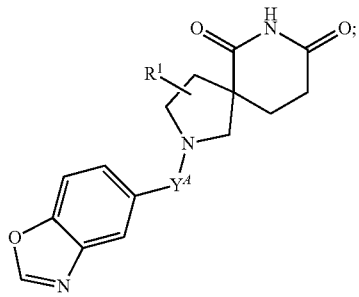

(XIV-t)

wherein all variables are as defined herein.

In one embodiment, a compound is provided of Formula XV-t:

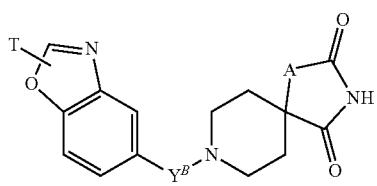

(XV-t)

wherein all variables are as defined herein.

In some embodiments of Formula XIV-t or XV-t,

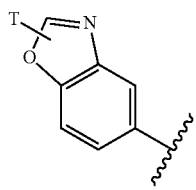

is selected from:

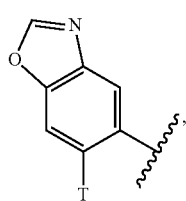

,

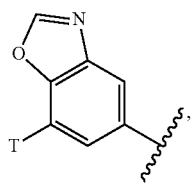

,

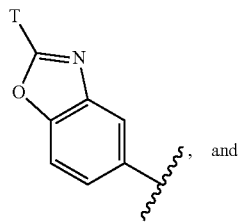

, and

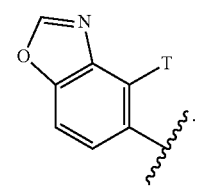

.

In one embodiment, a compound is provided of Formula XIV-u:

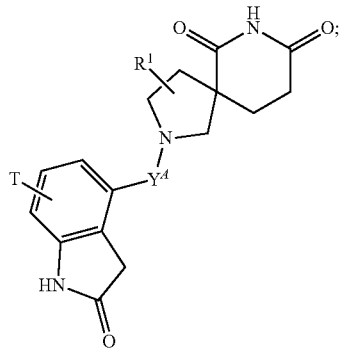

(XIV-u)

wherein all variables are as defined herein.

In some embodiments of Formula XIV-u,

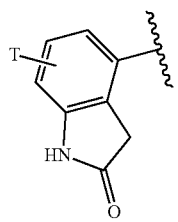

is selected from:

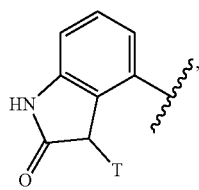

,

-continued
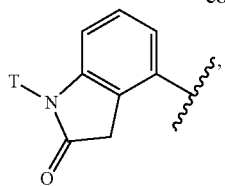
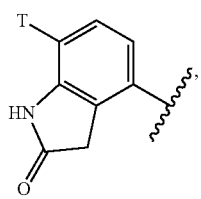
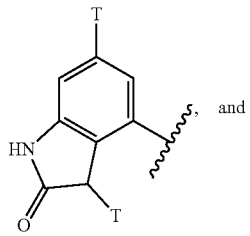, and
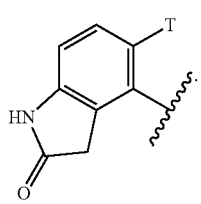
In one embodiment, a compound is provided of Formula XIV-v:
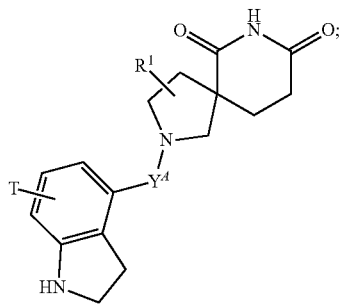
(XIV-v)
wherein all variables are as defined herein.
In some embodiments of Formla XIV-v,
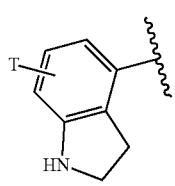
is selected from:
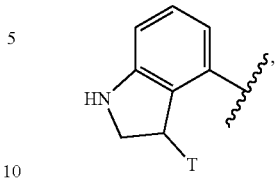
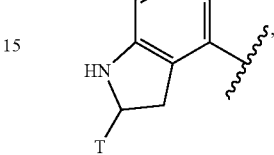
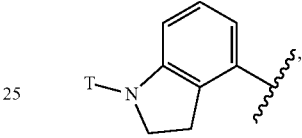
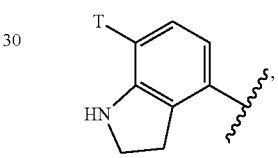
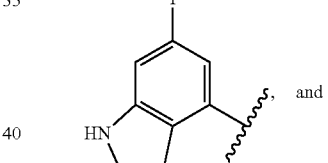, and
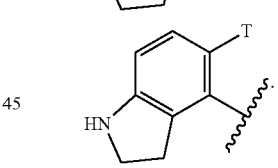
In one embodiment, a compound is provided of Formula XIV-w:
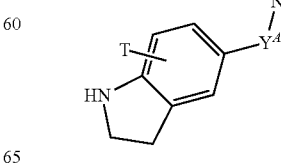
(XIV-w)
wherein all variables are as defined herein.

In some embodiments of Formula XIV-w,

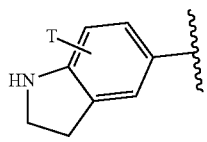

is selected from:

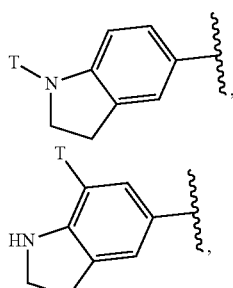

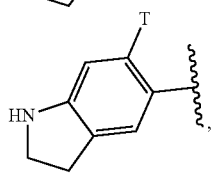

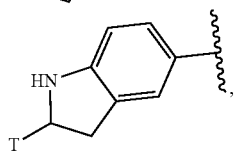

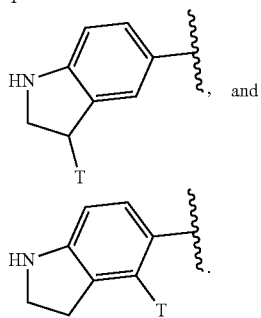, and

In one embodiment, a compound is provided of Formula XIV-x:

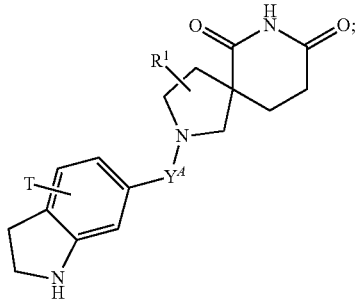

(XIV-x)

wherein all variables are as defined herein.

In some embodiments of Formula XIV-x,

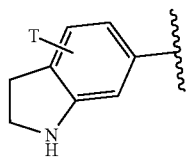

is selected from:

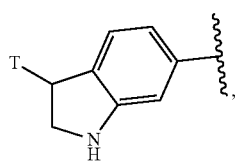

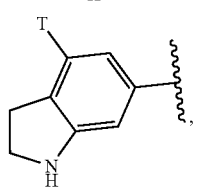

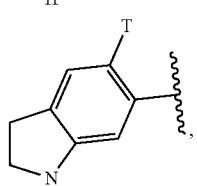

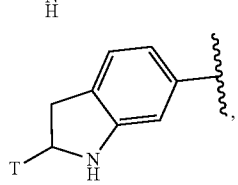

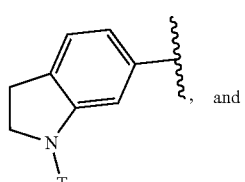

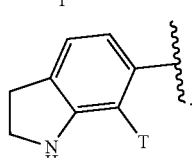, and

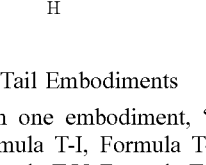

III. Tail Embodiments

In one embodiment, "Tail" is a moiety selected from Formula T-I, Formula T-II, Formula T-III, Formula T-IV, Formula T-V, Formula T-VI, and Formula T-VII:

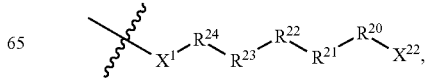

(T-I)

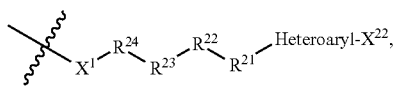
(T-II)

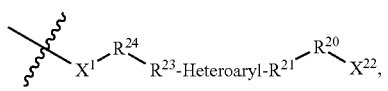
(T-III)

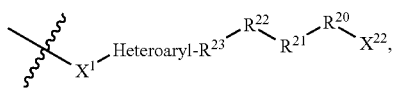
(T-IV)

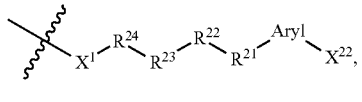
(T-V)

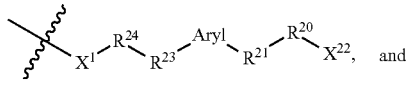
(T-VI) and

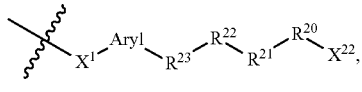
(T-VII)

wherein all variables are defined as above.

In an additional embodiment, "Tail" is a moiety selected from Formula T-VIII, T-IX, and T-X:

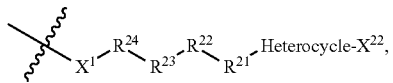
(T-VIII)

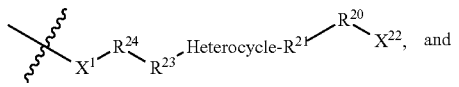
(T-IX) and

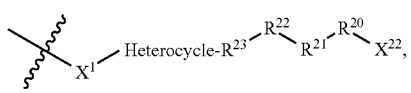
(T-X)

wherein all variables are defined as above. In other embodiments of T-VIII, T-IX and T-X, a carbocyclic ring is used in place of the heterocycle.

The following are non-limiting examples of "Tail" moieties that can be used in this invention. Based on this elaboration, those of skill in the art will understand how to use the full breadth of "Tail" moieties that will accomplish the goal of the invention.

As certain non-limiting examples, Formula T-I, Formula T-II, Formula T-III, Formula T-IV, Formula T-V, Formula T-VI, or Formula T-VII include:

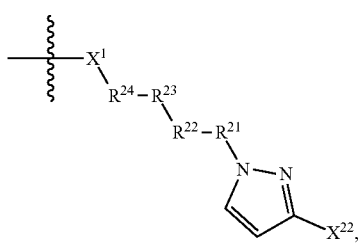

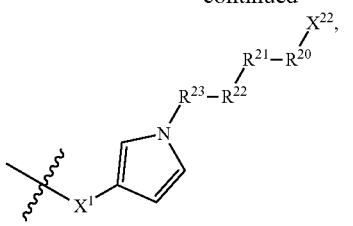

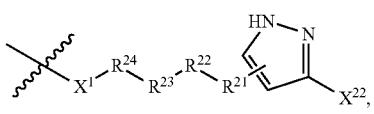

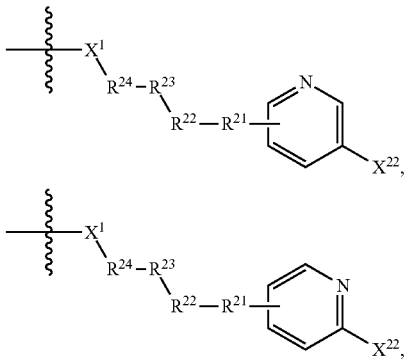

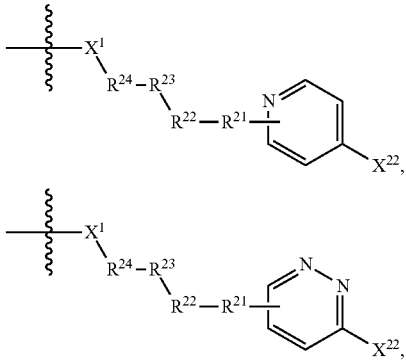

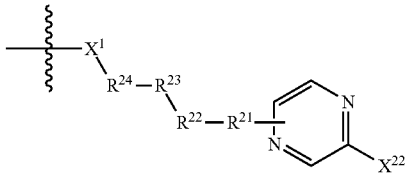

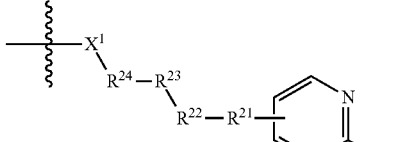

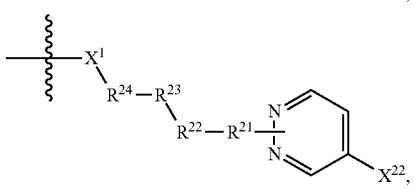

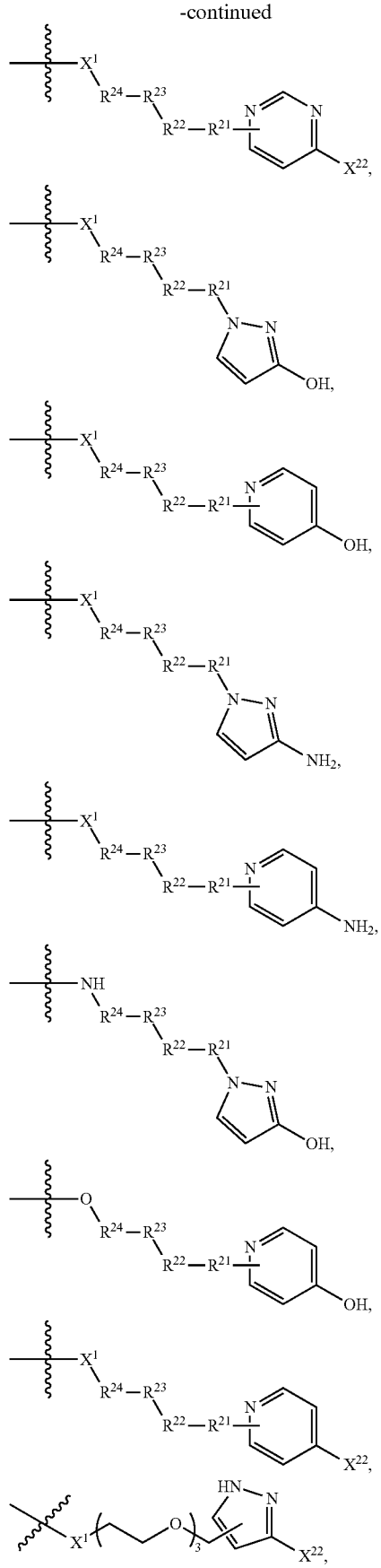
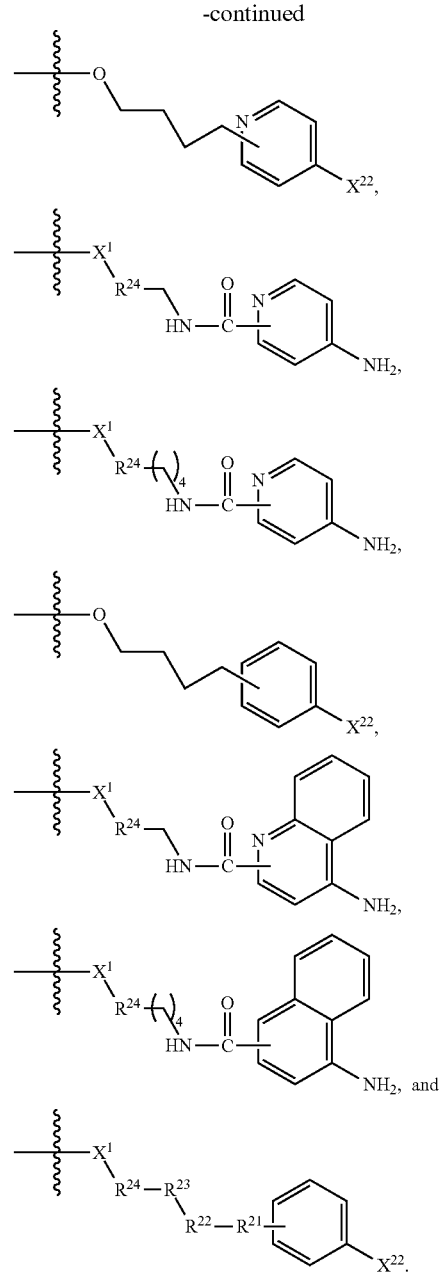
In an additional embodiment "Tail" is selected from:
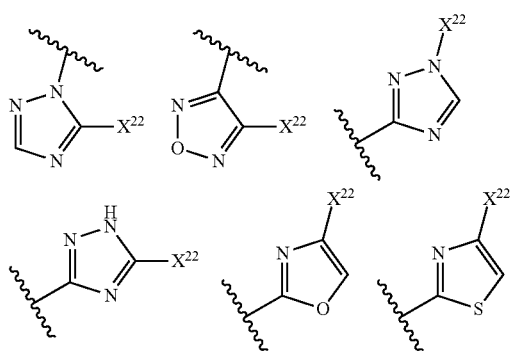

-continued
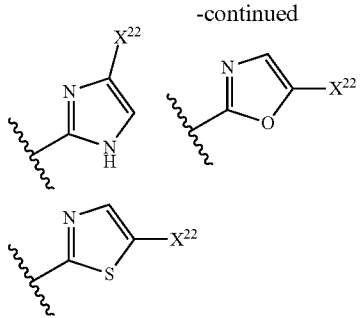
In an additional embodiment "Tail" is selected from:
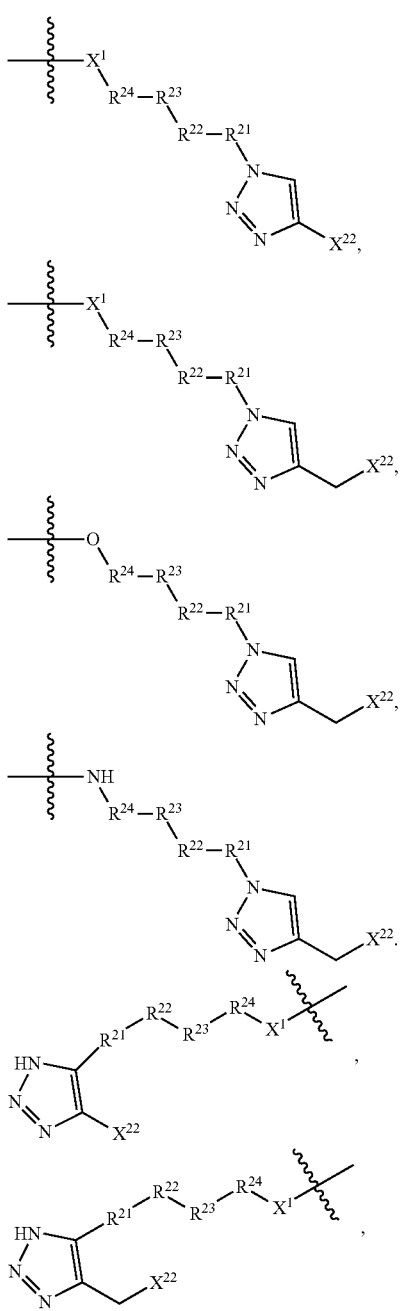
-continued
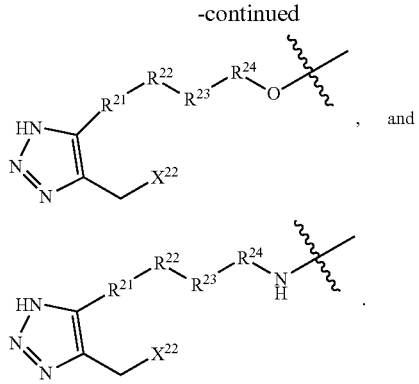
Non-limiting examples of moieties of $R^{20}$, $R^{21}$, $R^{22}$, $R^{23}$, and $R^{24}$ include:
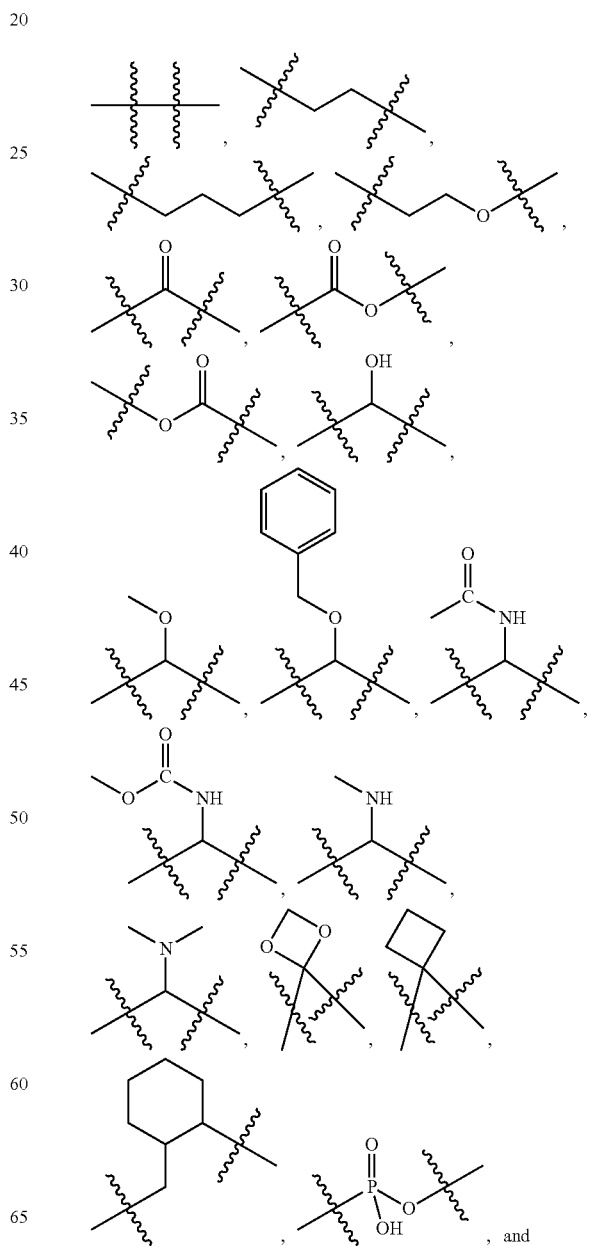

-continued
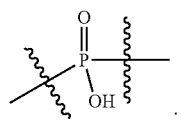
Additional non-limiting examples of moieties of $R^{20}$, $R^{21}$, $R^{22}$, $R^{23}$, and $R^{24}$ include:
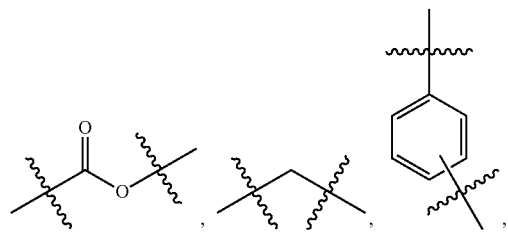
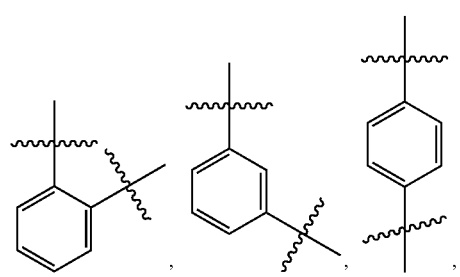
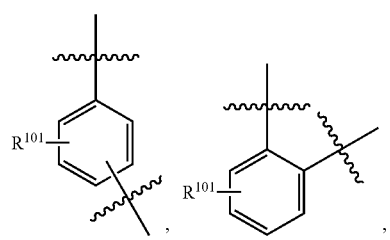
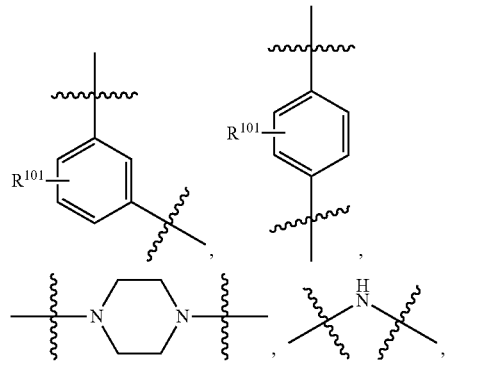
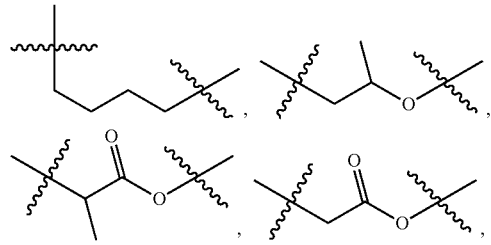
-continued
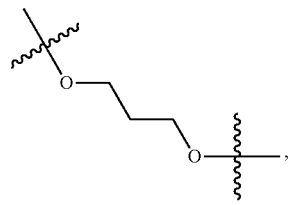
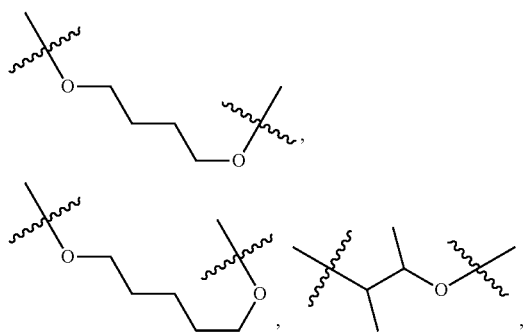
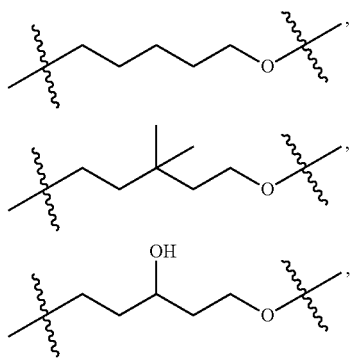
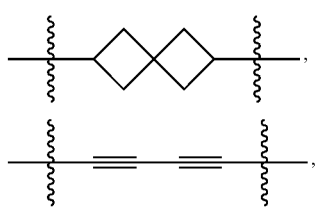
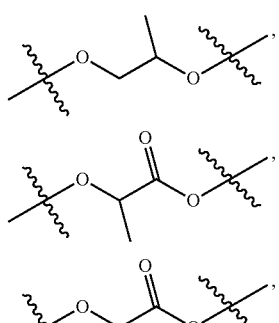
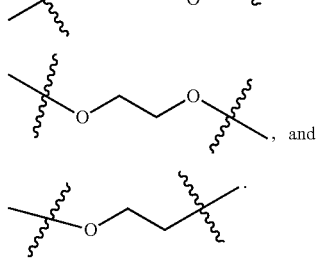
and Additional non-limiting examples of moieties of $R^{20}$, $R^{21}$, $R^{22}$, $R^{23}$, and $R^{24}$ include:
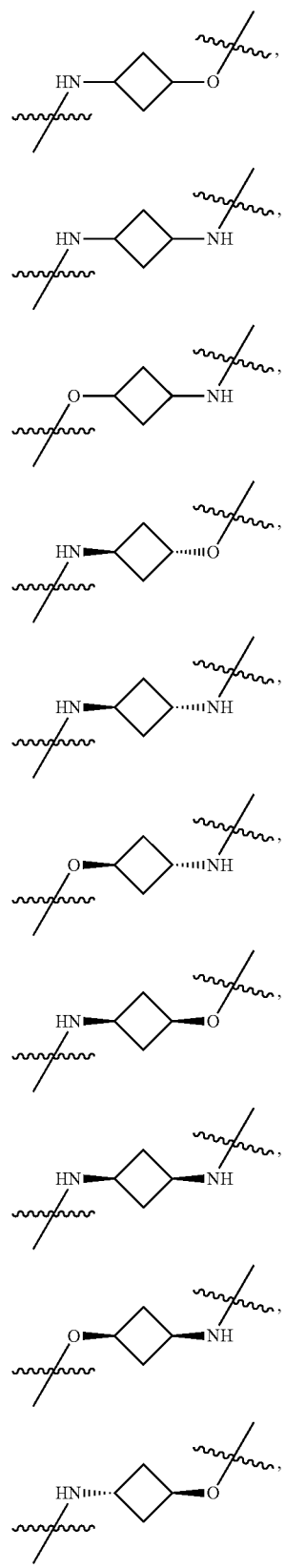
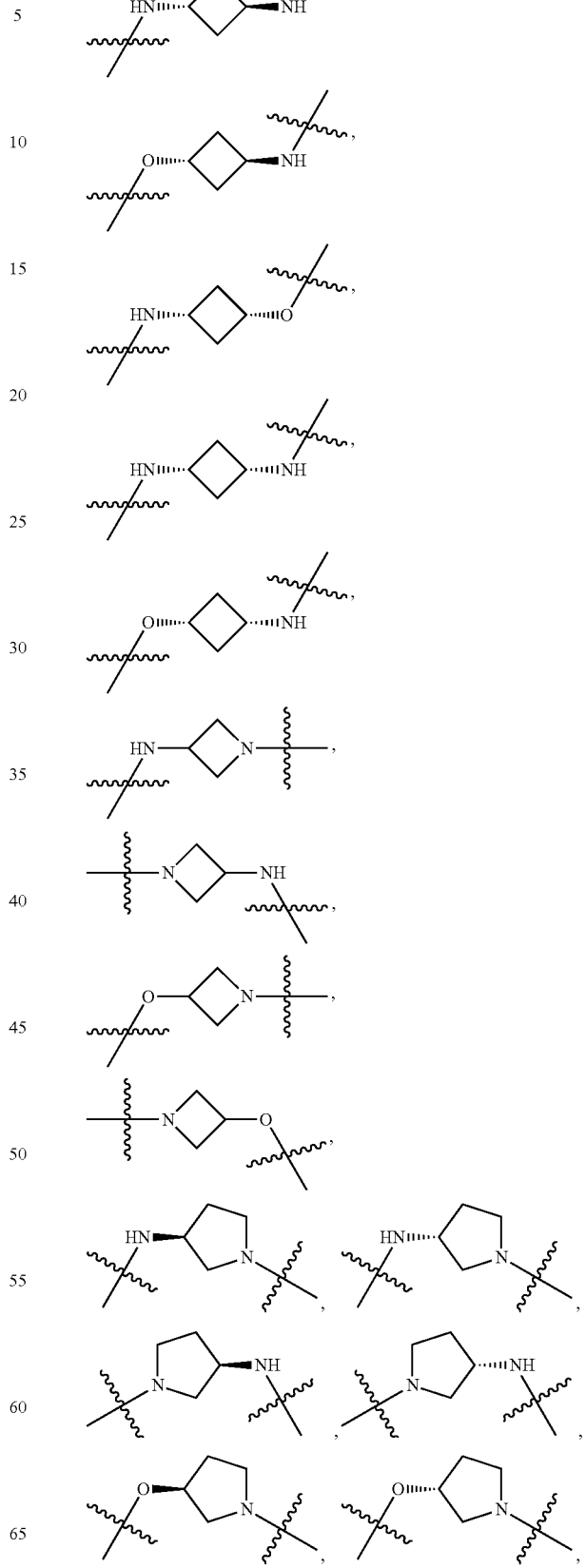

-continued

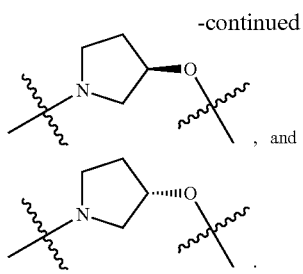
, and

In additional embodiments, "Tail" is an optionally substituted ethylene glycol having at least 1, at least 2, at least 3, at least 4, at least 5, at least 6, at least 7, at least 8, at least 9, at least 10, ethylene glycol units, or optionally substituted alkyl groups interspersed with optionally substituted, O, N, S, P or Si atoms. In certain embodiments, "Tail" is flanked, substituted, or interspersed with an aryl, phenyl, benzyl, alkyl, alkylene, or heterocycle group. In certain embodiments, "Tail" may be asymmetric or symmetrical. In some embodiments, "Tail" is a substituted or unsubstituted polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units. In any of the embodiments of the compounds described herein, "Tail" group may be any suitable moiety as described herein.

In additional embodiments, the "Tail" is selected from:
—NR$^{61}$(CH$_2$)$_{n1}$-(lower alkyl)-X$^{22}$, —NR$^{61}$(CH$_2$)$_{n1}$-(lower alkoxyl)-X$^{22}$,
—NR$^{61}$(CH$_2$)$_{n1}$-(lower alkoxyl)-OCH$_2$—X$^{22}$, —NR$^{61}$(CH$_2$)$_{n1}$-(lower alkoxyl)-(lower alkyl)-OCH$_2$—X$^{22}$,
—NR$^{61}$(CH$_2$)$_{n1}$-(cycloalkyl)-(lower alkyl)-OCH$_2$—X$^{22}$, —NR$^{61}$(CH$_2$)$_{n1}$-(heterocycloalkyl)-X$^{22}$,
—NR$^{61}$(CH$_2$CH$_2$O)$_{n1}$-(lower alkyl)-O—CH$_2$—X$^{22}$,
—NR$^{61}$(CH$_2$CH$_2$O)$_{n1}$-(heterocycloalkyl)-O—CH$_2$—X$^{22}$,
—NR$^{61}$(CH$_2$CH$_2$O)$_{n1}$-A-Aryl-O—CH$_2$—X$^{22}$, —NR$^{61}$(CH$_2$CH$_2$O)$_{n1}$-(heteroaryl)-O—CH$_2$—X$^{22}$,
—NR$^{61}$(CH$_2$CH$_2$O)$_{n1}$-(cycloalkyl)-O-(heteroaryl)-O—CH$_2$—X$^{22}$,
—NR$^{61}$(CH$_2$CH$_2$O)$_{n1}$-(cycloalkyl)-O-Aryl-O—CH$_2$—X$^{22}$,
—NR$^{61}$(CH$_2$CH$_2$O)$_{n1}$-(lower alkyl)-NH-Aryl-O—CH$_2$—X$^{22}$,
—NR$^{61}$(CH$_2$CH$_2$O)$_{n1}$-(lower alkyl)-O-Aryl-CH$_2$—X$^{22}$,
—NR$^{61}$(CH$_2$CH$_2$O)$_{n1}$-cycloalkyl-O-Aryl-X$^{22}$, —NR$^{61}$(CH$_2$CH$_2$O)$_{n1}$-cycloalkyl-O-heteroaryl-X$^{22}$,
—NR$^{61}$(CH$_2$CH$_2$)$_{n1}$-(cycloalkyl)-O-(heterocycle)-CH$_2$—X$^{22}$,
—NR$^{61}$(CH$_2$CH$_2$)$_{n1}$-(heterocycle)-(heterocycle)-CH$_2$—X$^{22}$, and —NR$^{61}$-(heterocycle)-CH$_2$—X$^{22}$;
wherein n1 is 0, 1, 2, 3, 4, 5, 6, 7, 8, 9, or 10; and R$^{61}$ is H, methyl, or ethyl.

In additional embodiments, "Tail" is selected from:
—N(R$^{61}$)—(CH$_2$)$_{m1}$—O(CH$_2$)$_{n2}$—O(CH$_2$)$_{o1}$—O(CH$_2$)$_{p1}$—O(CH$_2$)$_{q1}$—O(CH$_2$)$_{r1}$—OCH$_2$—X$^{22}$,
—O—(CH$_2$)$_{m1}$—O(CH$_2$)$_{n2}$—O(CH$_2$)$_{o1}$—O(CH$_2$)$_{p1}$—O(CH$_2$)$_{q1}$—O(CH$_2$)$_{r1}$—OCH$_2$—X$^{22}$,
—O—(CH$_2$)$_{m1}$—O(CH$_2$)$_{n2}$—O(CH$_2$)$_{o1}$—O(CH$_2$)$_{p1}$—O(CH$_2$)$_{q1}$—O(CH$_2$)$_{r1}$—OH;
—N(R$^{61}$)—(CH$_2$)$_{m1}$—O(CH$_2$)$_{n2}$—O(CH$_2$)$_{o1}$—O(CH$_2$)$_{p1}$—O(CH$_2$)$_{q1}$—O(CH$_2$)$_{r1}$—OH;
—(CH$_2$)$_{m1}$—O(CH$_2$)$_{n2}$—O(CH$_2$)$_{o1}$—O(CH$_2$)$_{p1}$—O(CH$_2$)$_{q1}$—O(CH$_2$)$_{r1}$—OH;
—(CH$_2$)$_{m1}$—O(CH$_2$)$_{n2}$—O(CH$_2$)$_{o1}$—O(CH$_2$)$_{p1}$—O(CH$_2$)$_{q1}$—O(CH$_2$)$_{r1}$—OCH$_2$—X$^{22}$;
—O(CH$_2$)$_{m1}$O(CH$_2$)$_{n2}$O(CH$_2$)$_{p1}$O(CH$_2$)$_{q1}$OCH$_2$—X$^{22}$;
—O(CH$_2$)$_{m1}$O(CH$_2$)$_{n2}$O(CH$_2$)$_{p1}$O(CH$_2$)$_{q1}$OCH$_2$—X$^{22}$;
wherein
m1, n2, o1, p1, q1, and r1 are independently 1, 2, 3, 4, or 5; and
R$^{61}$ is H, methyl, or ethyl.

In additional embodiments, "Tail" is selected from:

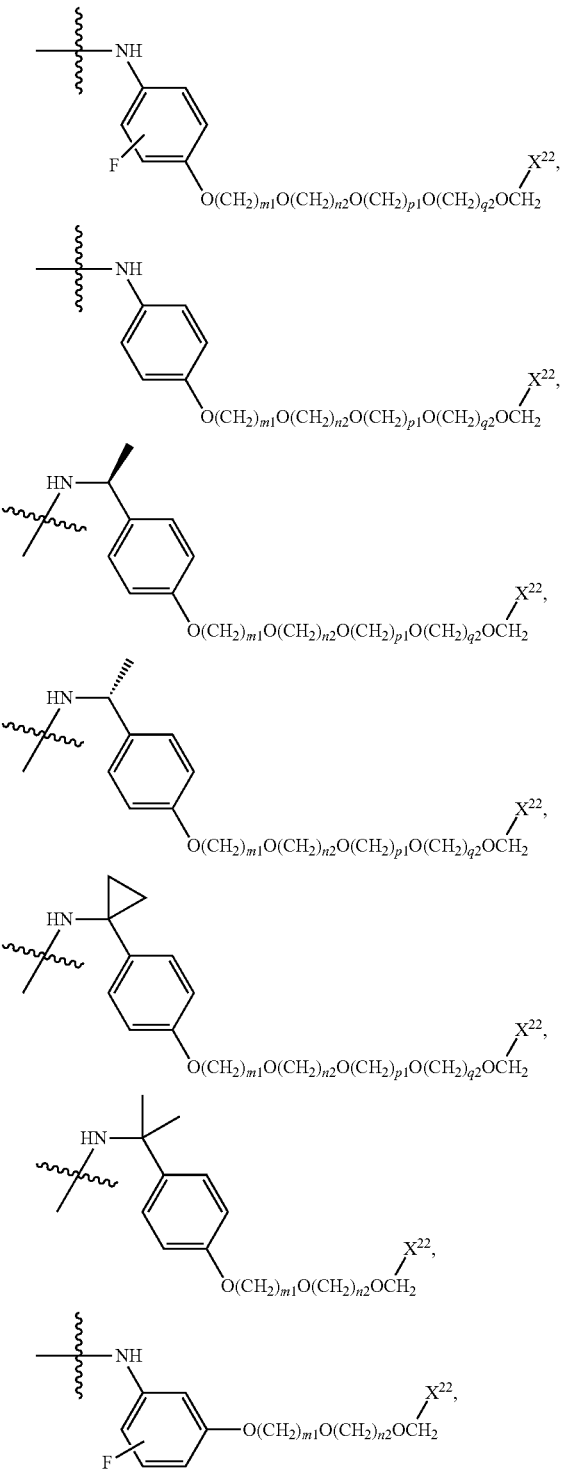

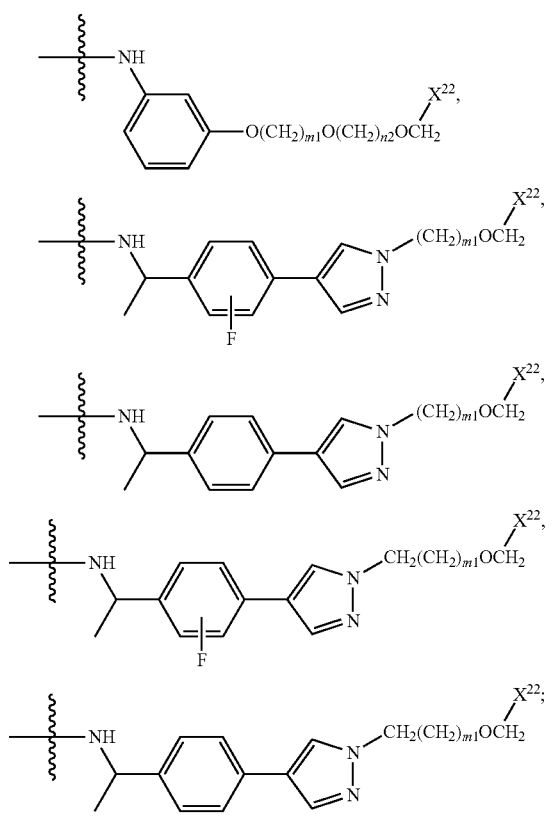
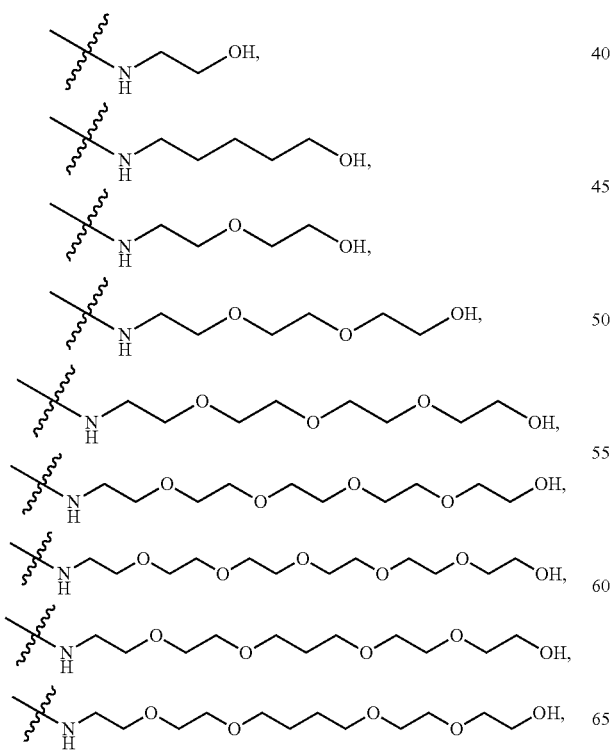
m1, n2, o1, p1, q2, and r1 are independently 1, 2, 3, 4, or 5.
In additional embodiments, "Tail" is selected from:
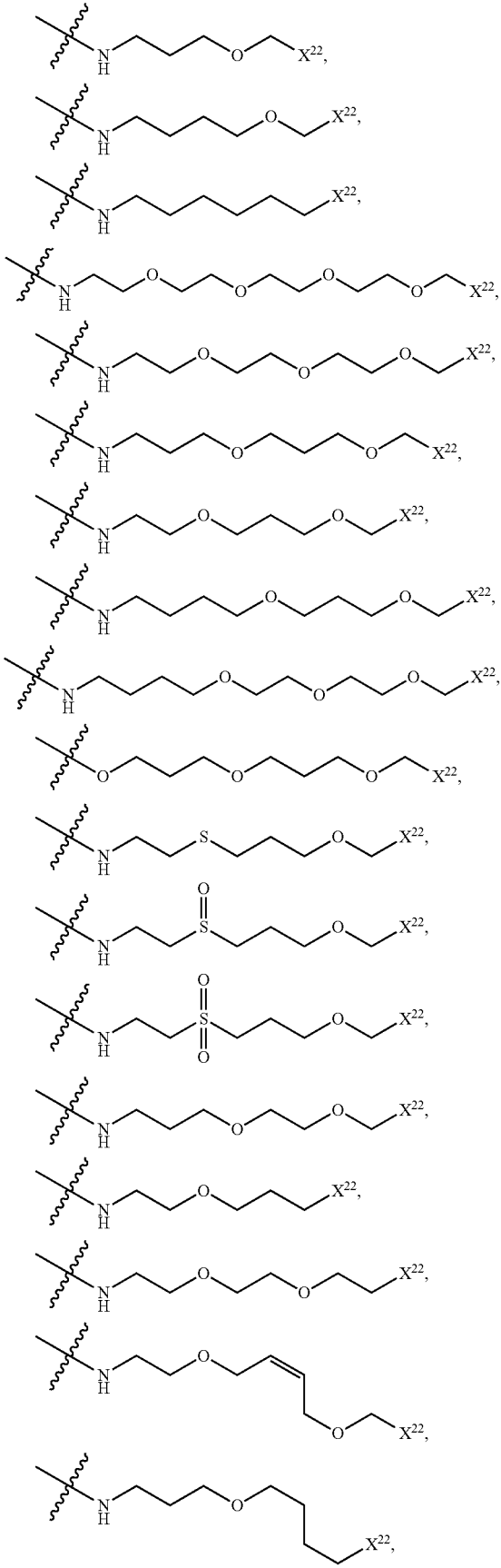

209
-continued
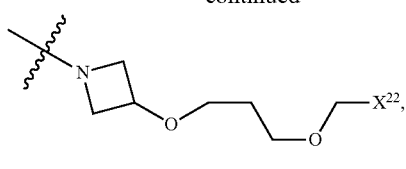
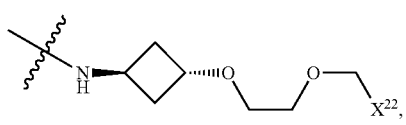
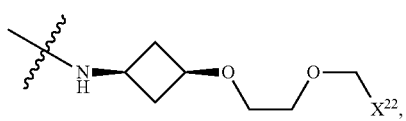
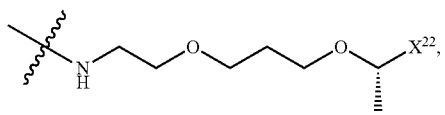
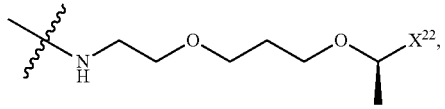
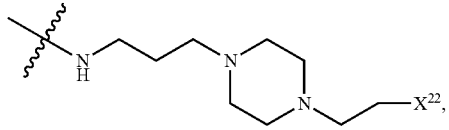
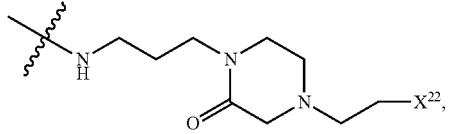
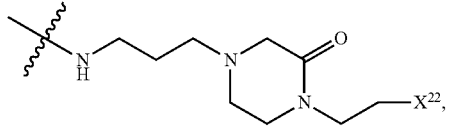
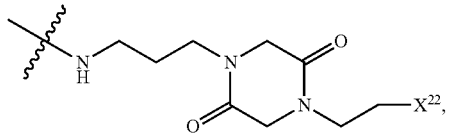
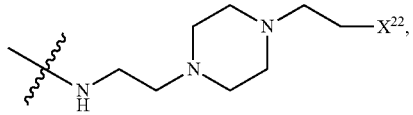
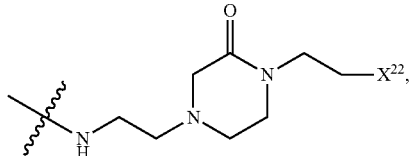
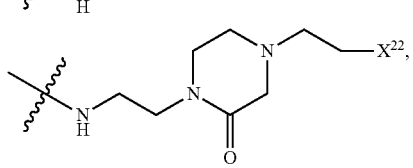
210
-continued
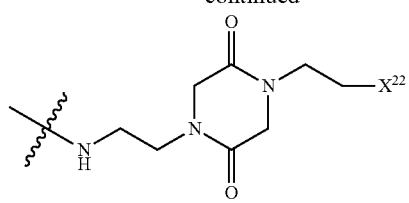
In additional embodiments, "Tail" is selected from:
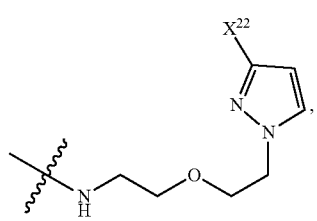
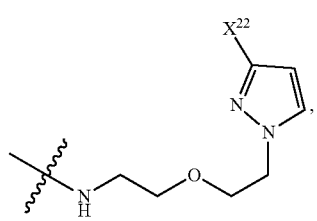
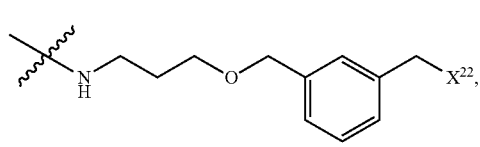
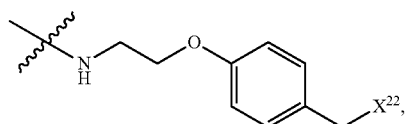
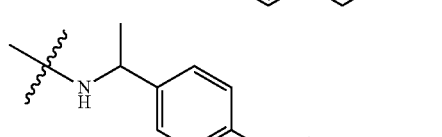
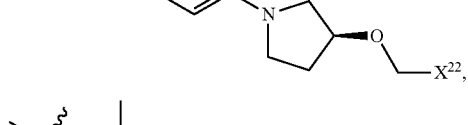
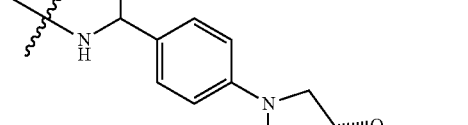
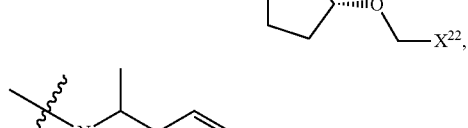
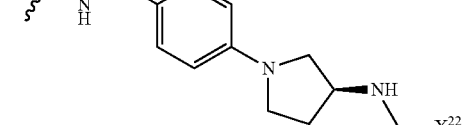
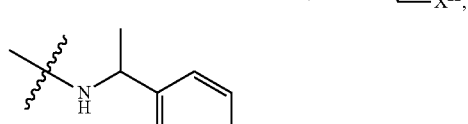
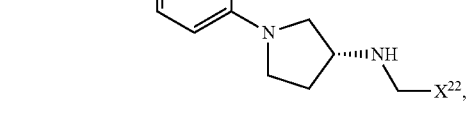

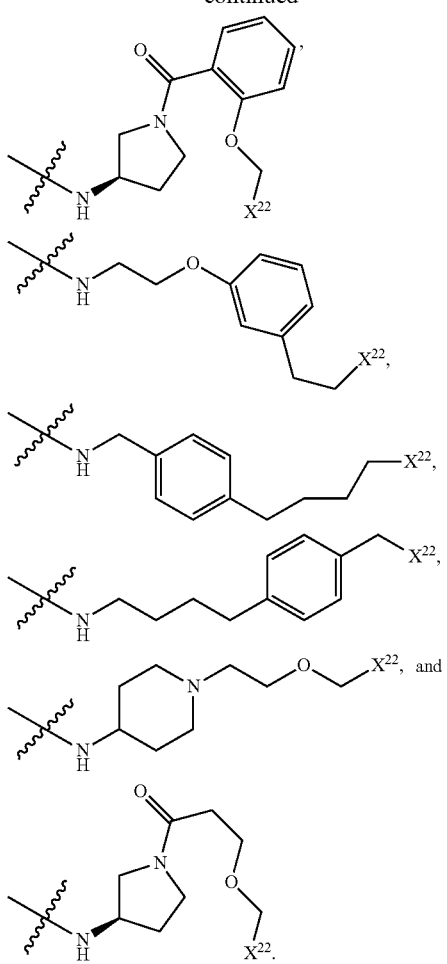
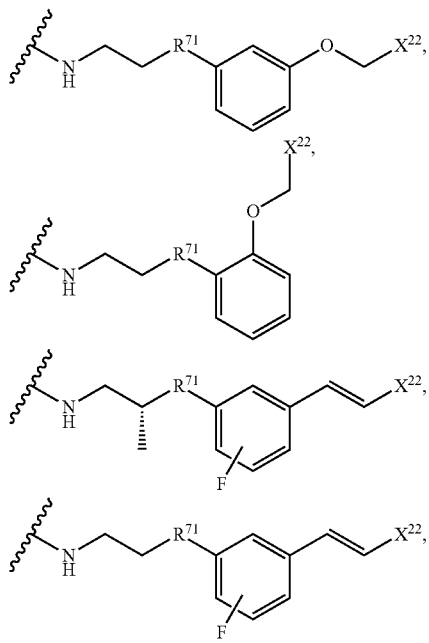
In additional embodiments, "Tail" is selected from:
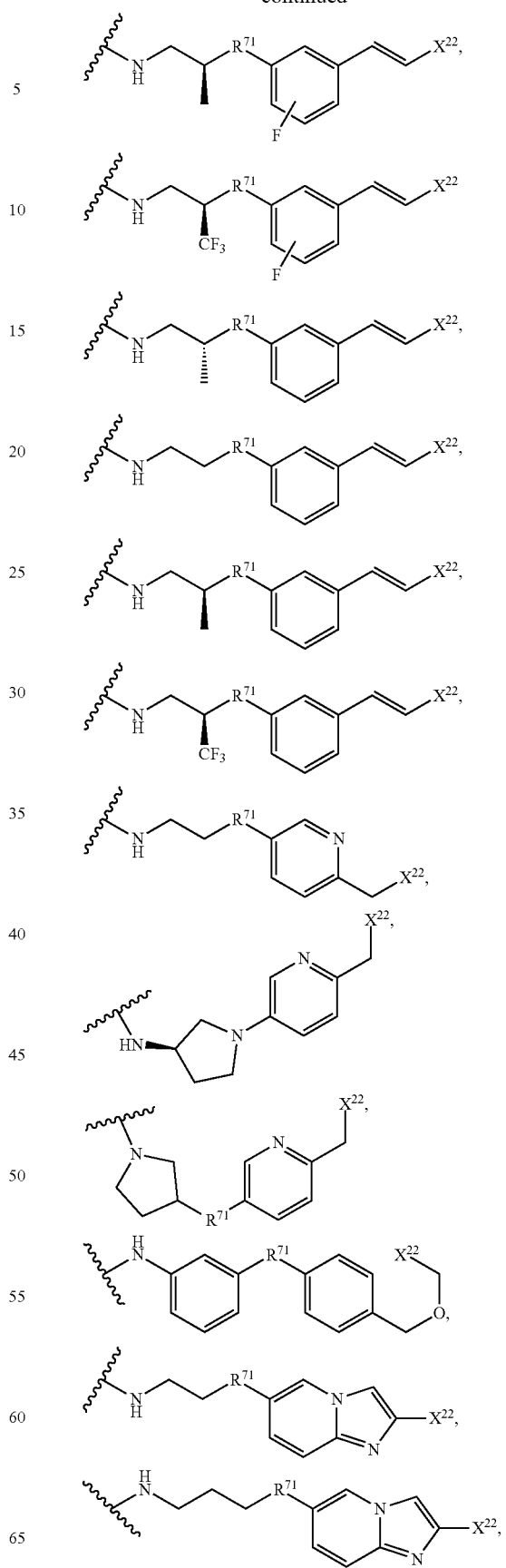

213
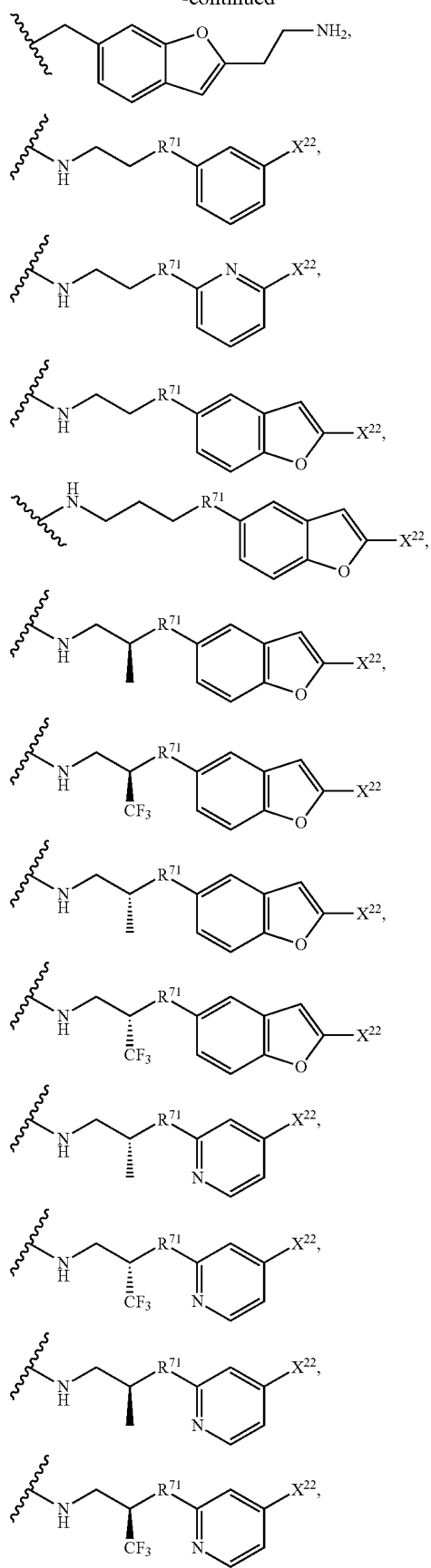
214
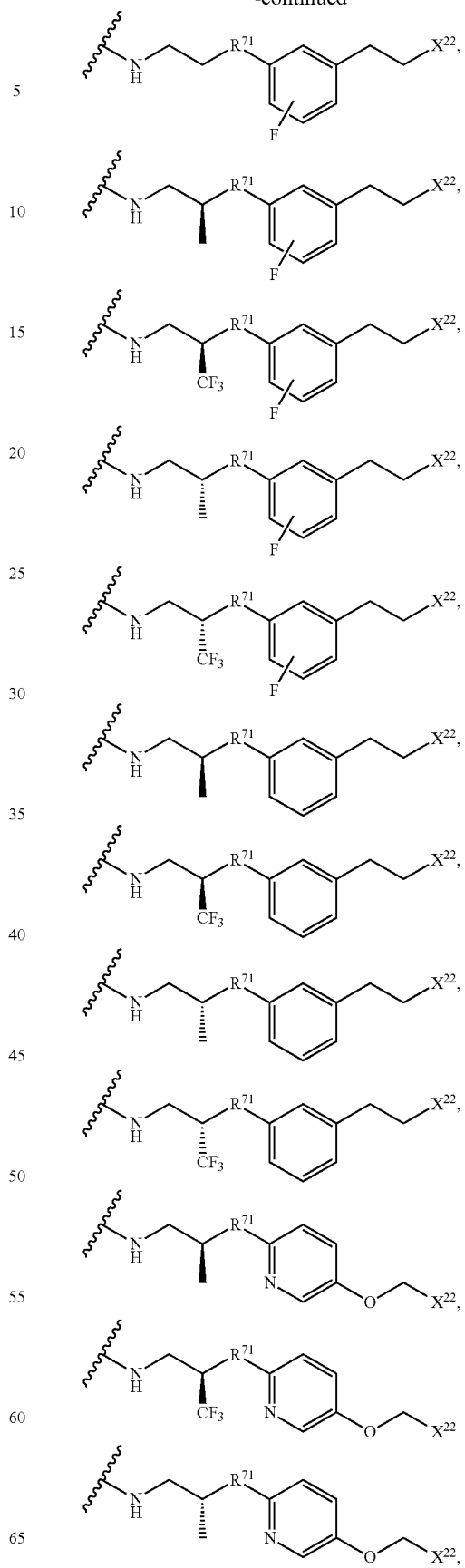

-continued
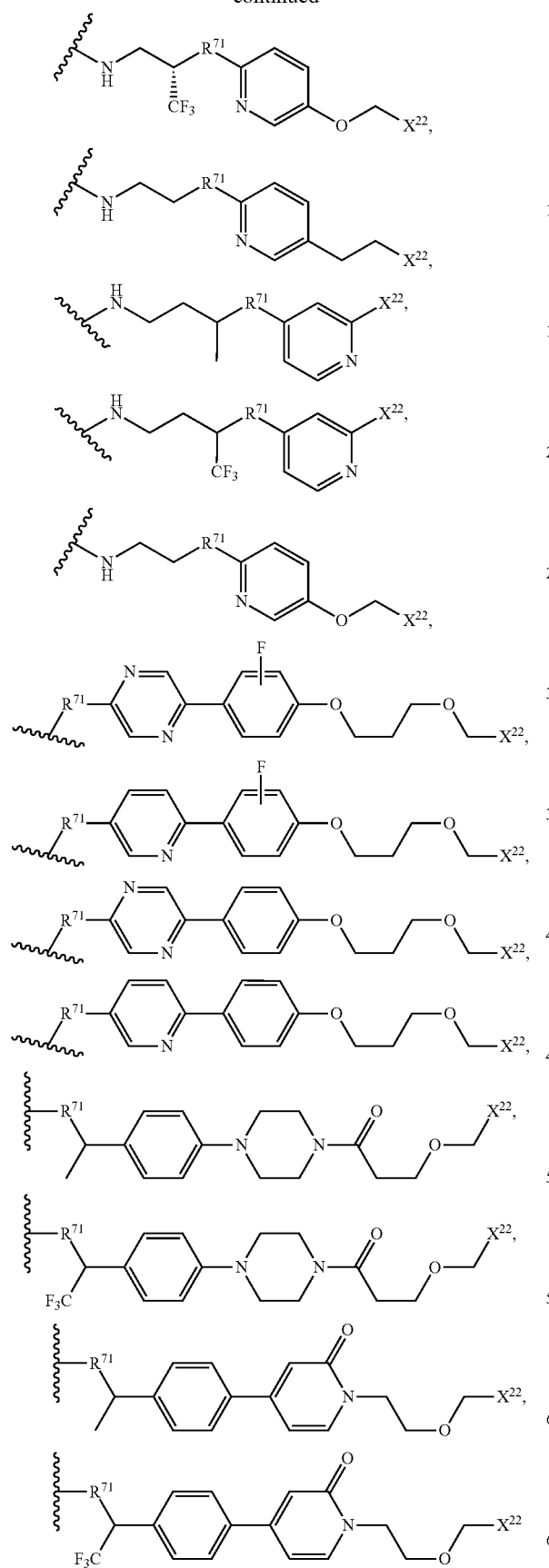
-continued
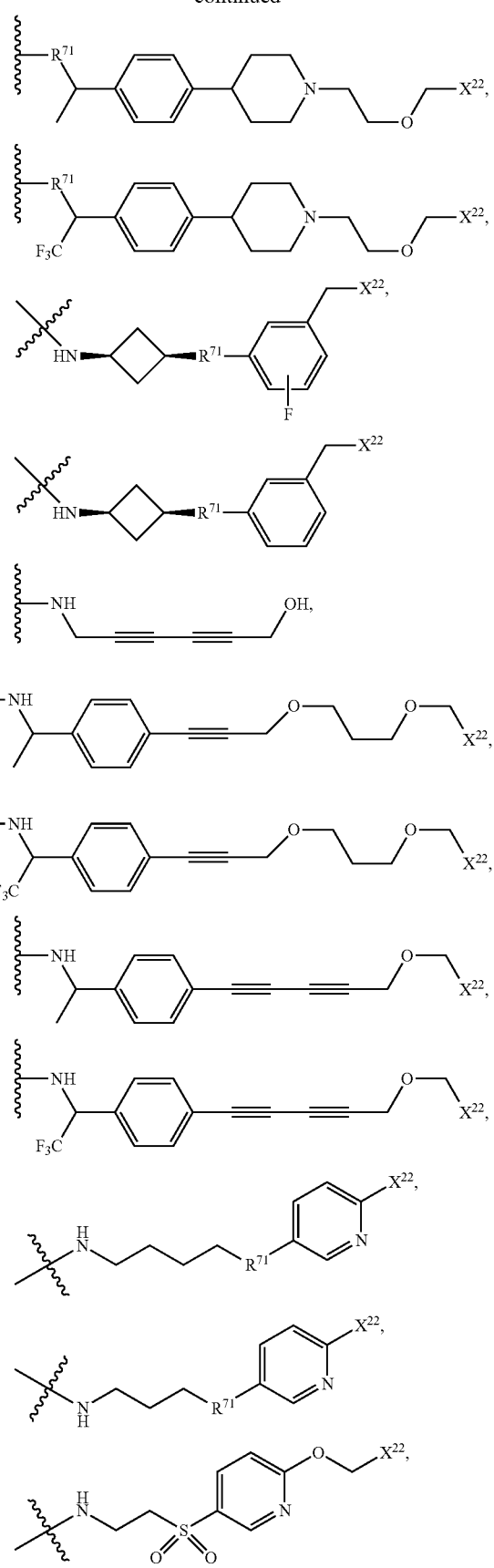

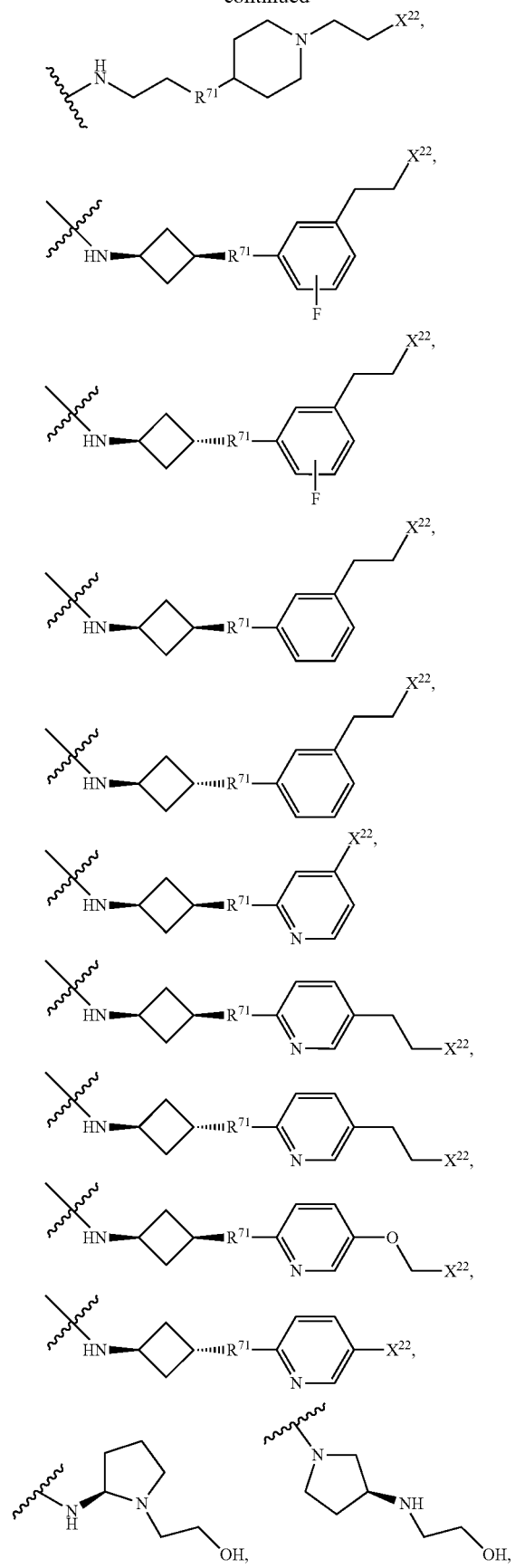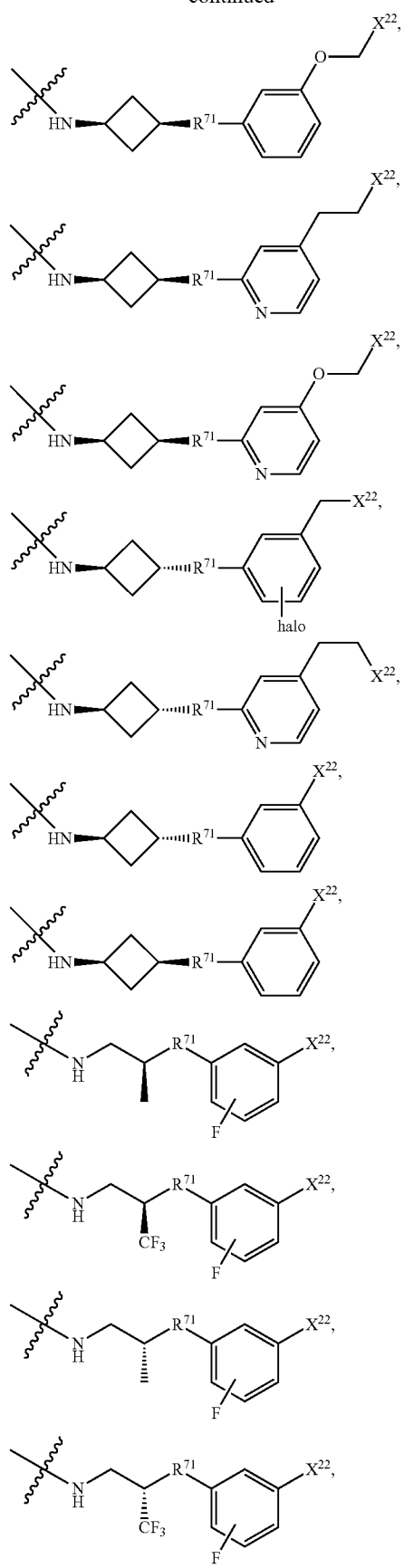

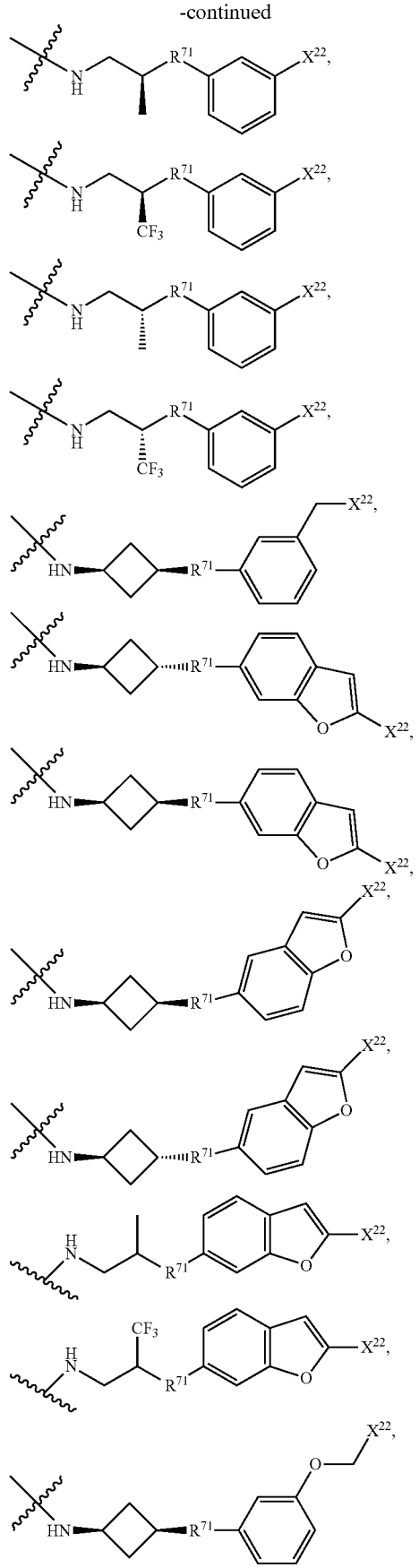
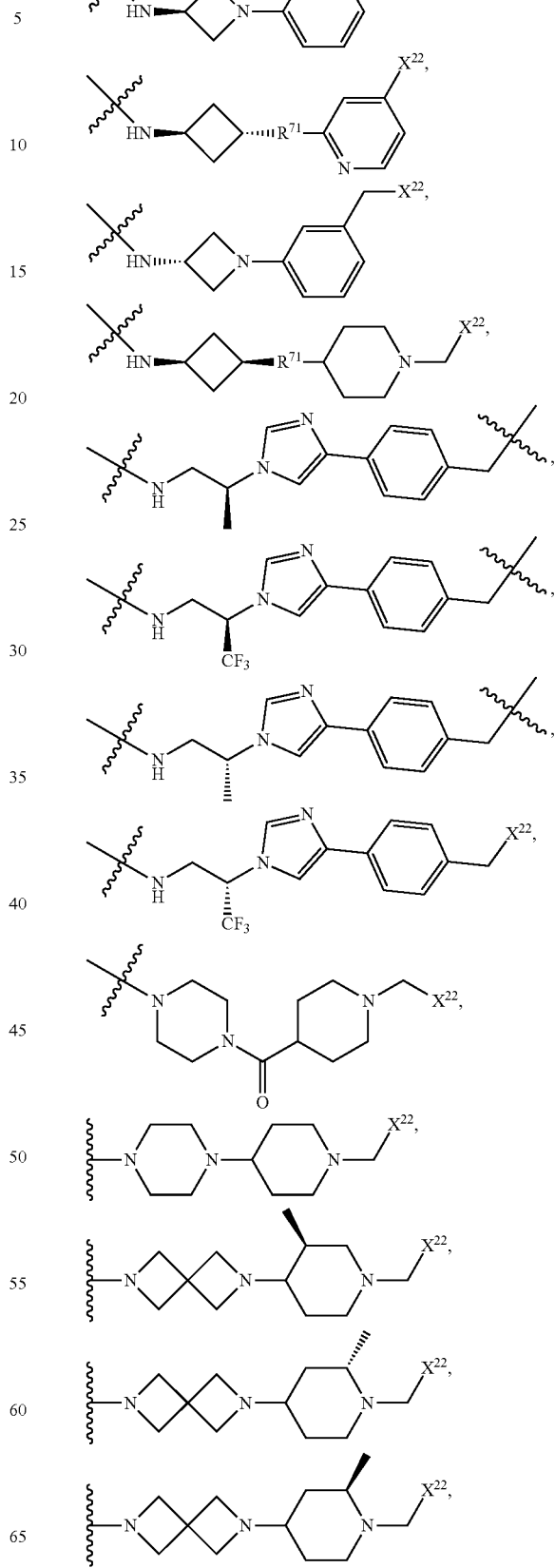

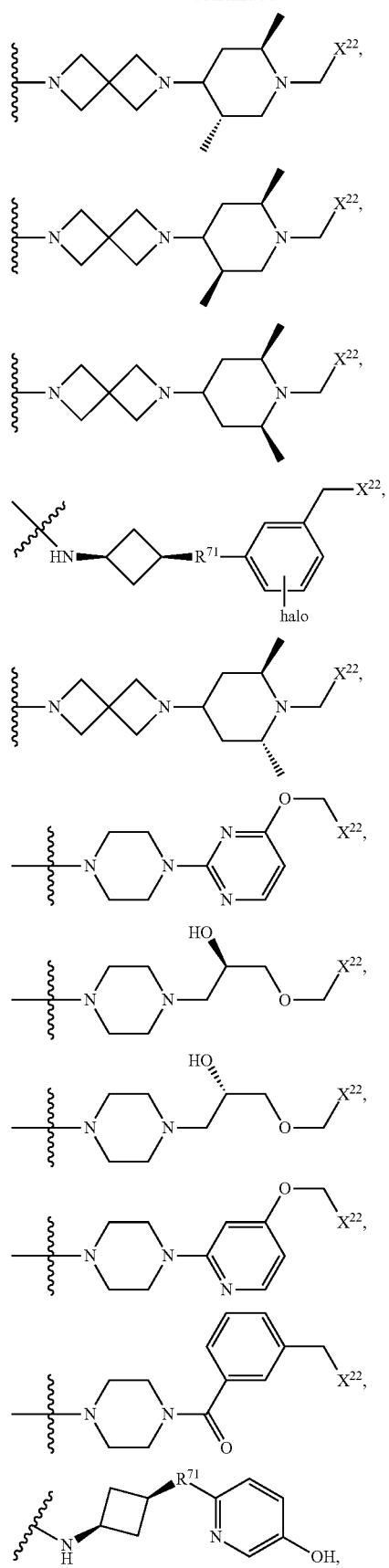
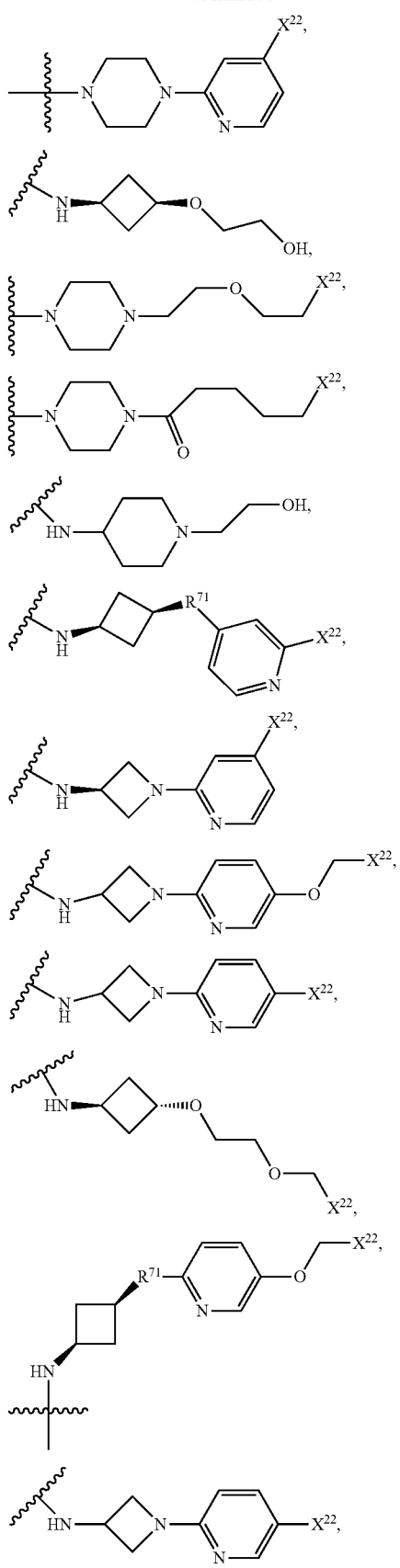

-continued
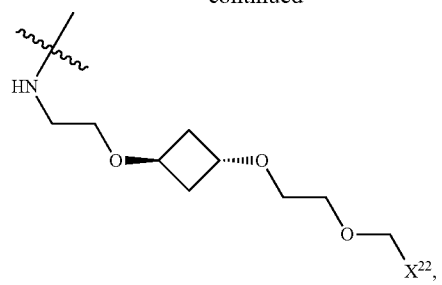
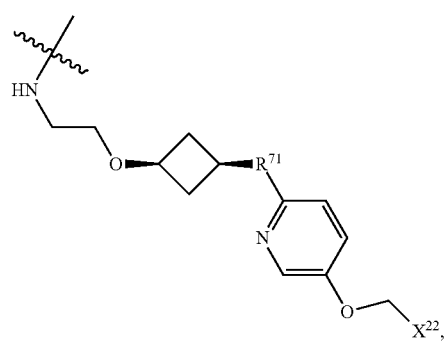
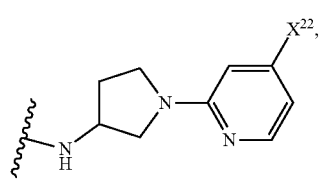
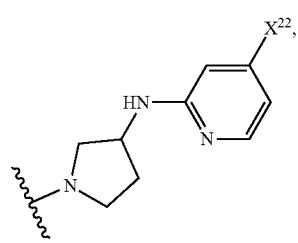
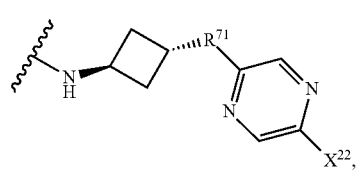
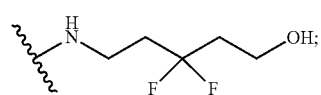
wherein $R^{71}$ is —O—, —NH, Nalkyl, heteroaliphatic, aliphatic, or —NMe.
In additional embodiments, "Tail" is selected from:
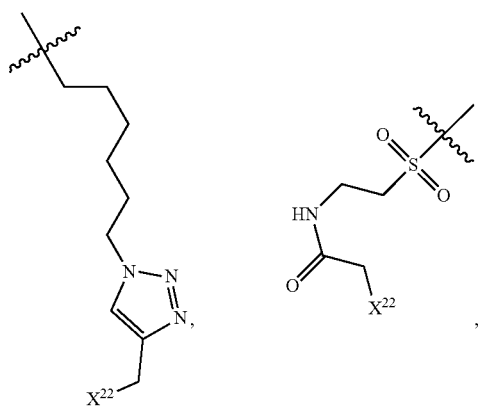
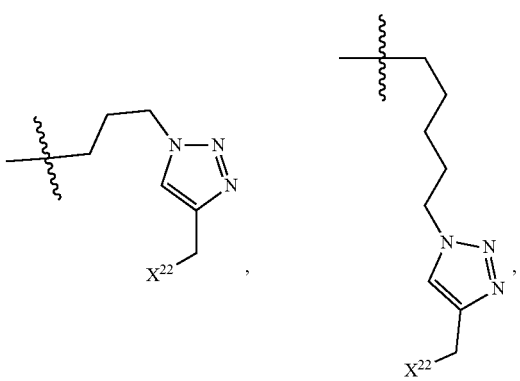

225
-continued
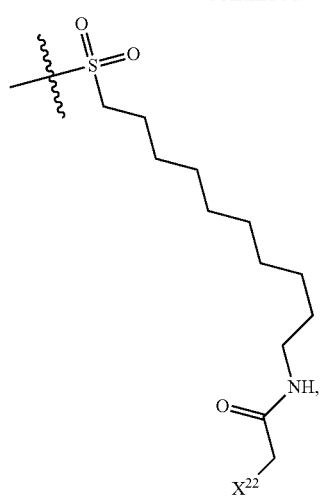
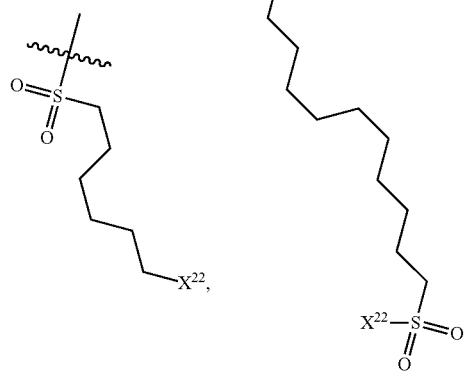
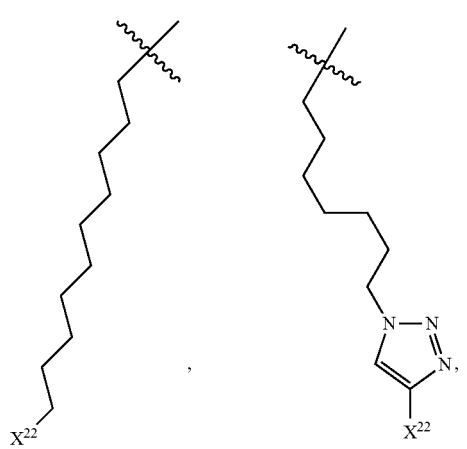
226
-continued
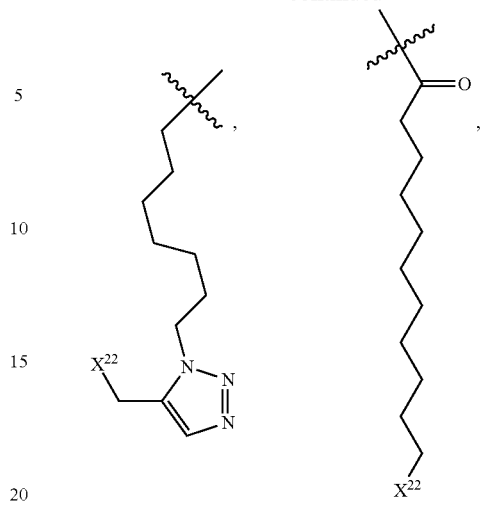
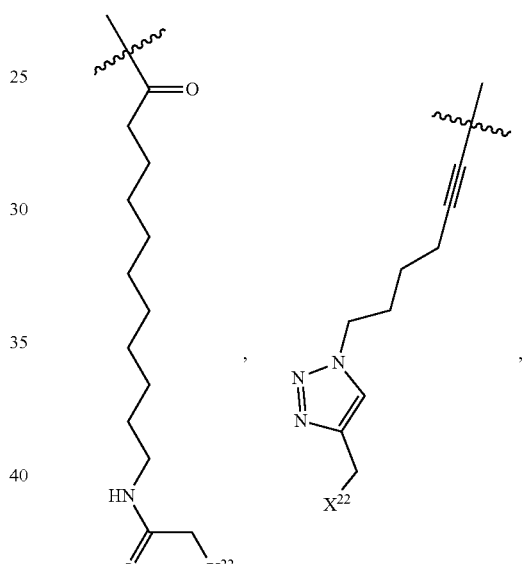
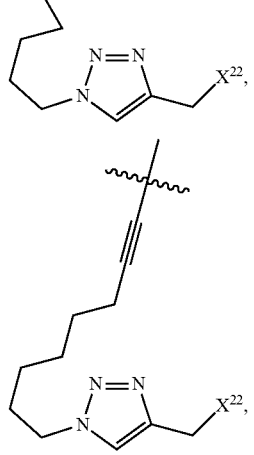

227
-continued
228
-continued
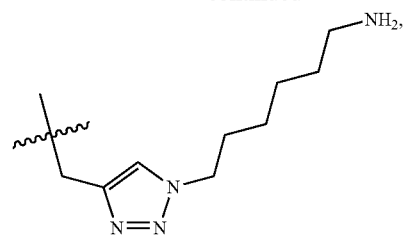
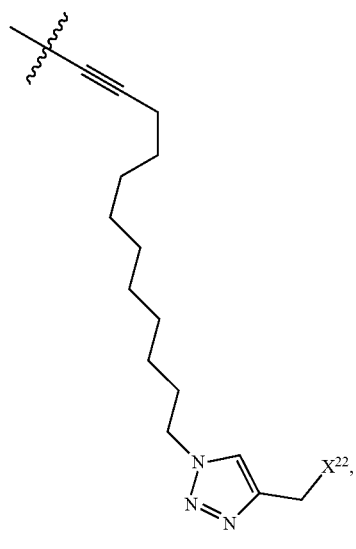
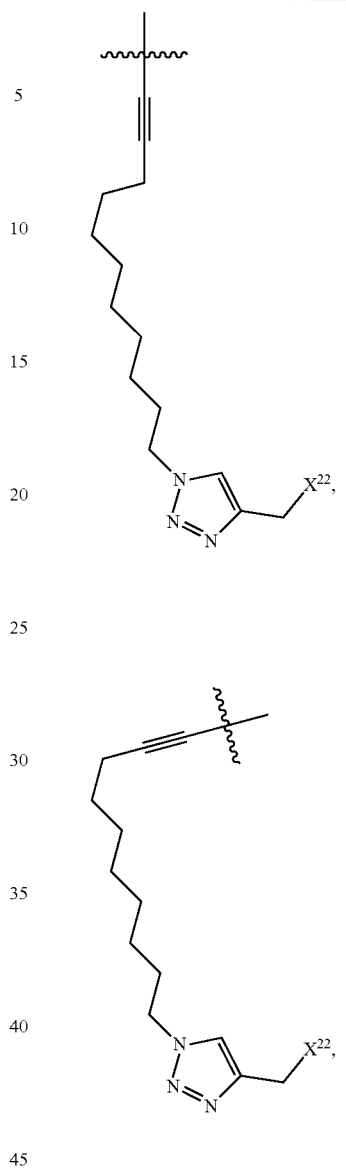

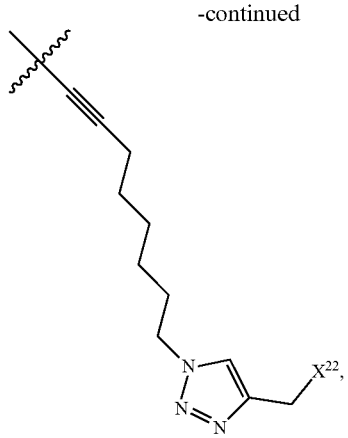
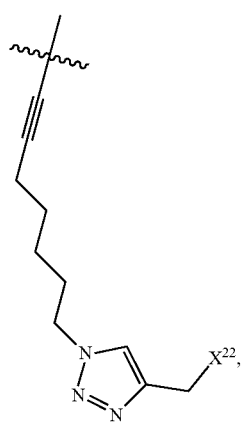
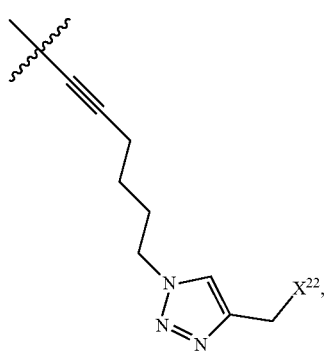
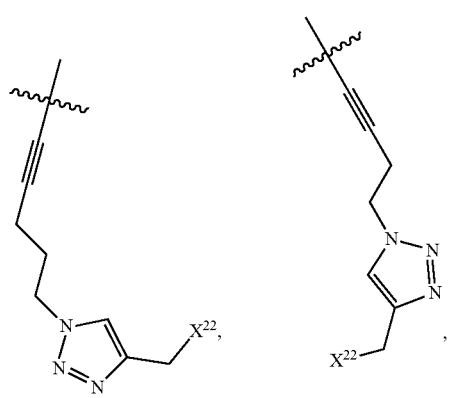
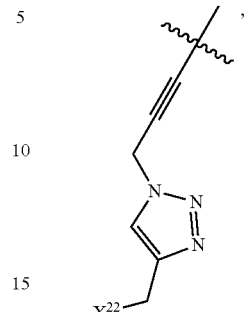
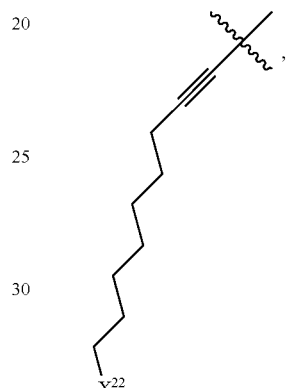
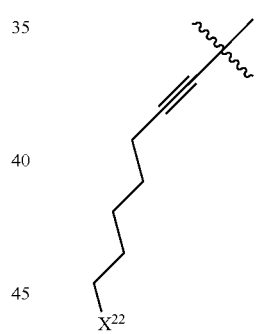
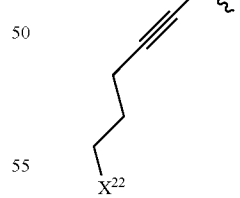

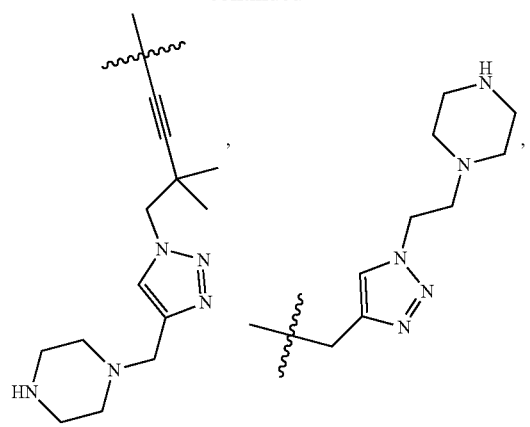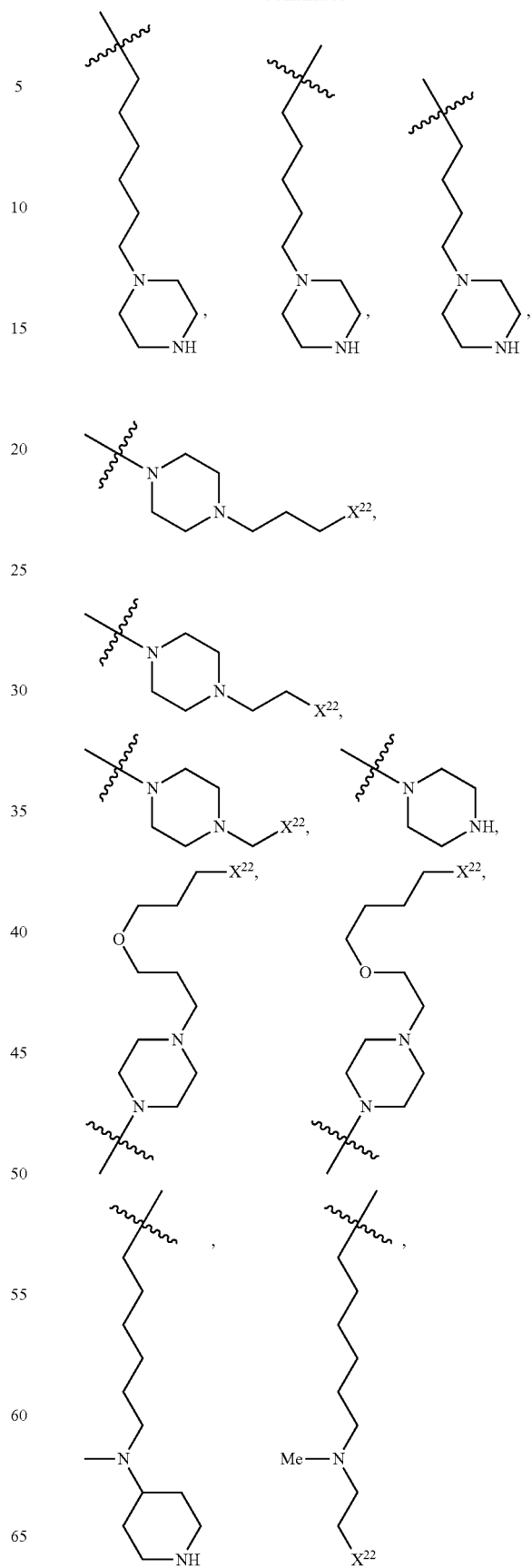

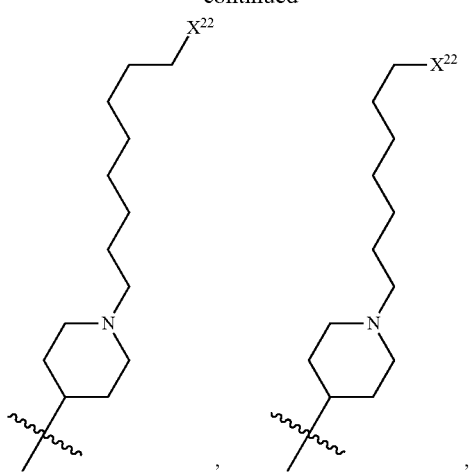
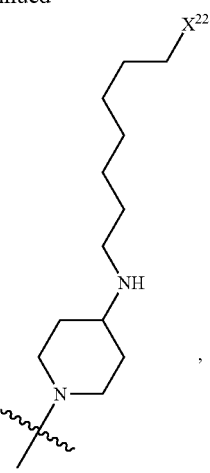
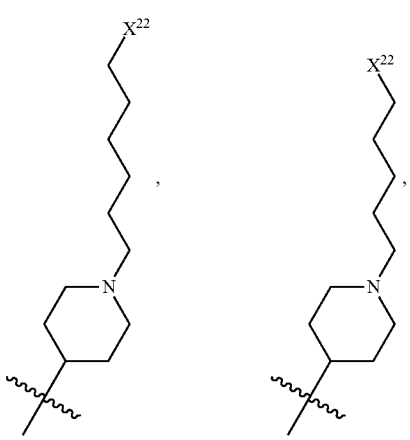
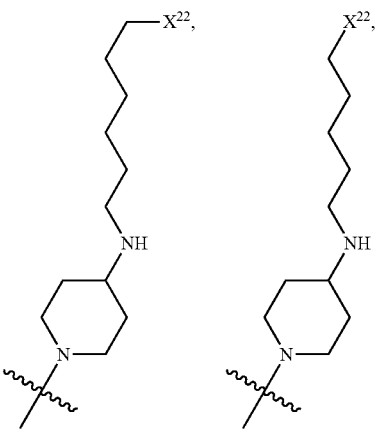
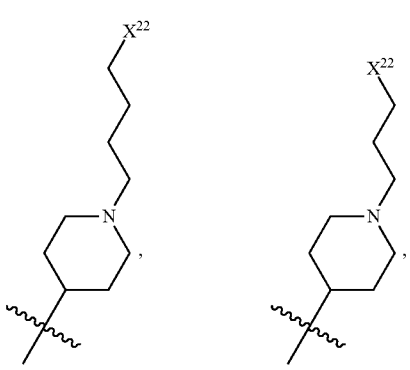
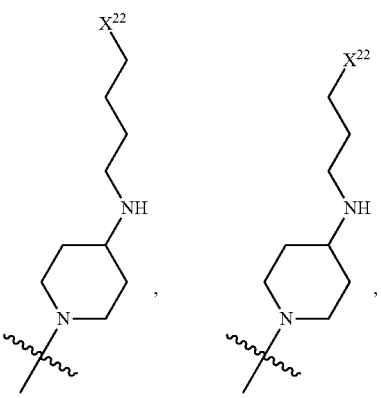
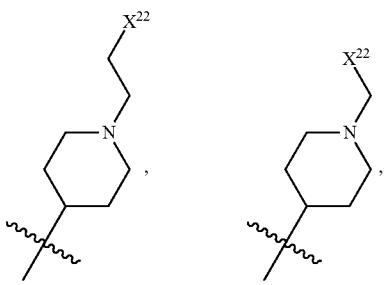
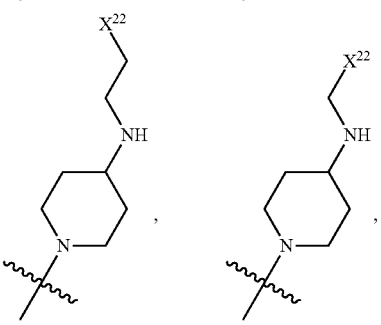

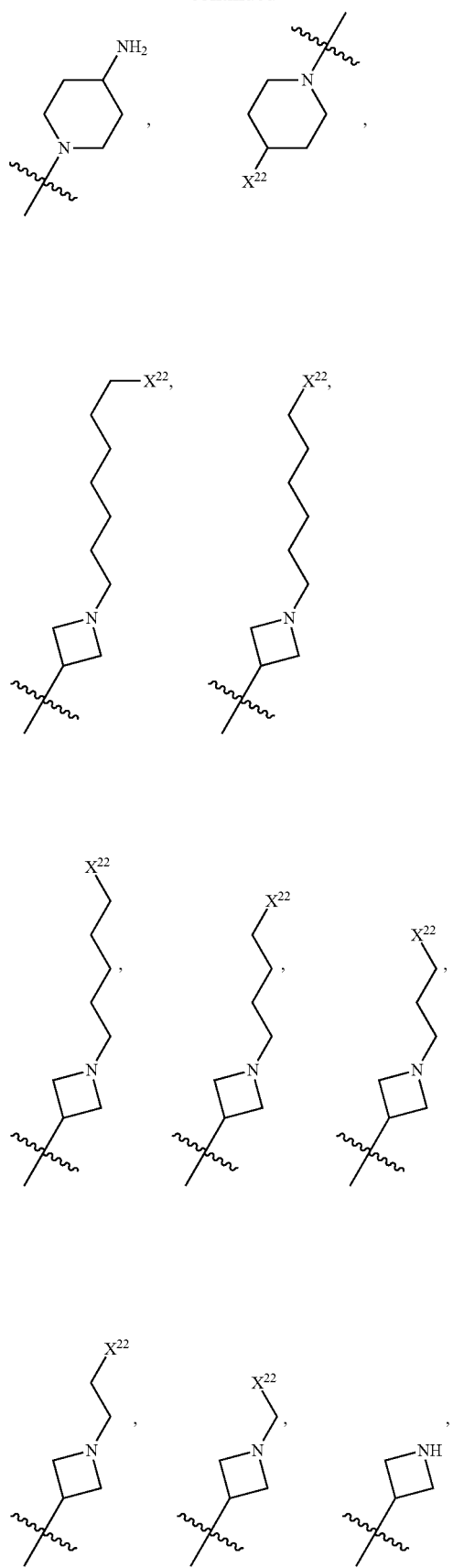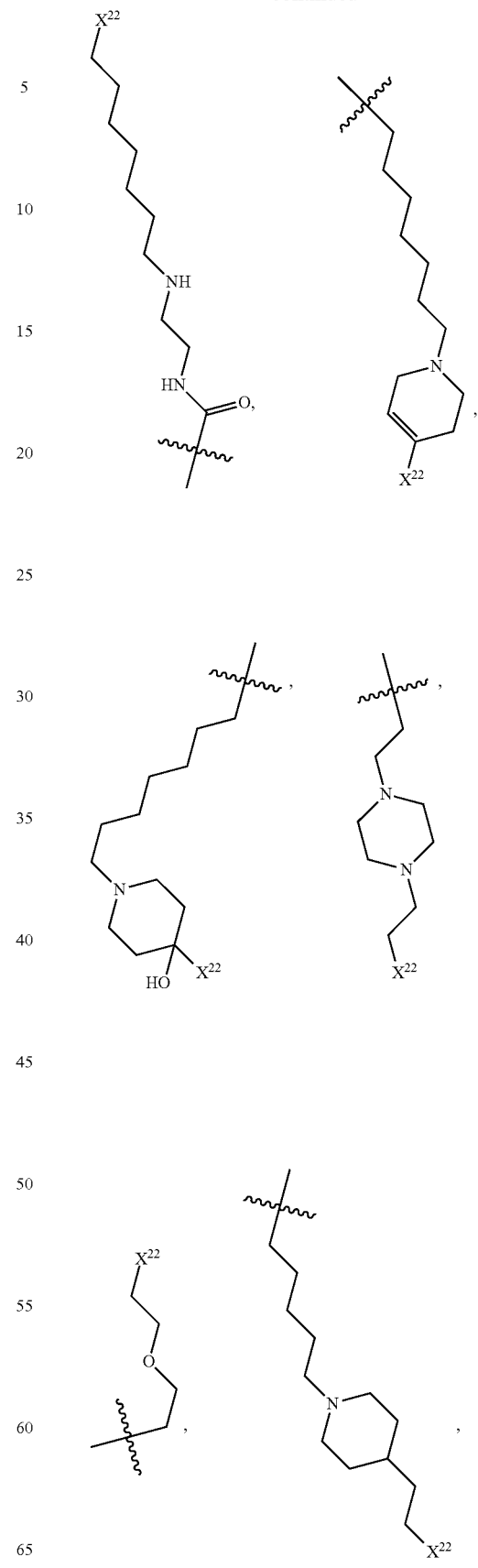

237
-continued
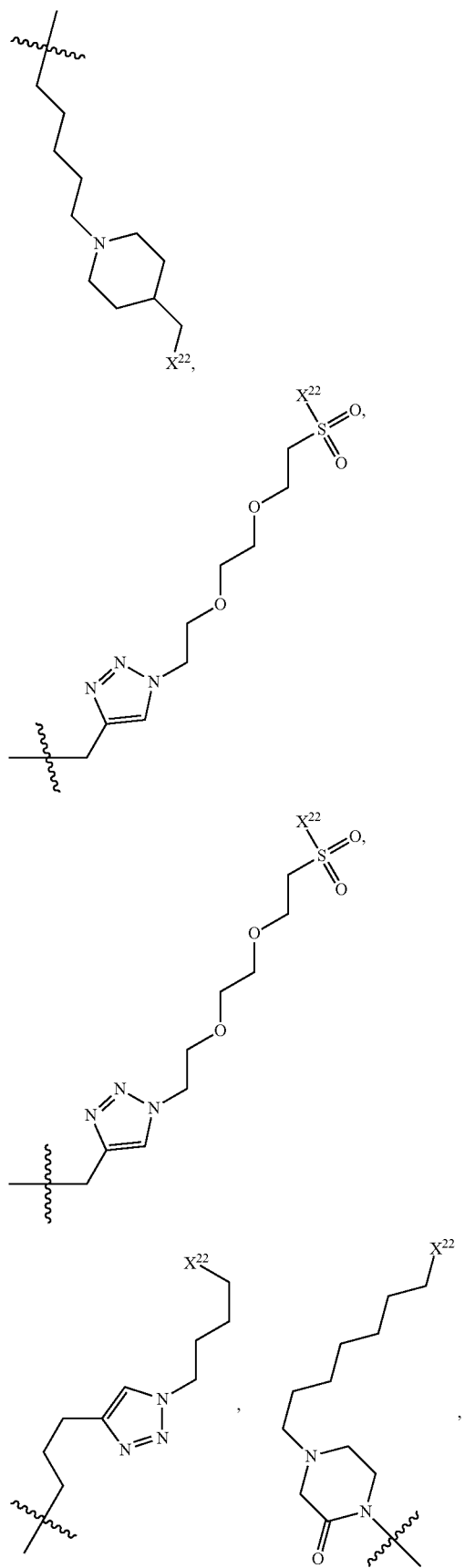
238
-continued
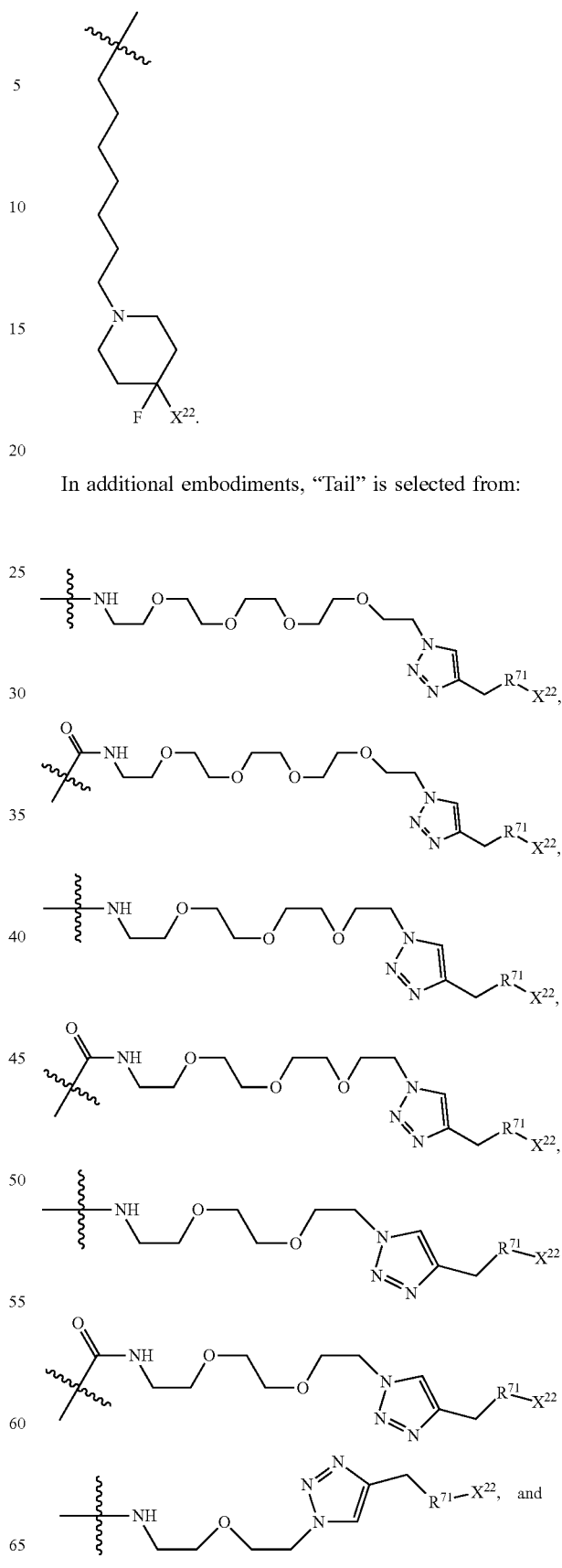
In additional embodiments, "Tail" is selected from:

-continued
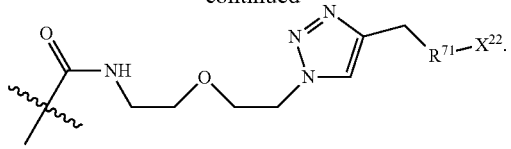
In additional embodiments, "Tail" is selected from:
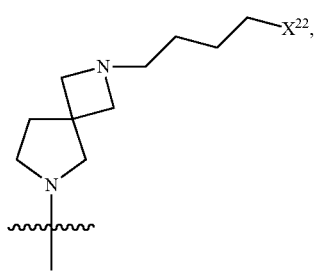
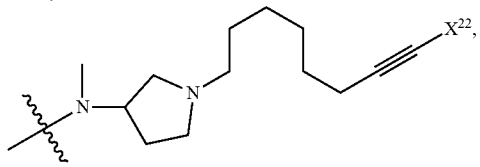
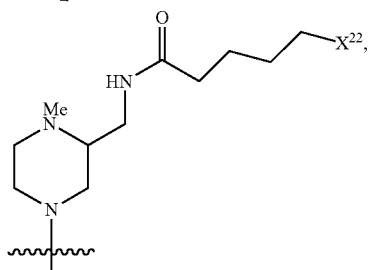
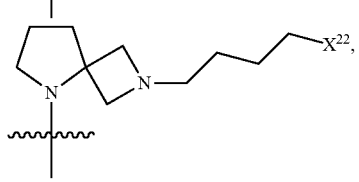
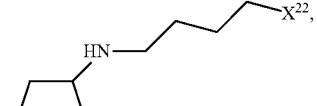
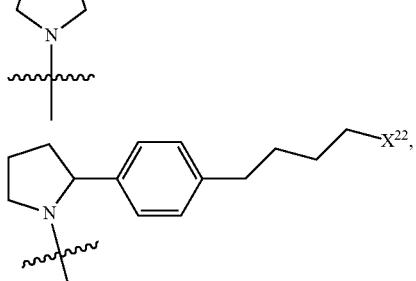
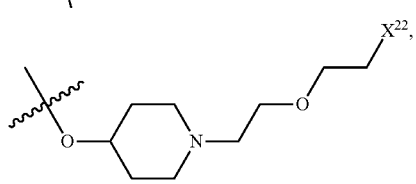
-continued
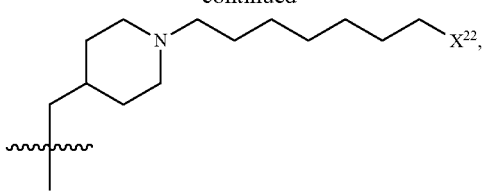
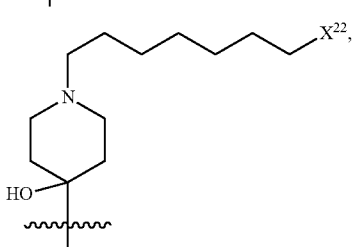
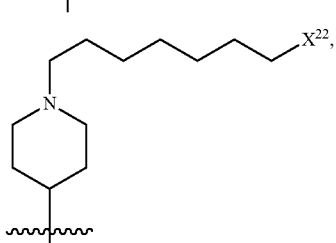
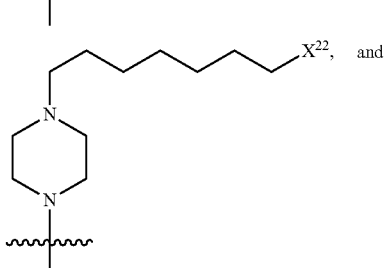
and
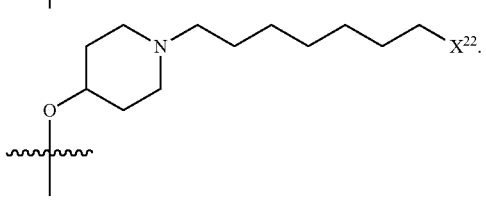
In additional embodiments, "Tail" is selected from:
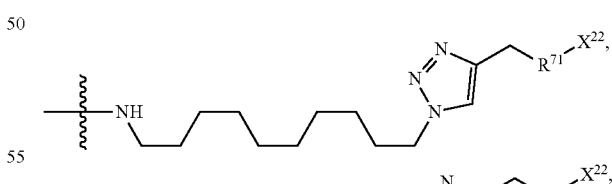
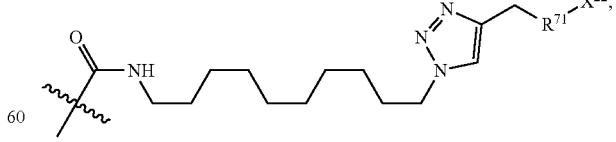
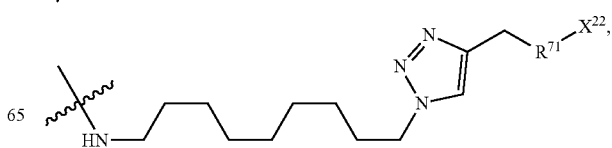

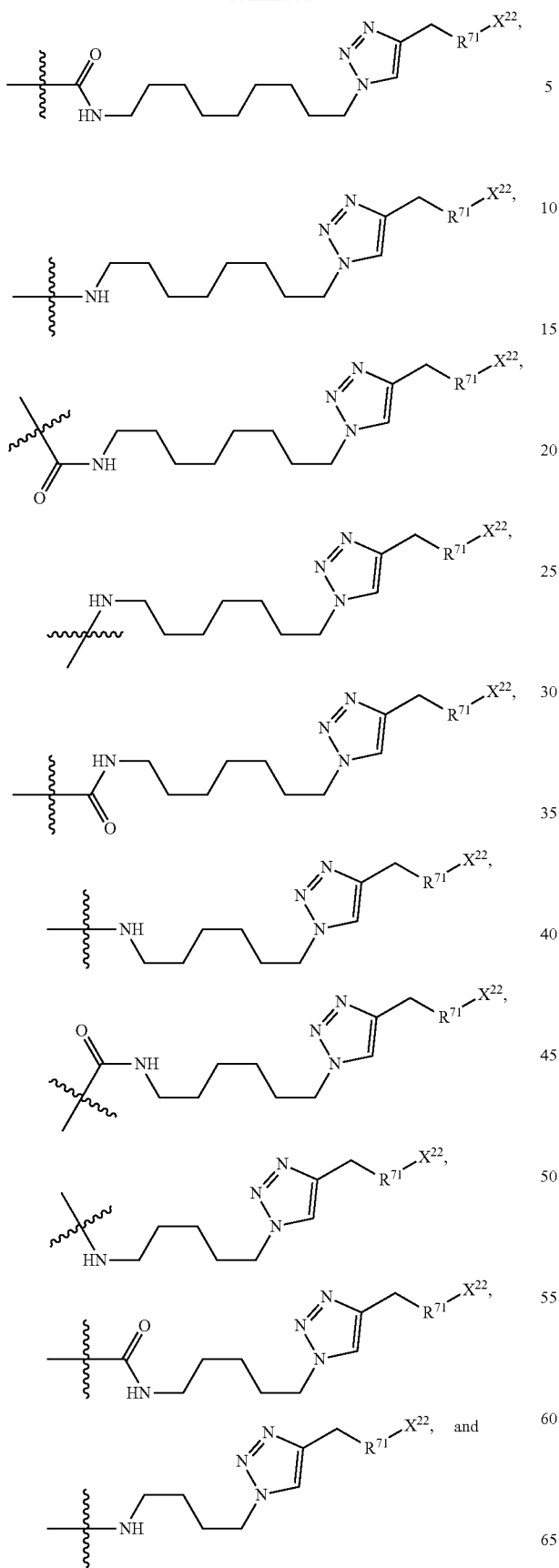
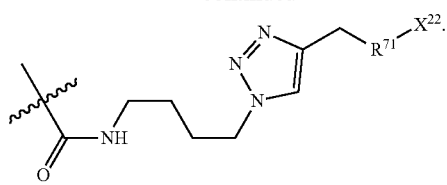
In additional embodiments, "Tail" is selected from:
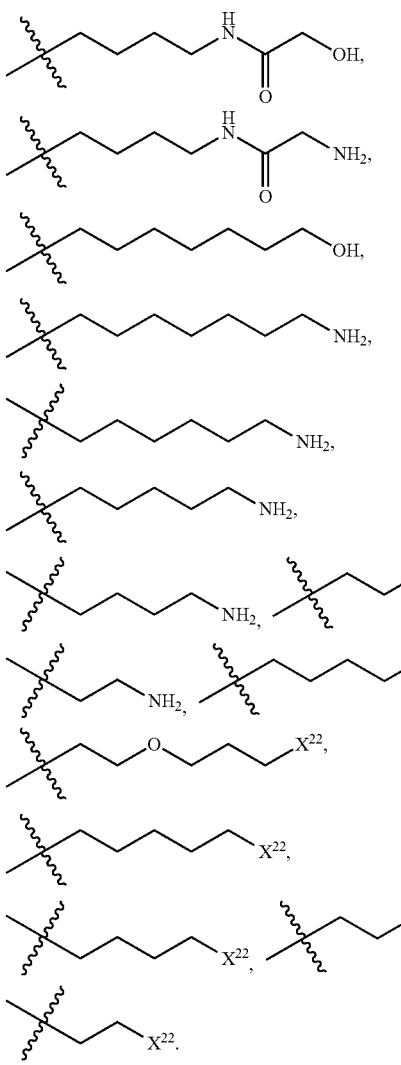
In the above embodiments $X^{22}$ is selected such that a compound sufficiently stable or the intended use results.
In additional embodiments, "Tail" is selected from:
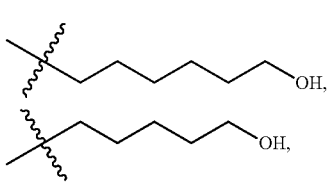

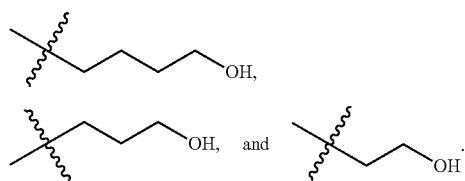
In certain embodiments, "Tail" is selected from:
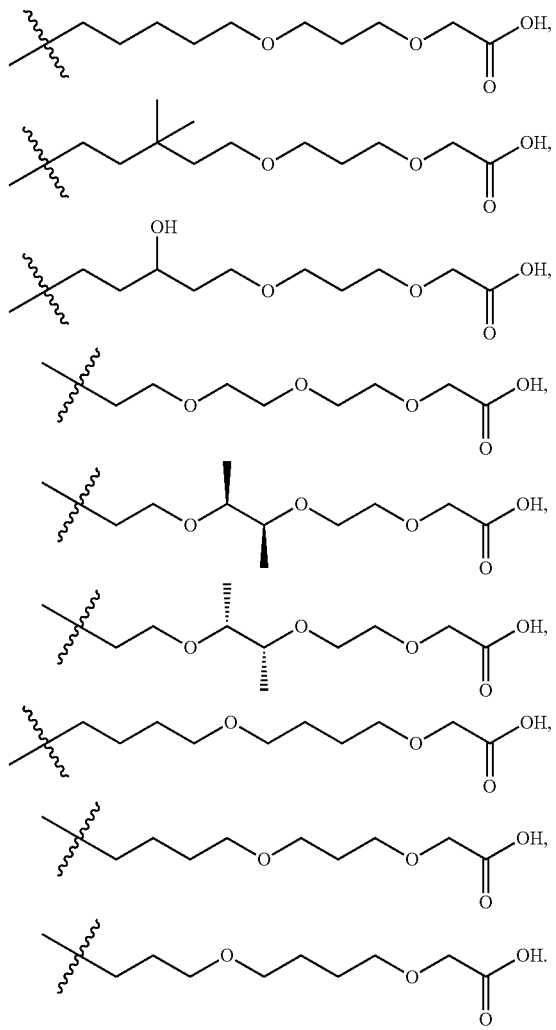
In certain embodiments "Tail" is selected from:
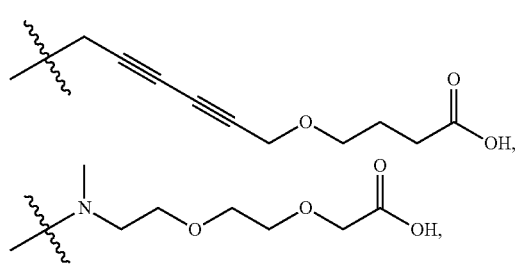
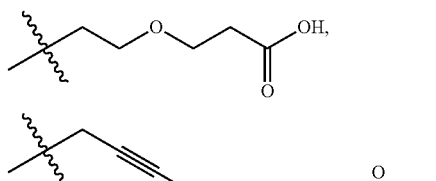
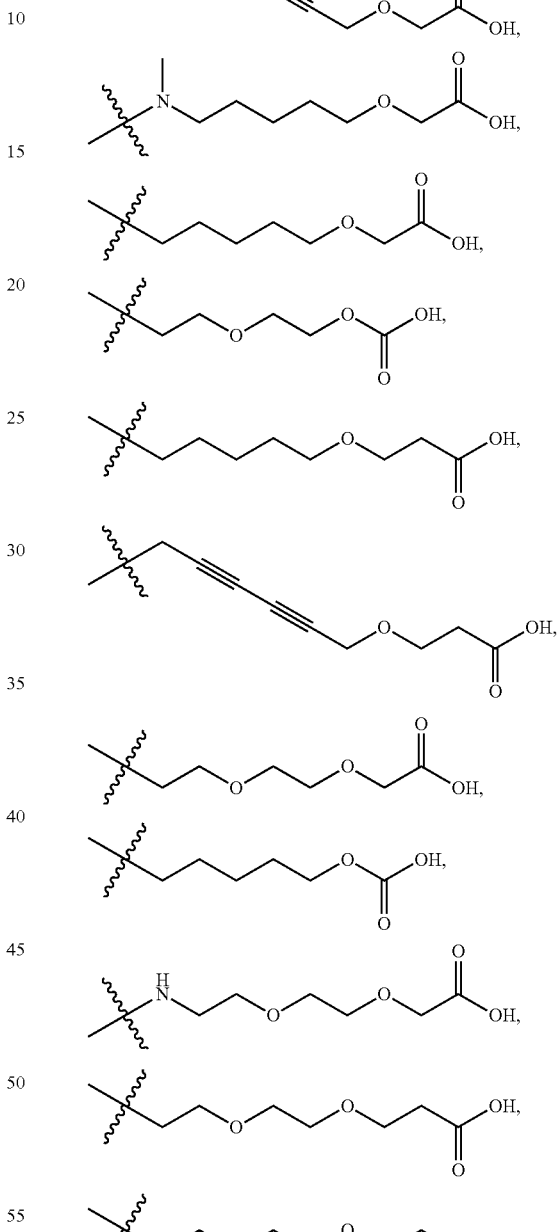
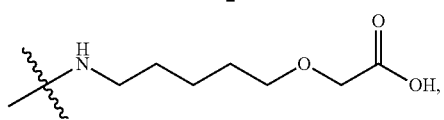

-continued
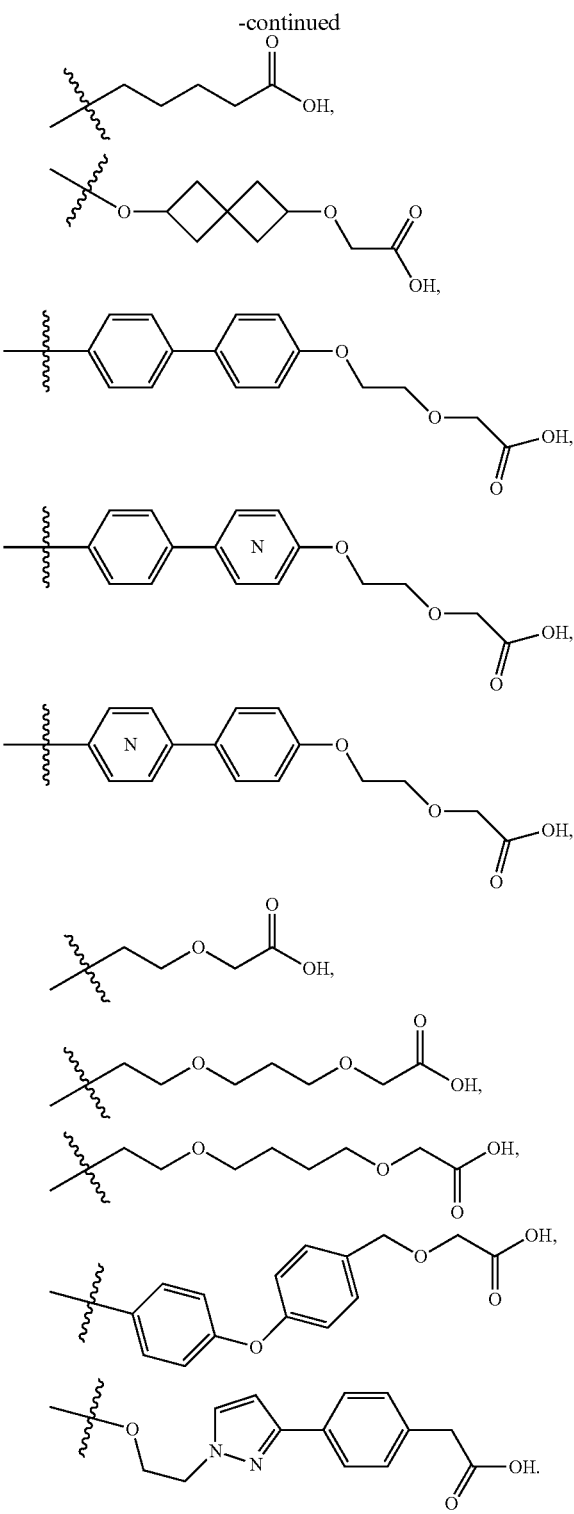
In the above structures
represents
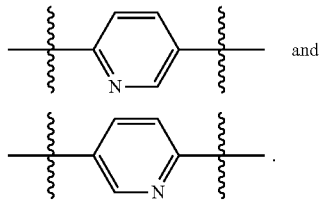
and
In certain embodiments, "Tail" can be a 4-24 carbon atom linear chains, wherein one or more the carbon atoms in the linear chain can be replaced or substituted with oxygen, nitrogen, amide, fluorinated carbon, etc., such as the following:
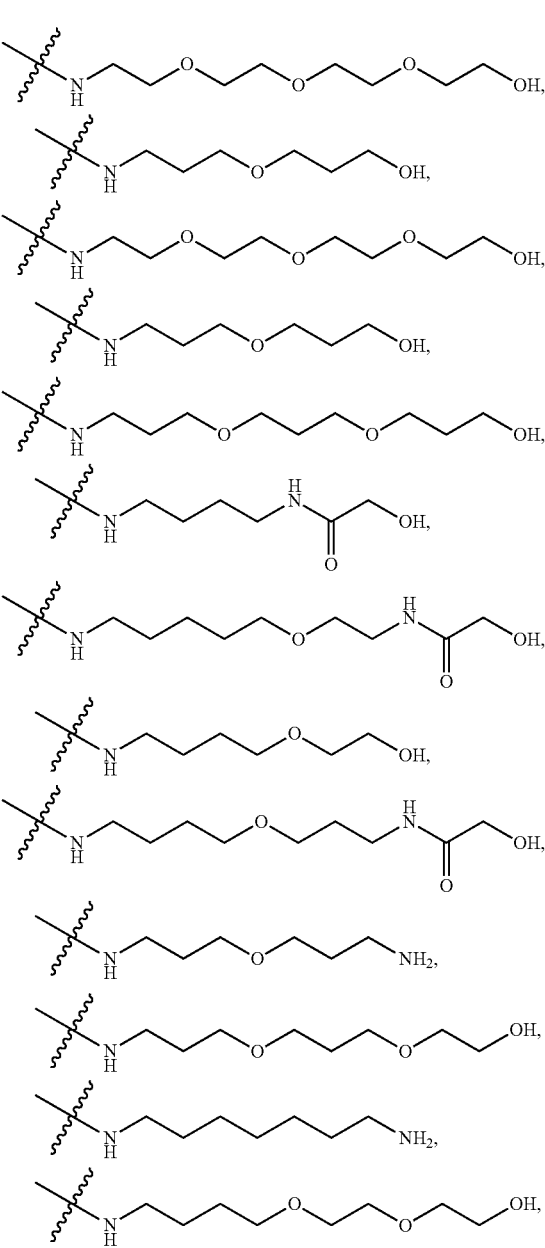

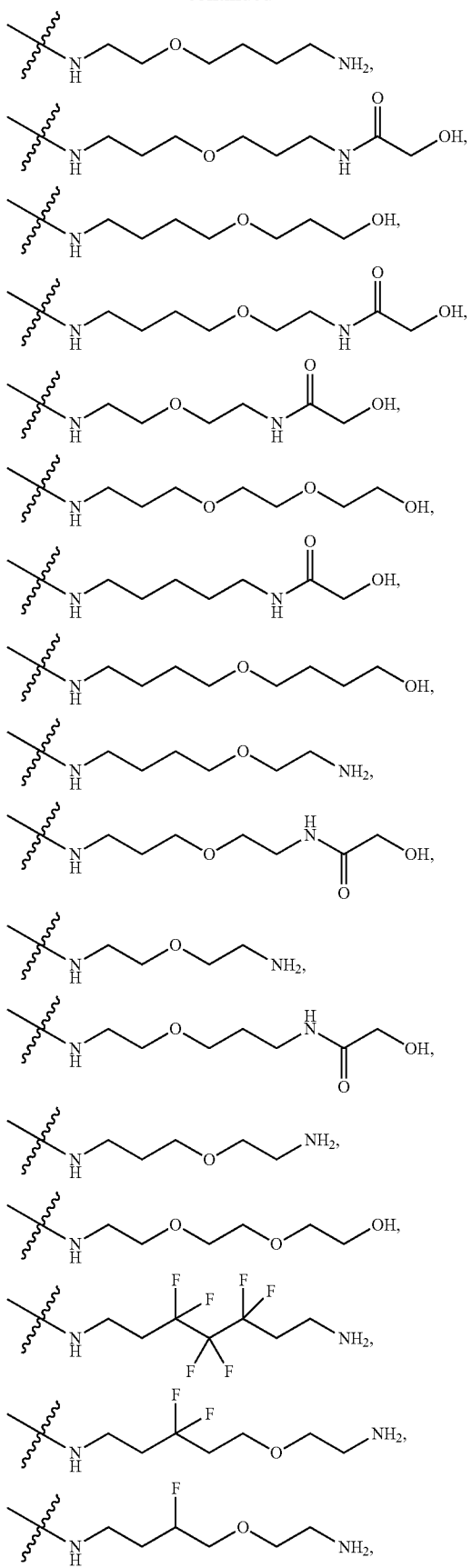
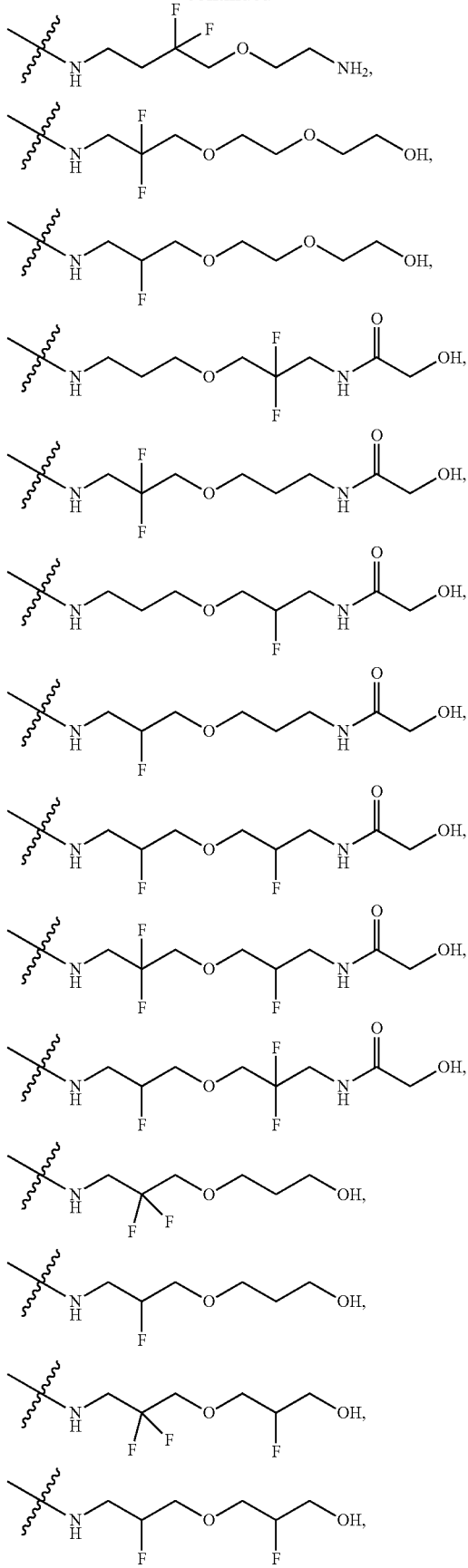

-continued

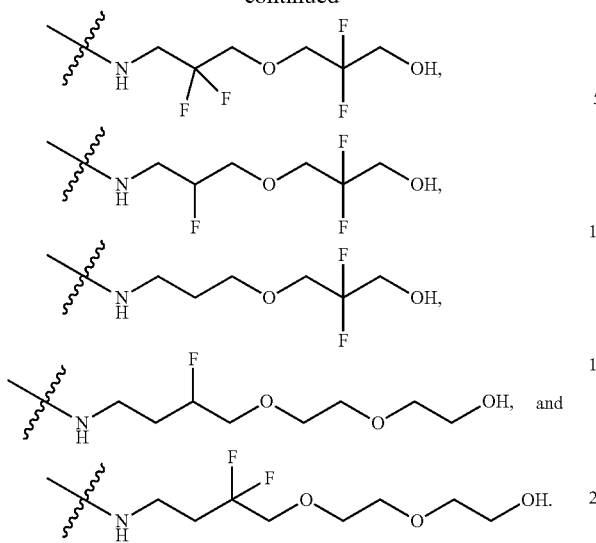

In certain embodiments, "Tail" can be a nonlinear chain, and can be, or include, aliphatic or aromatic or heteroaromatic cyclic moieties.

In certain embodiments, "Tail" may include contiguous, partially contiguous or non-contiguous ethylene glycol unit groups ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units, for example, 1, 2, 3, 4, 6, 6, 7, 8, 9, 10, 11 or 12 ethylene glycol units.

In certain embodiments, "Tail" may have 1, 2, 3, 4, 5, 6, 7, 8, 9, 10, 11, 12, 13, 14, or 15 fluorine substituents. In another embodiment "Tail" is perfluorinated. In yet another embodiment "Tail" is a partially or fully fluorinated poly ether. Nonlimiting examples of fluorinated "Tail" moieties include:

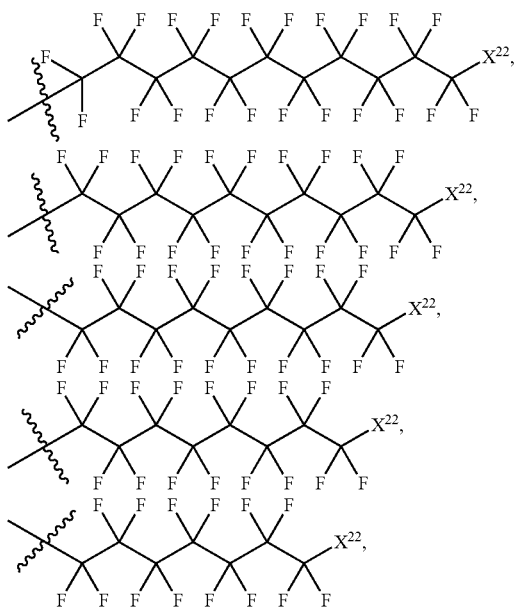

-continued

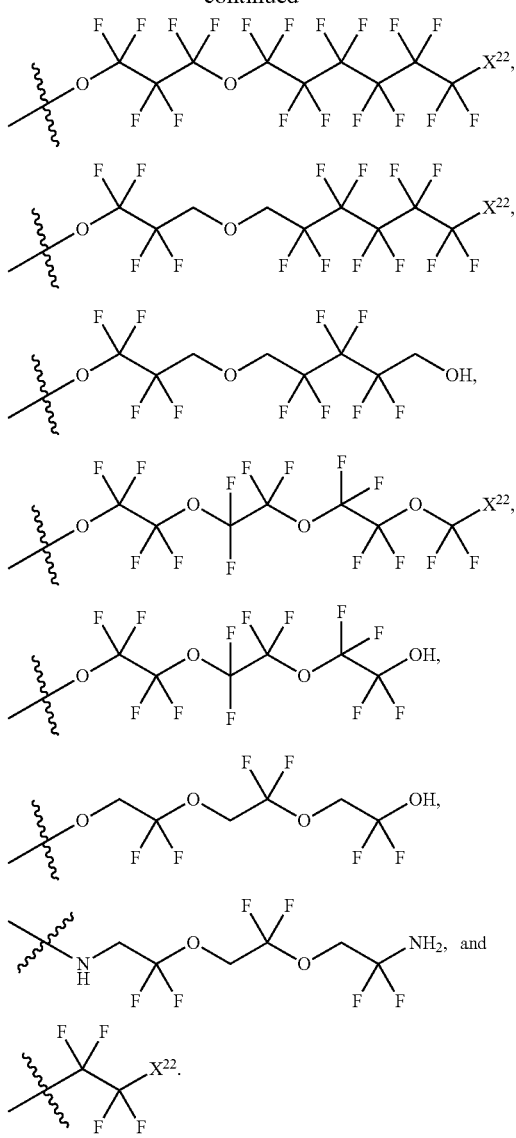

Representative examples of $X^{22}$ include:

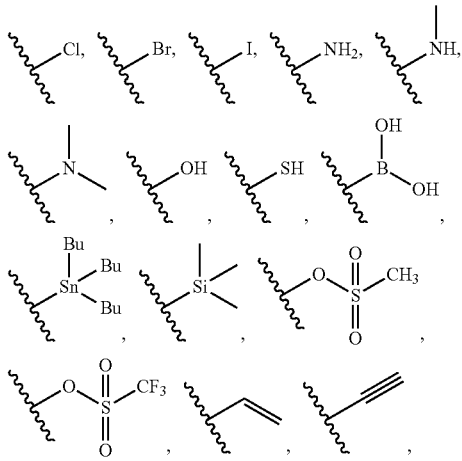

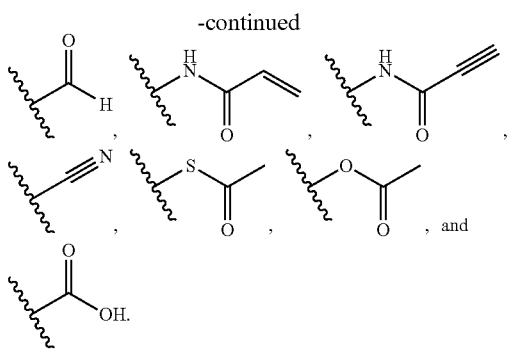

In certain embodiments, the length can be adjusted as desired or as found necessary for the desired application.

IV. Methods of Treatment

The compounds of Formula Ia, Formula Ib, Formula II, Formula IIIa, Formula IIIb, Formula IV, Formula V, Formula VI, Formula VII, Formula VIII, Formula IX, Formula X, Formula XI, Formula XII, Formula XIII, Formula XIV, Formula XV, Formula XIV-a to XIV-x, or Formula XV-a to XV-t can be used in an effective amount to treat a host, including a human, in need thereof, optionally in a pharmaceutically acceptable carrier to treat any of the disorders described herein.

The terms "treat", "treating", and "treatment", etc., as used herein, refer to any action providing a benefit to a patient for which the present compounds may be administered, including the treatment of any disease state or condition which is modulated through the protein to which the present compounds bind. Illustrative non-limiting disease states or conditions, including cancer, which may be treated using compounds according to the present invention are set forth hereinabove.

The term "disease state or condition" when used in connection with a Formula Ia, Formula Ib, Formula II, Formula IIIa, Formula IIIb, Formula IV, Formula V, Formula VI, Formula VII, Formula VIII, Formula IX, Formula X, Formula XI, Formula XII, Formula XIII, Formula XIV, Formula XV, Formula XIV-a to XIV-x, or Formula XV-a to XV-t compound for example, refers to any therapeutic indication which can be treated by decreasing the activity of cereblon or a cereblon-containing E3 Ligase. Nonlimiting examples of uses for cereblon binders are multiple myeloma, a hematological disorder such as myelodysplastic syndrome, cancer, tumor, abnormal cellular proliferation, HIV/AIDS, HBV, HCV, hepatitis, Crohn's disease, sarcoidosis, graft-versus-host disease, rheumatoid arthritis, Behcet's disease, tuberculosis, and myelofibrosis. Other indications include a myelo- or lymphoproliferative disorder such as B- or T-cell lymphomas, Waldenstrom's macroglobulinemia, Wiskott-Aldrich syndrome, or a post-transplant lymphoproliferative disorder; an immune disorder, including autoimmune disorders such as Addison disease, Celiac disease, dermatomyositis, Graves disease, thyroiditis, multiple sclerosis, pernicious anemia, arthritis, and in particular rheumatoid arthritis, lupus, or type I diabetes; a disease of cardiologic malfunction, including hypercholesterolemia; an infectious disease, including viral and/or bacterial infection, as described generally herein; an inflammatory condition, including asthma, chronic peptic ulcers, tuberculosis, rheumatoid arthritis, periodontitis and ulcerative colitis.

In certain embodiments, the present invention provides for administering a compound of Formula Ia, Formula Ib, Formula II, Formula IIIa, Formula IIIb, Formula IV, Formula V, Formula VI, Formula VII, Formula VIII, Formula IX, Formula X, Formula XI, Formula XII, Formula XIII, Formula XIV, Formula XV, Formula XIV-a to XIV-x, or Formula XV-a to XV-t to a patient, for example, a human, having an infectious disease, wherein the therapy targets a protein of the infectious agent, optionally in combination with another bioactive agent. The disease state or condition may be a disease caused by a microbial agent or other exogenous agent such as a virus (as non-limiting examples, HIV, HBV, HCV, HSV, HPV, RSV, CMV, Ebola, Flavivirus, Pestivirus, Rotavirus, Influenza, Coronavirus, EBV, viral pneumonia, drug-resistant viruses, Bird flu, RNA virus, DNA virus, adenovirus, poxvirus, Picornavirus, Togavirus, Orthomyxovirus, Retrovirus or Hepadnovirus), bacteria (Gram-negative, Gram-positive, fungus, protozoa, helminth, worms, prion, parasite, or other microbe or may be a disease state, which is caused by overexpression of a protein, which leads to a disease state and/or condition.

In certain embodiments, the condition treated with a compound of the present invention is a disorder related to abnormal cellular proliferation. Abnormal cellular proliferation, notably hyperproliferation, can occur as a result of a wide variety of factors, including genetic mutation, infection, exposure to toxins, autoimmune disorders, and benign or malignant tumor induction.

There are a number of skin disorders associated with cellular hyperproliferation. Psoriasis, for example, is a benign disease of human skin generally characterized by plaques covered by thickened scales. The disease is caused by increased proliferation of epidermal cells of unknown cause. Chronic eczema is also associated with significant hyperproliferation of the epidermis. Other diseases caused by hyperproliferation of skin cells include atopic dermatitis, lichen planus, warts, pemphigus vulgaris, actinic keratosis, basal cell carcinoma and squamous cell carcinoma.

Other hyperproliferative cell disorders include blood vessel proliferation disorders, fibrotic disorders, autoimmune disorders, graft-versus-host rejection, tumors and cancers.

Blood vessel proliferative disorders include angiogenic and vasculogenic disorders. Proliferation of smooth muscle cells in the course of development of plaques in vascular tissue cause, for example, restenosis, retinopathies and atherosclerosis. Both cell migration and cell proliferation play a role in the formation of atherosclerotic lesions.

Fibrotic disorders are often due to the abnormal formation of an extracellular matrix. Examples of fibrotic disorders include hepatic cirrhosis and mesangial proliferative cell disorders. Hepatic cirrhosis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role in hepatic cirrhosis.

Mesangial disorders are brought about by abnormal proliferation of mesangial cells. Mesangial hyperproliferative cell disorders include various human renal diseases, such as glomerulonephritis, diabetic nephropathy, malignant nephrosclerosis, thrombotic micro-angiopathy syndromes, transplant rejection, and glomerulopathies.

Another disease with a proliferative component is rheumatoid arthritis. Rheumatoid arthritis is generally considered an autoimmune disease that is thought to be associated with activity of autoreactive T cells, and to be caused by autoantibodies produced against collagen and IgE.

Other disorders that can include an abnormal cellular proliferative component include Bechet's syndrome, acute respiratory distress syndrome (ARDS), ischemic heart disease, post-dialysis syndrome, leukemia, acquired immune deficiency syndrome, vasculitis, lipid histiocytosis, septic shock and inflammation in general.

Cutaneous contact hypersensitivity and asthma are just two examples of immune responses that can be associated with significant morbidity. Others include atopic dermatitis, eczema, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, cutaneous lupus erythematosus, scleroderma, vaginitis, proctitis, and drug eruptions. These conditions may result in any one or more of the following symptoms or signs: itching, swelling, redness, blisters, crusting, ulceration, pain, scaling, cracking, hair loss, scarring, or oozing of fluid involving the skin, eye, or mucosal membranes.

In atopic dermatitis, and eczema in general, immunologically mediated leukocyte infiltration (particularly infiltration of mononuclear cells, lymphocytes, neutrophils, and eosinophils) into the skin importantly contributes to the pathogenesis of these diseases. Chronic eczema also is associated with significant hyperproliferation of the epidermis. Immunologically mediated leukocyte infiltration also occurs at sites other than the skin, such as in the airways in asthma and in the tear producing gland of the eye in keratoconjunctivitis sicca.

In one non-limiting embodiment compounds of the present invention are used as topical agents in treating contact dermatitis, atopic dermatitis, eczematous dermatitis, psoriasis, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, and drug eruptions. The novel method may also be useful in reducing the infiltration of skin by malignant leukocytes in diseases such as mycosis fungoides. These compounds can also be used to treat an aqueous-deficient dry eye state (such as immune mediated keratoconjunctivitis) in a patient suffering therefrom, by administering the compound topically to the eye.

Disease states of conditions which may be treated using compounds according to the present invention include, for example, asthma, autoimmune diseases such as multiple sclerosis, various cancers, ciliopathies, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter's syndrome, Neurofibromatosis, Phenylketonuria, Polycystic kidney disease 1 (PKD1) or 2 (PKD2) Prader-Willi syndrome, Sickle-cell disease, Tay-Sachs disease, Turner syndrome.

Further disease states or conditions which may be treated by compounds according to the present invention include Alzheimer's disease, Amyotrophic lateral sclerosis (Lou Gehrig's disease), Anorexia nervosa, Anxiety disorder, Atherosclerosis, Attention deficit hyperactivity disorder, Autism, Bipolar disorder, Chronic fatigue syndrome, Chronic obstructive pulmonary disease, Crohn's disease, Coronary heart disease, Dementia, Depression, Diabetes mellitus type 1, Diabetes mellitus type 2, Epilepsy, Guillain-Barré syndrome, Irritable bowel syndrome, Lupus, Metabolic syndrome, Multiple sclerosis, Myocardial infarction, Obesity, Obsessive-compulsive disorder, Panic disorder, Parkinson's disease, Psoriasis, Rheumatoid arthritis, Sarcoidosis, Schizophrenia, Stroke, Thromboangiitis obliterans, Tourette syndrome, Vasculitis.

Still additional disease states or conditions which can be treated by compounds according to the present invention include aceruloplasminemia, Achondrogenesis type II, achondroplasia, Acrocephaly, Gaucher disease type 2, acute intermittent porphyria, Canavan disease, Adenomatous Polyposis Coli, ALA dehydratase deficiency, adenylosuccinate lyase deficiency, Adrenogenital syndrome, Adrenoleukodystrophy, ALA-D porphyria, ALA dehydratase deficiency, Alkaptonuria, Alexander disease, Alkaptonuric ochronosis, alpha 1-antitrypsin deficiency, alpha-1 proteinase inhibitor, emphysema, amyotrophic lateral sclerosis Alström syndrome, Alexander disease, Amelogenesis imperfecta, ALA dehydratase deficiency, Anderson-Fabry disease, androgen insensitivity syndrome, Anemia Angiokeratoma Corporis Diffusum, Angiomatosis retinae (von Hippel-Lindau disease) Apert syndrome, Arachnodactyly (Marfan syndrome), Stickler syndrome, Arthrochalasis multiplex congenital (Ehlers-Danlos syndrome #arthrochalasia type) ataxia telangiectasia, Rett syndrome, primary pulmonary hypertension, Sandhoff disease, neurofibromatosis type II, Beare-Stevenson cutis gyrata syndrome, Mediterranean fever, familial, Benjamin syndrome, beta-thalassemia, Bilateral Acoustic Neurofibromatosis (neurofibromatosis type II), factor V Leiden thrombophilia, Bloch-Sulzberger syndrome (incontinentia pigmenti), Bloom syndrome, X-linked sideroblastic anemia, Bonnevie-Ullrich syndrome (Turner syndrome), Bourneville disease (tuberous sclerosis), prion disease, Birt-Hogg-Dube syndrome, Brittle bone disease (osteogenesis imperfecta), Broad Thumb-Hallux syndrome (Rubinstein-Taybi syndrome), Bronze Diabetes/Bronzed Cirrhosis (hemochromatosis), Bulbospinal muscular atrophy (Kennedy's disease), Burger-Grutz syndrome (lipoprotein lipase deficiency), CGD Chronic granulomatous disorder, Campomelic dysplasia, biotinidase deficiency, Cardiomyopathy (Noonan syndrome), Cri du chat, CAVD (congenital absence of the vas deferens), Caylor cardiofacial syndrome (CBAVD), CEP (congenital erythropoietic porphyria), cystic fibrosis, congenital hypothyroidism, Chondrodystrophy syndrome (achondroplasia), otospondylomegaepiphyseal dysplasia, Lesch-Nyhan syndrome, galactosemia, Ehlers-Danlos syndrome, Thanatophoric dysplasia, Coffin-Lowry syndrome, Cockayne syndrome, (familial adenomatous polyposis), Congenital erythropoietic porphyria, Congenital heart disease, Methemoglobinemia/Congenital methaemoglobinaemia, achondroplasia, X-linked sideroblastic anemia, Connective tissue disease, Conotruncal anomaly face syndrome, Cooley's Anemia (beta-thalassemia), Copper storage disease (Wilson's disease), Copper transport disease (Menkes disease), hereditary coproporphyria, Cowden syndrome, Craniofacial dysarthrosis (Crouzon syndrome), Creutzfeldt-Jakob disease (prion disease), Cockayne syndrome, Cowden syndrome, Curschmann-Batten-Steinert syndrome (myotonic dystrophy), Beare-Stevenson cutis gyrata syndrome, primary hyperoxaluria, spondyloepimetaphyseal dysplasia (Strudwick type), muscular dystrophy, Duchenne and Becker types (DBMD), Usher syndrome, Degenerative nerve diseases including de Grouchy syndrome and Dejerine-Sottas syndrome, developmental disabilities, distal spinal muscular atrophy, type V, androgen insensitivity syndrome, Diffuse Globoid Body Sclerosis (Krabbe disease), Di George's syndrome, Dihydrotestosterone receptor deficiency, androgen insensitivity syndrome, Down syndrome, Dwarfism, erythropoietic protoporphyria Erythroid 5-aminolevulinate synthetase deficiency, Erythropoietic porphyria, erythropoietic protoporphyria, erythropoietic uroporphyria, Friedreich's ataxia-familial paroxysmal polyserositis, porphyria cutanea tarda, familial pressure sensitive neuropathy, primary pulmonary hypertension (PPH), Fibrocystic disease of the pancreas, fragile X syndrome, galactosemia, genetic brain disorders, Giant cell hepatitis (Neonatal hemochromatosis), Gronblad-Strandberg syndrome (pseudoxanthoma elasticum), Gunther disease (congenital erythropoietic porphyria), haemochromatosis, Hallgren syndrome, sickle cell anemia, hemophilia, hepatoerythropoietic porphyria (HEP), Hippel-Lindau disease (von Hippel-Lindau disease), Huntington's disease, Hutchinson-Gilford progeria syndrome (progeria), Hyperandrogenism, Hypochondroplasia, Hypochromic anemia, Immune system disorders, including X-linked severe combined immunodeficiency, Insley-Astley syndrome, Jackson-Weiss syndrome, Joubert syndrome, Lesch-Nyhan syndrome, Jackson-Weiss syndrome, Kidney diseases, including hyperoxaluria, Klinefelter's syndrome, Kniest dysplasia, Lacunar dementia, Langer-Saldino achondrogenesis, ataxia telangiectasia, Lynch syndrome, Lysyl-hydroxylase deficiency, Machado-Joseph disease, Metabolic disorders, including Kniest dysplasia, Marfan syndrome, Movement disorders, Mowat-Wilson syndrome, cystic fibrosis, Muenke syndrome, Multiple neurofibromatosis, Nance-Insley syndrome, Nance-Sweeney chondrodysplasia, Niemann-Pick disease, Noack syndrome (Pfeiffer syndrome), Osler-Weber-Rendu disease, Peutz-Jeghers syndrome, Polycystic kidney disease, polyostotic fibrous dysplasia (McCune-Albright syndrome), Peutz-Jeghers syndrome, Prader-Labhart-Willi syndrome, hemochromatosis, primary hyperuricemia syndrome (Lesch-Nyhan syndrome), primary pulmonary hypertension, primary senile degenerative dementia, prion disease, progeria (Hutchinson Gilford Progeria Syndrome), progressive chorea, chronic hereditary (Huntington) (Huntington's disease), progressive muscular atrophy, spinal muscular atrophy, propionic acidemia, protoporphyria, proximal myotonic dystrophy, pulmonary arterial hypertension, PXE (pseudoxanthoma elasticum), Rb (retinoblastoma), Recklinghausen disease (neurofibromatosis type I), Recurrent polyserositis, Retinal disorders, Retinoblastoma, Rett syndrome, RFALS type 3, Ricker syndrome, Riley-Day syndrome, Roussy-Levy syndrome, severe achondroplasia with developmental delay and acanthosis nigricans (SADDAN), Li-Fraumeni syndrome, sarcoma, breast, leukemia, and adrenal gland (SBLA) syndrome, sclerosis tuberose (tuberous sclerosis), SDAT, SED congenital (spondyloepiphyseal dysplasia congenita), SED Strudwick (spondyloepimetaphyseal dysplasia, Strudwick type), SEDc (spondyloepiphyseal dysplasia congenita) SEMD, Strudwick type (spondyloepimetaphyseal dysplasia, Strudwick type), Shprintzen syndrome, Skin pigmentation disorders, Smith-Lemli-Opitz syndrome, South-African genetic porphyria (variegate porphyria), infantile-onset ascending hereditary spastic paralysis, Speech and communication disorders, sphingolipidosis, Tay-Sachs disease, spinocerebellar ataxia, Stickler syndrome, stroke, androgen insensitivity syndrome, tetrahydrobiopterin deficiency, beta-thalassemia, Thyroid disease, Tomaculous neuropathy (hereditary neuropathy with liability to pressure palsies), Treacher Collins syndrome, Triplo X syndrome (triple X syndrome), Trisomy 21 (Down syndrome), Trisomy X, VHL syndrome (von Hippel-Lindau disease), Vision impairment and blindness (Alström syndrome), Vrolik disease, Waardenburg syndrome, Warburg Sjo Fledelius Syndrome, Weissenbacher-Zweymuller syndrome, Wolf-Hirschhorn syndrome, Wolff Periodic disease, Weissenbacher-Zweymuller syndrome and Xeroderma pigmentosum, among others.

The term "neoplasia" or "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Exemplary cancers which may be treated by the present compounds either alone or in combination with at least one additional anti-cancer agent include squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using compounds according to the present invention include, for example, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML.

Additional cancers which may be treated using the disclosed compounds according to the present invention include, for example, acute granulocytic leukemia, acute lymphocytic leukemia (ALL), acute myelogenous leukemia (AML), adenocarcinoma, adenosarcoma, adrenal cancer, adrenocortical carcinoma, anal cancer, anaplastic astrocytoma, angiosarcoma, appendix cancer, astrocytoma, Basal cell carcinoma, B-Cell lymphoma, bile duct cancer, bladder cancer, bone cancer, bone marrow cancer, bowel cancer, brain cancer, brain stem glioma, breast cancer, triple (estrogen, progesterone and HER-2) negative breast cancer, double negative breast cancer (two of estrogen, progesterone and HER-2 are negative), single negative (one of estrogen, progesterone and HER-2 is negative), estrogen-receptor positive, HER2-negative breast cancer, estrogen receptor-negative breast cancer, estrogen receptor positive breast cancer, metastatic breast cancer, luminal A breast cancer, luminal B breast cancer, Her2-negative breast cancer, HER2-positive or negative breast cancer, progesterone receptor-negative breast cancer, progesterone receptor-positive breast cancer, recurrent breast cancer, carcinoid tumors, cervical cancer, cholangiocarcinoma, chondrosarcoma, chronic lymphocytic leukemia (CLL), chronic myelogenous leukemia (CML), colon cancer, colorectal cancer, craniopharyngioma, cutaneous lymphoma, cutaneous melanoma, diffuse astrocytoma, ductal carcinoma in situ (DCIS), endometrial cancer, ependymoma, epithelioid sarcoma, esophageal cancer, ewing sarcoma, extrahepatic bile duct cancer, eye cancer, fallopian tube cancer, fibrosarcoma, gallbladder cancer, gastric cancer, gastrointestinal cancer, gastrointestinal carcinoid cancer, gastrointestinal stromal tumors (GIST), germ cell tumor glioblastoma multiforme (GBM), glioma, hairy cell leukemia, head and neck cancer, hemangioendothelioma, Hodgkin lymphoma, hypopharyngeal cancer, infiltrating ductal carcinoma (IDC), infiltrating lobular carcinoma (MC), inflammatory breast cancer (IBC), intestinal Cancer, intrahepatic bile duct cancer, invasive/infiltrating breast cancer, Islet cell cancer, jaw cancer, Kaposi sarcoma, kidney cancer, laryngeal cancer, leiomyosarcoma, leptomeningeal metastases, leukemia, lip cancer, liposarcoma, liver cancer, lobular carcinoma in situ, low-grade astrocytoma, lung cancer, lymph node cancer, lymphoma, male breast cancer, medullary carcinoma, medulloblastoma, melanoma, meningioma, Merkel cell carcinoma, mesenchymal chondrosarcoma, mesenchymous, mesothelioma metastatic breast cancer, metastatic melanoma metastatic squamous neck cancer, mixed gliomas, monodermal teratoma, mouth cancer mucinous carcinoma, mucosal melanoma, multiple myeloma, Mycosis Fungoides, myelodysplastic syndrome, nasal cavity cancer, nasopharyngeal cancer, neck cancer, neuroblastoma, neuroendocrine tumors (NETs), non-Hodgkin's lymphoma, non-small cell lung cancer (NSCLC), oat cell cancer, ocular cancer, ocular melanoma, oligodendroglioma, oral cancer, oral cavity cancer, oropharyngeal cancer, osteogenic sarcoma, osteosarcoma, ovarian cancer, ovarian epithelial cancer ovarian germ cell tumor, ovarian primary peritoneal carcinoma, ovarian sex cord stromal tumor, Paget's disease, pancreatic cancer, papillary carcinoma, paranasal sinus cancer, parathyroid cancer, pelvic cancer, penile cancer, peripheral nerve cancer, peritoneal cancer, pharyngeal cancer, pheochromocytoma, pilocytic astrocytoma, pineal region tumor, pineoblastoma, pituitary gland cancer, primary central nervous system (CNS) lymphoma, prostate cancer, rectal cancer, renal cell carcinoma, renal pelvis cancer, rhabdomyosarcoma, salivary gland cancer, soft tissue sarcoma, bone sarcoma, sarcoma, sinus cancer, skin cancer, small cell lung cancer (SCLC), small intestine cancer, spinal cancer, spinal column cancer, spinal cord cancer, squamous cell carcinoma, stomach cancer, synovial sarcoma, T-cell lymphoma, testicular cancer, throat cancer, thymoma/thymic carcinoma, thyroid cancer, tongue cancer, tonsil cancer, transitional cell cancer, tubal cancer, tubular carcinoma, undiagnosed cancer, ureteral cancer, urethral cancer, uterine adenocarcinoma, uterine cancer, uterine sarcoma, vaginal cancer, vulvar cancer, T-cell lineage acute lymphoblastic leukemia (T-ALL), T-cell lineage lymphoblastic lymphoma (T-LL), peripheral T-cell lymphoma, Adult T-cell leukemia, Pre-B ALL, Pre-B lymphomas, large B-cell lymphoma, Burkitts lymphoma, B-cell ALL, Philadelphia chromosome positive ALL, Philadelphia chromosome positive CML, juvenile myelomonocytic leukemia (JMML), acute promyelocytic leukemia (a subtype of AML), large granular lymphocytic leukemia, Adult T-cell chronic leukemia, diffuse large B cell lymphoma, follicular lymphoma; Mucosa-Associated Lymphatic Tissue lymphoma (MALT), small cell lymphocytic lymphoma, mediastinal large B cell lymphoma, nodal marginal zone B cell lymphoma (NMZL); splenic marginal zone lymphoma (SMZL); intravascular large B-cell lymphoma; primary effusion lymphoma; or lymphomatoid granulomatosis; B-cell prolymphocytic leukemia; splenic lymphoma/leukemia, unclassifiable, splenic diffuse red pulp small B-cell lymphoma; lymphoplasmacytic lymphoma; heavy chain diseases, for example, Alpha heavy chain disease, Gamma heavy chain disease, Mu heavy chain disease, plasma cell myeloma, solitary plasmacytoma of bone; extraosseous plasmacytoma; primary cutaneous follicle center lymphoma, T cell/histocyte rich large B-cell lymphoma, DLBCL associated with chronic inflammation; Epstein-Barr virus (EBV)+ DLBCL of the elderly; primary mediastinal (thymic) large B-cell lymphoma, primary cutaneous DLBCL, leg type, ALK+ large B-cell lymphoma, plasmablastic lymphoma; large B-cell lymphoma arising in HHV8-associated multicentric, Castleman disease; B-cell lymphoma, unclassifiable, with features intermediate between diffuse large B-cell lymphoma, or B-cell lymphoma, unclassifiable, with features intermediate between diffuse large B-cell lymphoma and classical Hodgkin lymphoma.

In one embodiment the cancer is NUT midline carcinoma.

In one embodiment the cancer is adenoid cystic carcinoma.

The term "bioactive agent" is used to describe an agent, other than a compound according to the present invention, which is used in combination with the present compounds as an agent with biological activity to assist in effecting an intended therapy, inhibition and/or prevention/prophylaxis for which the present compounds are used. Preferred bioactive agents for use herein include those agents which have pharmacological activity similar to that for which the present compounds are used or administered and include for example, anti-cancer agents, antiviral agents, especially including anti-HIV agents and anti-HCV agents, antimicrobial agents, antifungal agents, etc.

In one embodiment, a method is provided for treating multiple myeloma comprising administering to a patient an effective amount of a compound described herein, or a pharmaceutically acceptable salt, isotopic analog, or prodrug thereof, optionally in a pharmaceutically acceptable carrier to form a composition. In another embodiment, a compound described herein or a pharmaceutically acceptable salt, isotopic analog, or prodrug thereof, optionally in a pharmaceutically acceptable carrier to form a composition, for use in a method of treating multiple myeloma, wherein the method comprises administering the compound to a patient.

In one embodiment, a method is provided for managing the progression of multiple myeloma comprising administering to a patient an effective amount of a compound described herein, or a pharmaceutically acceptable salt, isotopic analog, or prodrug thereof, optionally in a pharmaceutically acceptable carrier to form a composition. In another embodiment, a compound described herein, or a pharmaceutically acceptable salt, isotopic analog, or prodrug thereof, optionally in a pharmaceutically acceptable carrier to form a composition, for use in a method of managing the progression of multiple myeloma, wherein the method comprises administering the compound to a patient.

In one embodiment, a method is provided for inducing a therapeutic response as assessed by the International Uniform Response Criteria (IURC) for Multiple Myeloma (described in Durie B. G. M; et al. "International uniform response criteria for multiple myeloma. *Leukemia* 2006, 10(10):1-7) in a patient having multiple myeloma comprising administering to the patient an effective amount of a compound described herein, or a pharmaceutically acceptable salt, isotopic analog, or prodrug thereof, optionally in a pharmaceutically acceptable carrier to form a composition.

In another embodiment, a method is provided to achieve a stringent complete response, complete response, or very good partial response, as assessed by the IURC for Multiple Myeloma in a patient having multiple myeloma comprising administering to the patient an effective amount of a compound described herein, or a pharmaceutically acceptable salt, isotopic analog, or prodrug thereof, optionally in a pharmaceutically acceptable carrier to form a composition.

In another embodiment, a method is provided to achieve an increase in overall survival, progression-free survival, event-free survival, time to process, or disease-free survival in a patient having multiple myeloma comprising administering to the patient an effective amount of a compound described herein, or a pharmaceutically acceptable salt, isotopic analog, or prodrug thereof, optionally in a pharmaceutically acceptable carrier to form a composition.

In another embodiment, a method is provided to achieve an increase in overall survival in a patient having multiple myeloma comprising administering to the patient an effective amount of a compound described herein, or a pharmaceutically acceptable salt, isotopic analog, or prodrug thereof, optionally in a pharmaceutically acceptable carrier to form a composition.

In another embodiment, a method is provided to achieve an increase in progression-free survival in a patient having multiple myeloma comprising administering to the patient an effective amount of a compound described herein, or a pharmaceutically acceptable salt, isotopic analog, or prodrug thereof, optionally in a pharmaceutically acceptable carrier to form a composition.

In another embodiment, a method is provided to achieve an increase in event-free survival in a patient having multiple myeloma comprising administering to the patient an effective amount of a compound described herein, or a pharmaceutically acceptable salt, isotopic analog, or prodrug thereof, optionally in a pharmaceutically acceptable carrier to form a composition.

In another embodiment, a method is provided to achieve an increase in time to progression in a patient having multiple myeloma comprising administering to the patient an effective amount of a compound described herein, or a pharmaceutically acceptable salt, isotopic analog, or prodrug thereof, optionally in a pharmaceutically acceptable carrier to form a composition.

In another embodiment, a method is provided to achieve an increase in disease-free survival in a patient having multiple myeloma comprising administering to the patient an effective amount of a compound described herein, or a pharmaceutically acceptable salt, isotopic analog, or prodrug thereof, optionally in a pharmaceutically acceptable carrier to form a composition.

Methods are also provided to treat patients who have been previously treated for multiple myeloma but are non-responsive to standard therapies in addition to those who have not been previously treated. Additional methods are provided to treat patients who have undergone surgery in an attempt to treat multiple myeloma in addition to those who have not undergone surgery. Methods are also provided to treat patients who have previously undergone transplant therapy in addition to those who have not.

The compounds described herein may be used in the treatment or management of multiple myeloma that is relapsed, refractory, or resistant. In some embodiments, the multiple myeloma is primary, secondary, tertiary, quadruply or quintuply relapsed. In one embodiment, the compounds described herein may be used to reduce, maintain, or eliminate minimal residual disease (MRD).

The types of multiple myeloma that may be treated with the compounds described herein include, but are not limited to: monoclonal gammopathy of undetermined significance (MGUS); low risk, intermediate risk, or high risk multiple myeloma; newly diagnosed multiple myeloma, including low risk, intermediate risk, or high risk newly diagnosed multiple myeloma); transplant eligible and transplant ineligible multiple myeloma; smoldering (indolent) multiple myeloma (including low risk, intermediate risk, or high risk smoldering multiple myeloma); active multiple myeloma; solitary plasmocytoma; plasma cell leukemia; central nervous system multiple myeloma; light chain myeloma; nonsecretory myeloma; Immunoglobulin D myeloma; and Immunoglobulin E myeloma.

In some embodiments, the compounds described herein may be used in the treatment or management of multiple myeloma characterized by genetic abnormalities, for example but not limited to: Cyclin D translocations (for example, t(11;14)(q13; q32); t(6;14)(p21;32); t(12;14)(p13; q32); or t(6;20);); MMSET translocations (for example t(4;14)(p16; q32); MAF translocations (for example t(14; 16)(q32; a32); t(20;22); t(16;22)(q11; q13); or t(14;20)(q32; q11); or other chromosome factors (for example deletion of 17p13 or chromosome 13; del(17/17p), nonhyperdiploidy, and gain (1q)).

In one embodiment, a method is provided for treating or managing multiple myeloma comprising administering to a patient an effective amount of a compound described herein, or a pharmaceutically acceptable salt, isotopic analog, or prodrug thereof, optionally in a pharmaceutically acceptable carrier to form a composition, as induction therapy.

In one embodiment, a method is provided for treating or managing multiple myeloma comprising administering to a patient an effective amount of a compound described herein, or a pharmaceutically acceptable salt, isotopic analog, or prodrug thereof, optionally in a pharmaceutically acceptable carrier to form a composition, as consolidation therapy.

In one embodiment, a method is provided for treating or managing multiple myeloma comprising administering to a patient an effective amount of a compound described herein, or a pharmaceutically acceptable salt, isotopic analog, or prodrug thereof, optionally in a pharmaceutically acceptable carrier to form a composition, as maintenance therapy.

In one embodiment, the multiple myeloma is plasma cell leukemia.

In one embodiment, the multiple myeloma is high risk multiple myeloma. In some embodiments, the high risk multiple myeloma is relapsed or refractory. In one embodiment, the high risk multiple myeloma has relapsed within 12 months of the first treatment. In another embodiment, the high risk multiple myeloma is characterized by genetic abnormalities, for example, one or more of del(17/17p) and t(14;16)(q32; q32). In some embodiments, the high risk multiple myeloma is relapsed or refractory to one, two or three previous treatments.

In one embodiment, the multiple myeloma has a p53 mutation. In one embodiment, the p53 mutation is a Q331 mutation. In one embodiment, the p53 mutation is a R273H mutation. In one embodiment, the p53 mutation is a K132 mutation. In one embodiment, the p53 mutation is a K132N mutation. In one embodiment, the p53 mutation is a R337 mutation. In one embodiment, the p53 mutation is a R337L mutation. In one embodiment, the p53 mutation is a W146 mutation. In one embodiment, the p53 mutation is a S261 mutation. In one embodiment, the p53 mutation is a S261T mutation. In one embodiment, the p53 mutation is a E286 mutation. In one embodiment, the p53 mutation is a E286K mutation. In one embodiment, the p53 mutation is a R175 mutation.

In one embodiment, the p53 mutation is a R175H mutation. In one embodiment, the p53 mutation is a E258 mutation. In one embodiment, the p53 mutation is a E258K mutation. In one embodiment, the p53 mutation is a A161 mutation. In one embodiment, the p53 mutation is a A161T mutation.

In one embodiment, the multiple myeloma has a homozygous deletion of p53. In one embodiment, the multiple myeloma has a homozygous deletion of wild-type p53. In one embodiment, the multiple myeloma has wild-type p53.

In one embodiment, the multiple myeloma shows activation of one or more oncogenic drivers. In one embodiment, the one or more oncogenic drivers are selected from the group consisting of C-MAF, MAFB, FGFR3, MMset, Cyclin D1, and Cyclin D. In one embodiment, the multiple myeloma shows activation of C-MAF. In one embodiment, the multiple myeloma shows activation of MAFB. In one embodiment, the multiple myeloma shows activation of FGFR3 and MMset. In one embodiment, the multiple myeloma shows activation of C-MAF, FGFR3, and MMset. In one embodiment, the multiple myeloma shows activation of Cyclin D1. In one embodiment, the multiple myeloma shows activation of MAFB and Cyclin D1. In one embodiment, the multiple myeloma shows activation of Cyclin D.

In one embodiment, the multiple myeloma has one or more chromosomal translocations. In one embodiment, the chromosomal translocation is t(14;16). In one embodiment, the chromosomal translocation is t(14;20). In one embodiment, the chromosomal translocation is t(4; 14). In one embodiment, the chromosomal translocations are t(4;14) and t(14;16). In one embodiment, the chromosomal translocation is t(11;14). In one embodiment, the chromosomal translocation is t(6;20). In one embodiment, the chromosomal translocation is t(20;22). In one embodiment, the chromosomal translocations are t(6;20) and t(20;22). In one embodiment, the chromosomal translocation is t(16;22). In one embodiment, the chromosomal translocations are t(14; 16) and t(16;22). In one embodiment, the chromosomal translocations are t(14;20) and t(11;14).

In one embodiment, the multiple myeloma has a Q331 p53 mutation, activation of C-MAF, and a chromosomal translocation at t(14; 16). In one embodiment, the multiple myeloma has homozygous deletion of p53, activation of C-MAF, and a chromosomal translocation at t(14; 16). In one embodiment, the multiple myeloma has a K132N p53 mutation, activation of MAFB, and a chromosomal translocation at t(14;20). In one embodiment, the multiple myeloma has wild type p53, activation of FGFR3 and MMset, and a chromosomal translocation at t(4; 14). In one embodiment, the multiple myeloma has wild type p53, activation of C-MAF, and a chromosomal translocation at t(14;16). In one embodiment, the multiple myeloma has homozygous deletion of p53, activation of FGFR3, MMset, and C-MAF, and chromosomal translocations at t(4;14) and t(14;16). In one embodiment, the multiple myeloma has homozygous deletion of p53, activation of Cyclin D1, and a chromosomal translocation at t(11;14). In one embodiment, the multiple myeloma has a R337L p53 mutation, activation of Cyclin D1, and a chromosomal translocation at t(11;14). In one embodiment, the multiple myeloma has a W146 p53 mutation, activation of FGFR3 and MMset, and a chromosomal translocation at t(4; 14). In one embodiment, the multiple myeloma has a S261T p53 mutation, activation of MAFB, and chromosomal translocations at t(6;20) and t(20;22). In one embodiment, the multiple myeloma has a E286K p53 mutation, by activation of FGFR3 and MMset, and a chromosomal translocation at t(4; 14). In one embodiment, the multiple myeloma has a R175H p53 mutation, activation of FGFR3 and MMset, and a chromosomal translocation at t(4; 14). In one embodiment, the multiple myeloma has a E258K p53 mutation, activation of C-MAF, and chromosomal translocations at t(14;16) and t(16;22). In one embodiment, the multiple myeloma has wild type p53, activation of MAFB and Cyclin D1, and chromosomal translocations at t(14;20) and t(11;14). In one embodiment, the multiple myeloma has a A161T p53 mutation, activation of Cyclin D, and a chromosomal translocation at t(11;14).

In some embodiments, the multiple myeloma is transplant eligible newly diagnosed multiple myeloma. In other embodiments, the multiple myeloma is transplant ineligible newly diagnosed multiple myeloma.

In some embodiments, the multiple myeloma shows early progression (for example less than 12 months) following initial treatment. In other embodiments, the multiple myeloma shows early progression (for example less than 12 months) following autologous stem cell transplant. In another embodiment, the multiple myeloma is refractory to lenalidomide. In another embodiment, the multiple myeloma is refractory to pomalidomide. In some such embodiments, the multiple myeloma is predicted to be refractory to pomalidomide (for example, by molecular characterization). In another embodiment, the multiple myeloma is relapsed or refractory to 3 or more treatments and was exposed to a proteasome inhibitor (for example, bortezomib, carfilzomib, ixazomib, oprozomib, or marizomib) and an immunomodulatory compound (for example thalidomide, lenalidomide, pomalidomide, iberdomide, or avadomide), or double refractory to a proteasome inhibitor and an immunomodulatory compound. In still other embodiments, the multiple myeloma is relapsed or refractory to 3 or more prior therapies, including for example, a CD38 monoclonal antibody (CD38 mAb, for example, daratumumab or isatuximab), a proteasome inhibitor (for example, bortezomib, carfilzomib, ixazomib, or marizomib), and an immunomodulatory compound (for example thalidomide, lenalidomide, pomalidomide, iberdomide, or avadomide) or double refractory to a proteasome inhibitor or immunomodulatory compound and a CD38 mAb. In still other embodiments, the multiple myeloma is triple refractory, for example, the multiple myeloma is refractory to a proteasome inhibitor (for example, bortezomib, carfilzomib, ixazomib, oprozomib or marizomib), an immunomodulatory compound (for example thalidomide, lenalidomide, pomalidomide, iberdomide, or avadomide), and one other active agent, as described herein.

In one embodiment, a method is provided for treating or managing relapsed or refractory multiple myeloma in patients with impaired renal function or a symptom thereof comprising administering to a patient an effective amount of a compound described herein, or a pharmaceutically acceptable salt, isotopic analog, or prodrug thereof, optionally in a pharmaceutically acceptable carrier to form a composition.

In another embodiment, a method is provided for treating or managing relapsed or refractory multiple myeloma in frail patients comprising administering to a patient an effective amount of a compound described herein, or a pharmaceutically acceptable salt, isotopic analog, or prodrug thereof, optionally in a pharmaceutically acceptable carrier to form a composition, wherein the frail patient is characterized by ineligibility for induction therapy or intolerance to dexamethasone treatment. In other embodiments, the frail patient is elderly, for example, older than 65 years old.

In another embodiment, a method is provided for treating or managing fourth line relapsed or refractory multiple myeloma comprising administering to a patient an effective amount of a compound described herein, or a pharmaceutically acceptable salt, isotopic analog, or prodrug thereof, optionally in a pharmaceutically acceptable carrier to form a composition.

In another embodiment, a method is provided for treating or managing newly diagnosed, transplant-ineligible multiple myeloma comprising administering to a patient an effective amount of a compound described herein, or a pharmaceutically acceptable salt, isotopic analog, or prodrug thereof, optionally in a pharmaceutically acceptable carrier to form a composition.

In another embodiment, a method is provided for treating or managing newly diagnosed, transplant-ineligible multiple myeloma comprising administering to a patient an effective amount of a compound described herein, or a pharmaceutically acceptable salt, isotopic analog, or prodrug thereof, optionally in a pharmaceutically acceptable carrier to form a composition, as maintenance therapy after another therapy or transplant.

In another embodiment, a method is provided for treating or managing high risk multiple myeloma that is relapsed or refractory to one, two, or three previous treatments comprising administering to a patient an effective amount of a compound described herein, or a pharmaceutically acceptable salt, isotopic analog, or prodrug thereof, optionally in a pharmaceutically acceptable carrier to form a composition.

In some embodiments, the patient to be treated by one of the compounds described herein has not be treated with multiple myeloma therapy prior to administration. In some embodiments, the patient to be treated by one of the compounds described herein has been treated by multiple myeloma therapy prior to administration. In some embodiments, the patient to be treated by one of the compounds described herein has developed drug resistant to the multiple myeloma therapy.

In some embodiments, the patient to be treated by one of the compounds described herein has developed resistance to one, two, or three multiple myeloma therapies, wherein the therapies are selected from a CD38 antibody (CD38 mAB, for example, daratumumab or isatuximab), a proteasome inhibitor (for example, bortezomib, carfilzomib, ixazomib, or marizomib), and an immunomodulatory compound (for example thalidomide, lenalidomide, pomalidomide, iberdomide, or avodomide).

The compounds described herein can be used to treat a patient regardless of patient's age. In some embodiments, the subject is 18 years or older. In other embodiments, the subject is more than 18, 25, 35, 40, 45, 50, 55, 60, 65, or 70 years old. In other embodiments, the patient is less than 65 years old. In other embodiments, the patient is more than 65 years old. In one embodiment, the patient is an elderly multiple myeloma patient, such as a patient older than 65 years old. In one embodiment, the patient is an elderly multiple myeloma patient, such as a patient older than 75 years old.

V. Combination Therapy

The compounds of Formula Ia, Formula Ib, Formula II, Formula IIIa, Formula IIIb, Formula IV, Formula V, Formula VI, Formula VII, Formula VIII, Formula IX, Formula X, Formula XI, Formula XII, Formula XIII, Formula XIV, Formula XV, Formula XIV-a to XIV-x, or Formula XV-a to XV-t can be used in an effective amount alone or in combination to treat a host such as a human with a disorder as described herein.

The disclosed compounds described herein can be used in an effective amount alone or in combination with another compound of the present invention or another bioactive agent to treat a host such as a human with a disorder as described herein.

The term "bioactive agent" is used to describe an agent, other than the selected compound according to the present invention, which can be used in combination or alternation with a compound of the present invention to achieve a desired result of therapy. In one embodiment, the compound of the present invention and the bioactive agent are administered in a manner that they are active in vivo during overlapping time periods, for example, have time-period overlapping Cmax, Tmax, AUC or other pharmacokinetic parameter. In another embodiment, the compound of the present invention and the bioactive agent are administered to a host in need thereof that do not have overlapping pharmacokinetic parameter, however, one has a therapeutic impact on the therapeutic efficacy of the other.

In one aspect of this embodiment, the bioactive agent is an immune modulator, including but not limited to a checkpoint inhibitor, including as non-limiting examples, a PD-1 inhibitor, PD-L1 inhibitor, PD-L2 inhibitor, CTLA-4 inhibitor, LAG-3 inhibitor, TIM-3 inhibitor, V-domain Ig suppressor of T-cell activation (VISTA) inhibitors, small molecule, peptide, nucleotide, or other inhibitor. In certain aspects, the immune modulator is an antibody, such as a monoclonal antibody.

VI. Pharmaceutical Compositions

The compounds of Formula Ia, Formula Ib, Formula II, Formula IIIa, Formula IIIb, Formula IV, Formula V, Formula VI, Formula VII, Formula VIII, Formula IX, Formula X, Formula XI, Formula XII, Formula XIII, Formula XIV, Formula XV, Formula XIV-a to XIV-x, or Formula XV-a to XV-t as disclosed herein can be administered as the neat chemical, but are more typically administered as a pharmaceutical composition, that includes an effective amount for a host, typically a human, in need of such treatment for any of the disorders described herein. Accordingly, the disclosure provides pharmaceutical compositions comprising an effective amount of compound or pharmaceutically acceptable salt together with at least one pharmaceutically acceptable carrier for any of the uses described herein. The pharmaceutical composition may contain a compound or salt as the only active agent, or, in an alternative embodiment, the compound and at least one additional active agent.

In certain embodiments the pharmaceutical composition is in a dosage form that contains from about 0.1 mg to about 2000 mg, from about 10 mg to about 1000 mg, from about 100 mg to about 800 mg, or from about 200 mg to about 600 mg of the active compound and optionally from about 0.1 mg to about 2000 mg, from about 10 mg to about 1000 mg, from about 100 mg to about 800 mg, or from about 200 mg to about 600 mg of an additional active agent in a unit dosage form. Examples are dosage forms with at least 0.1, 1, 5, 10, 25, 50, 100, 200, 250, 300, 400, 500, 600, 700, or 750 mg of active compound, or its salt. The pharmaceutical composition may also include a molar ratio of the active compound and an additional active agent. For example the pharmaceutical composition may contain a molar ratio of about 0.5:1, about 1:1, about 2:1, about 3:1 or from about 1.5:1 to about 4:1 of an anti-inflammatory or immunosuppressing agent. Compounds disclosed herein may be administered orally, topically, parenterally, by inhalation or spray, sublingually, via implant, including ocular implant, transdermally, via buccal administration, rectally, as an ophthalmic solution, injection, including ocular injection, intraveneous, intra-aortal, intracranial, subdermal, intraperitioneal, subcutaneous, transnasal, sublingual, or rectal or by other means, in dosage unit formulations containing conventional pharmaceutically acceptable carriers. For ocular delivery, the compound can be administered, as desired, for example, via intravitreal, intrastromal, intracameral, sub-tenon, subretinal, retro-bulbar, peribulbar, suprachorodial, conjunctival, subconjunctival, episcleral, periocular, transcleral, retrobulbar, posterior juxtascleral, circumcorneal, or tear duct injections, or through a mucus, mucin, or a mucosal barrier, in an immediate or controlled release fashion or via an ocular device.

The pharmaceutical composition may be formulated as any pharmaceutically useful form, e.g., as an aerosol, a cream, a gel, a pill, an injection or infusion solution, a capsule, a tablet, a syrup, a transdermal patch, a subcutaneous patch, a dry powder, an inhalation formulation, in a medical device, suppository, buccal, or sublingual formulation, parenteral formulation, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, di sintegrants, emulsifiers, flavorants, glidents, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compound of the present invention.

The pharmaceutical compositions/combinations can be formulated for oral administration. These compositions can contain any amount of active compound that achieves the desired result, for example between 0.1 and 99 weight % (wt. %) of the compound and usually at least about 5 wt. % of the compound. Some embodiments contain from about 25 wt. % to about 50 wt. % or from about 5 wt. % to about 75 wt. % of the compound.

Formulations suitable for rectal administration are typically presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. In one embodiment, microneedle patches or devices are provided for delivery of drugs across or into biological tissue, particularly the skin. The microneedle patches or devices permit drug delivery at clinically relevant rates across or into skin or other tissue barriers, with minimal or no damage, pain, or irritation to the tissue.

Formulations suitable for administration to the lungs can be delivered by a wide range of passive breath driven and active power driven single/-multiple dose dry powder inhalers (DPI). The devices most commonly used for respiratory delivery include nebulizers, metered-dose inhalers, and dry powder inhalers. Several types of nebulizers are available, including jet nebulizers, ultrasonic nebulizers, and vibrating mesh nebulizers. Selection of a suitable lung delivery device depends on parameters, such as nature of the drug and its formulation, the site of action, and pathophysiology of the lung.

The compounds described herein and the pharmaceutically acceptable salts can be used as therapeutically active substances, e.g. in the form of pharmaceutical preparations. The pharmaceutical preparations can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds described herein and the pharmaceutically acceptable salts thereof can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of the present invention or a pharmaceutically acceptable salt thereof and a therapeutically inert carrier are also provided by the present invention, as is a process for their production, which comprises bringing one or more compounds of Formula I and/or pharmaceutically acceptable salts thereof and, if desired, one or more other therapeutically valuable substances into a galenical administration form together with one or more therapeutically inert carriers.

The dosage can vary within wide limits and will, of course, have to be adjusted to the individual requirements in each particular case. In the case of oral administration the dosage for adults can vary from about 0.01 mg to about 1000 mg per day of a compound of general Formula VII, Formula XIII, or of the corresponding amount of a pharmaceutically acceptable salt thereof. The daily dosage may be administered as single dose or in divided doses and, in addition, the upper limit can also be exceeded when this is found to be indicated.

The following examples illustrate the present invention without limiting it, but serve merely as representative thereof. The pharmaceutical preparations conveniently contain about 1-500 mg, particularly 1-100 mg, of a compound of Formula XIV. Examples of compositions according to the invention are:

EXAMPLE A

Tablets of the following composition are manufactured in the usual manner:

TABLE 1

| possible tablet composition | | | | |
|---|---|---|---|---|
| | mg/tablet | | | |
| ingredient | 5 | 25 | 100 | 500 |
| Compound of Formula VII or XIII | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure

1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

EXAMPLE B-1

Capsules of the following composition are manufactured:

TABLE 2

| possible capsule ingredient composition | | | | |
|---|---|---|---|---|
| | mg/capsule | | | |
| ingredient | 5 | 25 | 100 | 500 |
| Compound of Formula VII or XIII | 5 | 25 | 100 | 500 |
| Hydrous Lactose | 159 | 123 | 148 | — |
| Corn Starch | 25 | 35 | 40 | 70 |

TABLE 2-continued

| possible capsule ingredient composition | | | | |
|---|---|---|---|---|
| | mg/capsule | | | |
| ingredient | 5 | 25 | 100 | 500 |
| Talk | 10 | 15 | 10 | 25 |
| Magnesium Stearate | 1 | 2 | 2 | 5 |
| Total | 200 | 200 | 300 | 600 |

Manufacturing Procedure

1. Mix ingredients 1, 2 and 3 in a suitable mixer for 30 minutes.
2. Add ingredients 4 and 5 and mix for 3 minutes.
3. Fill into a suitable capsule.

The compound of Formula VII or XIII, lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

EXAMPLE B-2

Soft Gelatin Capsules of the following composition are manufactured:

TABLE 3

| possible soft gelatin capsule ingredient composition | |
|---|---|
| ingredient | mg/capsule |
| Compound of Formula VII or XIII | 5 |
| Yellow wax | 8 |
| Hydrogenated Soya bean oil | 8 |
| Partially hydrogenated plant oils | 34 |
| Soya bean oil | 110 |
| Total | 165 |

TABLE 4

| possible soft gelatin capsule composition | |
|---|---|
| ingredient | mg/capsule |
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure

The compound of Formula VII or XIII is dissolved in a warm melting of the other ingredients and the mixture is filled into soft gelatin capsules of appropriate size. The filled soft gelatin capsules are treated according to the usual procedures.

EXAMPLE C

Suppositories of the following composition are manufactured:

TABLE 5

| possible suppository composition | |
| --- | --- |
| ingredient | mg/supp. |
| Compound of Formula VII or XIII | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of Formula VII or XIII is added thereto and stirred until it has dispersed completely. The mixture is poured into suppository molds of suitable size, left to cool; the suppositories are then removed from the molds and packed individually in wax paper or metal foil.

EXAMPLE D

Injection solutions of the following composition are manufactured:

TABLE 6

| possible injection solution composition | |
| --- | --- |
| ingredient | mg/injection solution. |
| Compound of Formula VII or XIII | 3 |
| Polyethylene Glycol 400 | 150 |
| acetic acid | q.s. ad pH 5.0 |
| water for injection solutions | ad 1.0 ml |

Manufacturing Procedure

The compound of Formula VII or XIII is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

EXAMPLE E

Sachets of the following composition are manufactured:

TABLE 7

| possible sachet composition | |
| --- | --- |
| ingredient | mg/sachet |
| Compound of Formula VII or XIII | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesium stearate | 10 |
| Flavoring additives | 1 |
| Total | 2500 |

Manufacturing Procedure

The compound of Formula VII or XIII is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

VII. Use of Compounds

The compounds of Formula Ia, Formula Ib, Formula II, Formula IIIa, Formula IIIb, Formula IV, Formula V, Formula VI, Formula VII, Formula VIII, Formula IX, Formula X, Formula XI, Formula XII, Formula XIII, Formula XIV, Formula XV, Formula XIV-a to XIV-x, or Formula XV-a to XV-t of the present invention bind to the ubiquitously expressed E3 ligase protein cereblon (CRBN) and alter the substrate specificity of the CRBN E3 ubiquitin ligase complex, resulting in breakdown of intrinsic downstream proteins. The present compounds are thus useful for the treatment or prophylaxis of various cancers.

In one aspect, the present invention provides compounds Formula Ia, Formula Ib, Formula II, Formula IIIa, Formula IIIb, Formula IV, Formula V, Formula VI, Formula VII, Formula VIII, Formula IX, Formula X, Formula XI, Formula XII, Formula XIII, Formula XIV, Formula XV, Formula XIV-a to XIV-x, or Formula XV-a to XV-t as described herein for use as therapeutically active substance.

In a further aspect, the present invention provides compounds of Formula Ia, Formula Ib, Formula II, Formula IIIa, Formula IIIb, Formula IV, Formula V, Formula VI, Formula VII, Formula VIII, Formula IX, Formula X, Formula XI, Formula XII, Formula XIII, Formula XIV, Formula XV, Formula XIV-a to XIV-x, or Formula XV-a to XV-t as defined herein, for use in the treatment or prophylaxis of cancer.

In a further aspect, the present invention provides the use of a compound of Formula Ia, Formula Ib, Formula II, Formula IIIa, Formula IIIb, Formula IV, Formula V, Formula VI, Formula VII, Formula VIII, Formula IX, Formula X, Formula XI, Formula XII, Formula XIII, Formula XIV, Formula XV, Formula XIV-a to XIV-x, or Formula XV-a to XV-t as defined herein for the treatment or prophylaxis of cancer.

In a further aspect, the present invention provides a method of treating or preventing cancer, comprising administering a therapeutically effective amount of a compound of Formula Ia, Formula Ib, Formula II, Formula IIIa, Formula IIIb, Formula IV, Formula V, Formula VI, Formula VII, Formula VIII, Formula IX, Formula X, Formula XI, Formula XII, Formula XIII, Formula XIV, Formula XV, Formula XIV-a to XIV-x, or Formula XV-a to XV-t as defined herein to a subject.

In a further aspect, the present invention provides the use of a compound of Formula Ia, Formula Ib, Formula II, Formula IIIa, Formula IIIb, Formula IV, Formula V, Formula VI, Formula VII, Formula VIII, Formula IX, Formula X, Formula XI, Formula XII, Formula XIII, Formula XIV, Formula XV Formula XIV-a to XIV-x, or Formula XV-a to XV-t as defined herein for the manufacture of a medicament for the treatment or prophylaxis of cancer.

The compounds of Formula Ia, Formula Ib, Formula II, Formula IIIa, Formula IIIb, Formula IV, Formula V, Formula VI, Formula VII, Formula VIII, Formula IX, Formula X, Formula XI, Formula XII, Formula XIII, Formula XIV, Formula XV, Formula XIV-a to XIV-x, or Formula XV-a to XV-t may also be used to prepare bifunctional degrader compounds by linking them to a protein-targeting moiety that binds to a target protein or to a target polypeptide, in analogy to the bifunctional compounds which have been described e.g. in WO2013020557, WO2013063560, WO 2013106643, WO2015160845, WO2016011906, WO2016105518, WO2017007612, WO2017024318, and WO2017117473.

GENERAL SYNTHETIC EXAMPLES

The preparation of compounds of the present invention may be carried out in sequential or convergent synthetic routes. Syntheses of the compounds of the invention are shown in the following schemes in the description of the specific examples. The skills required for carrying out the reactions and purification of the resulting products are known to those skilled in the art. The substituents and indices used in the following description of the processes have the significance given herein before unless indicated to the contrary.

In more detail, the compounds of the invention can be manufactured by the methods given below, by the methods given in the examples or by analogous methods. Appropriate reaction conditions for the individual reaction steps are known to a person skilled in the art. The reaction sequence is not limited to the one displayed in the schemes below, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

Step A: Formation of the glutarimide ring of 3 can be accomplished by reaction between (2-amino-2-oxo-ethyl)-phosphonium salt 1 (CAS 25361-54-0) and ethyl acrylate 2 in the presence of an aqueous base such as lithium hydroxide, sodium hydroxide or potassium hydroxide in protic organic solvents such as methanol or ethanol. Preferred conditions are NaOH in methanol at room temperature for 16 hours.

Step B: Conjugated olefin 4 can be prepared by Wittig-Horner-Emmons reaction of phosphanylidene 3 with paraformaldehyde. The reaction is carried out at elevated temperatures in halogenated solvents such as dichloromethane or 1,2-dichloroethane. Preferred conditions are dichloroethane at 80° C. for 30 minutes.

Step C: Formation of the pyrrolidine ring of 6 can be accomplished by a 1,3-cycloaddition reaction between dipolarophile 4 and an azomethine ylide which is generated in situ from precursor N-(methoxymethyl)-1-phenyl-N-(trimethylsilylmethyl)methanamine 5 (CAS 93102-05-7) by treatment with an acid catalyst such as trifluoracetic acid or triflic acid, according to the method of Terao et al. *Chem. Pharm. Bull.* 1985, 33, 2762. The reaction is carried out in halogenated solvents such as dichloromethane or 1,2-dichloroethane. Preferred conditions are trifluoracetic acid in dichloromethane at room temperature for 16 hours.

Step D: Removal of the benzyl protecting group of 6 to afford secondary amine 7 can be accomplished by a two-step procedure according to the method of Olofson et al. *J. Org. Chem.* 1984, 49, 2081. The first step involves treatment of tertiary amine 6 with 1-chloroethyl chloroformate (CAS 50893-53-3). The reaction is carried out in halogenated solvents such as dichloromethane or 1,2-dichloroethane at elevated temperature. In a second step, the carbamate compound resulting from the first step is thermally decomposed by heating in an alcoholic solvent such as methanol or ethanol at elevated temperature. Preferred conditions are dichloromethane at 80° C. for 12 hours for the first step, and methanol at 65° C. for 2 hours for the second step.

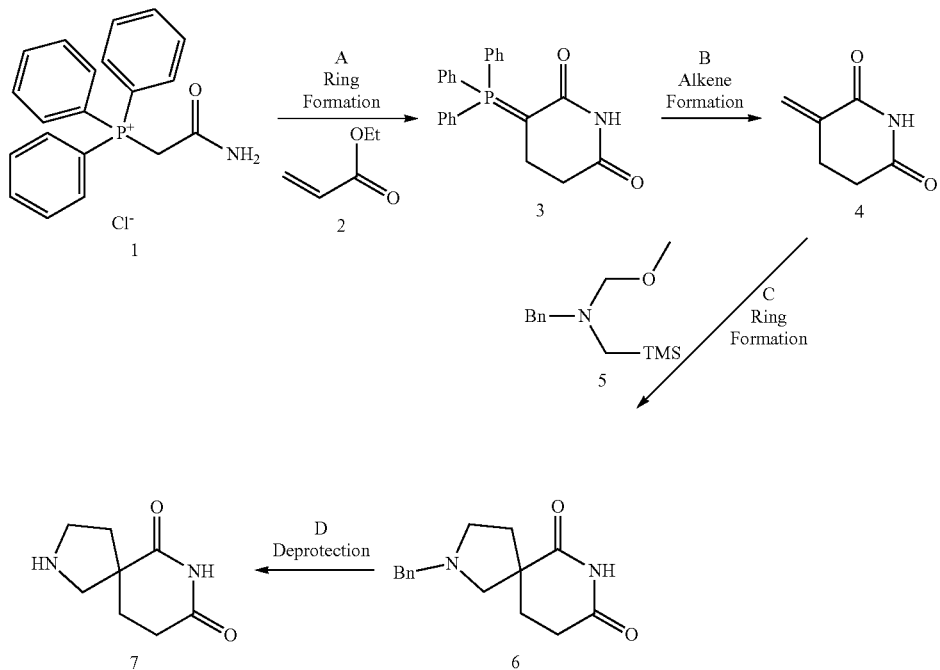

General Scheme 2

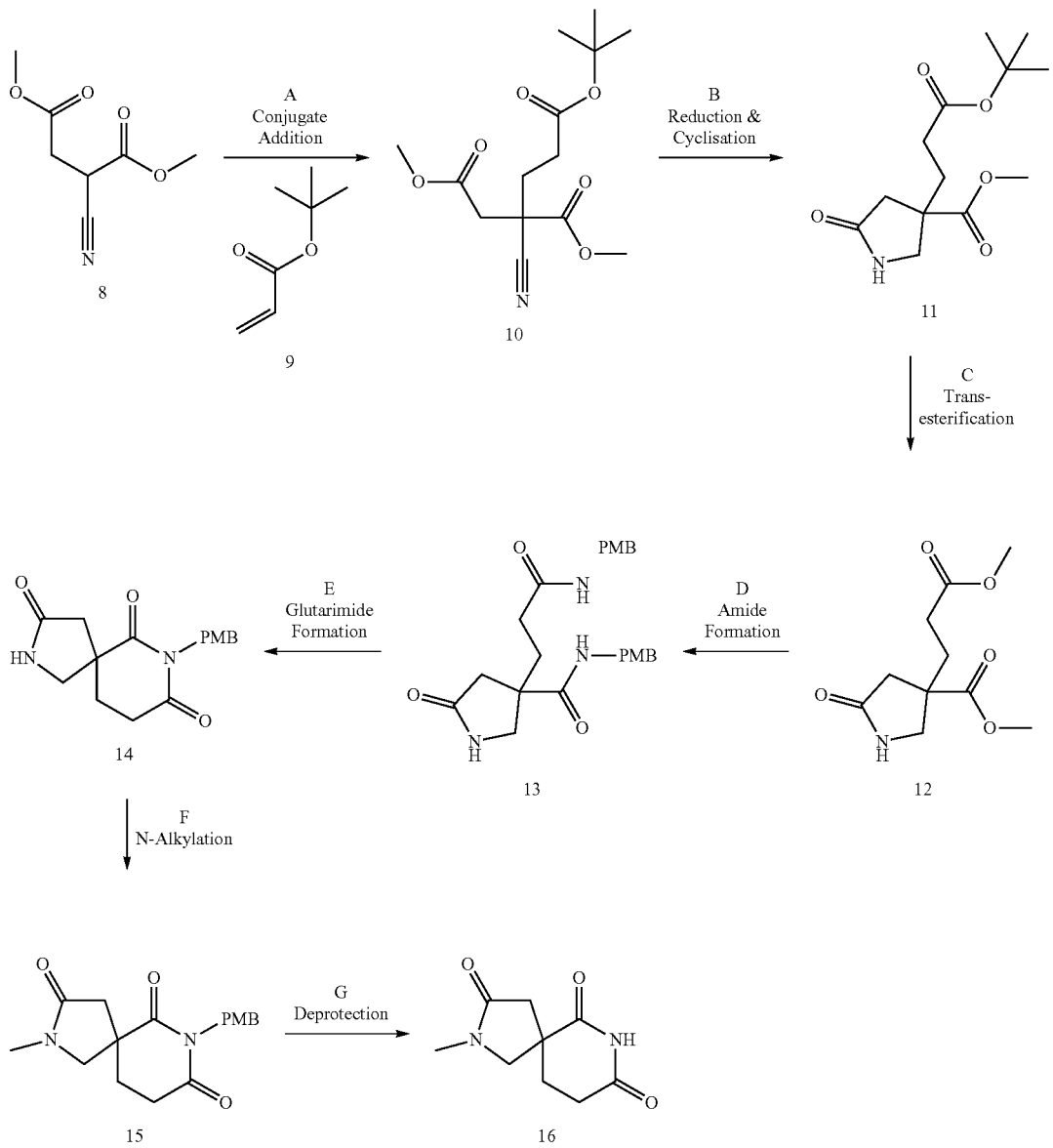

Step A: Nitrile ester 10 can be prepared by conjugate addition of the enolate of nitrile ester 8 (CAS 6283-71-2) to unsaturated ester 9 (CAS 1663-39-4). The enolate of 8 can be pre-formed in situ by treatment of 8 with a tertiary amine base such as triethylamine or N,N-diisopropylethylamine prior to addition of unsaturated ester 9 to the reaction mixture. Preferred conditions for enolisation are triethylamine in a mixture of methanol and water at 0-5° C. for 30 minutes. Preferred conditions for the conjugate addition are 0-5° C. for 90 minutes followed by warming to room temperature for 2 hours.

Step B: Lactam 11 can be prepared by selective reduction of the nitrile group of nitrile ester 10 to afford the corresponding primary amine which can then be cyclised in situ to afford lactam 11. The selective reduction of the nitrile group in the presence of the ester groups can be accomplished by catalytic hydrogenation. Preferred conditions are treatment with Raney nickel as hydrogenation catalyst under a hydrogen atmosphere at elevated pressure, preferably at a pressure of 40 atm, in methanol at room temperature for 16 hours.

Step C: Transesterification of mixed methyl/tent-butyl ester 11 to all methyl ester 12 can be accomplished by reaction with methanol in the presence of an acid catalyst such as hydrochloric acid, sulphuric acid or p-toluenesulphonic acid. The reaction is preferably carried out using neat methanol as solvent. Preferred conditions are hydrochloric acid in methanol at 60° C. for 2 hours.

Step D: Conversion of di-ester 12 to di-amide 13 can be accomplished by reaction with 4-methoxybenzylamine at elevated temperature and pressure. The reaction is preferably carried out using neat methoxybenzylamine as solvent. Preferred conditions are stirring the reaction mixture at 200° C. in a sealed vessel under microwave irradiation for 2 hours.

Step E: Formation of the glutarimide ring of 14 can be accomplished by cyclisation of di-amide 13 in the presence of an acid such as p-toluenesulphonic acid in an aromatic solvent such as benzene, toluene or xylene at elevated temperature. Preferred conditions are p-toluenesulphonic acid in xylene at 145° C. for 2 hours.

Step F: N-alkylation of lactam 14 can be accomplished by treatment with an alkyl halide, such as an alkyl bromide or an alkyl iodide, in the presence of a base such as sodium hydride or potassium hydride in an aprotic organic solvent such as tetrahydrofuran, dioxane, toluene or N,N-dimethylformamide at elevated temperature. In the case where the alkyl halide reagent is methyl iodide, preferred conditions are sodium hydride in toluene at 60° C. for 1 hour.

Step G: Removal of the 4-methoxybenzyl protecting group of 15 to afford glutarimide 16 can be accomplished by treatment with an oxidising agent such as ammonium cerium(IV) nitrate in a mixture of water and a miscible polar organic solvent such as acetonitrile or dioxane. Preferred conditions are ammonium cerium(IV) nitrate in aqueous acetonitrile at room temperature for 1 hour.

General Scheme 3

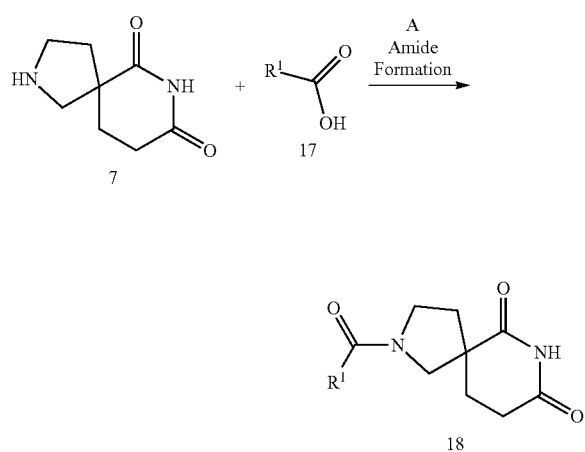

The substituents are as described herein and in the claims.

Step A: Amide bond formation can be accomplished by a coupling reaction between a carboxylic acid 17 and pyrrolidine-glutarimide 7 in the presence of a coupling reagent such as DCC, EDC, TBTU or HATU in the presence of an organic base such as triethylamine, N,N-diisopropylethylamine or N-methylmorpholine in halogenated solvents such as dichloromethane or 1,2-dichloroethane or ethereal solvents such as diethyl ether, dioxane, THF, DME or TBME or polar non-protic organic solvent such as N,N-dimethylformamide at room temperature or at elevated temperatures for 2-18 hours. Preferred conditions are HATU with N,N-diisopropylethylamine in N,N-dimethylformamide at room temperature for 3 hours.

General Scheme 4

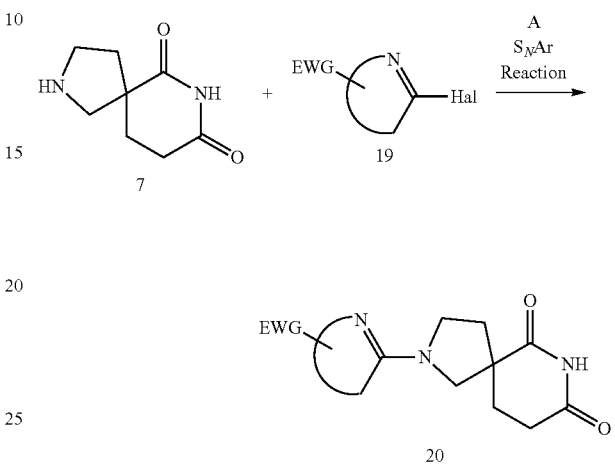

The substituents are as described in the claims, EWG is an electron-withdrawing group such as —CN, —CO$_2$R, —SO$_2$R or —NO$_2$ and hal is F or Cl.

Step A: Nucleophilic aromatic substitution (S$_N$Ar) reaction can be accomplished by reaction of pyrrolidine-glutarimide 7 with an electron-deficient mono- or fused bicyclic heteroaromatic compound 19 bearing a suitable leaving group such as fluorine or chlorine, in the presence of an organic base such as triethylamine, N,N-diisopropylethylamine or N-methylmorpholine in polar non-protic organic solvent such as N,N-dimethylformamide or N-methylpyrrolidone at elevated temperature.

Examples of suitable electron-deficient heteroaromatic compounds 19 bearing a suitable leaving group include, but are not limited to, methyl 6-chloronicotinate (CAS 73781-91-6), 2-chlorothiazolo[4,5-b]pyridine (CAS 152170-30-4), 1-fluoro-4-nitrobenzene (CAS 350-46-9), 2-chloro-5-nitro-1H-benzo[d]imidazole (CAS 5955-72-6), 2-chlorobenzo[d]thiazole (CAS 615-20-3), methyl 2-chloro-1H-benzo[d]imidazole-7-carboxylate (CAS 1171129-05-7), methyl 2-chloropyrimidine-4-carboxylate (CAS 149849-94-5), 2-chloroquinoline (CAS 612-62-4), 2-chlorobenzo[d]thiazol-6-amine (CAS 2406-90-8), 2-chlorooxazolo[4,5-b]pyridine (CAS 325976-45-2), 2-chloro-1-methyl-1H-benzo[d]imidazole (CAS 1849-02-1), 2-chlorothiazolo[4,5-c]pyridine (CAS 884860-63-3), methyl 2-chlorobenzo[d]thiazole-6-carboxylate (CAS 90792-69-1), methyl 2-chlorothiazole-4-carboxylate (CAS 850429-61-7), methyl 2-chlorothiazole-5-carboxylate (CAS 72605-86-8), tent-butyl 6-chloronicotinate (CAS 115309-57-4), 2-chloro-5-nitropyridine (CAS 4548-45-2), or methyl 6-chloro-2-picolinic acid methyl ester (CAS 6636-55-1). Preferred conditions are N,N-diisopropylethylamine in N,N-dimethylformamide at 110° C. for 24 hours.

General Scheme 5

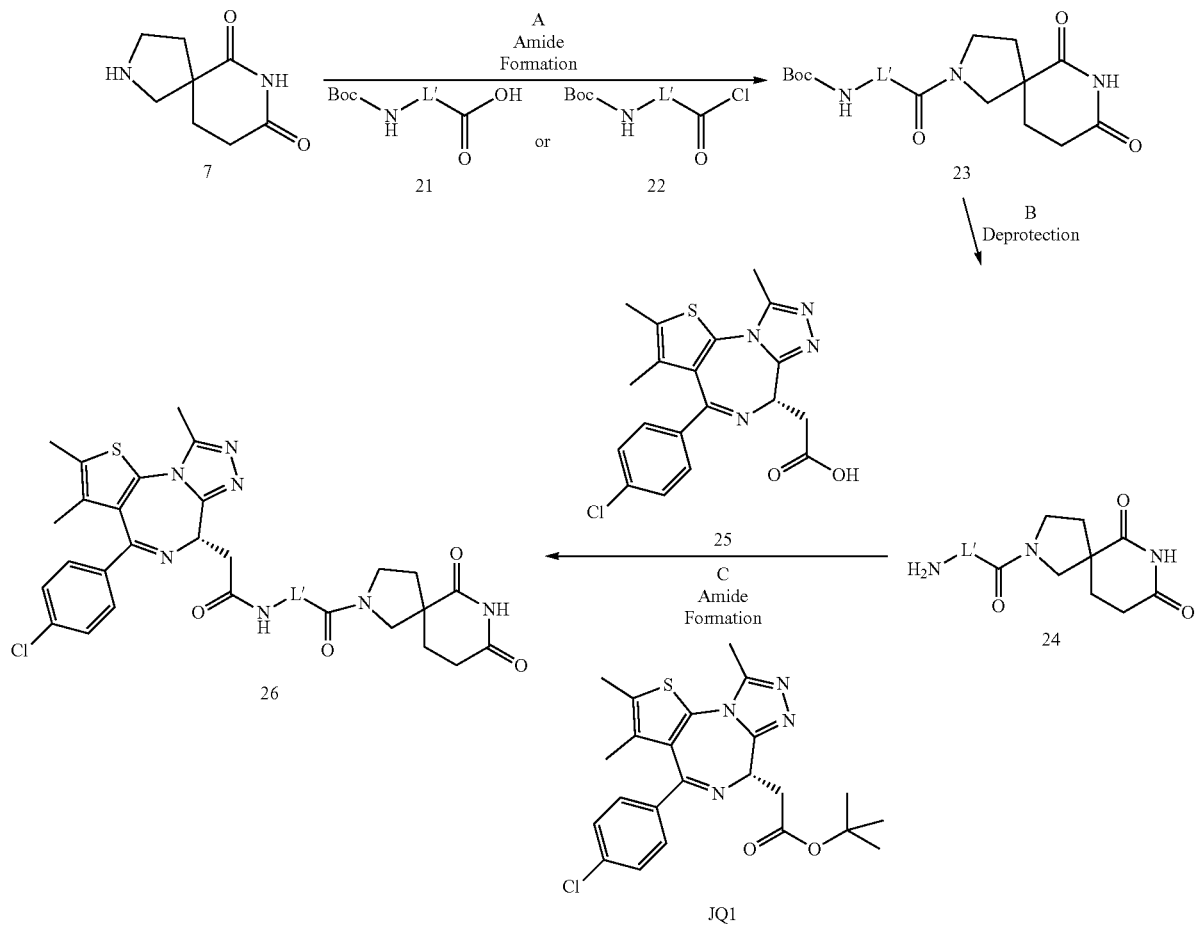

L = as defined in the claims

As an illustrative example, degrader compounds targeting the BET bromodomain BRD4 can be prepared based on the known BRD4 ligand JQ1 (Filippakopoulos, P. et al. Nature 2010, 468, 1067-1073, CAS 1268524-70-4). The synthesis employs the corresponding carboxylic acid derivative 25 (CAS 202592-23-2).

Step A: Amide bond formation can be accomplished by a coupling reaction between amine 7 and a linker-containing compound 21 bearing a terminal carboxylic acid functionality and a terminal BOC-protected amine functionality. The reaction is carried out in the presence of a coupling reagent such as DCC, EDC, TBTU or HATU in the presence of an organic base such as triethylamine, N,N-diisopropylethylamine, N-methylmorpholine or 4-(N,N-dimethylamino)pyridine in halogenated solvents such as dichloromethane or 1,2-dichloroethane or ethereal solvents such as diethyl ether, dioxane, THF, DME or TBME or polar non-protic organic solvent such as N,N-dimethylformamide at room temperature or at elevated temperatures for 2-18 hours. Preferred conditions are HATU with N,N-diisopropylethylamine in N,N-dimethylformamide at room temperature for 18 hours.

Alternatively, amide bond formation can be accomplished by a coupling reaction between amine 7 and an acyl chloride compound 22 which has been performed in situ from a linker-containing compound 21 bearing a terminal carboxylic acid functionality and a terminal BOC-protected amine functionality. The acyl chloride compound 22 can be prepared in situ from the corresponding carboxylic acid 21 by treatment with 1-chloro-N,N,2-trimethylpropenylamine (CAS 26189-59-3) in halogenated solvents such as dichloromethane or 1,2-dichloroethane at a temperature between 0° C. and room temperature, according to the method of Ghosez and co-workers (J. Chem. Soc., Chem. Commun. 1979, 1180; Org. Synth. 1980, 59, 26-34). Amide bond formation can then be accomplished by reaction of the acyl chloride compound 22 with amine 7 in halogenated solvents such as dichloromethane or 1,2-dichloroethane. Preferred conditions are dichoromethane at room temperature for 2 hours.

Step B: Removal of the Boc N-protecting group of 23 can be effected with mineral acids such as HCl, $H_2SO_4$ or $H_3PO_4$ or organic acids such as $CF_3COOH$, $CHCl_2COOH$, HOAc or p-toluenesulfonic acid in solvents such as $CH_2Cl_2$, $CHCl_3$, THF, EtOAc, Dioxane, MeOH, EtOH or $H_2O$ at 0° C. to reflux temperature. Preferred conditions are 4 M aq. HCl in dioxane and ethyl acetate at room temperature for 1 hour.

Step C: Amide bond formation can be accomplished by a coupling reaction between carboxylic acid 25 and amine 24 in the presence of a coupling reagent such as DCC, EDC, TBTU or HATU in the presence of an organic base such as triethylamine, N,N-diisopropylethylamine or N-methylmorpholine in halogenated solvents such as dichloromethane or 1,2-dichloroethane or ethereal solvents such as diethyl ether, dioxane, THF, DME or TBME or polar non-protic organic solvent such as N,N-dimethylformamide at room temperature or at elevated temperatures for 2-18 hours. Preferred conditions are HATU with N,N-diisopropylethylamine in N,N-dimethylformamide at room temperature for 3 hours.

between 0° C. and room temperature, according to the method of Ghosez and co-workers (J. Chem. Soc., Chem. Commun. 1979, 1180; Org. Synth. 1980, 59, 26-34). Amide bond formation can then be accomplished by reaction of the acyl chloride compound 29a with spiro-piperidine 28 in the presence of an organic base such as triethylamine, N,N-diisopropylethylamine or N-methylmorpholine in halogenated solvents such as dichloromethane or 1,2-dichloroethane, or in ethereal solvents such as diethyl ether, dioxane, THF, DME or TBME. Preferred conditions are N,N-diisopropylethylamine in THF at room temperature for 2 hours.

General Scheme 6

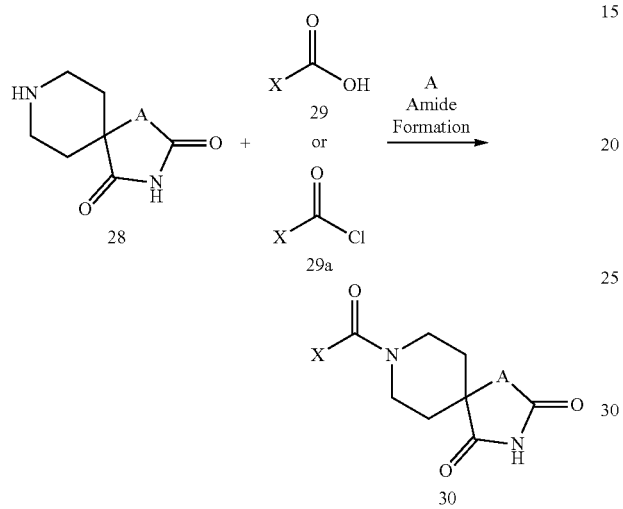

General Scheme 7

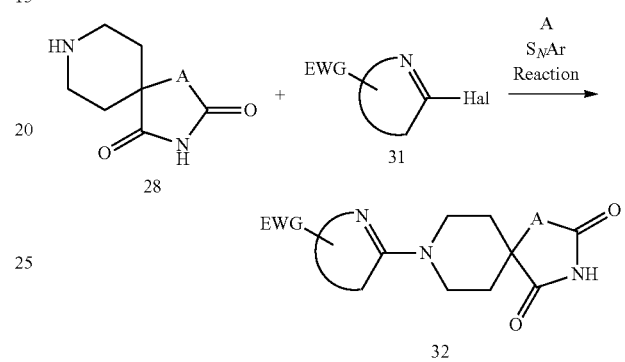

The substituents X are as described in the claims and A is NH or CH$_2$

Step A: Amide bond formation can be accomplished by a coupling reaction between a spiro-piperidine 28 and a carboxylic acid 29 in the presence of a coupling reagent such as DCC, EDC, TBTU or HATU in the presence of an organic base such as triethylamine, N,N-diisopropylethylamine or N-methylmorpholine in halogenated solvents such as dichloromethane or 1,2-dichloroethane or ethereal solvents such as diethyl ether, dioxane, THF, DME or TBME or polar non-protic organic solvent such as N,N-dimethylformamide at room temperature or at elevated temperatures for 2-18 hours.

Preferred conditions are HATU with N,N-diisopropylethylamine in N,N-dimethylformamide at room temperature for 15 hours.

Examples of suitable spiro-piperidine compounds 28 include, but are not limited to, 1,3,8-triazaspiro[4.5]decane-2,4-dione (CAS 13625-39-3) or 2,8-diazaspiro[4 5]decane-1,3-dione (CAS 2079-25-6), or their corresponding salts 1,3,8-triazaspiro[4.5]decane-2,4-dione hydrochloride (CAS 13625-48-4) or 2,8-diazaspiro[4.5]decane-1,3-dione hydrochloride (CAS 2696-03-9). Alternatively, amide bond formation can be accomplished by a coupling reaction between a spiro-piperidine 28 and an acyl chloride compound 29a which has been preformed in situ from a carboxylic acid 29. The acyl chloride compound 29a can be prepared in situ from the corresponding carboxylic acid 29 by treatment with 1-chloro-N,N, 2-trimethylpropenylamine (CAS 26189-59-3) in halogenated solvents such as dichloromethane or 1,2-dichloroethane, or in ethereal solvents such as diethyl ether, dioxane, THF, DME or TBME, at a temperature The substituents are as described in the claims, A is NH or CH$_2$, EWG is an electron-withdrawing group such as —CN, —CO$_2$R, —SO$_2$R or —NO$_2$ and hal is F or Cl.

Step A: Nucleophilic aromatic substitution (SNAr) reaction can be accomplished by reaction of a spiro-piperidine 28 with an electron-deficient mono- or fused bicyclic heteroaromatic compound 31 bearing a suitable leaving group such as fluorine or chlorine, in the presence of an organic base such as triethylamine, N,N-diisopropylethylamine or N-methylmorpholine in polar non-protic organic solvent such as N,N-dimethylformamide or N-methylpyrrolidone at elevated temperature.

Examples of suitable spiro-piperidine compounds 28 include, but are not limited to, 1,3,8-triazaspiro[4.5]decane-2,4-dione (CAS 13625-39-3) or 2,8-diazaspiro[4.5]decane-1,3-dione (CAS 2079-25-6), or their corresponding salts 1,3,8-triazaspiro[4.5]decane-2,4-dione hydrochloride (CAS 13625-48-4) or 2,8-diazaspiro[4.5]decane-1,3-dione hydrochloride (CAS 2696-03-9).

Examples of suitable electron-deficient heteroaromatic compounds 21 bearing a suitable leaving group include, but are not limited to, 2-chlorobenzo[d]thiazole (CAS 615-20-3), 2-chlorothiazolo[4,5-b]pyridine (CAS 152170-30-4), methyl 6-chloronicotinate (CAS 73781-91-6), 2-chloro-5-nitropyridine (CAS 4548-45-2), or 1-fluoro-4-nitrobenzene (CAS 350-46-9). Preferred conditions are N,N-diisopropylethylamine in N,N-dimethylformamide at 120° C. for 2 hours.

REPRESENTATIVE EXAMPLES OF THE PRESENT INVENTION

The following examples are provided for illustration of the invention. They should not be considered as limiting the scope of the invention, but merely as being representative thereof.

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC. Racemic mixtures of chiral synthetic intermediates may also be separated using chiral HPLC.

EXAMPLE 1

2,7-Diazaspiro[4.5]decane-6,8-dione

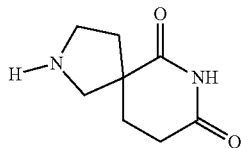

a) 3-(Triphenyl-λ$^5$-phosphanyhdene)piperidine-2,6-dione

To a solution of (2-amino-2-oxo-ethyl)-triphenyl-phosphonium chloride (CAS 25361-54-0, 70.0 g, 219 mmol, 1.00 eq, and NaOH (8.04 g, 201 mmol, 0.92 eq) in methanol (300 mL) was added ethyl acrylate (20.7 g, 240 mmol, 21.6 mL, 1.10 eq). The reaction mixture was stirred at 25° C. for 16 hours. The starting material was consumed and the product was detected by LC/MS. The reaction mixture was filtered, washed with methanol (2×20 mL) and petrol ether (100 mL), and dried to afford 3-(triphenyl-λ$^5$-phosphanylidene)piperidine-2,6-dione (35.0 g, crude) as a white solid that was used directly for the next step without further purification. MS (ISP): 374.1 ([M+H]$^+$).

b) 3-Methylenepiperidine-2,6-dione

A solution of 3-(triphenyl-λ$^5$-phosphanylidene)piperidine-2,6-dione (35.0 g, 93.7 mmol, 1.00 eq) and paraformaldehyde (10.1 g, 112 mmol, 1.20 eq) in dichloroethane (200 mL) was stirred at 80° C. for 30 minutes. The starting material was consumed and the product was detected by LC/MS. The reaction was filtered and concentrated in vacuo. The residue was purified by preparative HPLC to afford 3-methylenepiperidine-2,6-dione (4.30 g, 34.4 mmol, 36.7% yield) as an off-white solid. MS (ISP): 126.0 ([M+H]$^+$).

c) 2-Benzyl-2,7-diazaspiro[4.5]decane-6,8-dione

To a solution of 3-methylenepiperidine-2,6-dione (4.30 g, 34.36 mmol, 1.00 eq) and N-(methoxymethyl)-1-phenyl-N-(trimethylsilylmethyl)methanamine (CAS 93102-05-7, 8.97 g, 37.8 mmol, 1.10 eq) in dichloromethane (200 mL) was added trifluoroacetic acid (2.55 g, 22.3 mmol, 1.65 mL, 0.65 eq). The reaction was stirred at 25° C. for 16 hours. The starting material was consumed and the product was detected by LC/MS. The reaction was quenched with saturated NaHCO$_3$ (200 mL), extracted with dichloromethane (50 mL), washed with brine (100 mL), dried with Na$_2$SO$_4$, filtered and concentrated in vacuo. The solid residue obtained was triturated with a mixture of ethyl acetate and petrol ether (1:10) and purified by preparative HPLC to afford 2-benzyl-2,7-diazaspiro[4.5]decane-6,8-dione (3.00 g, 11.6 mmol, 33.8% yield) as a white solid. MS (ISP): 259.1 ([M+H]$^+$).

d) 2,7-Diazaspiro[4.5]decane-6,8-dione

To a solution of 2-benzyl-2,7-diazaspiro[4.5]decane-6,8-dione (1.50 g, 5.81 mmol, 1.00 eq) in dichloroethane (50.0 mL) was added 1-chloroethyl chloroformate (CAS 50893-53-3, 1.66 g, 11.6 mmol, 2.00 eq). The reaction mixture was stirred at 80° C. for 12 hours. The solution was concentrated in vacuo, the residue was dissolved in methanol (50.0 mL) and stirred at 65° C. for 2 hours. After concentration in vacuo, $^1$H NMR showed the presence of starting material. The residue was dissolved in dichloroethane (100 ml) and treated again with 1-chloroethyl chloroformate (1.66 g, 11.6 mmol, 4.00 eq) at 80° C. for 12 hours. After evaporation of the solvent, methanol was added and the solution was stirred at 65° C. for 2 hours. The solvent was evaporated and the residue was dissolved in dichloromethane, stirred for 5 hours and filtered to afford 2,7-diazaspiro[4.5]decane-6,8-dione as its hydrochloride salt (300 mg, 1.78 mmol, 30.7% yield) as a grey solid. MS (ISP): 169.1 ([M+H]$^+$).

EXAMPLE 2

2-Methyl-2,7-diazaspiro[4.5]decane-3,6,8-trione

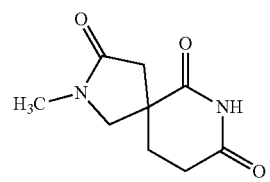

a) 4-O-tert-Butyl 1-0,2-O-dimethyl 2-cyanobutane-1,2,4-tricarboxylate

To a solution of dimethyl 2-cyanobutanedioate (CAS 6283-71-2, 10.0 g, 58.4 mmol, 1.00 eq) in methanol (60.0 mL) and water (60.0 mL) was added triethylamine (8.87 g, 87.6 mmol, 12.1 mL, 1.50 eq) at 0-5° C. After stirring for 30 minutes, tent-butyl prop-2-enoate (CAS 1663-39-4, 8.99 g, 70.1 mmol, 10.2 mL, 1.20 eq) was added to the reaction mixture. The mixture was stirred at 0-5° C. for 1.5 hours and was allowed to warm to 25° C. and stirred for a further 2 hours. TLC showed that starting material was consumed and one new spot was detected. The reaction mixture was acidified with 2 N aq HCl to pH=4 and extracted with EtOAc (3×50 mL). The combined organic layers were washed with brine (50 mL), dried over Na$_2$SO$_4$, filtered, and the filtrate was concentrated under reduced pressure. The residue was purified by chromatography (SiO$_2$, petrol ether: ethyl acetate=20:1 to 4:1) to afford 4-O-tert-butyl 1-O,2-O-dimethyl 2-cyanobutane-1,2,4-tricarboxylate (10.0 g, 33.4 mmol, 57.2%) as a yellow gum. $^1$H NMR: 400 MHz, CDCl$_3$: δ3.82-3.87 (m, 3H), 3.73 (s, 3H), 3.09 (d, J=17.07 Hz, 1H), 2.83 (d, J=17.32 Hz, 1H), 2.47-2.61 (m, 1H), 2.31-2.43 (m, 1H), 2.10-2.25 (m, 2H), 2.03 (s, 1H), 1.43 (s, 9H).

b) Methyl 3-(3-tert-butoxy-3-oxo-propyl)-5-oxo-pyrrolidine-3-carboxylate

4-O-tert-butyl 1-O,2-O-dimethyl 2-cyanobutane-1,2,4-tricarboxylate (5.00 g, 16.7 mmol, 1.00 eq) was dissolved in methanol (200 mL) and Raney-Ni (143 mg, 1.67 mmol, 0.10 eq) was added to the mixture. The reaction mixture was hydrogenated with $H_2$ (40 psi) for 16 hours. According to LC/MS, the starting material was consumed and the desired compound was detected. The solution was decanted with a pipette and the catalyst was washed with methanol. The filtrate was concentrated under reduced pressure to afford methyl 3-(3-tert-butoxy-3-oxo-propyl)-5-oxo-pyrrolidine-3-carboxylate (4.00 g, 14.7 mmol, 88.3%) as a yellow solid that was used directly for the next reaction. MS (ISP): 543.2 ([2M+H]$^+$).

c) Methyl 3-(3-methoxy-3-oxo-propyl)-5-oxo-pyrrolidine-3-carboxylate

To a solution of methyl 3-(3-tert-butoxy-3-oxo-propyl)-5-oxo-pyrrolidine-3-carboxylate (2.00 g, 7.37 mmol, 1.00 eq) in methanol (25.0 mL) was added concentrated HCl (0.8 ml) while stirring. The mixture was heated at 60° C. for 2 hours. LC/MS showed the starting material was consumed and the desired compound was detected. The reaction mixture was quenched by the addition of saturated $NaHCO_3$ (50 mL) and extracted with ethyl acetate (3×50 ml). The combined organic layers were washed with brine (50 mL), dried over $Na_2SO_4$, filtered, and the filtrate was concentrated under reduced pressure to afford crude methyl 3-(3-methoxy-3-oxo-propyl)-5-oxo-pyrrolidine-3-carboxylate (1.60 g) as a yellow gum, which was used directly for the next reaction without further purification. MS (ISP): 459.2 ([2M+H]$^+$).

d) N-[(4-Methoxyphenyl)methyl]-3-[3-[(4-methoxyphenyl)methylamino]-3-oxo-propyl]-5-oxo-pyrrolidine-3-carboxamide A mixture of methyl 3-(3-methoxy-3-oxo-propyl)-5-oxo-pyrrolidine-3-carboxylate (800 mg, 3.49 mmol, 1.00 eq) and 4-methoxybenzylamine (CAS 2393-23-9, 15.0 g, 109 mmol, 14.2 mL, 31.3 eq.) were heated together at 200° C. for 2 hours under microwave irradiation. LC/MS showed the starting material was consumed and the desired compound was detected. The reaction mixture was diluted with water (100 mL), acidified to pH=7 with 1 N aqueous HCl, and extracted with dichloromethane (3×200 mL). The combined organic layers were washed with brine (100 mL), dried over $Na_2SO_4$, filtered, and was evaporated in vacuo. The residue was purified by preparative HPLC to afford N-[(4-methoxyphenyl)methyl]-3-[3-[(4-methoxyphenyl)methylamino]-3-oxo-propyl]-5-oxo-pyrrolidine-3-carboxamide (1.00 g, 2.28 mmol, 32.7%) as a yellow gum. MS (ISP): 440.1 ([M+H]$^+$).

e) 7-[(4-Methoxyphenyl)methyl]-2,7-diazaspiro[4.5]decane-3,6,8-trione

To a solution of N-[(4-methoxyphenyl)methyl]-3-[3-[(4-methoxyphenyl)methylamino]-3-oxo-propyl]-5-oxo-pyrrolidine-3-carboxamide (1.00 g, 2.28 mmol, 1.00 eq) in xylene (20.0 mL) was added p-toluene sulfonic acid monohydrate (500 mg, 2.63 mmol, 1.15 eq). The reaction mixture was degassed and purged with nitrogen three times and was then stirred at 145° C. for 2 hours under $N_2$ atmosphere. LC/MS showed the starting material was consumed and the desired compound was detected. The reaction mixture was diluted with water (50 mL) and extracted with dichloromethane (3×50 mL). The combined organic layers were washed with brine (50 mL), dried over $Na_2SO_4$, filtered, and the filtrate was concentrated under reduced pressure. The residue was purified by flash silica gel chromatography to afford 7-[(4-methoxyphenyl)methyl]-2,7-diazaspiro[4.5]decane-3,6,8-trione (200 mg, 662 μmol, 29%) as a yellow gum. MS (ISP): 303.2 ([M+H]$^+$).

f) 7-[(4-Methoxyphenyl)methyl]-2-methyl-2,7-diazaspiro[4.5] decane-3,6,8-trione To a solution of 7-[(4-methoxyphenyl)methyl]-2,7-diazaspiro[4.5]decane-3,6,8-trione (200 mg, 662 μmol, 1.00 eq) in toluene (20.0 mL) was added sodium hydride (66.0 mg, 1.65 mmol, 60% purity, 2.49 eq) followed by methyl iodide (235 mg, 1.66 mmol, 2.50 eq). The reaction mixture was stirred at 60° C. for 1 hour under $N_2$ atmosphere. LC/MS showed the starting material was consumed and the desired compound was detected. The reaction mixture was quenched by addition of a saturated solution of aqueous $NH_4Cl$ (50 mL) and extracted with dichloromethane (3×50 mL). The combined organic layers were washed with brine (50 mL), dried over $Na_2SO_4$, filtered, and concentrated in vacuo. The crude material was purified by flash column chromatography (silica gel, eluent: 0 to 5% of methanol in dichloromethane) to afford 7-[(4-methoxyphenyl) methyl]-2-methyl-2,7-diazaspiro[4.5]decane-3,6,8-trione (100 mg, 316 μmol, 47.8%) as a yellow gum. MS (ISP): 317.1 ([M+H]$^+$).

g) 2-Methyl-2,7-diazaspiro[4.5]decane-3,6,8-trione

A solution of 7-[(4-methoxyphenyl)methyl]-2-methyl-2,7-diazaspiro[4.5]decane-3,6,8-trione (300 mg, 948 μmol, 1.00 eq) in acetonitrile (10.0 mL) was treated with ammonium cerium (IV) nitrate (1.04 g, 1.90 mmol, 2.00 eq) in $H_2O$ (5.00 mL). The mixture was stirred at 25° C. for 1 hour. LC/MS showed the starting material was consumed and the desired compound was detected. The reaction mixture was diluted with water (20 ml) and set to pH=7 by adding a saturated solution of aqueous $NaHCO_3$. The solid was filtered, concentrated under reduced pressure, dissolved in anhydrous methanol (20 ml) and filtered. The filtrate was concentrated in vacuo. The crude was purified by prep-HPLC to afford 2-methyl-2,7-diazaspiro[4.5]decane-3,6,8-trione (35.0 mg, 178 μmol, 18.8%) as a white solid. MS (ISP): 197.1 ([M+H]$^+$).

EXAMPLE 3

(2-(2-Phenylacetyl)-2,7-diazaspiro[4.5]decane-6,8-dione

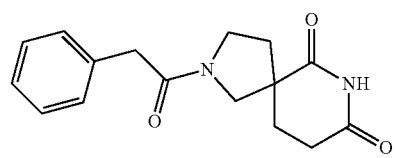 [SMILES: O=C1CCC2(CCN(C(=O)Cc3ccccc3)C2)C(=O)N1]

a) 2-(2-(4-Bromophenyl)acetyl)-2,7-diazaspiro[4.5]decane-6,8-dione

To a suspension of 2-(4-bromophenyl) acetic acid (84.4 mg, 392 µmol, eq. 1.1) and 2,7-diazaspiro[4.5]decane-6,8-dione hydrochloride (60 mg, 357 µmol, eq. 1) in N,N-dimethylformamide (1.5 ml) were added DIPEA (138 mg, 187 µl, 1.07 mmol, eq. 3) and HATU (271 mg, 713 µmol, eq. 2) at room temperature. The reaction mixture was stirred for 3 hours. The reaction mixture was partitioned between ethyl acetate (40 ml) and 0.5 M aqueous sodium hydroxide solution (20 ml). The layers were separated. The aqueous layer was extracted with ethyl acetate (2×25 ml). The combined organic layers were washed with brine (20 ml), dried over anhydrous sodium sulfate and concentrated in vacuo. The product was purified by reversed phase HPLC followed by lyophilisation to afford 2-(2-(4-bromophenyl)acetyl)-2,7-diazaspiro[4.5]decane-6,8-dione (44 mg, 120 µmol, 34%) as an off-white solid. MS (ISP): 366.9 ([M+H]$^+$).

b) 2-(2-Phenylacetyl)-2,7-diazaspiro[4.5]decane-6,8-dione

To a stirred suspension of 2-(2-(4-bromophenyl)acetyl)-2,7-diazaspiro[4.5]decane-6,8-dione (39 mg, 107 µmol, eq. 1) in methanol (5 ml) was added 10% palladium on charcoal (11.4 mg, 10.7 µmol, Eq. 0.1). The reaction mixture was stirred for 4 hours at room temperature under an atmosphere of hydrogen. The catalyst was collected by filtration, washing with methanol. The filtrate was then concentrated in vacuo. The crude material was purified by flash chromatography (silica gel, eluent: 0 to 10% of methanol in dichloromethane) to afford 2-(2-phenylacetyl)-2,7-diazaspiro[4.5]decane-6,8-dione (8.5 mg, 107 µmol, 28%) as an off-white solid. MS (ISP): 287 ([M+H]$^+$).

EXAMPLE 4

2-(2,3-Dihydro-1H-indene-1-carbonyl)-2,7-diazaspiro[4.5]decane-6,8-dione

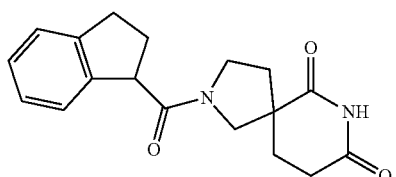

The title compound was obtained as a white solid in analogy to Example 3(a) using 2,3-dihydro-1H-indene-1-carboxylic acid (CAS 14381-42-1) in place of 2-(4-bromophenyl)acetic acid. MS (ISP): 374.1 ([M+H]$^+$).

EXAMPLE 5

2-(3-Nitrobenzoyl)-2,7-diazaspiro[4.5]decane-6,8-dione

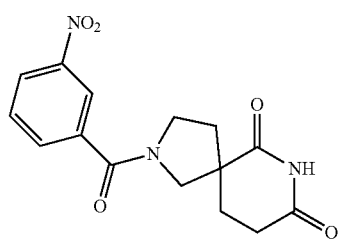 [SMILES: O=C1CCC2(CCN(C(=O)c3cccc([N+](=O)[O-])c3)C2)C(=O)N1]

To a mixture of 2,7-diazaspiro[4.5]decane-6,8-dione hydrochloride (200 mg, 1.19 mmol, eq. 1) and a solution of HATU in N,N-dimethylformamide 0.269 M (4.87 ml, 1.31 mmol, eq. 1.34) was added 3-nitrobenzoic acid (238 mg, 1.43 mmol, eq. 1.2) followed by DIPEA (615 mg, 831 µl, 4.76 mmol, eq. 4). The reaction mixture was stirred for 3 hours and stayed overnight at room temperature. The reaction mixture was partitioned between ethyl acetate and water. The layers were separated. The aqueous phase was extracted a second time with ethyl acetate. The combined organic layer was dried over MgSO$_4$ and concentrated in vacuo. The product was purified via column chromatography (silica gel, eluent: 0 to 10% of methanol in dichloromethane) to afford 2-(3-nitrobenzoyl)-2,7-diazaspiro[4.5]decane-6,8-dione as a pink powder (50 mg, 158 µmol, 13.3%). MS (ISP): 318.1 ([M+H]$^+$).

EXAMPLE 6

Methyl 6-(6,8-dioxo-2,7-diazaspiro[4.5]decan-2-yl)nicotinate

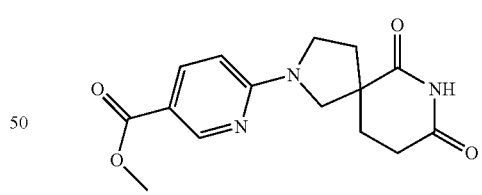

To a stirred solution of 2,7-diazaspiro[4.5]decane-6,8-dione hydrochloride (50 mg, 244 µmol, Eq. 1) in N,N-dimethylformamide (0.6 ml) was added methyl 6-chloronicotinate (CAS 73781-91-6, 41.9 mg, 244 µmol, eq. 1) and DIPEA (94.7 mg, 128 µl, 733 µmol, eq. 3). The reaction mixture was shaken for 24 hours at 110° C. and was directly purified by preparative HPLC followed by lyophilisation to afford methyl 6-(6,8-dioxo-2,7-diazaspiro[4.5]decan-2-yl)nicotinate (30.2 mg, 99.6 µmol, 40.8% yield) as a white solid. MS (ISP): 304.3 ([M+H]$^+$).

EXAMPLE 7

2-(Thiazolo[4,5-b]pyridin-2-yl)-2,7-diazaspiro[4.5]decane-6,8-dione

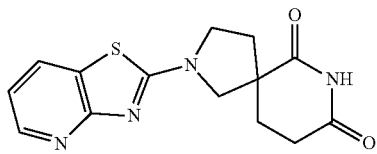 [SMILES: O=C1CCC2(CCN(c3nc4ncccc4s3)C2)C(=O)N1]

The title compound was obtained as a white solid in analogy to Example 6 using 2-chlorothiazolo[4,5-b]pyridine (CAS 152170-30-4) in place of methyl 6-chloronicotinate. MS (ISP): 304.3 ([M+H]$^+$).

EXAMPLE 8

2-(4-Nitrophenyl)-2,7-diazaspiro[4.5]decane-6,8-dione

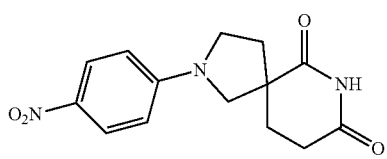 [SMILES: O=C1CCC2(CCN(c3ccc([N+](=O)[O-])cc3)C2)C(=O)N1]

The title compound was obtained as a white solid in analogy to Example 6 using 1-fluoro-4-nitrobenzene (CAS 350-46-9) in place of methyl 6-chloronicotinate. MS (ISP): 290.3 ([M+H]$^+$).

EXAMPLE 9

2-(5-Nitro-1H-benzo[d]imidazol-2-yl)-2,7-diazaspiro[4.5]decane-6,8-dione

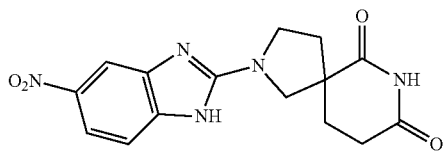 [SMILES: O=C1CCC2(CCN(c3nc4cc([N+](=O)[O-])ccc4[nH]3)C2)C(=O)N1]

The title compound was obtained as a white solid in analogy to Example 6 using 2-chloro-5-nitro-1H-benzo[d]imidazole (CAS 5955-72-6) in place of methyl 6-chloronicotinate. MS (ISP): 330.3 ([M+H]$^+$).

EXAMPLE 10

(+)-2-(4-Nitrophenyl)-2,7-diazaspiro[4.5]decane-6,8-dione (Enantiomer 1)

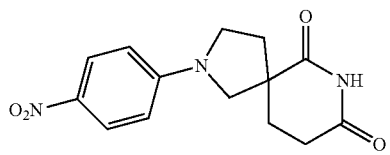 [SMILES: O=C1CCC2(CCN(c3ccc([N+](=O)[O-])cc3)C2)C(=O)N1]

a) 2-(4-Nitrophenyl)-2,7-diazaspiro[4.5]decane-6,8-dione

The title compound was obtained as a white solid in analogy to Example 6 using 1-fluoro-4-nitrobenzene (CAS 350-46-9) in place of methyl 6-chloronicotinate. MS (ISP): 330.3 ([M+H]$^+$).

b) (+)-2-(4-Nitrophenyl)-2,7-diazaspiro[4.5]decane-6,8-dione (Enantiomer 1)

The enantiomers of 2-(4-nitrophenyl)-2,7-diazaspiro[4.5]decane-6,8-dione (415 mg) were separated using chiral HPLC (column: Chiralcel OD, eluent: heptane/ethanol+NH$_4$OAc (60:40), pressure: 18 bar; flow rate: 35 ml/min) affording (+)-2-(4-nitrophenyl)-2,7-diazaspiro[4.5]decane-6,8-dione (62 mg, yellow solid), retention time=19.0 min. MS (ISP): 290.3 ([M+H]$^+$).

EXAMPLE 11

(+2-(4-Nitrophenyl)-2,7-diazaspiro[4.5]decane-6,8-dione (Enantiomer 2)

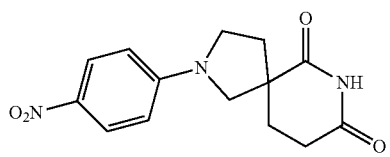 [SMILES: O=C1CCC2(CCN(c3ccc([N+](=O)[O-])cc3)C2)C(=O)N1]

The enantiomers of 2-(4-nitrophenyl)-2,7-diazaspiro[4.5]decane-6,8-dione (415 mg) were separated using chiral HPLC (column: Reprosil Chiral-NR, eluent: heptane/ethanol+NH$_4$OAc (60:40), pressure: 18 bar; flow rate: 35 ml/min) affording (−)-2-(4-nitrophenyl)-2,7-diazaspiro[4.5]decane-6,8-dione (65 mg, yellow solid), retention time=25.5 min. MS (ISP): 290.3 ([M+H]$^+$).

EXAMPLE 12

2-(Benzo[d]thiazol-2-yl)-2,7-diazaspiro[4.5]decane-6,8-dione

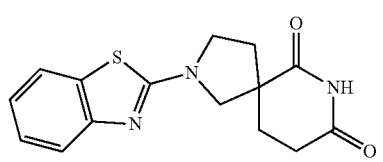

To a suspension of 2,7-diazaspiro[4.5]decane-6,8-dione hydrochloride (23 mg, 112 μmol, Eq. 1) and DIPEA (43.6 mg, 58.9 337 μmol, Eq. 3) in DMF (0.5 ml) was added 2-chlorobenzo[d]thiazole (CAS 615-20-3, 21 mg, 16.1 μl, 124 μmol, eq. 1.1). The reaction mixture was stirred at 100° C. for 1 hour. The reaction mixture was poured into a mixture of ethylacetate/tetrahydrofuran (1:1). The organic layer was washed with water followed by brine, dried over Na$_2$SO$_4$ and concentrated in vacuo. The crude material was purified by flash column chromatography (silica gel, eluent: 0 to 5% of methanol in dichloromethane) to afford 2-(benzo[d]thiazol-2-yl)-2,7-diazaspiro[4.5]decane-6,8-dione (10 mg, 33.2 μmol, 29.5%) as a white solid. MS (ISP): 302.1 ([M+H]$^+$).

EXAMPLE 13

Methyl 2-(6,8-dioxo-2,7-diazaspiro[4.5]decan-2-yl)-1H-benzo[d]imidazole-7-carboxylate

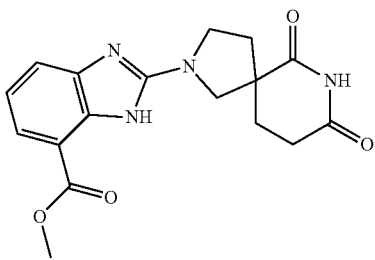 [SMILES: COC(=O)c1cccc2nc(N3CCC4(CCC(=O)NC4=O)C3)[nH]c12]

To a stirred solution of 2,7-diazaspiro[4.5]decane-6,8-dione hydrochloride (50 mg, 244 μmol, Eq. 1) in N,N-dimethylformamide (600 μl) were added methyl 2-chloro-1H-benzo[d]imidazole-7-carboxylate (CAS 1171129-05-7, 51.5 mg, 244 μmol, eq. 1) and DIPEA (94.7 mg, 128 733 μmol, eq. 3). The reaction mixture was shaken at 110° C. for 17 hours. The reaction mixture was partitioned between water and a 1:1 mixture of ethyl acetate and THF. The organic layer was washed with brine, dried over Na$_2$SO$_4$, filtered and concentrated in vacuo. The crude product was taken in CH$_2$Cl$_2$ and stirred at room temperature for 30 minutes. The product was collected by filtration, washed with CH$_2$Cl$_2$ and dried to afford methyl 2-(6,8-dioxo-2,7-diazaspiro[4.5]decan-2-yl)-1H-benzo[d]imidazole-7-carboxylate (19 mg, 55.5 μmol, 22.7% yield) as light brown solid. MS (ISP): 343.3 ([M+H]$^+$).

EXAMPLE 14

Methyl 2-(6,8-dioxo-2,7-diazaspiro[4.5]decan-2-yl)pyrimidine-4-carboxylate

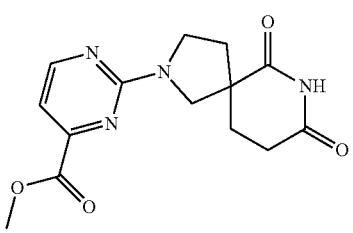 [SMILES: COC(=O)c1ccnc(N2CCC3(CCC(=O)NC3=O)C2)n1]

The title compound was obtained as a light brown solid in analogy to Example 13 using methyl 2-chloropyrimidine-4-carboxylate (CAS 149849-94-5) in place of methyl 2-chloro-1H-benzo[d]imidazole-7-carboxylate. MS (ISP): 305.3 ([M+H]$^+$).

EXAMPLE 15

2-(Quinolin-2-yl)-2,7-diazaspiro[4.5]decane-6,8-dione

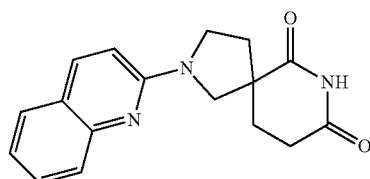

The title compound was obtained as a light brown solid in analogy to Example 13 using 2-chloroquinoline (CAS 612-62-4) in place of methyl 2-chloro-1H-benzo[d]imidazole-7-carboxylate. MS (ISP): 296.3 ([M+H]$^+$).

EXAMPLE 16

2-(6-Aminobenzo[d]thiazol-2-yl)-2,7-diazaspiro[4.5]decane-6,8-dione

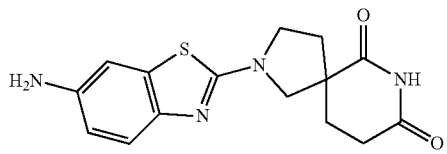 [SMILES: Nc1ccc2nc(N3CCC4(CCC(=O)NC4=O)C3)sc2c1]

To a suspension of 2,7-diazaspiro[4.5]decane-6,8-dione hydrochloride (23 mg, 112 μmol, Eq. 1) and 2-chlorobenzo[d]thiazol-6-amine (CAS 2406-90-8, 20.8 mg, 112 μmol, eq. 1) in N,N-dimethylformamide (0.5 ml) was added DIPEA (43.6 mg, 58.9 337 μmol, eq. 3). The reaction mixture was stirred at 100° C. for 1 hour then at 120° C. for 1 hour and finally at 130° C. overnight. The reaction mixture was poured into a mixture of ethylacetate/tetrahydrofuran (1:1), the organic layer was washed with water followed by brine, dried over Na$_2$SO$_4$ and concentrated in vacuo. The crude material was purified by flash column chromatography (silica gel, eluent: 0 to 5% of methanol in dichloromethane) to afford 2-(6-aminobenzo[d]thiazol-2-yl)-2,7-diazaspiro[4.5]decane-6,8-dione (3 mg, 9.48 μmol, 8.44%) as a yellow solid. MS (ISP): 317.1 ([M+H]$^+$).

EXAMPLE 17

2-(Oxazolo[4,5-b]pyridin-2-yl)-2,7-diazaspiro[4.5]decane-6,8-dione

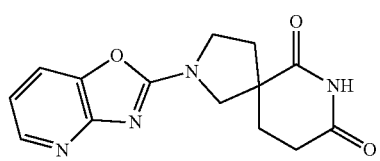 [SMILES: O=C1CCC2(CCN(c3nc4ncccc4o3)C2)C(=O)N1]

The title compound was obtained as awhite solid in analogy to Example 12 using 2-chlorooxazolo[4,5-b]pyridine (CAS 325976-45-2) in place of 2-chlorobenzo[d]thiazole. MS (ISP): 287.1 ([M+H]⁺).

EXAMPLE 18

2-(Benzo[d]oxazol-2-yl)-2,7-diazaspiro[4.5]decane-6,8-dione

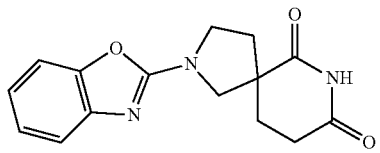 [SMILES: O=C1CCC2(CCN(c3nc4ccccc4o3)C2)C(=O)N1]

The title compound was obtained as a white solid in analogy to Example 12 using 2-chlorobenzo[d]oxazole (CAS 615-18-9) in place of 2-chlorobenzo[d]thiazole. MS (ISP): 286.1 ([M+H]⁺).

EXAMPLE 19

2-(1-Methyl-1H-benzo[d]imidazol-2-yl)-2,7-diazaspiro[4.5]decane-6,8-dione

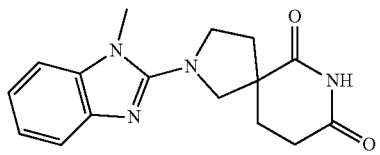 [SMILES: Cn1c(N2CCC3(CCC(=O)NC3=O)C2)nc2ccccc21]

The title compound was obtained as a brown solid in analogy to Example 12 using 2-chloro-1-methyl-1H-benzo[d]imidazole (CAS 1849-02-1) in place of 2-chlorobenzo[d]thiazole and heating at 135° C. overnight instead of at 100° C. for 1 hour. MS (ISP): 299.1 ([M+H]⁺).

EXAMPLE 20

2-(Thiazolo[4,5-c]pyridin-2-yl)-2,7-diazaspiro[4.5]decane-6,8-dione

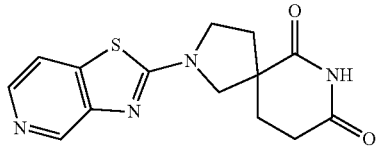 [SMILES: O=C1CCC2(CCN(c3nc4cnccc4s3)C2)C(=O)N1]

The title compound was obtained as a white solid in analogy to example 12 using 2-chlorothiazolo[4,5-c]pyridine (CAS 884860-63-3) in place of 2-chlorobenzo[d]thiazole. MS (ISP): 303.2 ([M+H]⁺).

EXAMPLE 21

Methyl 2-(6,8-dioxo-2,7-diazaspiro[4.5]decan-2-yl)benzo[d]thiazole-6-carboxylate

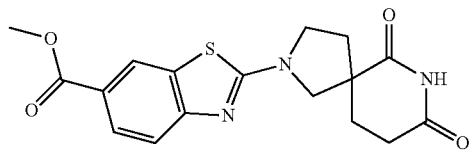 [SMILES: COC(=O)c1ccc2nc(N3CCC4(CCC(=O)NC4=O)C3)sc2c1]

The title compound was obtained as a yellow solid in analogy to Example 12 using methyl 2-chlorobenzo[d]thiazole-6-carboxylate (CAS 90792-69-1) in place of 2-chlorobenzo[d]thiazole and heating at 125° C. overnight instead at 100° C. for 1 hour. MS (ISP): 360.1 ([M+H]⁺).

EXAMPLE 22

Methyl 2-(6,8-dioxo-2,7-diazaspiro[4.5]decan-2-yl)thiazole-4-carboxylate

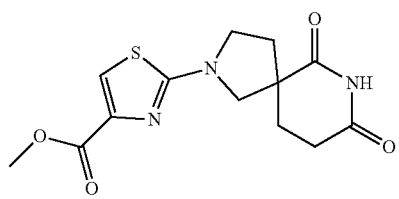 [SMILES: COC(=O)c1csc(N2CCC3(CCC(=O)NC3=O)C2)n1]

The title compound was obtained as a white solid in analogy to Example 12 using methyl 2-chlorothiazole-4-carboxylate (CAS 850429-61-7) in place of 2-chlorobenzo[d]thiazole. MS (ISP): 310.1 ([M+H]⁺).

EXAMPLE 23

Methyl 2-(6,8-dioxo-2,7-diazaspiro[4.5]decan-2-yl)thiazole-5-carboxylate

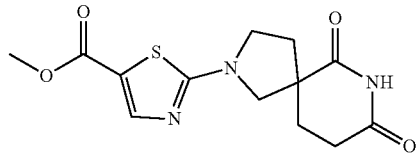 [SMILES: COC(=O)c1cnc(N2CCC3(CCC(=O)NC3=O)C2)s1]

The title compound was obtained as a white solid in analogy to Example 12 using methyl 2-chlorothiazole-5-carboxylate (CAS 72605-86-8) in place of 2-chlorobenzo[d]thiazole. MS (ISP): 310.1 ([M+H]⁺).

EXAMPLE 24 tert-Butyl 6-(6,8-dioxo-2,7-diazaspiro[4.5]decan-2-yl)nicotinate

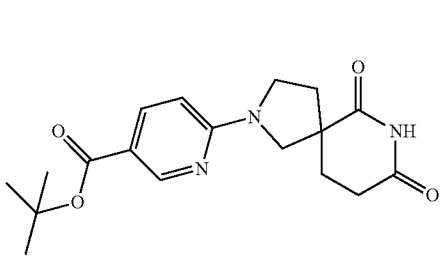 [SMILES: CC(C)(C)OC(=O)c1ccc(N2CCC3(CCC(=O)NC3=O)C2)nc1]

The title compound was obtained as a white solid in analogy to Example 13 using tert-butyl 6-chloronicotinate (CAS 115309-57-4) in place of methyl 2-chloro-1H-benzo[d]imidazole-7-carboxylate. MS (ISP): 346.2 ([M+H]$^+$).

EXAMPLE 25

2-(Benzo[d]thiazole-6-carbonyl)-2,7-diazaspiro[4.5]decane-6,8-dione

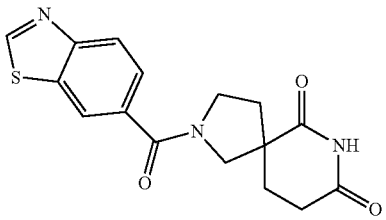 [SMILES: O=C1CCC2(CCN(C(=O)c3ccc4ncsc4c3)C2)C(=O)N1]

To a mixture of 2,7-diazaspiro[4.5]decane-6,8-dione hydrochloride (30 mg, 147 µmol, eq. 1) and benzo[d]thiazole-6-carboxylic acid (CAS 3622-35-3, 28.9 mg, 161 µmol, eq. 1.1) were added a solution of HATU in N,N-dimethylformamide 0.358 M (491 µl, 176 µmol, eq. 1.2) and N,N-diisopropylethylamine (75.8 mg, 100 586 eq. 4). The reaction mixture was shaken at 25° C. for 4 hours. The reaction mixture was partitioned between water and a 1:1 mixture of ethyl acetate and tetrahydrofuran. The organic layer was washed with brine, dried over Na$_2$SO$_4$, filtered and concentrated in vacuo. The crude material was purified by flash chromatography (silica gel, 4 g, eluent: 0 to 10% of methanol in dichloromethane) to afford 2-(benzo[d]thiazole-6-carbonyl)-2,7-diazaspiro[4.5]decane-6,8-dione (17 mg, 51.6 µmol, 35.2%) as a white solid. MS (ISP): 330.1 ([M+H]$^+$)

EXAMPLE 26

2-(4-Nitropicolinoyl)-2,7-diazaspiro[4.5]decane-6,8-dione

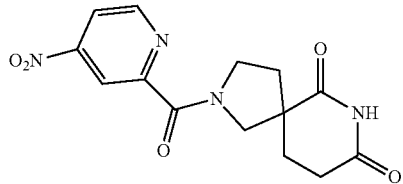 [SMILES: O=C1CCC2(CCN(C(=O)c3cc([N+](=O)[O-])ccn3)C2)C(=O)N1]

The title compound was obtained as a white solid in analogy to Example 25 using 4-nitropicolinic acid (CAS 13509-19-8) in place of benzo[d]thiazole-6-carboxylic acid. MS (ISP): 319.1 ([M+H]$^+$).

EXAMPLE 27

2-(2-Oxoindoline-4-carbonyl)-2,7-diazaspiro[4.5]decane-6,8-dione

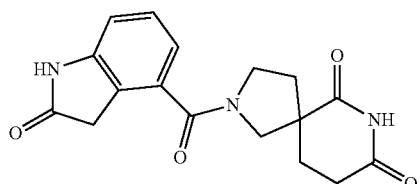

The title compound was obtained as a light brown viscous oil in analogy to Example 25 using 2-oxoindoline-4-carboxylic acid (CAS 90322-37-5) in place of benzo[d]thiazole-6-carboxylic acid. MS (ISP): 328.2 ([M+H]$^+$).

EXAMPLE 28

Methyl 4-(6,8-dioxo-2,7-diazaspiro[4.5]decane-2-carbonyl)benzoate

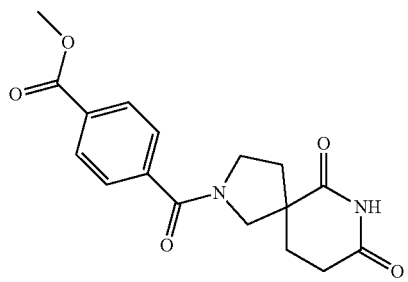 [SMILES: COC(=O)c1ccc(C(=O)N2CCC3(CCC(=O)NC3=O)C2)cc1]

To a mixture of 2,7-diazaspiro[4.5]decane-6,8-dione hydrochloride (30 mg, 147 µmol, eq. 1.2) and ethyl acetate (187 µl) were added 4-(methoxycarbonyl)benzoic acid (CAS 1679-64-7, 22 mg, 122 µmol, eq. 1), pyridine (93.4 µl) and a solution of 50% 1-propanephosphonic anhydride in ethyl acetate (155 mg, 145 µl, 244 µmol, eq. 2). The reaction mixture was shaken at 60° C. for 17 hours. The reaction mixture was partitioned between water and a 1:1 mixture of ethyl acetate and tetrahydrofuran. The organic layer was washed with brine, dried over Na₂SO₄, filtered and concentrated in vacuo. The crude material was purified by flash chromatography (silica gel, 4 g, eluent: 0 to 10% of methanol in dichloromethane) to afford methyl 4-(6,8-dioxo-2,7-diazaspiro[4.5]decane-2-carbonyl)benzoate (27 mg, 81.7 µmol, 66.9%) as a white solid. MS (ISP): 331.2 ([M+H]⁺).

EXAMPLE 29

2-(Benzo[d]thiazole-5-carbonyl)-2,7-diazaspiro[4.5]decane-6,8-dione

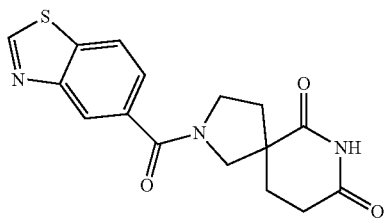 [SMILES: O=C1CCC2(CCN(C(=O)c3ccc4scnc4c3)C2)C(=O)N1]

To a solution of 2,7-diazaspiro[4.5]decane-6,8-dione hydrochloride (50 mg, 244 µmol, eq. 1) and benzo[d]thiazole-5-carboxylic acid (CAS 68867-17-4, 48.2 mg, 269 µmol, eq. 1.1) in N,N-dimethylformamide (1.5 ml) were added HATU (204 mg, 537 µmol, Eq. 2.2) and DIPEA (94.7 mg, 128 µl, 733 µmol, eq. 3.0) at room temperature. The reaction mixture was stirred for 2 hours and was then partitioned between ethyl acetate (30 ml) and water (15 ml). The layers were separated. The aqueous layer was extracted with ethyl acetate (30 ml). The combined organic layers were washed with brine (25 ml), dried over anhydrous sodium sulfate and concentrated in vacuo. The crude material was purified by flash column chromatography (silica gel, eluent: 0 to 5% of methanol in dichloromethane) to afford 2-(benzo[d]thiazole-5-carbonyl)-2,7-diazaspiro[4.5]decane-6,8-dione (14 mg, 34 µmol, 13.9%) as a white solid. MS (ISP): 330.0 ([M+H]⁺).

EXAMPLE 30

2-(5-Nitropyridin-2-yl)-2,7-diazaspiro[4.5]decane-6,8-dione

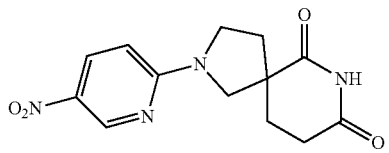 [SMILES: O=C1CCC2(CCN(c3ccc([N+](=O)[O-])cn3)C2)C(=O)N1]

The title compound was obtained as a yellow solid in analogy to Example 12 using 2-chloro-5-nitropyridine (CAS 4548-45-2) in place of 2-chlorobenzo[d]thiazole and heating at 100° C. for five hours instead of one. MS (ISP): 291.1 ([M+H]⁺).

EXAMPLE 31

2-(2-(Pyridin-3-yl)propanoyl)-2,7-diazaspiro[4.5]decane-6,8-dione

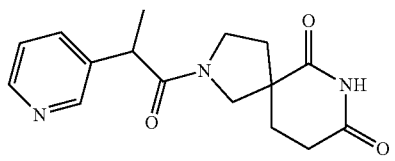 [SMILES: CC(C(=O)N1CCC2(CCC(=O)NC2=O)C1)c1cccnc1]

To a mixture of 2,7-diazaspiro[4.5]decane-6,8-dione hydrochloride (50 mg, 244 µmol, eq. 1) and 2-(pyridin-3-yl)propanoic acid (CAS 90005-62-2, 44.3 mg, 293 µmol, eq. 1.2) in ethyl acetate (560 µl) were added a solution of 1-propanephosphonic anhydride 50% in ethyl acetate (311 mg, 291 µl, 489 µmol, eq. 2) and triethylamine (98.9 mg, 136 µl, 977 µmol, eq. 4). The reaction mixture was shaken at 60° C. for 3 hours. According to LC/MS, the reaction was complete. The reaction mixture was filtered and the filtrate was directly purified by flash column chromatography (silica gel, 10 g, eluent: 0 to 20% of methanol in dichloromethane) to afford 2-(2-(pyridin-3-yl)propanoyl)-2,7-diazaspiro[4.5]decane-6,8-dione (57.2 mg, 190 µmol, 77.7%) as a white solid. MS (ISP): 302.15 ([M+H]⁺).

EXAMPLE 32

Methyl 6-(6,8-dioxo-2,7-diazaspiro[4.5]decan-2-yl)picolinate

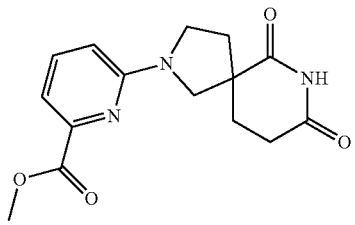 [SMILES: COC(=O)c1cccc(N2CCC3(CCC(=O)NC3=O)C2)n1]

The title compound was obtained as a brown solid in analogy to Example 6 using methyl 6-chloro-2-picolinic acid methyl ester (CAS 6636-55-1) in place of methyl 6-chloronicotinate. MS (ISP): 304.3 ([M+H]⁺).

EXAMPLE 33

2-(5-Nitro-1H-benzo[d]imidazol-2-yl)-2,7-diazaspiro[4.5]decane-6,8-dione (Enantiomer 1)

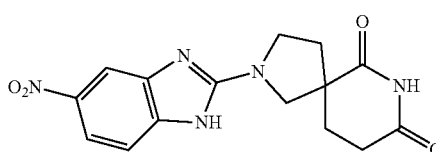

The enantiomers of 2-(5-nitro-1H-benzo[d]imidazol-2-yl)-2,7-diazaspiro[4.5]decane-6,8-dione (example 9) were separated using chiral SFC (column:IC, 12 nm, 5 µm, 250×4.6 mm, 20% ethanol) affording 2-(5-nitro-1H-benzo[d]imidazol-2-yl)-2,7-diazaspiro[4.5]decane-6,8-dione (Enantiomer 1) (24 mg, white solid), retention time=4.07 min. MS (ISP): 330.3 ([M+H]⁺).

EXAMPLE 34

2-(5-Nitro-1H-benzo[d]imidazol-2-yl)-2,7-diazaspiro[4.5]decane-6,8-dione (Enantiomer 2)

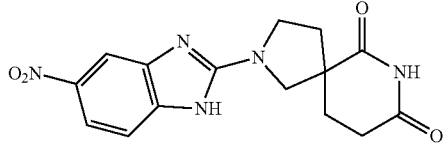 [SMILES: O=C1CCC2(CCN(c3nc4cc([N+](=O)[O-])ccc4[nH]3)C2)C(=O)N1]

The enantiomers of 245-nitro-1H-benzo[d]imidazol-2-yl)-2,7-diazaspiro[4.5]decane-6,8-dione (example 9) were separated using chiral SFC (column:IC, 12 nm, 5 µm, 250×4.6 mm, 20% ethanol) affording 2-(5-nitro-1H-benzo[d]imidazol-2-yl)-2,7-diazaspiro[4.5]decane-6,8-dione (Enantiomer 2) (24 mg, white solid), retention time=4.55 min. MS (ISP): 330.3 ([M+H]⁺).

EXAMPLE 35

2-(1-Acetylindoline-4-carbonyl)-2,7-diazaspiro[4.5]decane-6,8-dione

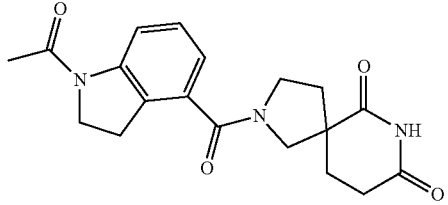 [SMILES: CC(=O)N1CCc2c(C(=O)N3CCC4(CCC(=O)NC4=O)C3)cccc21]

a) tert-Butyl 4-(6,8-dioxo-2,7-diazaspiro[4.5]decane-2-carbonyl)indoline-1-carboxylate The title compound was obtained as a light yellow solid in analogy to Example 29 using 1-(tert-butoxycarbonyl)indoline-4-carboxylic acid (CAS 208774-11-2) in place of benzo[d]thiazole-5-carboxylic acid. MS (ISP): 330.0 0 ([M+H]⁺).

b) 2-(Indoline-4-carbonyl)-2,7-diazaspiro[4.5]decane-6,8-dione

To a solution of tent-butyl 4-(6,8-dioxo-2,7-diazaspiro[4.5]decane-2-carbonyl)indoline-1-carboxylate (194 mg, 469 µmol, eq. 1) in 1,4-dioxane (2 ml) was added 4 M hydrogen chloride solution in 1,4-dioxane (1.17 ml, 4.69 mmol, eq. 10) at room temperature. The reaction mixture was stirred for 3 days. The reaction mixture was then partitioned between ethyl acetate/tetrahydrofuran (1:1) (50 ml) and 2 M aqueous sodium carbonate (30 ml). The layers were separated. The organic layer was dried over anhydrous sodium sulfate and concentrated in vacuo. The crude material was purified by flash chromatography (silica gel, eluent: 0 to 10% of methanol in dichloromethane) to afford 2-(indoline-4-carbonyl)-2,7-diazaspiro[4.5]decane-6,8-dione (102 mg, 326 µmol, 69.4%) as a yellow solid. MS (ISP): 314.0 ([M+H]⁺).

c) 2-(1-Acetylindoline-4-carbonyl)-2,7-diazaspiro[4.5]decane-6,8-dione

To a solution of 2-(indoline-4-carbonyl)-2,7-diazaspiro[4.5]decane-6,8-dione (30 mg, 95.7 µmol, Eq. 1) and triethylamine (19.4 mg, 26.7 µl, 191 µmol, Eq. 2.0) in dichloromethane (0.5 ml) was added acetic anhydride (10.8 mg, 9.94 µl, 105 µmol, Eq. 1.1) at room temperature. The reaction mixture was stirred for 15 hours. The crude material was directly purified by flash chromatography (loaded as an impregnate, silica gel, eluent: 0 to 10% of methanol in dichloromethane) to afford 2-(1-acetylindoline-4-carbonyl)-2,7-diazaspiro[4.5]decane-6,8-dione (34 mg, 95.7 µmol, 99.9% yield) as a white solid. MS (ISP): 356.0 ([M+H]⁺).

EXAMPLE 36

2-Benzoyl-2,7-diazaspiro[4.5]decane-6,8-dione

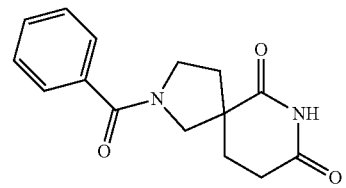 [SMILES: O=C1CCC2(CCN(C(=O)c3ccccc3)C2)C(=O)N1]

The title compound was obtained as a orange solid in analogy to Example 29 using benzoic acid (CAS 65-85-0) in place of benzo[d]thiazole-5-carboxylic acid. MS (ISP): 273.0 ([M+H]⁺).

EXAMPLE 37

N-(3-(6,8-Dioxo-2,7-diazaspiro[4.5]decane-2-carbonyl)phenyl)acetamide

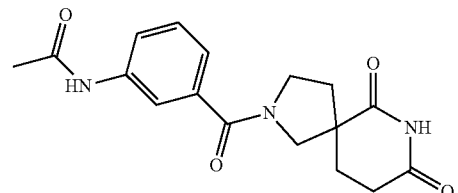

The title compound was obtained as a white solid in analogy to Example 29 using 3-acetamidobenzoic acid (CAS 587-48-4) in place of benzo[d]thiazole-5-carboxylic acid. MS (ISP): 330.0 ([M+H]⁺).

EXAMPLE 38

2-(1H-Indazole-4-carbonyl)-2,7-diazaspiro[4.5]decane-6,8-dione

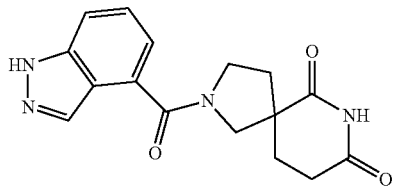 [SMILES: O=C1CCC2(CCN(C(=O)c3cccc4[nH]ncc34)C2)C(=O)N1]

The title compound was obtained as a white solid in analogy to Example 29 using 1H-indazole-4-carboxylic acid (CAS 677306-38-6) in place of benzo[d]thiazole-5-carboxylic acid. MS (ISP): 313.1 ([M+H]$^+$).

EXAMPLE 39

2-(5-Aminopyridin-2-yl-2,7-diazaspiro[4.5]decane-6,8-dione

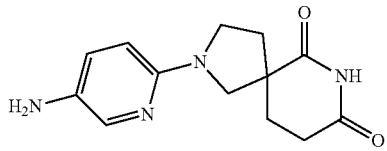

To a solution of 2-(5-nitropyridin-2-yl)-2,7-diazaspiro[4.5]decane-6,8-dione (189 mg, 651 µmol, eq. 1) in methanol (30 ml) and tetrahydrofuran (30 ml) was added 10% palladium on charcoal (34.6 mg, 32.6 µmol, eq. 0.05). The reaction mixture was stirred at room temperature for 2 hours under an atmosphere of hydrogen. The catalyst was collected by filtration, washing with methanol. The filtrate was then concentrated in vacuo. The crude material was purified by flash chromatography (silica gel, eluent: 0 to 10% of methanol in dichloromethane) to afford 2-(5-aminopyridin-2-yl)-2,7-diazaspiro[4.5]decane-6,8-dione (101 mg, 388 µmol, 59.6%) as an off-white solid. MS (ISP): 287.0 ([M+H]$^+$).

EXAMPLE 40

2-(Indoline-4-carbonyl)-2,7-diazaspiro[4.5]decane-6,8-dione

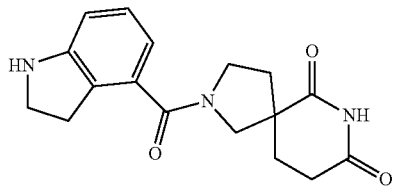 [SMILES: O=C1CCC2(CCN(C(=O)c3cccc4c3CCN4)C2)C(=O)N1]

The title compound was described in Example 35 (a) and (b) and was obtained as a yellow solid. MS (ISP): 314.0 ([M+H]$^+$).

EXAMPLE 41

2-(Indoline-6-carbonyl)-2,7-diazaspiro[4.5]decane-6,8-dione

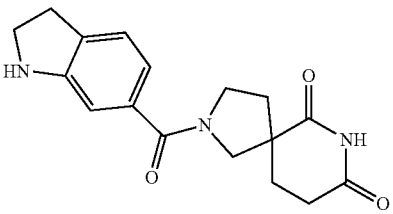 [SMILES: O=C1CCC2(CCN(C(=O)c3ccc4c(c3)NCC4)C2)C(=O)N1]

The title compound was obtained as a white solid in analogy to example 35 a) and b) using 1-(tert-butoxycarbonyl)indoline-6-carboxylic acid (CAS 208772-41-2) in place of benzo[d]thiazole-5-carboxylic acid. MS (ISP): 314.0 ([M+H]$^+$).

EXAMPLE 42

2-(1-Acetylindoline-6-carbonyl)-2,7-diazaspiro[4.5]decane-6,8-dione

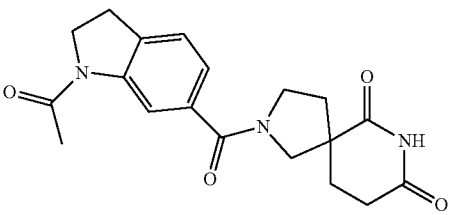 [SMILES: CC(=O)N1CCc2ccc(C(=O)N3CCC4(CCC(=O)NC4=O)C3)cc21]

The title compound was obtained as a white solid in analogy to Example 35 (c) using 2-(indoline-6-carbonyl)-2,7-diazaspiro[4.5]decane-6,8-dione (from example 41) in place of 2-(indoline-4-carbonyl)-2,7-diazaspiro[4.5]decane-6,8-dione. MS (ISP): 356.0 ([M+H]$^+$).

EXAMPLE 43

N-(6-(6,8-Dioxo-2,7-diazaspiro[4.5]decan-2-yl)pyridin-3-yl)acetamide

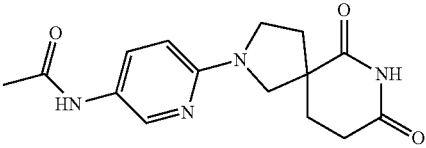 [SMILES: CC(=O)Nc1ccc(N2CCC3(CCC(=O)NC3=O)C2)nc1]

To a suspension of 2-(5-aminopyridin-2-yl)-2,7-diazaspiro[4.5]decane-6,8-dione (17 mg, 65.3 µmol, eq. 1) and Et$_3$N (16.5 mg, 22.8 µl, 163 µmol, eq. 2.5) in dichloromethane (1 ml) was added acetic anhydride (10 mg, 9.24 µl, 98 µmol, eq. 1.5). The reaction mixture was stirred at room temperature for 30 minutes. The reaction mixture was poured into a mixture of ethylactate/tetrahydrofuran (1:2) and washed with water and brine. The organic layer was dried over sodium sulfate and concentrated in vacuo. The crude material was purified by flash chromatography (silica gel, eluent: 0 to 10% of methanol in dichloromethane) to afford N-(6-(6,8-dioxo-2,7-diazaspiro[4.5]decan-2-yl)pyridin-3-yl)acetamide (11 mg, 36.4 μmol, 55.7%) as a light brown solid. MS (ISP): 303.1 ([M+H]$^+$).

EXAMPLE 44

2-(Benzofuran-3-carbonyl)-2,7-diazaspiro[4.5]decane-6,8-dione

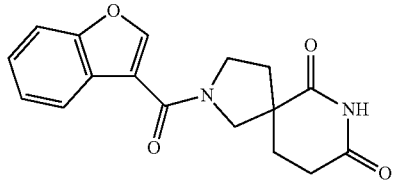 [SMILES: O=C1CCC2(CCN(C(=O)c3coc4ccccc34)C2)C(=O)N1]

The title compound was obtained as an off-white solid in analogy to Example 29 using benzofuran-3-carboxylic acid (CAS 26537-68-8) in place of benzo[d]thiazole-5-carboxylic acid. MS (ISP): 313.1 ([M+H]$^+$).

EXAMPLE 45

2-(Pyrazolo[1,5-a]pyridine-3-carbonyl)-2,7-diazaspiro[4.5]decane-6,8-dione

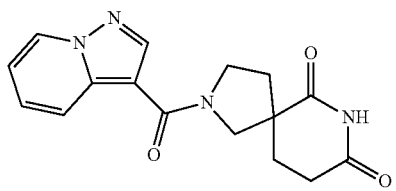 [SMILES: O=C1CCC2(CCN(C(=O)c3cnn4ccccc34)C2)C(=O)N1]

The title compound was obtained as an off-white solid in analogy to Example 29 using pyrazolo[1,5-a]pyridine-3-carboxylic acid (CAS 16205-46-2) in place of benzo[d]thiazole-5-carboxylic acid. MS (ISP): 313.1 ([M+H]$^+$).

EXAMPLE 46

2-(Benzo[d]oxazole-6-carbonyl)-2,7-diazaspiro[4.5]decane-6,8-dione

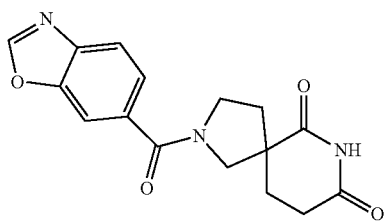 [SMILES: O=C1CCC2(CCN(C(=O)c3ccc4ncoc4c3)C2)C(=O)N1]

The title compound was obtained as an off-white solid in analogy to Example 29 using 1,3-benzoxazole-6-carboxylic acid (CAS 154235-77-5) in place of benzo[d]thiazole-5-carboxylic acid. MS (ISP): 314.1 ([M+H]$^+$).

EXAMPLE 47

2-(Indoline-5-carbonyl)-2,7-diazaspiro[4.5]decane-6,8-dione

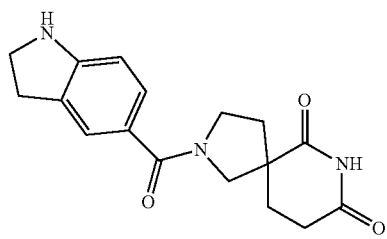 [SMILES: O=C1CCC2(CCN(C(=O)c3ccc4c(c3)CCN4)C2)C(=O)N1]

The title compound was obtained as an off-white solid in analogy to Example 29 using indoline-5-carboxylic acid (CAS 15861-30-0) in place of benzo[d]thiazole-5-carboxylic acid. MS (ISP): 314.1 ([M+H]$^+$).

EXAMPLE 48

(+)-2-((R)-1,2,3,4-Tetrahydronaphthalene-1-carbonyl)-2,7-diazaspiro[4.5]decane-6,8-dione

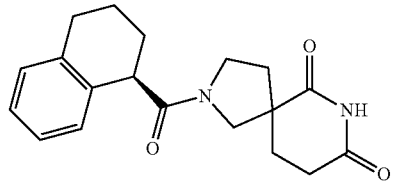 [SMILES: O=C1CCC2(CCN(C(=O)[C@@H]3CCCc4ccccc43)C2)C(=O)N1]

To a mixture of 2,7-diazaspiro[4.5]decane-6,8-dione hydrochloride (50 mg, 244 μmol, eq. 1) and (R)-1,2,3,4-tetrahydronaphthalene-1-carboxylic acid (51.7 mg, 293 μmol, eq. 1.2) in ethyl acetate (560 μl) was added a solution of 50% 1-propanephosphonic anhydride in ethyl acetate (311 mg, 291 μl, 489 μmol, eq. 2) followed by triethylamine (98.9 mg, 136 977 μmol, eq. 4). The reaction mixture was shaken at 60° C. for 3 hours. According to LC/MS, the reaction was finished. The reaction mixture was filtered and the filtrate was directly purified by flash column chromatography (silica gel, 10 g, eluent: 0 to 20% of methanol in dichloromethane). According to chiral HPLC, the compound obtained was a racemic mixture of four diastereomers. The sample was purified with chiral HPLC (column: Reprosil Chiral-NR, eluent: heptane/ethanol+NH$_4$OAc (70:30), pressure: 18 bar; flow rate: 35 ml/min) to afford (+)-2-((R)-1,2,3,4-tetrahydronaphthalene-1-carbonyl)-2,7-diazaspiro[4.5]decane-6,8-dione (25.6 mg, 78.4 μmol, 32.1% yield, mixture of epimers) as a white solid. Retention time=46.8 min MS (ISP): 327.3 ([M+H]$^+$).

EXAMPLE 49

(+2-((S)-1,2,3,4-Tetrahydronaphthalene-1-carbonyl)-2,7-diazaspiro[4.5]decane-6,8-dione

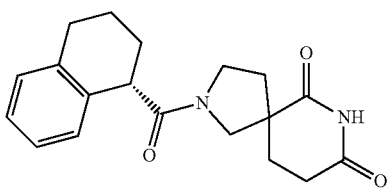 [SMILES: O=C1CCC2(CCN(C(=O)[C@H]3CCCc4ccccc43)C2)C(=O)N1]

The mixture of diastereomers from Example 48 was purified with chiral HPLC (column: Reprosil Chiral-NR, eluent: heptane/ethanol+NH$_4$OAc (70:30), pressure: 18 bar; flow rate: 35 ml/min) to afford (−)-2-((S)-1,2,3,4-tetrahydronaphthalene-1-carbonyl)-2,7-diazaspiro[4.5]decane-6,8-dione (27.9 mg, 85.5 mol, 35% yield, mixture of epimers) as a white solid. Retention time=68 min MS (ISP): 327.3 ([M+H]$^+$).

EXAMPLE 50

N-(5-(6,8-Dioxo-2,7-diazaspiro[4.5]decane-2-carbonyl)benzo[d]thiazol-2-yl)acetamide

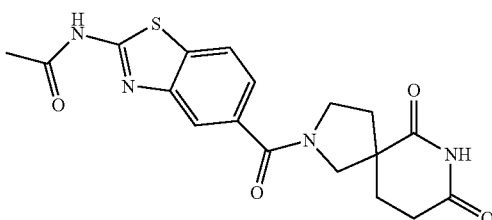

The title compound was obtained as an off-white solid in analogy to Example 29 using 2-acetamidobenzo[d]thiazole-5-carboxylic acid (CAS 77850-40-9) in place of benzo[d]thiazole-5-carboxylic acid. MS (ISP): 387.1 ([M+H]$^+$).

EXAMPLE 51

N-(6-(6,8-Dioxo-2,7-diazaspiro[4.5]decane-2-carbonyl)benzo[d]thiazol-2-yl)acetamide

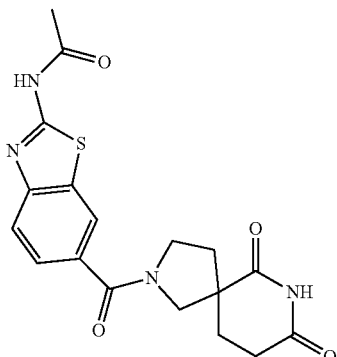

The title compound was obtained as an off-white solid in analogy to Example 29 using 2-acetamidobenzo[d]thiazole-6-carboxylic acid (CAS 100817-94-5) in place of benzo[d]thiazole-5-carboxylic acid. MS (ISP): 387.1 ([M+H]+).

EXAMPLE 52

2-(1-Acetylindoline-5-carbonyl)-2,7-diazaspiro[4.5]decane-6,8-dione

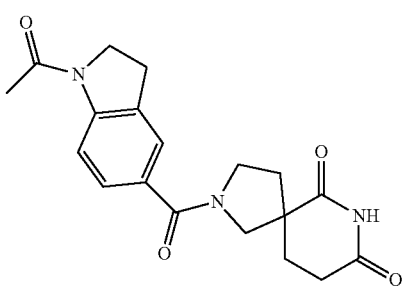 [SMILES: CC(=O)N1CCc2cc(C(=O)N3CCC4(CCC(=O)NC4=O)C3)ccc21]

The title compound was obtained as a white solid in analogy to Example 35 (c) using 2-(indoline-5-carbonyl)-2,7-diazaspiro[4.5]decane-6,8-dione (from example 47) in place of 2-(indoline-4-carbonyl)-2,7-diazaspiro[4.5]decane-6,8-dione. MS (ISP): 356.1 ([M+H]$^+$).

EXAMPLE 53 tert-Butyl (5-(6,8-dioxo-2,7-diazaspiro[4.5]decane-2-carbonyl)benzo[d]thiazol-2-yl)carbamate

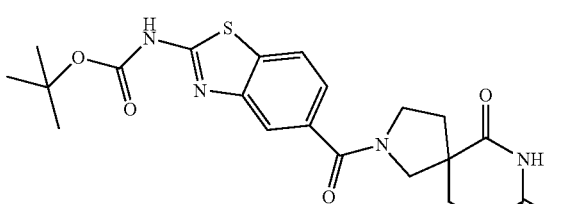

The title compound was obtained as a white solid in analogy to Example 29 using 2-((tert-butoxycarbonyl)amino)benzo[d]thiazole-5-carboxylic acid (CAS 1824350-51-7) in place of benzo[d]thiazole-5-carboxylic acid. MS (ISP): 445.1 ([M+H]+).

EXAMPLE 54 tert-Butyl (6-(6,8-dioxo-2,7-diazaspiro[4.5]decane-2-carbonyl)benzo[d]thiazol-2-yl)carbamate

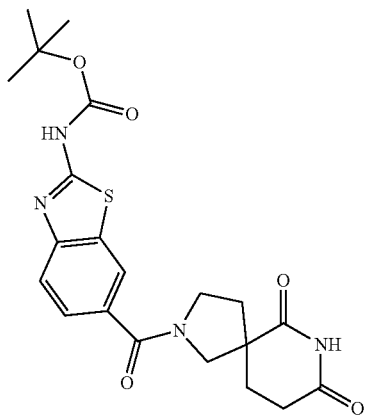 [SMILES: CC(C)(C)OC(=O)Nc1nc2ccc(C(=O)N3CCC4(CCC(=O)NC4=O)C3)cc2s1]

The title compound was obtained as an off-white solid in analogy to Example 29 using 2-((tert-butoxycarbonyl)amino)benzo[d]thiazole-6-carboxylic acid (CAS 225525-50-8) in place of benzo[d]thiazole-5-carboxylic acid. MS (ISP): 445.1 ([M+H]+).

EXAMPLE 55

2-(2-Aminobenzo[d]thiazole-6-carbonyl)-2,7-diazaspiro[4.5]decane-6,8-dione

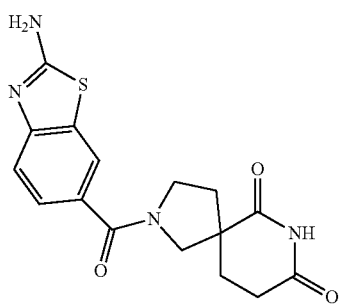 [SMILES: Nc1nc2ccc(C(=O)N3CCC4(CCC(=O)NC4=O)C3)cc2s1]

To a stirred solution of tent-butyl (6-(6,8-dioxo-2,7-diazaspiro[4.5]decane-2-carbonyl)benzo[d]thiazol-2-yl)carbamate (43 mg, 96.7 μmol, eq. 1) in dichloromethane (1 ml) at room temperature was added dropwise trifluoroacetic acid (298 3.87 mmol, eq. 40). The reaction mixture was stirred at room temperature for 1 h. LC-MS showed the reaction was complete. The reaction mixture was concentrated in vacuo. The residue was taken up in EtOAc/THF (1:3) and extracted sequentially with water and with brine. The organic layer was dried over $Na_2SO_4$ and concentrated in vacuo. The crude material was purified by flash chromatography (silica gel, 4 g, 0% to 10% MeOH in DCM) to afford 2-(2-aminobenzo[d]thiazole-6-carbonyl)-2,7-diazaspiro[4.5]decane-6,8-dione (14 mg, 40.7 μmol, 42% yield) as a white solid. MS (ISP): 345.0 ([M+H]+).

EXAMPLE 56

2-(Benzo[d]thiazole-6-carbonyl)-2,7-diazaspiro[4.5]decane-6,8-dione

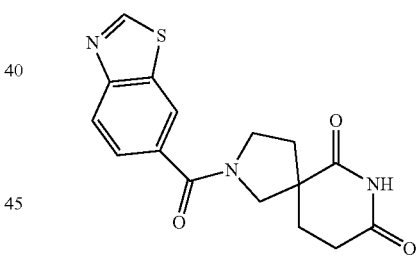

The title compound was obtained as an off-white solid in analogy to Example 29 using benzo[d]thiazole-6-carboxylic acid (CAS 3622-35-3) in place of benzo[d]thiazole-5-carboxylic acid. MS (ISP): 330.1 ([M+H]+).

EXAMPLE 57

8-(2-((R)-4-(4-Chlorophenyl)-2,3,9-trimethyl-6H-thieno[3,2-f][1,2,4]triazolo[4,3-a][1,4]diazepin-6-yl)acetamido)-N-(3-(6,8-dioxo-2,7-diazaspiro[4.5]decane-2-carbonyl)phenyl)octanamide

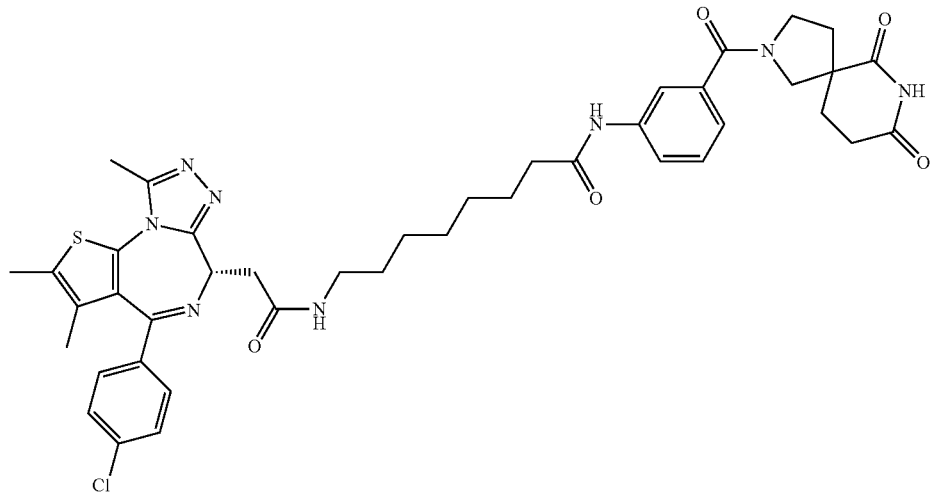 [SMILES: Cc1sc2c(c1C)C(c1ccc(Cl)cc1)=N[C@@H](CC(=O)NCCCCCCCC(=O)Nc1cccc(C(=O)N3CCC4(CCC(=O)NC4=O)C3)c1)c1nnc(C)n1-2]

a) tert-Butyl (8-((3-(6,8-dioxo-2,7-diazaspiro[4.5]decane-2-carbonyl)phenyl)amino)-8-oxooctyl)carbamate 2,7-Diazaspiro[4.5]decane-6,8-dione (200 mg, 1.19 mmol, eq. 1) was dissolved in a solution of HATU in N,N-dimethylformamide (4.86 ml, 1.31 mmol, eq. 1.1, 0.269 mol/l) and 3-(8-(((tert-butoxycarbonyl)amino)octanamido)benzoic acid (540 mg, 1.43 mmol, eq. 1.2) followed by DIPEA (615 mg, 831 µl, 4.76 mmol, eq. 4) were added. The reaction mixture was stirred at room temperature for 3 hours and then left overnight at room temperature. Water and ethyl acetate were added. The aqueous phase was extracted a second time with ethyl acetate. The combined organic layer was dried over sodium sulfate and concentrated in vacuo. The crude material was purified by flash chromatography (silica gel, eluent: 0 to 50% of ethyl acetate in heptane) to afford tent-butyl (8-((3-(6,8-dioxo-2,7-diazaspiro[4.5]decane-2-carbonyl)phenyl)amino)-8-oxooctyl)carbamate (90 mg, 170 µmol, 14.3% yield) as an off-white powder. MS (ISP): 529.4 ([M+H]$^+$).

b) 8-Amino-N-(3-(6,8-dioxo-2,7-diazaspiro[4.5]decane-2-carbonyl)phenyl)octanamide hydrochloride To a solution of tent-butyl (8-((3-(6,8-dioxo-2,7-diazaspiro[4.5]decane-2-carbonyl)phenyl)amino)-8-oxooctyl)carbamate (90 mg, 170 µmol, eq. 1) in ethyl acetate (1 ml) was added a solution of 4 M HCl in dioxane (638 µl, 2.55 mmol, eq. 15. The reaction was stirred at room temperature for 1 hour. According to LC-MS, the reaction was finished. The solvent was evaporated. The crude was dissolved in a minimum of ethanol and diethyl ether was added. The suspension obtained was filtered to afford 8-amino-N-(3-(6,8-dioxo-2,7-diazaspiro[4.5]decane-2-carbonyl)phenyl)octanamide hydrochloride (40 mg, 86 µmol, 50.5% yield) and was directly used in the next step.

c) 8-(2-((R)-4-(4-Chlorophenyl)-2,3,9-trimethyl-6H-thieno[3,2-f][1,2,4]triazolo[4,3-a][1,4]diazepin-6-yl)acetamido)-N-(3-(6,8-dioxo-2,7-diazaspiro[4.5]decane-2-carbonyl)phenyl)octanamide (S)-2-(4-(4-Chlorophenyl)-2,3,9-trimethyl-6H-thieno[3,2-f][1,2,4]triazolo[4,3-a][1,4]diazepin-6-yl)acetic acid (CAS 202592-23-2, 40 mg, 99.8 µmol, eq. 1) and 8-amino-N-(3-(6,8-dioxo-2,7-diazaspiro[4.5]decane-2-carbonyl)phenyl)octanamide hydrochloride (51 mg, 110 µmol, eq. 1.1) were dissolved in a solution of HATU (445 µl, 120 µmol, eq. 1.2, 0.269 mol/l) N,N-dimethylformamide and DIPEA (51.6 mg, 69.7 µl, 399 µmol, eq. 4) was added. The reaction mixture was shaken at room temperature for 3 hours. According to LC/MS, the reaction was finished. Water and dichloromethane were added. The organic layer was dried over sodium sulfate and concentrated in vacuo. The crude material was purified by flash chromatography (silica gel, eluent: 0 to 20% of methanol in dichloromethane) to afford 8-(2-((R)-4-(4-chlorophenyl)-2,3,9-trimethyl-6H-thieno[3,2-f][1,2,4]triazolo[4,3-a][1,4]diazepin-6-yl)acetamido)-N-(3-(6,8-dioxo-2,7-diazaspiro[4.5]decane-2-carbonyl)phenyl)octanamide (39.8 mg, 49.1 µmol, 49.2% yield) as an off-white solid. MS (ISP): 811.3 ([M+H]$^+$).

EXAMPLE 58

(S)-8-(1,2,3,4-Tetrahydronaphthalene-1-carbonyl)-1,3,8-triazaspiro[4.5]decane-2,4-dione

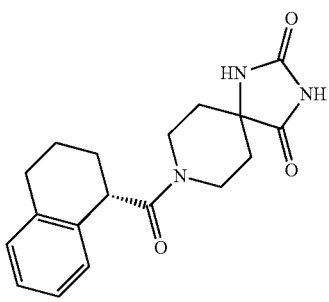 [SMILES: O=C1NC(=O)C2(CCN(C(=O)[C@H]3CCCc4ccccc43)CC2)N1]

To a solution of 1,3,8-triazaspiro[4.5]decane-2,4-dione (CAS 13625-39-3, 100 mg, 591 µmol, eq. 1) and (S)-1,2,3,4-tetrahydronaphthalene-1-carboxylic acid (CAS 85977-52-2, 109 mg, 621 µmol, eq. 1.05) in N,N-dimethylformamide (1 ml) were added HATU (449 mg, 1.18 mmol, eq. 2.0) and DIPEA (229 mg, 310 µl, 1.77 mmol, eq. 3.0) at room temperature. The reaction mixture was stirred for 15 hours and was then partitioned between ethyl acetate (50 ml) and water (30 ml). The layers were separated. The aqueous layer was extracted with ethyl acetate (2×20 ml). The combined organic layers were washed with brine (30 ml), dried over anhydrous sodium sulfate and concentrated in vacuo. The crude material was purified by reversed phase HPLC followed by lyophilisation to afford (S)-8-(1,2,3,4-tetrahydronaphthalene-1-carbonyl)-1,3,8-triazaspiro[4.5]decane-2,4-dione (45 mg, 137 µmol, 23.3%) as a white solid. MS (ISP): 328.0 ([M+H]$^+$).

EXAMPLE 59

(R)-8-(1,2,3,4-Tetrahydronaphthalene-1-carbonyl)-1,3,8-triazaspiro[4.5]decane-2,4-dione

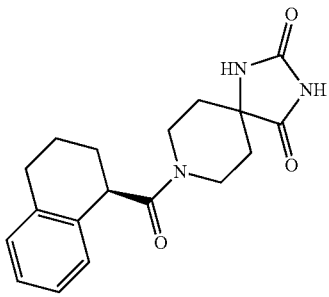 [SMILES: O=C1NC(=O)C2(CCN(C(=O)[C@@H]3CCCc4ccccc43)CC2)N1]

The title compound was obtained as a white solid in analogy to Example 58 using (R)-1,2,3,4-tetrahydronaphthalene-1-carboxylic acid (CAS 23357-47-3) in place of (9-1,2,3,4-tetrahydronaphthalene-1-carboxylic acid. MS (ISP): 328.0 ([M+H]$^+$).

EXAMPLE 60

8-Benzoyl-1,3,8-triazaspiro[4.5]decane-2,4-dione

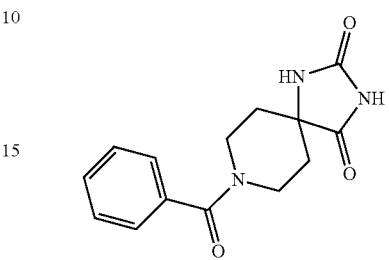

The title compound was obtained as a white solid in analogy to Example 58 using benzoic acid (CAS 65-85-0) in place of (S)-1,2,3,4-tetrahydronaphthalene-1-carboxylic acid. White solid. MS (ISP): 274.1 ([M⇌H]$^+$).

EXAMPLE 61

8-(Benzo[d]thiazol-2-yl)-1,3,8-triazaspiro[4.5]decane-2,4-dione

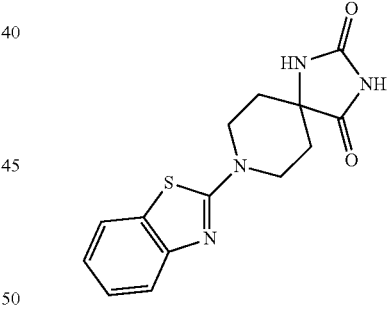

To a suspension of 1,3,8-triazaspiro[4.5]decane-2,4-dione (CAS 13625-39-3, 20 mg, 118 µmol, eq. 1) and DIPEA (45.8 mg, 61.9 µl, 355 mol, eq. 3) in N,N-dimethylformamide (0.5 ml) was added 2-chlorobenzo[d]thiazole (22.1 mg, 130 µmol, eq. 1.1). The reaction mixture was stirred at 120° C. for 2 hours. The reaction mixture was poured into a mixture of ethylacetate/tetrahydrofuran (1:1) and the organic layer was washed with water and brine, dried over Na$_2$SO$_4$ and concentrated in vacuo. The crude material was purified by flash column chromatography (silica gel, eluent: 0 to 5% of methanol in dichloromethane) to afford 8-(benzo[d]thiazol-2-yl)-1,3,8-triazaspiro[4.5]decane-2,4-dione (11 mg, 36.4 µmol, 30.8%) as a white solid. MS (ISP): 303.1 ([M+H]$^+$).

EXAMPLE 62

8-(Thiazolo[4,5-b]pyridin-2-yl)-1,3,8-triazaspiro[4.5]decane-2,4-dione

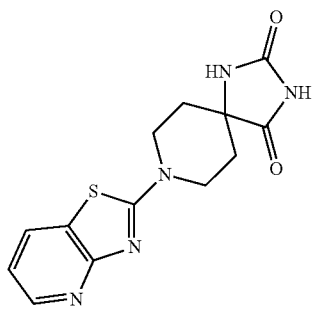 [SMILES: O=C1NC(=O)C2(CCN(c3nc4ncccc4s3)CC2)N1]

The title compound was obtained as a brown solid in analogy to Example 62 using 2-chlorothiazolo[4,5-b]pyridine (CAS 152170-30-4) in place of 2-chlorobenzo[d]thiazole. MS (ISP): 304.1 ([M+H]$^+$).

EXAMPLE 63

Methyl 6-(2,4-dioxo-1,3,8-triazaspiro[4.5]decan-8-yl)nicotinate

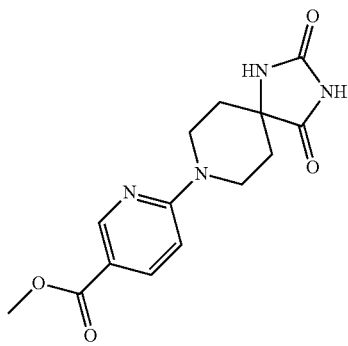 [SMILES: COC(=O)c1ccc(N2CCC3(CC2)NC(=O)NC3=O)nc1]

The title compound was obtained as a brown solid in analogy to Example 62 using methyl 6-chloronicotinate (CAS 73781-91-6) in place of 2-chlorobenzo[d]thiazole and stirring for 16 hours instead of 2 hours. MS (ISP): 305.1 ([M+H]$^+$).

EXAMPLE 64

N-(4-(2,4-Dioxo-1,3,8-triazaspiro[4.5]decane-8-carbonyl)phenyl)acetamide

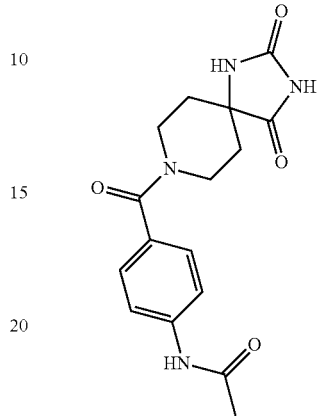

To a solution of 1,3,8-triazaspiro[4.5]decane-2,4-dione (36 mg, 213 µmol, eq. 1) and 4-acetamidobenzoic acid (CAS 556-08-1, 40 mg, 223 µmol, eq. 1.05) in N,N-dimethylformamide (1 ml) were added DIPEA (110 mg, 149 µl, 851 µmol, eq. 4) and HATU (121 mg, 319 µmol, eq. 1.5). The reaction mixture was stirred at room temperature overnight. The reaction mixture was poured into ethyl acetate/tetrahydrofuran (1:1) and extracted with water followed with brine. The organic layer was dried over Na$_2$SO$_4$ and concentrated in vacuo. The crude material was purified by flash chromatography (silica gel, 4 g, 0% to 10% methanol in dichloromethane) to afford N-(4-(2,4-dioxo-1,3,8-triazaspiro[4.5]decane-8-carbonyl)phenyl)acetamide (10 mg, 30.3 µmol, 14.2%) as a white solid. MS (ISP): 331.1 ([M+H]$^+$).

EXAMPLE 65

N-(3-(2,4-Dioxo-1,3,8-triazaspiro[4.5]decane-8-carbonyl)phenyl)acetamide

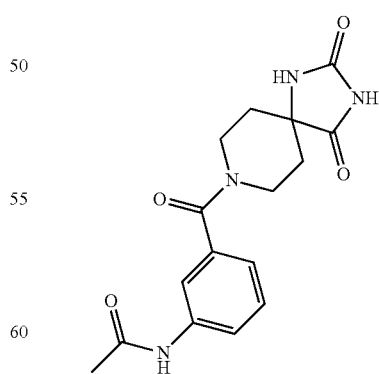

The title compound was obtained as a white solid in analogy to Example 64 using 3-acetamidobenzoic acid (CAS 587-48-4) in place of 4-acetamidobenzoic acid. MS (ISP): 329.1 ([M−H]$^-$).

EXAMPLE 66

8-(Benzofuran-3-carbonyl)-1,3,8-triazaspiro[4.5]decane-2,4-dione

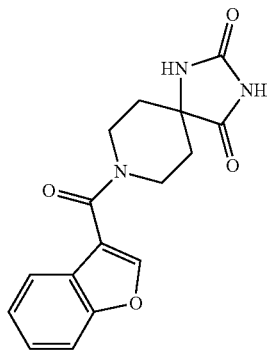

To a solution of 1,3,8-triazaspiro[4.5]decane-2,4-dione hydrochloride (CAS 13625-48-4, 30 mg, 146 µmol, eq. 1) and benzofuran-3-carboxylic acid (CAS 26537-68-8, 31.6 mg, 195 µmol, eq. 1.1) in N,N-dimethylformamide (0.5 ml) were added DIPEA (68.8 mg, 92.9 µL, 532 µmol, eq. 3) and HATU (169 mg, 443 µmol, eq. 2.5). The reaction mixture was stirred at room temperature for 2 hours and was poured into ethyl acetate/tetrahydrofuran (2:1) (30 ml). The aqueous layer was extracted with two portions of ethyl acetate (2×20 ml). The combined organic layer was dried over $Na_2SO_4$ and concentrated in vacuo. The crude material was purified by flash chromatography (silica gel, 4 g, 0% to 10% methanol in dichloromethane) followed by a preparative RP-HPLC and lyophilisation to afford 8-(benzofuran-3-carbonyl)-1,3,8-triazaspiro[4.5]decane-2,4-dione (3.3 mg, 10.5 µmol, 7.22%) as a yellow solid. MS (ISP): 314.1 ([M+H]$^+$).

EXAMPLE 67

8-(Pyrazolo[1,5-a]pyridine-3-carbonyl)-1,3,8-triazaspiro[4.5]decane-2,4-dione

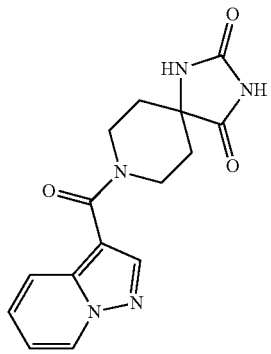 [SMILES: O=C1NC(=O)C2(CCN(C(=O)c3cnn4ccccc34)CC2)N1]

The title compound was obtained as a white solid in analogy to Example 66 using pyrazolo[1,5-a]pyridine-3-carboxylic acid (CAS 16205-46-2) in place of benzofuran-3-carboxylic acid. MS (ISP): 314 ([M+H]$^+$).

EXAMPLE 68

8-(Thiazolo[4,5-b]pyridin-2-yl)-2,8-diazaspiro[4.5]decane-1,3-dione

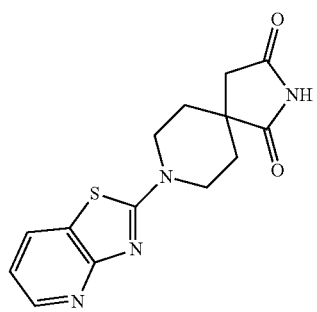 [SMILES: O=C1CC2(CCN(c3nc4ncccc4s3)CC2)C(=O)N1]

The title compound was obtained as a grey solid in analogy to Example 61 using 2-chlorothiazolo[4,5-b]pyridine (CAS 152170-30-4) in place of 2-chlorobenzo[d]thiazole and using 2,8-diazaspiro[4.5]decane-1,3-dione hydrochloride (CAS 2696-03-9) instead of 1,3,8-triazaspiro[4.5]decane-2,4-dione. MS (ISP): 303.1 ([M+H]$^+$).

EXAMPLE 69

8-(5-Nitropyridin-2-yl)-1,3,8-triazaspiro[4.5]decane-2,4-dione

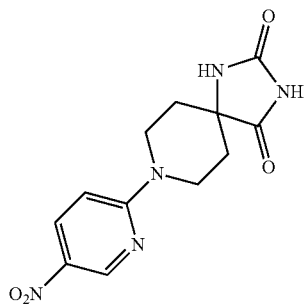 [SMILES: O=C1NC(=O)C2(CCN(c3ccc([N+](=O)[O-])cn3)CC2)N1]

The title compound was obtained as a yellow solid in analogy to Example 61 using 2-chloro-5-nitropyridine (CAS 4548-45-2) in place of 2-chlorobenzo[d]thiazole. MS (ISP): 292.1 ([M+H]$^+$).

EXAMPLE 70

8-(5-Nitropyridin-2-yl)-2,8-diazaspiro[4.5]decane-1,3-dione

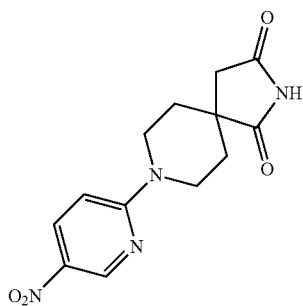 [SMILES: O=C1CC2(CCN(c3ccc([N+](=O)[O-])cn3)CC2)C(=O)N1]

The title compound was obtained as a grey solid in analogy to Example 61 using 2-chloro-5-nitropyridine (CAS 4548-45-2) in place of 2-chlorobenzo[d]thiazole and using 2,8-diazaspiro[4.5]decane-1,3-dione hydrochloride (CAS 2696-03-9) instead of 1,3,8-triazaspiro[4.5]decane-2,4-dione. MS (ISP): 291.1 ([M+H]$^+$).

EXAMPLE 71

8-(Benzo[d]thiazol-2-yl)-2,8-diazaspiro[4.5]decane-1,3-dione

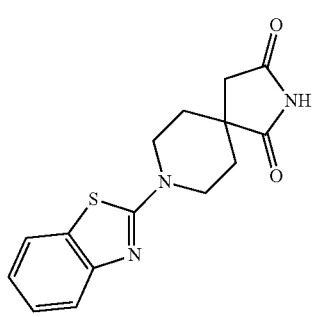

The title compound was obtained as a grey solid in analogy to Example 61 using 2,8-diazaspiro[4.5]decane-1,3-dione hydrochloride (CAS 2696-03-9) instead of 1,3,8-triazaspiro[4.5]decane-2,4-dione. MS (ISP): 302.0 ([M+H]$^+$).

EXAMPLE 72

8-(4-Nitrophenyl)-1,3,8-triazaspiro[4.5]decane-2,4-dione

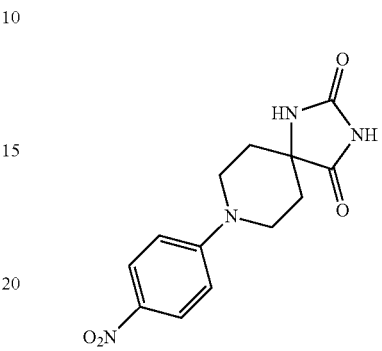

The title compound was obtained as a yellow solid in analogy to Example 61 using 1-fluoro-4-nitrobenzene (CAS 350-46-9) in place of 2-chlorobenzo[d]thiazole. MS (ISP): 291.0 ([M+H]$^+$).

EXAMPLE 73

8-(4-Nitrophenyl)-2,8-diazaspiro[4.5]decane-1,3-dione

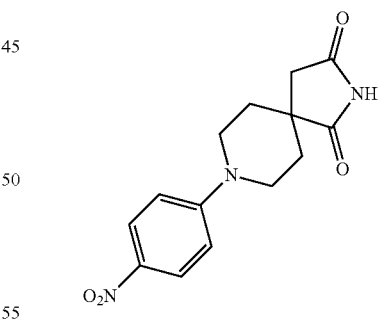

The title compound was obtained as a grey solid in analogy to Example 61 using 1-fluoro-4-nitrobenzene (CAS 350-46-9) in place of 2-chlorobenzo[d]thiazole and using 2,8-diazaspiro[4.5]decane-1,3-dione hydrochloride (CAS 2696-03-9) instead of 1,3,8-triazaspiro[4.5]decane-2,4-dione. MS (ISP): 291.1 ([M+H]$^+$).

317

EXAMPLE 74

Methyl 6-(1,3-dioxo-2,8-diazaspiro[4.5]decan-8-yl)nicotinate

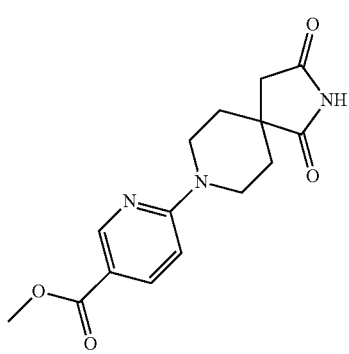 [SMILES: COC(=O)c1ccc(N2CCC3(CC2)CC(=O)NC3=O)nc1]

The title compound was obtained as an off-white solid in analogy to Example 61 using methyl 6-chloronicotinate (CAS 73781-91-6) in place of 2-chlorobenzo[d]thiazole and using 2,8-diazaspiro[4.5]decane-1,3-dione hydrochloride (CAS 2696-03-9) instead of 1,3,8-triazaspiro[4.5]decane-2,4-dione. MS (ISP): 304.1 ([M+H]$^+$).

EXAMPLE 75

8-Benzoyl-2,8-diazaspiro[4.5]decane-1,3-dione

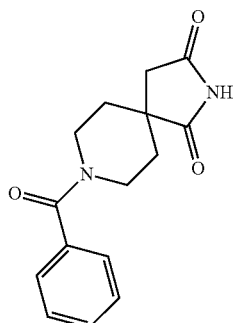

To a solution of 2,8-diazaspiro[4.5]decane-1,3-dione hydrochloride (60 mg, 293 µmol, eq. 1) and triethylamine (89 mg, 123 µl, 880 µmol, eq. 3) in tetrahydrofuran (1.5 ml) was added benzoyl chloride (CAS 98-88-4, 49.5 mg, 40.9 352 µmol, eq. 1.2) at 5° C. The reaction mixture was stirred for 3 hours. LC/MS showed the reaction was finished. The reaction mixture was partitioned between ethyl acetate/tetrahydrofuran 1:1 (20 ml) and brine (25 ml). The layers were separated. The aqueous layer was extracted with one portion of ethyl acetate (15 ml). The combined organic layers were dried over anhydrous sodium sulfate and concentrated in vacuo. The crude material was purified by flash chromatography (silica gel, 4 g, 0% to 10% methanol in dichloromethane) to afford 8-benzoyl-2,8-diazaspiro[4.5]decane-1,3-dione (25.2 mg, 92.5 µmol, 31.6%) as a white solid. MS (ISP): 273.1 ([M+H]$^+$).

318

EXAMPLE 76

8-(Benzo[d]thiazole-5-carbonyl)-2,8-diazaspiro[4.5]decane-1,3-dione

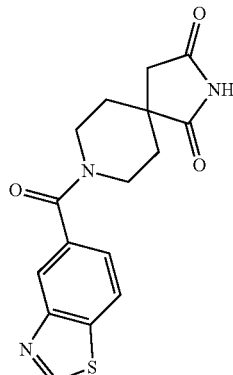

To a suspension of benzo[d]thiazole-5-carboxylic acid (55.2 mg, 308 µmol, eq. 1.05) in tetrahydrofuran (1 ml) was added 1-chloro-N,N,2-trimethyl-1-propenylamine (47 mg, 46.5 µL, 352 µmol, Eq. 1.2). The mixture was stirred for 1.5 hours and was added at room temperature in one portion to a pre-stirred suspension of 2,8-diazaspiro[4.5]decane-1,3-dione hydrochloride (60 mg, 293 µmol, eq. 1) and DIPEA (114 mg, 154 µl, 880 µmol, eq. 3.0) in tetrahydrofuran (1 ml). The reaction mixture was stirred for 1.5 hours. LC/MS showed the reaction was finished. The reaction mixture was partitioned between ethyl acetate (30 ml) and 1 M aqueous sodium carbonate (15 ml). The aqueous layer was extracted with one portion of ethyl acetate (30 ml). The combined organic layers were washed with one portion of brine (20 ml), dried over anhydrous sodium sulfate and concentrated in vacuo. The crude material was purified by preparative RP-HPLC followed by lyophilisation to afford 8-(benzo[d]thiazole-5-carbonyl)-2,8-diazaspiro[4.5]decane-1,3-dione (16 mg, 48.6 µmol, 16.6%) as a white solid. MS (ISP): 330.1 ([M+H]$^+$).

EXAMPLE 77

(S)-8-(1,2,3,4-Tetrahydronaphthalene-1-carbonyl)-2,8-diazaspiro[4.5]decane-1,3-dione (or enantiomer)

a) (R)-1,2,3,4-Tetrahydronaphthalene-1-carbonyl chloride

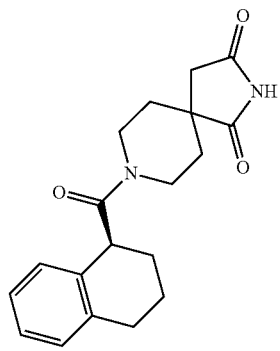 [SMILES: O=C1CC2(CCN(C(=O)[C@H]3CCCc4ccccc43)CC2)C(=O)N1]

To a solution of (R)-1,2,3,4-tetrahydronaphthalene-1-carboxylic acid (250 mg, 1.42 mmol, eq. 1) in dichloromethane (11 ml) was added thionyl chloride (203 mg, 124 μl, 1.7 mmol, eq. 1.2) at room temperature and a catalytic amount of N,N-dimethylformamide. The reaction mixture was stirred for 3 hours. The solvent was concentrated in vacuo to afford (R)-1,2,3,4-tetrahydronaphthalene-1-carbonyl chloride as a colorless oil (276 mg, 1.42 mmol, 99.9%), which was used in the next step without further purification.

b) 8-(Benzo[d]thiazole-5-carbonyl)-2,8-diazaspiro[4.5]decane-1,3-dione

To a suspension of 2,8-diazaspiro[4.5]decane-1,3-dione hydrochloride (60 mg, 293 μmol, eq. 1) and triethylamine (89 mg, 123 μl, 880 μmol, eq. 3.0) in tetrahydrofuran (1.5 ml) was added dropwise (R)-1,2,3,4-tetrahydronaphthalene-1-carbonyl chloride (62.8 mg, 322 μmol, eq. 1.1) at 0° C.-5° C. The cooling bath was removed after 5 minutes and the reaction mixture was stirred for 15 hours. The reaction was quenched by addition of a solution of 2 M aqueous sodium carbonate (5 ml). The reaction mixture was partitioned between ethyl acetate (30 ml) and a solution of 2 M aqueous sodium carbonate (15 ml). The layers were separated. The aqueous layer was extracted with ethyl acetate (2×30 ml). The combined organic layers were washed with brine (20 ml), dried over anhydrous sodium sulfate, and concentrated in vacuo. Analytical chiral HPLC of the product revealed that some racemization had occurred during the reaction. The crude material was purified by flash column chromatography (silica gel, 4 g, 0% to 5% methanol in dichloromethane) to afford 8-(1,2,3,4-tetrahydronaphthalene-1-carbonyl)-2,8-diazaspiro[4.5]decane-1,3-dione (16 mg, 41.7 μmol, 14.2%) as a white solid. MS (ISP): 327.1 ([M+H]$^+$).

c) (S)-8-(Benzo[d]thiazole-5-carbonyl)-2,8-diazaspiro[4.5]decane-1,3-dione (or enantiomer)

The enantiomers of 8-(benzo[d]thiazole-5-carbonyl)-2,8-diazaspiro[4.5]decane-1,3-dione were separated using chiral HPLC (column: Reprosil Chiral-NR, eluent: heptane/ethanol+NH$_4$OAc (60:40), pressure: 18 bar; flow rate: 35 ml/min) affording (S)-8-(benzo[d]thiazole-5-carbonyl)-2,8-diazaspiro[4.5]decane-1,3-dione (or ENANTIOMER) (9.4 mg, white solid), retention time=8.87 min. MS (ISP): 327.1 ([M+H]$^+$).

EXAMPLE 78

(R)-8-(1,2,3,4-Tetrahydronaphthalene-1-carbonyl)-2,8-diazaspiro[4.5]decane-1,3-dione (or enantiomer)

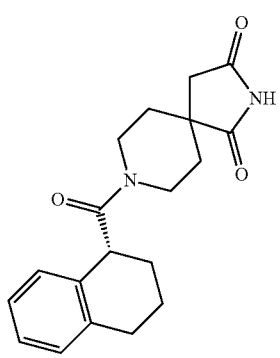 [SMILES: O=C1CC2(CCN(C(=O)[C@@H]3CCCc4ccccc43)CC2)C(=O)N1]

The enantiomers of 8-(benzo[d]thiazole-5-carbonyl)-2,8-diazaspiro[4.5]decane-1,3-dione were separated using chiral HPLC (column: Reprosil Chiral-NR, eluent: heptane/ethanol+NH$_4$OAc (60:40), pressure: 18 bar; flow rate: 35 ml/min) affording (R)-8-(benzo[d]thiazole-5-carbonyl)-2,8-diazaspiro[4.5]decane-1,3-dione (or ENANTIOMER) (9.4 mg, white solid), retention time=11.28 min. MS (ISP): 327.1 ([M+H]$^+$).

EXAMPLE 79

8-(Pyrazolo[1,5-a]pyridine-3-carbonyl)-2,8-diazaspiro[4.5]decane-1,3-dione

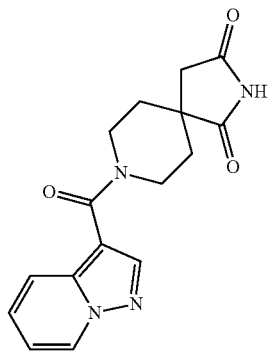 [SMILES: O=C1CC2(CCN(C(=O)c3cnn4ccccc34)CC2)C(=O)N1]

To a suspension of pyrazolo[1,5-a]pyridine-3-carboxylic acid (CAS 68867-17-4) 40 mg, 247 μmol, eq. 1) in tetrahydrofuran (0.5 ml) was added 1-chloro-N,N,2-trimethylpropenylamine (39.6 mg, 39.2 μl, 296 μmol, Eq. 1.2) at 0° C.-5° C. The reaction mixture was stirred at 0° C. for 30 minutes to afford a white suspension. The reaction mixture was stirred at room temperature for 15 minutes and was then added to a suspension of 2,8-diazaspiro[4.5]decane-1,3-dione hydrochloride (50.5 mg, 247 μmol, eq. 1) and DIPEA (95.7 mg, 129 μl, 740 μmol, eq. 3) in tetrahydrofuran (0.5 ml). The reaction mixture was stirred at room temperature for 30 minutes. The reaction mixture was poured into ethyl acetate/tetrahydrofuran (1:3) and extracted with brine. The organic layer was dried over Na$_2$SO$_4$ and concentrated in vacuo. The crude material was purified by flash chromatography (silica gel, 4 g, 0% to 10% MeOH in dichloromethane) to afford 8-(pyrazolo[1,5-a]pyridine-3-carbonyl)-2,8-diazaspiro[4.5]decane-1,3-dione (42 mg, 134 μmol, 54.5%) as a white solid. MS (ISP): 313.1 ([M+H]$^+$).

EXAMPLE 80

8-(Benzofuran-3-carbonyl)-2,8-diazaspiro[4.5]decane-1,3-dione

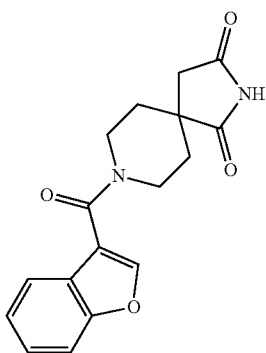 [SMILES: O=C1CC2(CCN(C(=O)c3coc4ccccc34)CC2)C(=O)N1]

The title compound was obtained as a yellow solid in analogy to Example 79 using benzofuran-3-carboxylic acid (CAS 26537-68-8) in place of pyrazolo[1,5-a]pyridine-3-carboxylic acid. MS (ISP): 291.0 ([M+H]$^+$).

EXAMPLE 81

8-(Benzo[d]thiazole-5-carbonyl)-1,3,8-triazaspiro[4.5]decane-2,4-dione

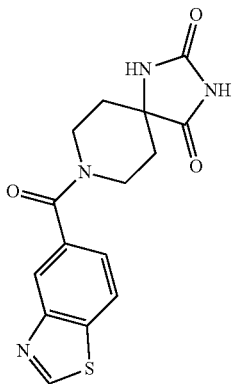 [SMILES: O=C1NC(=O)C2(CCN(C(=O)c3ccc4scnc4c3)CC2)N1]

The title compound was obtained as a white solid in analogy to Example 66 using benzo[d]thiazole-5-carboxylic acid (CAS 68867-17-4) in place of benzofuran-3-carboxylic acid and stirring overnight instead of for 2 hours. MS (ISP): 331.1 ([M+H]$^+$).

Pharmacological Tests

The compounds described herein and their pharmaceutically acceptable salt possess valuable pharmacological properties. The compounds were investigated in accordance with the test given hereinafter.

Fluorescence Direct Binding Protocol

Determination of the affinities of compounds to protein containing one or more tryptophan is measurable by monitoring the fluorescence emission in direct mode. The measurements, depending on the protein available amounts, were performed either manually in a cuvette on ISS-PCI photon counting spectrofluorometer or automatically in well plates on a fluorescence plate reader device. Fluorescence titrations were performed at 20° C. in the chosen binding assay buffer by using a defined constant protein concentration against ligand concentration variations. Small aliquots of known ligand concentration solubilized in DMSO were added and the fluorescence, excited at 280 nm, was recorded at 340 nm. The fluorescence intensity was corrected for protein dilution and for the filter effect (Birdsall, B., King, R. W., Wheeler, M. R., Lewis, C. A. Jr, Goode, S. R., Dunlap, R. B. & Roberts, G. C. (1983). *Anal. Biochem.* 132, 353-361). The corrected fluorescence intensity was plotted against the ligand concentration and fitted using a four-parameter sigmoidal function from which the equilibrium dissociation constant $K_d$ was computed using the law of mass action assuming a 1:1 protein—ligand complex (Eftink, Methods Enzymol. 1997; 278:221-57). The process includes:

1) Optimization of measurement parameters to minimize protein consumption and to minimize the dilution effect and the DMSO content
2) Titration measurements of the protein against ligand by at least 12 titration steps to obtain an s-curve fit
3) Repeat the same titration measurements with the ligand alone to enable correction
4) Check the stability of the protein once by titration against DMSO alone
5) Determination of the molar extinction coefficients of the ligand at 280 and 340 nm with help of an UV-spectrophotometer
6) Use Excel template for the correction of the measured raw data
7) Use GraphPad Prism software for the quadratic binding fit and the KD evaluation.

TABLE 8

Parameters of Fluorescence Direct Binding Protocol

| | |
|---|---|
| Construct name | hCereblon(M1-L442)_hDDB1(M1-H1140) |
| Concentration | 2.54 mg/ml |
| MW | 180180 Da |
| Molar extinction coefficient | $\lambda_{280} = 165045$ M$^{-1}$ · cm$^{-1}$ |
| Storage buffer | 20 mM MES pH 6.5 200 mM NaCl 1 mM TCEP |
| Assay buffer | 50 mM Hepes 7.4 200 mM NaCl |
| Reference Compound | Thalidomide |

TABLE 2

Settings for ISS-PC1 Device

| | |
|---|---|
| Excitation wavelength [nm] | 280 |
| Emission wavelength [nm] | 340 |
| Cuvette | Hellma 115F-QS |
| Volume [µL] | 500 |

TABLE 9

Protein Preparation

| Volume Protein [µL] | Volume buffer [µL] | Protein concentration [M] |
|---|---|---|
| 1.8 @ 2.54 mg/ml | 498.2 | 5.0E−8 |

TABLE 10

Titration Steps to determine S-Curve Fit

| C Lig [M] | C Aliquot [M] | V Aliquot [μL] | C Prot [M] | Dilution factor |
|---|---|---|---|---|
| 1E−10 | 1.0E−07 | 0.5 | 4.995E−08 | 1.001 |
| 1.1E−09 | 1.0E−06 | 0.5 | 4.990E−08 | 1.002 |
| 3.1E−09 | 1.0E−06 | 1 | 4.980E−08 | 1.004 |
| 5.1E−09 | 1.0E−06 | 1 | 4.970E−08 | 1.006 |
| 1.51E−08 | 1.0E−05 | 0.5 | 4.965E−08 | 1.007 |
| 2.51E−08 | 1.0E−05 | 0.5 | 4.960E−08 | 1.008 |
| 4.51E−08 | 1.0E−05 | 1 | 4.950E−08 | 1.01 |
| 6.51E−08 | 1.0E−05 | 1 | 4.941E−08 | 1.012 |
| 1.651E−07 | 1.0E−04 | 0.5 | 4.936E−08 | 1.013 |
| 3.651E−07 | 1.0E−04 | 1 | 4.926E−08 | 1.015 |
| 5.651E−07 | 1.0E−04 | 1 | 4.916E−08 | 1.017 |
| 7.651E−07 | 1.0E−04 | 1 | 4.907E−08 | 1.019 |
| 9.651E−07 | 1.0E−04 | 1 | 4.897E−08 | 1.021 |
| 1.9651E−06 | 1.0E−03 | 0.5 | 4.892E−08 | 1.022 |
| 2.9651E−06 | 1.0E−03 | 0.5 | 4.888E−08 | 1.023 |
| 1.29651E−05 | 1.0E−02 | 0.5 | 4.883E−08 | 1.024 |
| 2.29651E−05 | 1.0E−02 | 0.5 | 4.878E−08 | 1.025 |
| 4.29651E−05 | 1.0E−02 | 1 | 4.869E−08 | 1.027 |
| 6.29651E−05 | 1.0E−02 | 1 | 4.859E−08 | 1.029 |
| 8.29651E−05 | 1.0E−02 | 1 | 4.850E−08 | 1.031 |

TABLE 11A

Affinities of Select Compounds for Cereblon

| Ex. | Name | Structure | Fluorescence h-Cereblon_DDB1 Mean $K_d$_EQ(μM) |
|---|---|---|---|
| 1 | 2,7-diazaspiro[4.5]decane-6,8-dione | 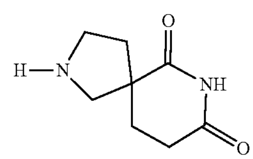 [SMILES: O=C1CCC2(CCNC2)C(=O)N1] | 0.084 |
| 2 | 2-methyl-2,7-diazaspiro[4.5]decane-3,6,8-trione | 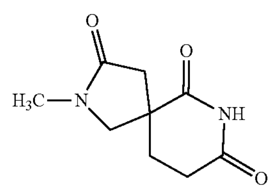 | 0.159 |
| 3 | 2-(2-phenylacetyl)-2,7-diazaspiro[4.5]decane-6,8-dione | 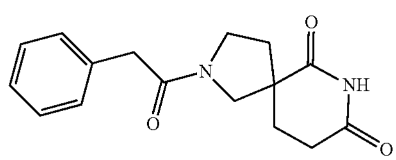 [SMILES: O=C1CCC2(CCN(C(=O)Cc3ccccc3)C2)C(=O)N1] | 0.369 |
| 4 | 2-(2,3-dihydro-1$H$-indene-1-carbonyl)-2,7-diazaspiro[4.5]decane-6,8-dione | 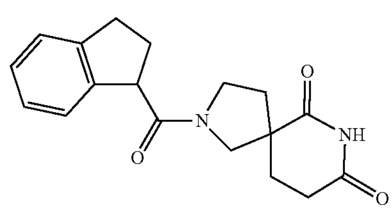 [SMILES: O=C1CCC2(CCN(C(=O)C3CCc4ccccc43)C2)C(=O)N1] | 0.316 |
| 5 | 2-(3-nitrobenzoyl)-2,7-diazaspiro[4.5]decane-6,8-dione | 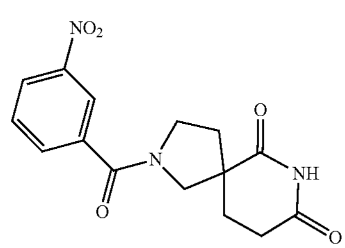 [SMILES: O=C1CCC2(CCN(C(=O)c3cccc([N+](=O)[O-])c3)C2)C(=O)N1] | 0.023 |

TABLE 11A-continued

Affinities of Select Compounds for Cereblon

| Ex. | Name | Structure | Fluorescence h-Cereblon_DDB1 Mean $K_d$_EQ(μM) |
|---|---|---|---|
| 6 | methyl 6-(6,8-dioxo-2,7-diazaspiro[4.5]decan-2-yl) nicotinate | 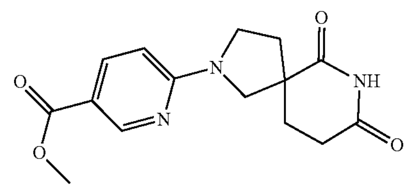 [SMILES: COC(=O)c1ccc(N2CCC3(CCC(=O)NC3=O)C2)nc1] | <0.001 |
| 7 | 2-(thiazolo[4,5-b]pyridin-2-yl)-2,7-diazaspiro[4.5]decane-6,8-dione | 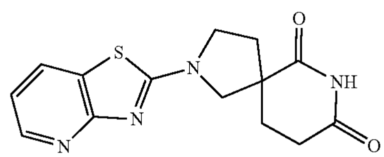 [SMILES: O=C1CCC2(CCN(c3nc4ncccc4s3)C2)C(=O)N1] | <0.001 |
| 8 | 2-(4-nitrophenyl)-2,7-diazaspiro[4.5]decane-6,8-dione | 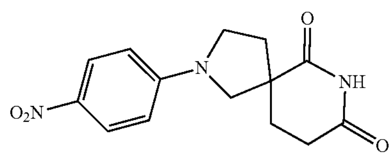 [SMILES: O=C1CCC2(CCN(c3ccc([N+](=O)[O-])cc3)C2)C(=O)N1] | 0.014 |
| 9 | 2-(5-nitro-1H-benzo[d]imidazol-2-yl)-2,7-diazaspiro[4.5]decane-6,8-dione | 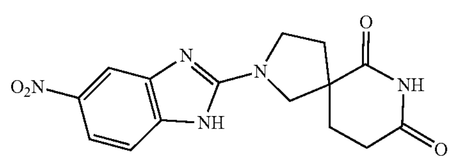 [SMILES: O=C1CCC2(CCN(c3nc4cc([N+](=O)[O-])ccc4[nH]3)C2)C(=O)N1] | 0.008 |
| 10 | 2-(4-nitrophenyl)-2,7-diazaspiro[4.5]decane-6,8-dione | [1 enantiomer] [entity A] | 0.001 |
| 11 | 2-(4-nitrophenyl)-2,7-diazaspiro[4.5]decane-6,8-dione | [1 enantiomer] [entity B] | 0.005 |
| 12 | 2-(benzo[d]thiazol-2-yl)-2,7-diazaspiro[4.5]decane-6,8-dione | 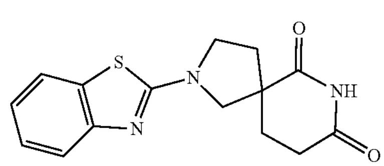 [SMILES: O=C1CCC2(CCN(c3nc4ccccc4s3)C2)C(=O)N1] | 0.001 |

TABLE 11A-continued

Affinities of Select Compounds for Cereblon

| Ex. | Name | Structure | Fluorescence h-Cereblon_DDB1 Mean $K_d\_EQ(\mu M)$ |
|---|---|---|---|
| 13 | methyl 2-(6,8-dioxo-2,7-diazaspiro[4.5]decan-2-yl)-1H-benzo[d]imidazole-7-carboxylate | 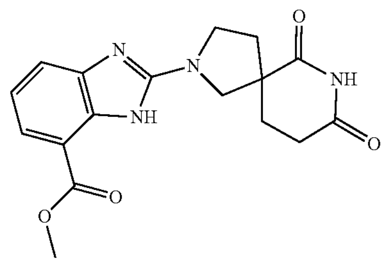 [SMILES: COC(=O)c1cccc2nc(N3CCC4(CCC(=O)NC4=O)C3)[nH]c12] | 0.096 |
| 14 | methyl 2-(6,8-dioxo-2,7-diazaspiro[4.5]decan-2-yl)pyrimidine-4-carboxylate | 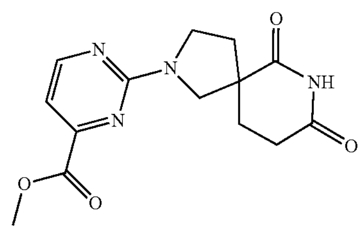 [SMILES: COC(=O)c1ccnc(N2CCC3(CCC(=O)NC3=O)C2)n1] | 0.015 |
| 15 | 2-(quinolin-2-yl)-2,7-diazaspiro[4.5]decane-6,8-dione | 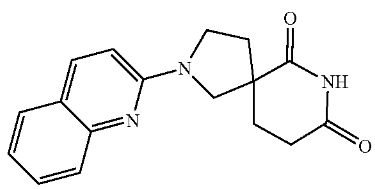 [SMILES: O=C1CCC2(CCN(c3ccc4ccccc4n3)C2)C(=O)N1] | 0.006 |
| 16 | 2-(6-aminobenzo[d]thiazol-2-yl)-2,7-diazaspiro[4.5]decane-6,8-dione | 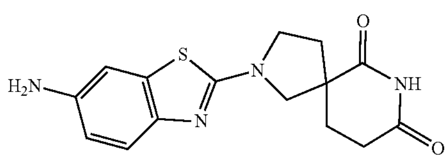 [SMILES: Nc1ccc2nc(N3CCC4(CCC(=O)NC4=O)C3)sc2c1] | 0.010 |
| 17 | 2-(oxazolo[4,5-b]pyridin-2-yl)-2,7-diazaspiro[4.5]decane-6,8-dione | 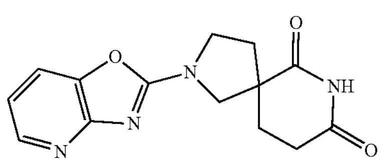 [SMILES: O=C1CCC2(CCN(c3nc4ncccc4o3)C2)C(=O)N1] | 0.026 |
| 18 | 2-(benzo[d]oxazol-2-yl)-2,7-diazaspiro[4.5]decane-6,8-dione | 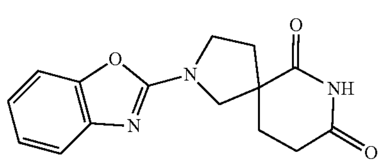 [SMILES: O=C1CCC2(CCN(c3nc4ccccc4o3)C2)C(=O)N1] | 0.046 |
| 19 | 2-(1-methyl-1H-benzo[d]imidazol-2-yl)-2,7-diazaspiro[4.5]decane-6,8-dione | 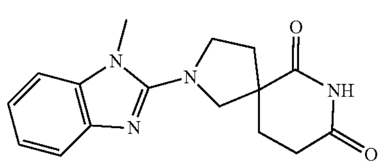 [SMILES: Cn1c(N2CCC3(CCC(=O)NC3=O)C2)nc2ccccc21] | 0.030 |
| 20 | 2-(thiazolo[4,5-c]pyridin-2-yl)-2,7-diazaspiro[4.5]decane-6,8-dione | 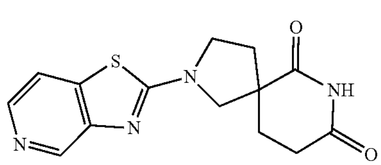 | 0.006 |

TABLE 11A-continued

Affinities of Select Compounds for Cereblon

| Ex. | Name | Structure | Fluorescence h-Cereblon_DDB1 Mean $K_d\_EQ(\mu M)$ |
|---|---|---|---|
| 21 | methyl 2-(6,8-dioxo-2,7-diazaspiro[4.5]decan-2-yl)benzo[d]thiazole-6-carboxylate | 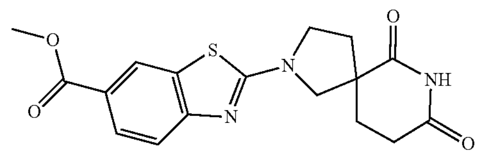 [SMILES: COC(=O)c1ccc2nc(N3CCC4(CCC(=O)NC4=O)C3)sc2c1] | 0.008 |
| 22 | methyl 2-(6,8-dioxo-2,7-diazaspiro[4.5]decan-2-yl)thiazole-4-carboxylate | 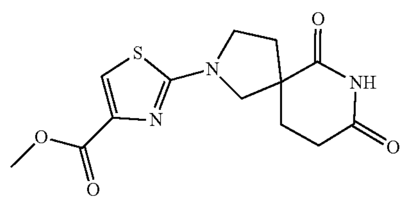 [SMILES: COC(=O)c1csc(N2CCC3(CCC(=O)NC3=O)C2)n1] | 0.044 |
| 23 | methyl 2-(6,8-dioxo-2,7-diazaspiro[4.5]decan-2-yl)thiazole-5-carboxylate | 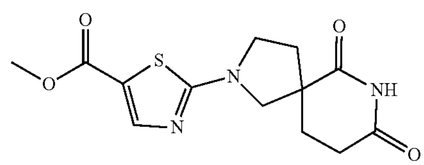 [SMILES: COC(=O)c1cnc(N2CCC3(CCC(=O)NC3=O)C2)s1] | 0.008 |
| 24 | tert-butyl 6-(6,8-dioxo-2,7-diazaspiro[4.5]decan-2-yl)nicotinate | 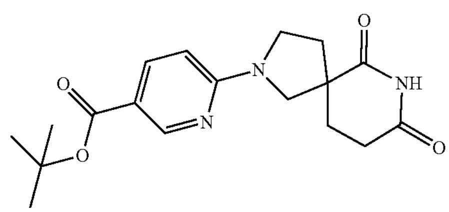 [SMILES: CC(C)(C)OC(=O)c1ccc(N2CCC3(CCC(=O)NC3=O)C2)nc1] | 0.002 |
| 25 | 2-(benzo[d]thiazole-6-carbonyl)-2,7-diazaspiro[4.5]decane-6,8-dione | 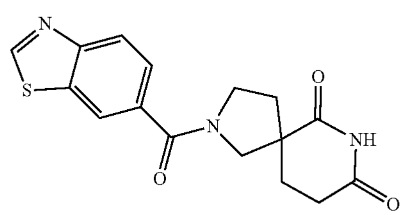 [SMILES: O=C1CCC2(CCN(C(=O)c3ccc4ncsc4c3)C2)C(=O)N1] | 0.002 |
| 26 | 2-(4-nitropicolinoyl)-2,7-diazaspiro[4.5]decane-6,8-dione | 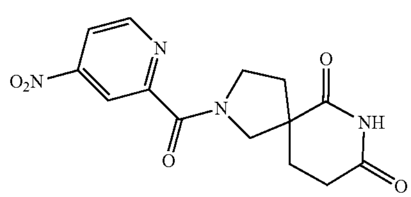 [SMILES: O=C1CCC2(CCN(C(=O)c3cc([N+](=O)[O-])ccn3)C2)C(=O)N1] | 0.019 |
| 27 | 2-(2-oxoindoline-4-carbonyl)-2,7-diazaspiro[4.5]decane-6,8-dione | 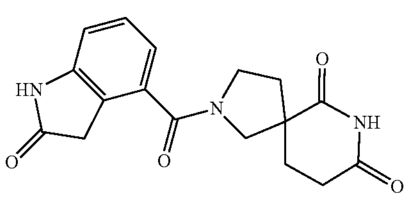 [SMILES: O=C1CCC2(CCN(C(=O)c3cccc4c3CC(=O)N4)C2)C(=O)N1] | 0.047 |

TABLE 11A-continued

Affinities of Select Compounds for Cereblon

| Ex. | Name | Structure | Fluorescence h-Cereblon_DDB1 Mean $K_d\_EQ(\mu M)$ |
|---|---|---|---|
| 28 | methyl 4-(6,8-dioxo-2,7-diazaspiro[4.5]decane-2-carbonyl)benzoate | 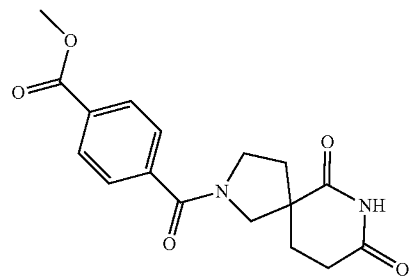 [SMILES: COC(=O)c1ccc(C(=O)N2CCC3(CCC(=O)NC3=O)C2)cc1] | 0.013 |
| 29 | 2-(benzo[d]thiazole-5-carbonyl)-2,7-diazaspiro[4.5]decane-6,8-dione | 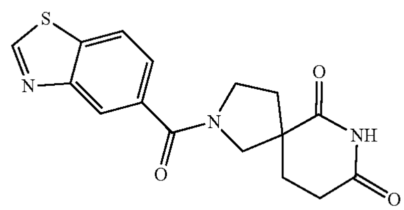 [SMILES: O=C1CCC2(CCN(C(=O)c3ccc4scnc4c3)C2)C(=O)N1] | <0.001 |
| 30 | 2-(5-nitropyridin-2-yl)-2,7-diazaspiro[4.5]decane-6,8-dione | 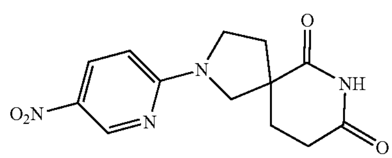 [SMILES: O=C1CCC2(CCN(c3ccc([N+](=O)[O-])cn3)C2)C(=O)N1] | 0.001 |
| 31 | 2-(2-(pyridin-3-yl)propanoyl)-2,7-diazaspiro[4.5]decane-6,8-dione | 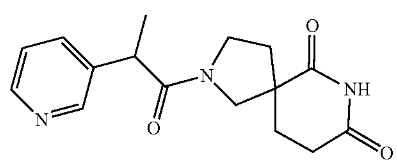 [SMILES: CC(C(=O)N1CCC2(CCC(=O)NC2=O)C1)c1cccnc1] | 0.077 |
| 32 | methyl 6-(6,8-dioxo-2,7diazaspiro[4.5]decan-2-yl)picolinate | 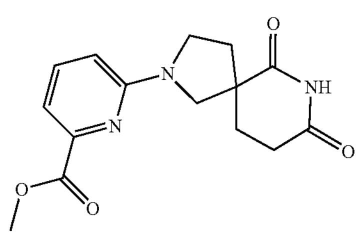 | 0.001 |
| 33 | 2-(5-nitro-1H-benzo[d]imidazol-2-yl)-2,7-diazaspiro[4.5]decane-6,8-dione [1 enantiomer] [entity A] | 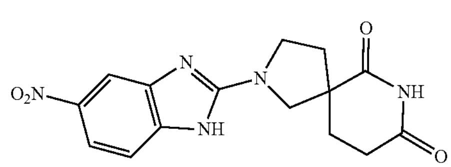 | <0.001 |
| 34 | 2-(5-nitro-1H-benzo[d]imidazol-2-yl)-2,7-diazaspiro[4.5]decane-6,8-dione [1 enantiomer] [entity B] | 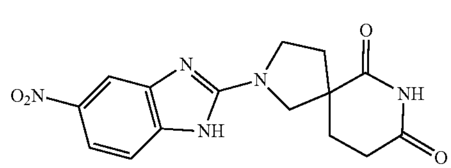 | 0.005 |

TABLE 11A-continued

Affinities of Select Compounds for Cereblon

| Ex. | Name | Structure | Fluorescence h-Cereblon_DDB1 Mean $K_d\_EQ(\mu M)$ |
|---|---|---|---|
| 35 | 2-(1-acetylindoline-4-carbonyl)-2,7-diazaspiro[4.5]decane-6,8-dione | 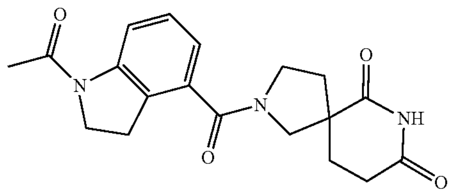 [SMILES: CC(=O)N1CCc2c(C(=O)N3CCC4(CCC(=O)NC4=O)C3)cccc21] | <0.001 |
| 36 | 2-benzoyl-2,7-diazaspiro[4.5]decane-6,8-dione | 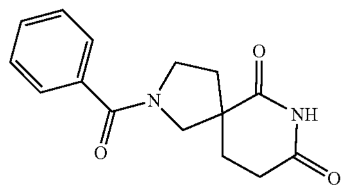 [SMILES: O=C1CCC2(CCN(C(=O)c3ccccc3)C2)C(=O)N1] | <0.001 |
| 37 | N-(3-(6,8-dioxo-2,7-diazaspiro[4.5]decane-2-carbonyl)phenyl)acetamide | 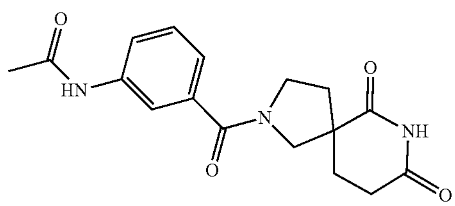 [SMILES: CC(=O)Nc1cccc(C(=O)N2CCC3(CCC(=O)NC3=O)C2)c1] | 0.006 |
| 38 | 2-(1H-indazole-4-carbonyl)-2,7-diazaspiro[4.5]decane-6,8-dione | 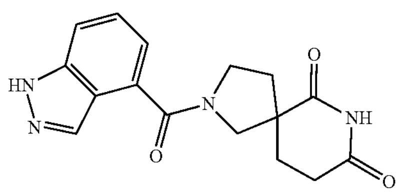 [SMILES: O=C1CCC2(CCN(C(=O)c3cccc4[nH]ncc34)C2)C(=O)N1] | 0.084 |
| 39 | 2-(5-aminopyridin-2-yl)-2,7-diazaspiro[4.5]decane-6,8-dione | 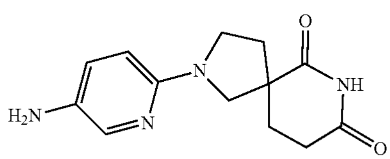 | <0.001 |
| 40 | 2-(indoline-4-carbonyl)-2,7-diazaspiro[4.5]decane-6,8-dione | 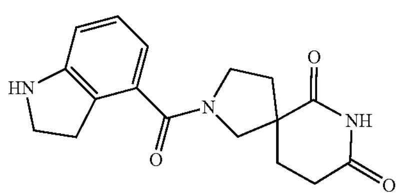 [SMILES: O=C1CCC2(CCN(C(=O)c3cccc4c3CCN4)C2)C(=O)N1] | 0.006 |
| 41 | 2-(indoline-6-carbonyl)-2,7-diazaspiro[4.5]decane-6,8-dione | 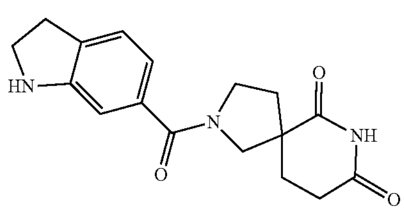 [SMILES: O=C1CCC2(CCN(C(=O)c3ccc4c(c3)NCC4)C2)C(=O)N1] | 0.075 |

TABLE 11A-continued

Affinities of Select Compounds for Cereblon

| Ex. | Name | Structure | Fluorescence h-Cereblon_DDB1 Mean $K_d\_EQ(\mu M)$ |
|---|---|---|---|
| 42 | 2-(1-acetylindoline-6-carbonyl)-2,7-diazaspiro[4.5]decane-6,8-dione | 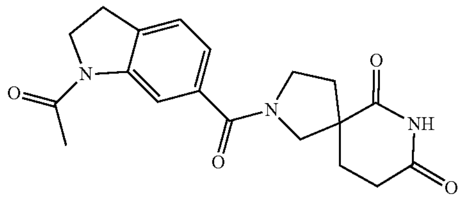 [SMILES: CC(=O)N1CCc2ccc(C(=O)N3CCC4(CCC(=O)NC4=O)C3)cc21] | 0.008 |
| 43 | N-(6-(6,8-dioxo-2,7-diazaspiro[4.5]decan-2-yl)pyridin-3-yl)acetamide | 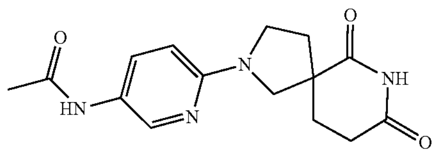 [SMILES: CC(=O)Nc1ccc(N2CCC3(CCC(=O)NC3=O)C2)nc1] | 0.012 |
| 44 | 2-(benzofuran-3-carbonyl)-2,7-diazaspiro[4.5]decane-6,8-dione | 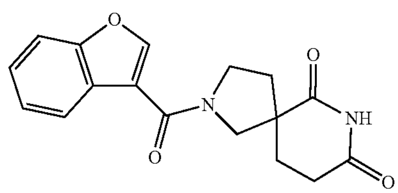 [SMILES: O=C1CCC2(CCN(C(=O)c3coc4ccccc34)C2)C(=O)N1] | 0.009 |
| 45 | 2-(pyrazolo[1,5-a]pyridine-3-carbonyl)-2,7-diazaspiro[4.5]decane-6,8-dione | 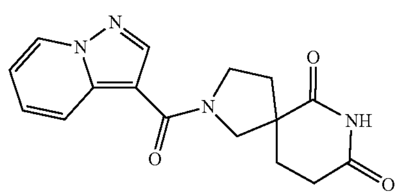 [SMILES: O=C1CCC2(CCN(C(=O)c3cnn4ccccc34)C2)C(=O)N1] | <0.001 |
| 46 | 2-(benzo[d]oxazole-6-carbonyl)-2,7-diazaspiro[4.5]decane-6,8-dione | 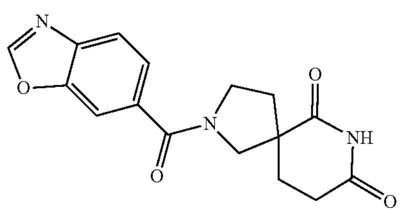 | 0.010 |
| 47 | 2-(indoline-5-carbonyl)-2,7-diazaspiro[4.5]decane-6,8-dione | 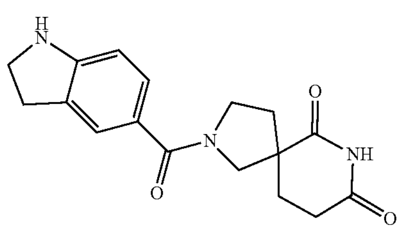 [SMILES: O=C1CCC2(CCN(C(=O)c3ccc4c(c3)CCN4)C2)C(=O)N1] | 0.004 |
| 48 | 2-((R)-1,2,3,4-tetrahydro-naphthalene-1-carbonyl)-2,7-diazaspiro[4.5]decane-6,8-dione | 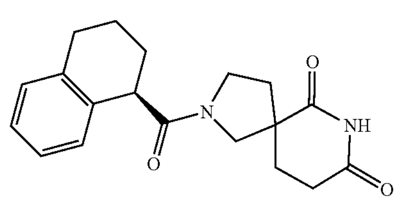 [SMILES: O=C1CCC2(CCN(C(=O)[C@@H]3CCCc4ccccc43)C2)C(=O)N1] | 0.028 |

TABLE 11A-continued

Affinities of Select Compounds for Cereblon

| Ex. | Name | Structure | Fluorescence h-Cereblon_DDB1 Mean $K_d\_EQ(\mu M)$ |
|---|---|---|---|
| 49 | 2-((S)-1,2,3,4-tetrahydro-naphthalene-1-carbonyl)-2,7-diazaspiro[4.5]decane-6,8-dione | 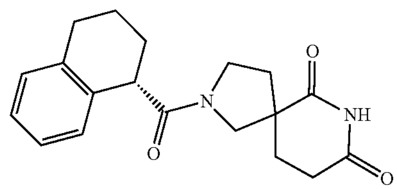 [SMILES: O=C1CCC2(CCN(C(=O)[C@H]3CCCc4ccccc43)C2)C(=O)N1] | 0.014 |
| 50 | N-(5-(6,8-dioxo-2,7-diazaspiro[4.5]decane-2-carbonyl)benzo[d]thiazol-2-yl)acetamide | 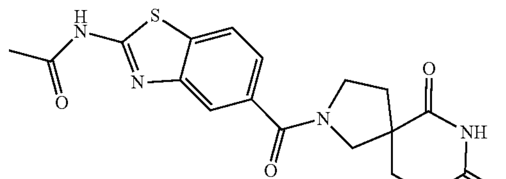 | 0.045 |
| 51 | N-(6-(6,8-dioxo-2,7-diazaspiro[4.5]decane-2-carbonyl)benzo[d]thiazol-2-yl)acetamide | 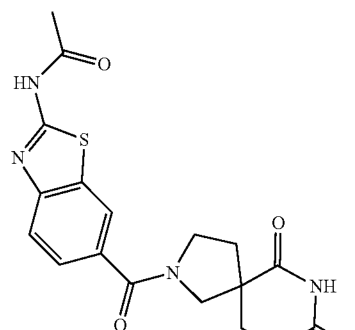 | 0.094 |
| 52 | 2-(1-acetylindoline-5-carbonyl)-2,7-diazaspiro[4.5]decane-6,8-dione | 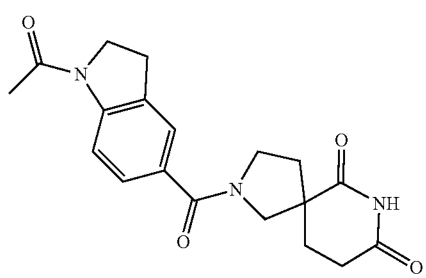 [SMILES: CC(=O)N1CCc2cc(C(=O)N3CCC4(CCC(=O)NC4=O)C3)ccc21] | 0.041 |
| 53 | tert-butyl (5-(6,8-dioxo-2,7-diazaspiro[4.5]decane-2-carbonyl)benzo[d]thiazol-2-yl)carbamate | 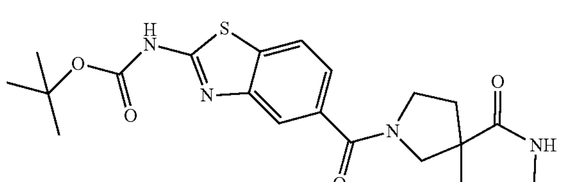 | 0.006 |

TABLE 11A-continued

Affinities of Select Compounds for Cereblon

| Ex. | Name | Structure | Fluorescence h-Cereblon_DDB1 Mean $K_d\_EQ(\mu M)$ |
|---|---|---|---|
| 54 | tert-butyl (6-(6,8-dioxo-2,7-diazaspiro[4.5]decane-2-carbonyl)benzo[d]thiazol-2-yl)carbamate | 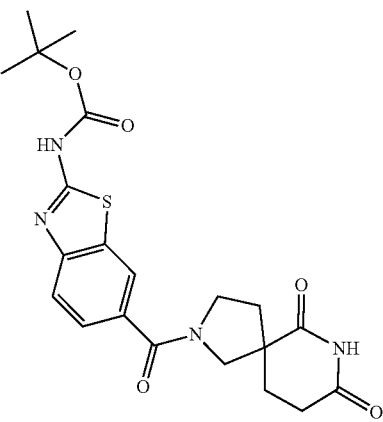 [SMILES: CC(C)(C)OC(=O)Nc1nc2ccc(C(=O)N3CCC4(CCC(=O)NC4=O)C3)cc2s1] | 0.004 |
| 55 | 2-(2-aminobenzo[d]thiazole-6-carbonyl)-2,7-diazaspiro[4.5]decane-6,8-dione | 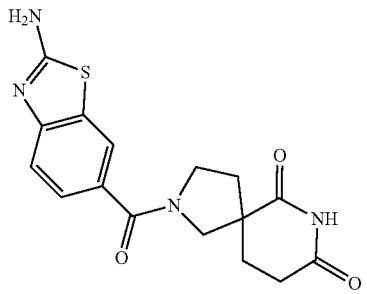 [SMILES: Nc1nc2ccc(C(=O)N3CCC4(CCC(=O)NC4=O)C3)cc2s1] | 0.026 |
| 56 | 2-(benzo[d]thiazole-6-carbonyl)-2,7-diazaspiro[4.5]decane-6,8-dione | 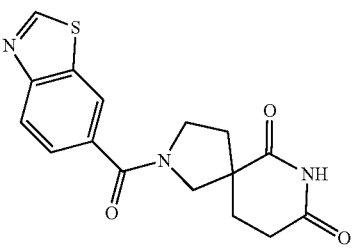 [SMILES: O=C1CCC2(CCN(C(=O)c3ccc4ncsc4c3)C2)C(=O)N1] | 0.002 |
| 57 | 8-(2-((R)-4-(4-chlorophenyl)-2,3,9-trimethyl-6H-thieno[3,2-f][1,2,4]triazolo[4,3-a][1,4]diazepin-6-yl)acetamido)-N-(3-(6,8-dioxo-2,7-diazaspiro[4.5]decane-2-carbonyl)phenyl)octanamide | 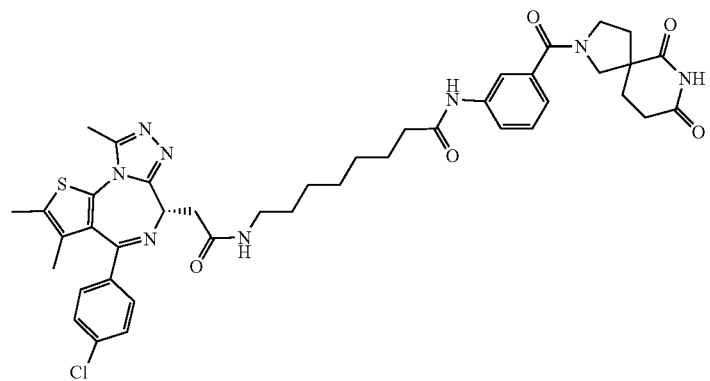 [SMILES: Cc1sc2c(c1C)C(c1ccc(Cl)cc1)=N[C@@H](CC(=O)NCCCCCCCC(=O)Nc1cccc(C(=O)N3CCC4(CCC(=O)NC4=O)C3)c1)c1nnc(C)n1-2] | 0.106 |

TABLE 5B

Affinities of Select Compounds for Cereblon

| Ex. | Name | Structure | Fluorescence h-Cereblon_DDB1 Mean $K_d\_EQ(\mu M)$ |
|---|---|---|---|
| 58 | (S)-8-(1,2,3,4-tetrahydronaphthalene-1-carbonyl)-1,3,8-triazaspiro[4.5]decane-2,4-dione | 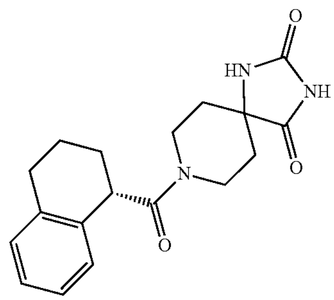 [SMILES: O=C1NC(=O)C2(CCN(C(=O)[C@H]3CCCc4ccccc43)CC2)N1] | 0.004 |
| 59 | (R)-8-(1,2,3,4-tetrahydronaphthalene-1-carbonyl)-1,3,8-triazaspiro[4.5]decane-2,4-dione | 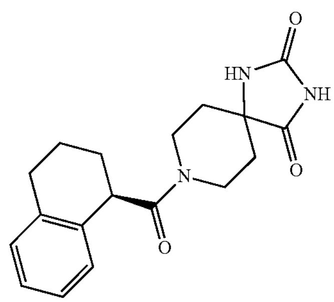 [SMILES: O=C1NC(=O)C2(CCN(C(=O)[C@@H]3CCCc4ccccc43)CC2)N1] | 0.005 |
| 60 | 8-benzoyl-1,3,8-triazaspiro[4.5]decane-2,4-dione | 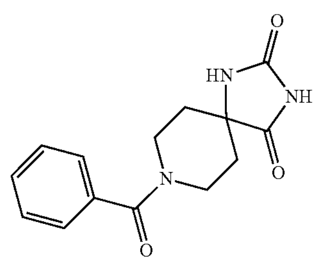 [SMILES: O=C1NC(=O)C2(CCN(C(=O)c3ccccc3)CC2)N1] | 0.002 |
| 61 | 8-(benzo[d]thiazol-2-yl)-1,3,8-triazaspiro[4.5]decane-2,4-dione | 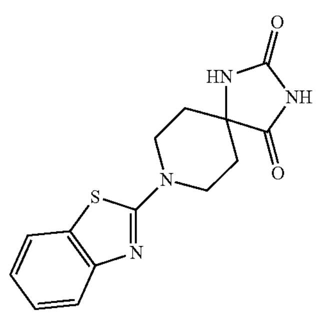 [SMILES: O=C1NC(=O)C2(CCN(c3nc4ccccc4s3)CC2)N1] | 0.002 |
| 62 | 8-(thiazolo[4,5-b]pyridin-2-yl)-1,3,8-triazaspiro[4.5]decane-2,4-dione | 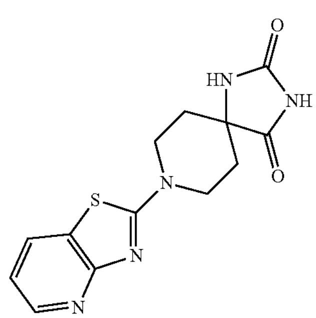 [SMILES: O=C1NC(=O)C2(CCN(c3nc4ncccc4s3)CC2)N1] | 0.017 |

TABLE 5B-continued

Affinities of Select Compounds for Cereblon

| Ex. | Name | Structure | Fluorescence h-Cereblon_DDB1 Mean $K_d\_EQ(\mu M)$ |
|---|---|---|---|
| 63 | methyl 6-(2,4-dioxo-1,3,8-triazaspiro[4.5]decan-8-yl)nicotinate | 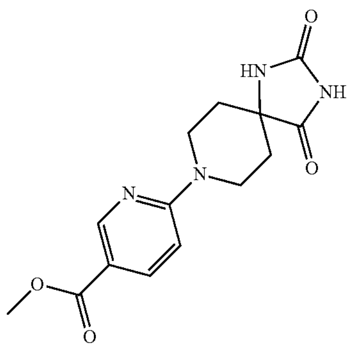 [SMILES: COC(=O)c1ccc(N2CCC3(CC2)NC(=O)NC3=O)nc1] | 0.034 |
| 64 | N-(4-(2,4-dioxo-1,3,8-triazaspiro[4.5]decane-8-carbonyl)phenyl)acetamide | 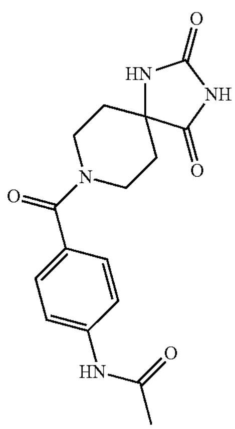 [SMILES: CC(=O)Nc1ccc(C(=O)N2CCC3(CC2)NC(=O)NC3=O)cc1] | 0.027 |
| 65 | N-(3-(2,4-dioxo-1,3,8-triazaspiro[4.5]decane-8-carbonyl)phenyl)acetamide | 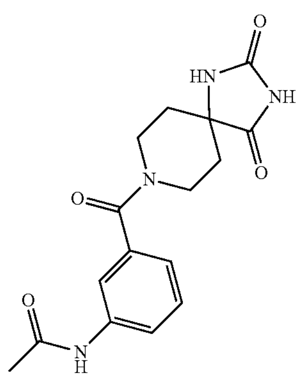 [SMILES: CC(=O)Nc1cccc(C(=O)N2CCC3(CC2)NC(=O)NC3=O)c1] | 0.021 |
| 66 | 8-(benzofuran-3-carbonyl)-1,3,8-triazaspiro[4.5]decane-2,4-dione | 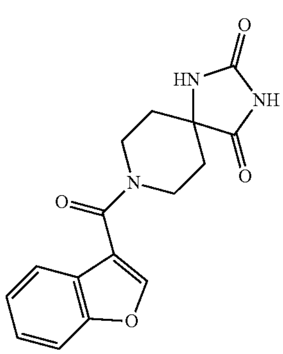 [SMILES: O=C1NC(=O)C2(CCN(C(=O)c3coc4ccccc34)CC2)N1] | 0.001 |

TABLE 5B-continued

Affinities of Select Compounds for Cereblon

| Ex. | Name | Structure | Fluorescence h-Cereblon_DDB1 Mean $K_d$_EQ(μM) |
|---|---|---|---|
| 67 | 8-(pyrazolo[1,5-a]pyridine-3-carbonyl)-1,3,8-triazaspiro[4.5]decane-2,4-dione | 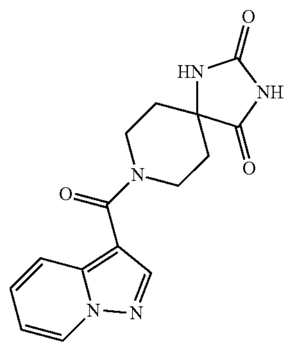 [SMILES: O=C1NC(=O)C2(CCN(C(=O)c3cnn4ccccc34)CC2)N1] | <0.001 |
| 68 | 8-(thiazolo[4,5-b]pyridin-2-yl)-2,8-diazaspiro[4.5]decane-1,3-dione | 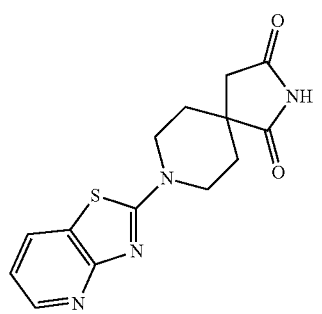 [SMILES: O=C1CC2(CCN(c3nc4ncccc4s3)CC2)C(=O)N1] | 0.016 |
| 69 | 8-(5-nitropyridin-2-yl)-1,3,8-triazaspiro[4.5]decane-2,4-dione | 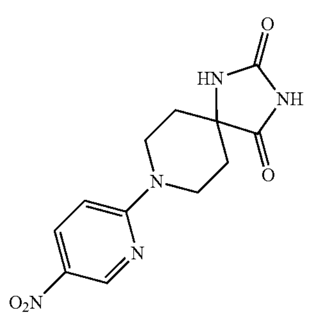 [SMILES: O=C1NC(=O)C2(CCN(c3ccc([N+](=O)[O-])cn3)CC2)N1] | 0.007 |
| 70 | 8-(5-nitropyridin-2-yl)-2,8-diazaspiro[4.5]decane-1,3-dione | 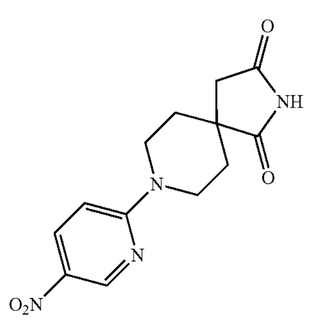 [SMILES: O=C1CC2(CCN(c3ccc([N+](=O)[O-])cn3)CC2)C(=O)N1] | 0.023 |

TABLE 5B-continued

Affinities of Select Compounds for Cereblon

| Ex. | Name | Structure | Fluorescence h-Cereblon_DDB1 Mean $K_d$_EQ(μM) |
|---|---|---|---|
| 71 | 8-(benzo[d]thiazol-2-yl)-2,8-diazaspiro[4.5]decane-1,3-dione | 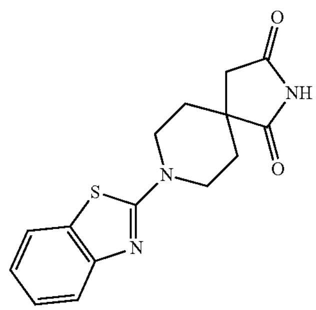 | 0.002 |
| 72 | 8-(4-nitrophenyl)-1,3,8-triazaspiro[4.5]decane-2,4-dione | 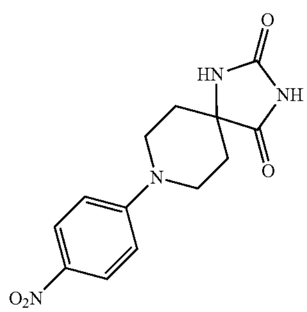 [SMILES: O=C1NC(=O)C2(CCN(c3ccc([N+](=O)[O-])cc3)CC2)N1] | <0.001 |
| 73 | 8-(4-nitrophenyl)-2,8-diazaspiro[4.5]decane-1,3-dione | 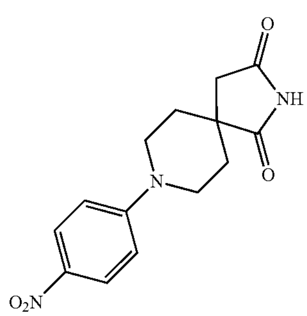 [SMILES: O=C1CC2(CCN(c3ccc([N+](=O)[O-])cc3)CC2)C(=O)N1] | 0.006 |
| 74 | methyl 6-(1,3-dioxo-2,8-diazaspiro[4.5]decan-8-yl)nicotinate | 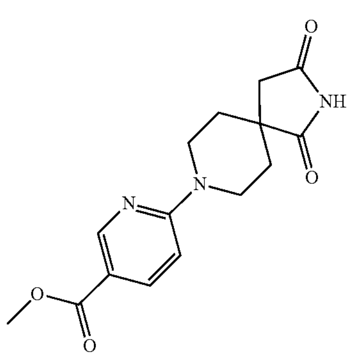 [SMILES: COC(=O)c1ccc(N2CCC3(CC2)CC(=O)NC3=O)nc1] | 0.011 |

TABLE 5B-continued

Affinities of Select Compounds for Cereblon

| Ex. | Name | Structure | Fluorescence h-Cereblon_DDB1 Mean $K_d$_EQ(μM) |
|---|---|---|---|
| 75 | 8-benzoyl-2,8-diazaspiro[4.5]decane-1,3-dione | 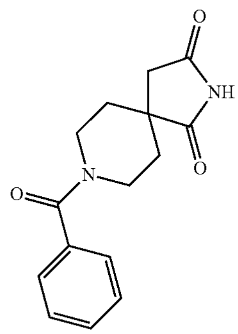 [SMILES: O=C1CC2(CCN(C(=O)c3ccccc3)CC2)C(=O)N1] | <0.001 |
| 76 | 8-(benzo[d]thiazole-5-carbonyl)-2,8-diazaspiro[4.5]decane-1,3-dione | 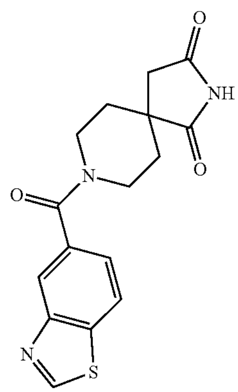 [SMILES: O=C1CC2(CCN(C(=O)c3ccc4scnc4c3)CC2)C(=O)N1] | 0.015 |
| 77 | (S)-8-(1,2,3,4-tetrahydronaphthalene-1-carbonyl)-2,8-diazaspiro[4.5]decane-1,3-dione [OR ENANTIOMER] | 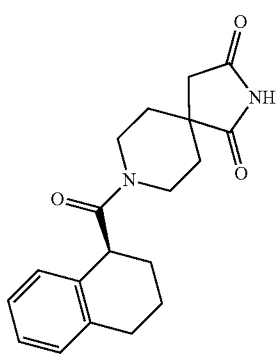 [SMILES: O=C1CC2(CCN(C(=O)[C@H]3CCCc4ccccc43)CC2)C(=O)N1] | 0.006 |
| 78 | (R)-8-(1,2,3,4-tetrahydronaphthalene-1-carbonyl)-2,8-diazaspiro[4.5]decane-1,3-dione [OR ENANTIOMER] | 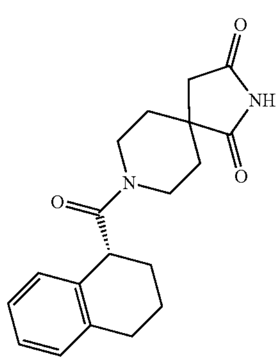 [SMILES: O=C1CC2(CCN(C(=O)[C@@H]3CCCc4ccccc43)CC2)C(=O)N1] | 0.004 |

TABLE 5B-continued

Affinities of Select Compounds for Cereblon

| Ex. | Name | Structure | Fluorescence h-Cereblon_DDB1 Mean $K_d$_EQ(μM) |
|---|---|---|---|
| 79 | 8-(pyrazolo[1,5-a]pyridine-3-carbonyl)-2,8-diazaspiro[4.5]decane-1,3-dione | 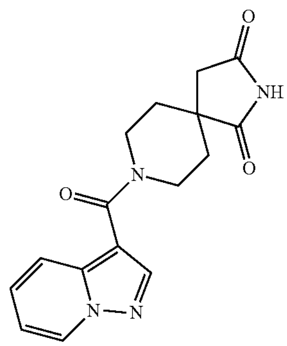 [SMILES: O=C1CC2(CCN(C(=O)c3cnn4ccccc34)CC2)C(=O)N1] | 0.028 |
| 80 | 8-(benzofuran-3-carbonyl)-2,8-diazaspiro[4.5]decane-1,3-dione | 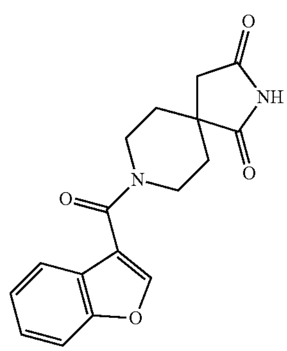 [SMILES: O=C1CC2(CCN(C(=O)c3coc4ccccc34)CC2)C(=O)N1] | 0.006 |
| 81 | 8-(benzo[d]thiazole-5-carbonyl)-1,3,8-triazaspiro[4.5]decane-2,4-dione | 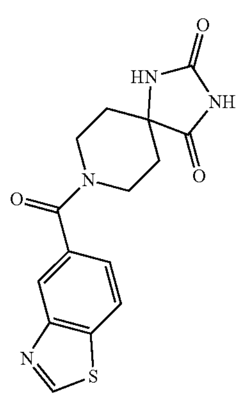 [SMILES: O=C1NC(=O)C2(CCN(C(=O)c3ccc4scnc4c3)CC2)N1] | 0.0060 |

All publications and patent applications cited in this specification are herein incorporated by reference as if each individual publication or patent application were specifically and individually indicated to be incorporated by reference.

Although the foregoing invention has been described in some detail by way of illustration and example for the purposes of clarity of understanding, it will be readily apparent to one of ordinary skill in the art in light of the teaching of this invention that certain changes and modification may be made thereto without departing from the spirit or scope of the invention as defined in the claims.

We claim:

1. A compound of formula:

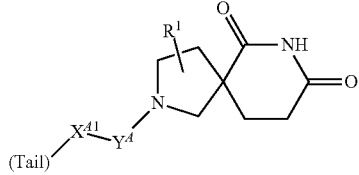

(XIV)

or a pharmaceutically acceptable salt thereof;
wherein:
$R^1$ is absent or $=O$;
$X^{A1}$ is heteroarylene;
$Y^A$ is absent or selected from the group consisting of: —C(=O)—; —C(=O)—C(H,C$_{1-6}$-alkyl)-; and —C(=O)—CH$_2$—;

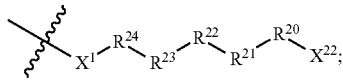

$X^1$ is selected from bond, $NR^{34}$, $CH_2$, $CHR^{34}$, $C(R^{34})_2$, O, and S;
$X^{22}$ is selected from halo, —NH$_2$, —NHR$^{34}$, —N(R$^{34}$)$_2$, hydroxyl, thiol, —B(OH)$_2$, —Sn(R$^{36}$)$_3$, —Si(R$^{36}$)$_3$, —OS(O)$_2$alkyl, —OS(O)$_2$haloalkyl, alkenyl, alkynyl, ethynyl, ethenyl, —C(O)H, —NR$^{34}$C(O)alkene, —NR$^{34}$C(O)alkyne, cyano, —SC(O)alkyl, OC(O)alkyl, heterocycle, —C(O)OH, hydrogen, alkyl, aryl, heteroaryl, aliphatic, heteroaliphatic, and carbocyclic;
$R^{34}$ and $R^{34'}$ are independently selected at each occurrence from hydrogen, C$_1$-C$_6$alkyl, C$_1$-C$_6$haloalkyl, C$_2$-C$_6$alkenyl, C$_2$-C$_6$alkynyl, C$_3$-C$_6$cycloalkyl, C$_3$-C$_6$heterocycle, aryl, heteroaryl, —(CO)R$^{36}$, —(CS)R$^{36}$, —(C=NH)R$^{36}$, —(SO)R$^{36}$, and —(SO$_2$)R$^{36}$;
$R^{36}$ is independently selected at each occurrence from hydrogen, C$_1$-C$_6$alkyl, C$_1$-C$_6$haloalkyl, C$_2$-C$_6$alkenyl, C$_2$-C$_6$alkynyl, C$_3$-C$_6$cycloalkyl, C$_3$-C$_6$heterocycle, aryl, heteroaryl, hydroxyl, C$_1$-C$_6$alkoxy, thio, C$_1$-C$_6$thioalkyl, —NH$_2$, —NH(C$_1$-C$_6$alkyl, C$_3$-C$_7$cycloalkyl, C$_3$-C$_7$heterocycle, aryl, or heteroaryl), and —N(independently C$_1$-C$_6$alkyl, C$_3$-C$_7$cycloalkyl, C$_3$-C$_7$heterocycle, aryl, or heteroaryl)$_2$;
$R^{20}$, $R^{21}$, $R^{22}$, $R^{23}$ and $R^{24}$ are independently selected from bond, alkyl, —C(O)—, —C(O)O—, —OC(O)—, —C(O)alkyl, —C(O)Oalkyl, —C(S)—, —SO$_2$—, —S(O)—, —C(S)—, —C(O)NH—, —NHC(O)—, —N(alkyl)C(O)—, —C(O)N(alkyl)-, —O—, —S—, —NH—, —N(alkyl)-, —CH(—O—R$^{26}$)—, —CH(—NR$^{34}$R$^{34'}$)—, —C(—O—R$^{26}$)alkyl-, —C(—NR$^{34}$R$^{34'}$)alkyl-, —C(R$^{40}$R$^{40}$)—, -alkyl(R$^{27}$)-alkyl(R$^{28}$)—, —C(R$^{27}$R$^{28}$)—, —P(O)(OR$^{26}$)O—, —P(O)(OR$^{26}$)—, —NR$^{34}$C(O)NR$^{34'}$—, alkene, haloalkyl, alkoxy, alkyneheteroarylalkyl, aryl, arylalkyl, heterocycle, aliphatic, heteroaliphatic, heteroaryl, lactic acid, glycolic acid, carbocycle, -(ethylene glycol)$_{1-6}$-, -(lactic-co-glycolic acid)$_{1-6}$-, -(propylene glycol)$_{1-6}$-, —O—(CH$_2$)$_{1-12}$—O—, —NH—(CH$_2$)$_{1-12}$—NH—, —NH—(CH$_2$)$_{1-12}$—O—, —O—(CH$_2$)$_{1-12}$—NH—, —S—(CH$_2$)$_{1-12}$—O—, —O—(CH$_2$)$_{1-12}$—S—, —S—(CH$_2$)$_{1-12}$—S—, —S—(CH$_2$)$_{1-12}$—NH—, and —NH—(CH$_2$)$_{1-12}$—S—;
each of which $R^{20}$, $R^{21}$, $R^{22}$, $R^{23}$, and $R^{24}$ is optionally substituted with one or more substituents selected from $R^{101}$;
wherein at least one of $R^{20}$, $R^{21}$, $R^{22}$, $R^{23}$, and $R^{24}$ is not a bond;
$R^{101}$ is independently selected at each occurrence from hydrogen, alkyl, alkene, alkyne, haloalkyl, alkoxy, hydroxyl, aryl, heteroaryl, heterocycle, arylalkyl, heteroarylalkyl, heterocycloalkyl, aryloxy, heteroaryloxy, CN, —COOalkyl, COOH, NO$_2$, F, Cl, Br, I, CF$_3$, NH$_2$, NHalkyl, N(alkyl)$_2$, aliphatic, and heteroaliphatic;
$R^{26}$ is selected from hydrogen, alkyl, silane, arylalkyl, heteroarylalkyl, alkene, alkyne, aryl, heteroaryl, heterocyclic, aliphatic and heteroaliphatic;
$R^{27}$ and $R^{28}$ are independently selected from hydrogen, alkyl, amine, or together with the carbon atom to which they are attached, form C(O), C(S), C=CH$_2$, a C$_3$-C$_6$ spirocarbocycle, or a 4-, 5-, or 6-membered spiroheterocycle comprising 1 or 2 heteroatoms selected from N and O, or form a 1 or 2 carbon bridged ring; and
$R^{40}$ is selected at each instance from: hydrogen, alkyl, alkene, alkyne, halogen, hydroxyl, alkoxy, azide, amino, cyano, —NH(aliphatic), —N(aliphatic)$_2$, —NHSO$_2$(aliphatic), —N(aliphatic)SO$_2$alkyl, —NHSO$_2$(aryl, heteroaryl or heterocyclic), —N(alkyl)SO$_2$(aryl, heteroaryl or heterocyclic) —NHSO$_2$alkenyl, —N(alkyl)SO$_2$alkenyl, —NHSO$_2$alkynyl, —N(alkyl)SO$_2$alkynyl, haloalkyl, aliphatic, heteroaliphatic, aryl, heteroaryl, heteroalkyl, heterocyclic, and carbocyclic.

2. The compound of claim 1, wherein the compound is of the formula:

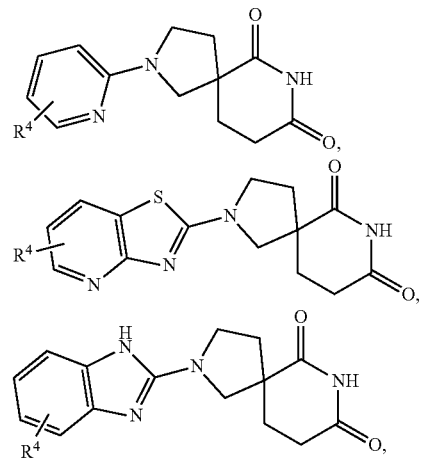

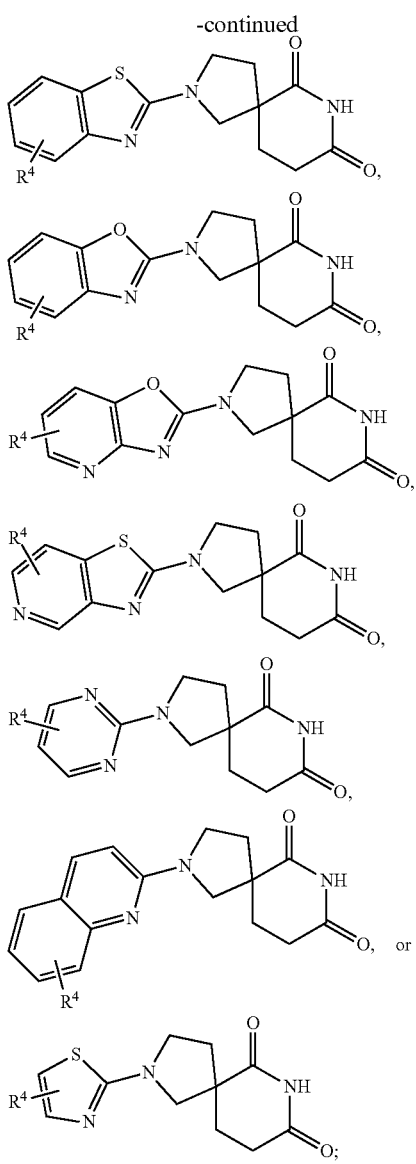

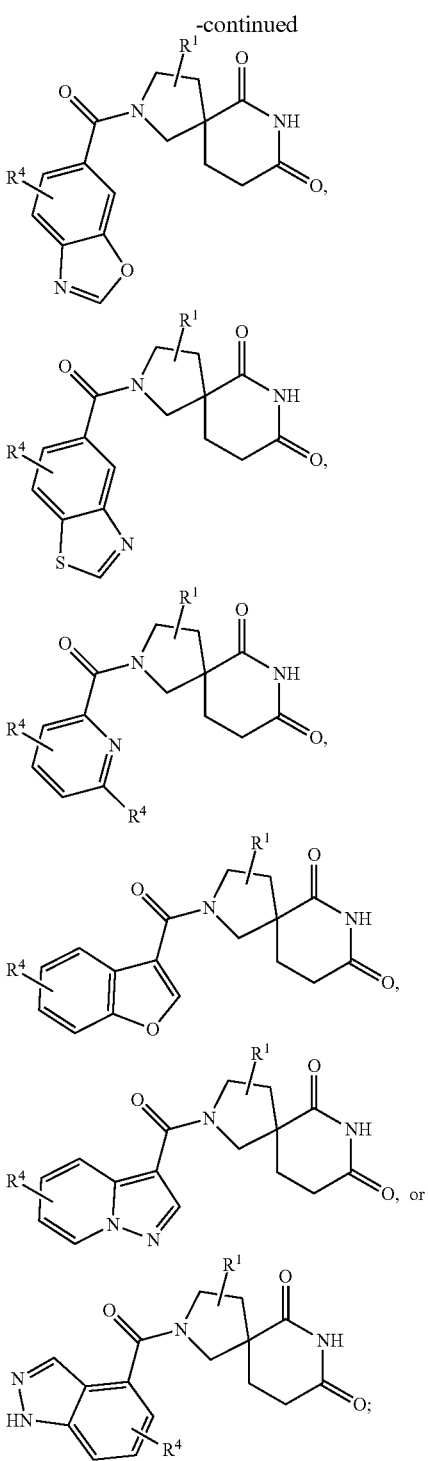

wherein
R⁴ is selected from the group consisting of —C(=O)—O—C$_{1-6}$-alkyl; C$_{1-6}$alkyl; —NH$_2$; and —NH—C(=O)—C$_{1-6}$-alkyl;
or a pharmaceutically acceptable salt thereof.

3. The compound of claim 1, wherein the compound is of the formula:

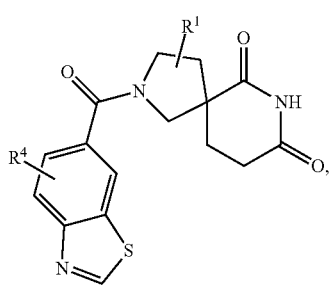

wherein
R⁴ is selected from the group consisting of —C(=O)—O—C$_{1-6}$-alkyl; C$_{1-6}$alkyl; —NH$_2$; and —NH—C(=O)—C$_{1-6}$-alkyl;
or a pharmaceutically acceptable salt thereof.

4. The compound of claim 2, wherein R⁴ is —C(=O)—OCH$_3$, —NHC(=O)CH$_3$, or —C(=O)—OC(CH$_3$)$_3$.

5. The compound of claim 2, wherein R⁴ is —NH$_2$, or —C(=O)—O—C$_{1-6}$-alkyl.

6. The compound of claim 2, wherein R⁴ is C$_{1-6}$-alkyl or —NH—C(=O)—C$_{1-6}$-alkyl.

7. The compound of claim 3, wherein $R^4$ is $-NH_2$, or $-C(=O)-O-C_{1-6}$-alkyl.
8. The compound of claim 3, wherein $R^4$ is $C_{1-6}$-alkyl or $-NH-C(=O)-C_{1-6}$-alkyl.
9. The compound of claim 1 selected from:
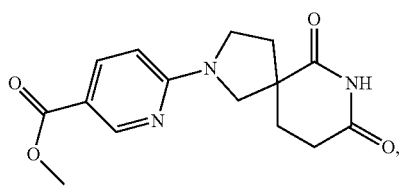
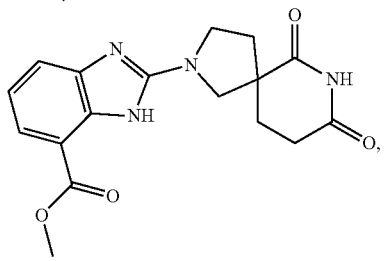
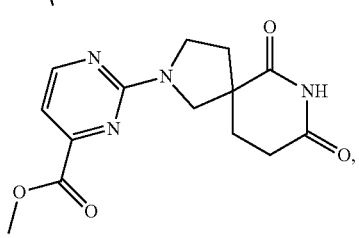
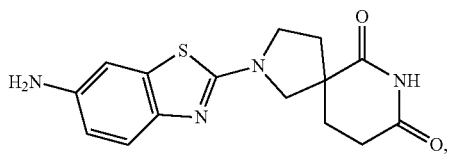
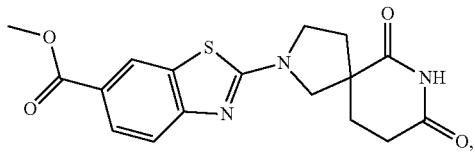
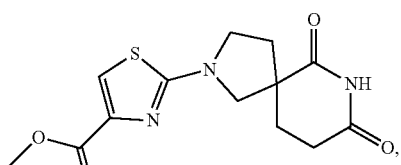
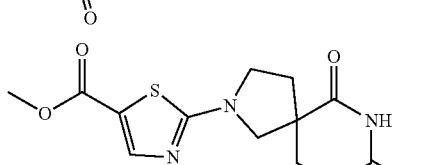
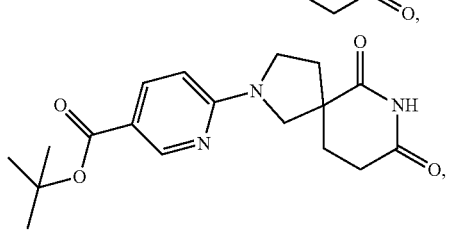
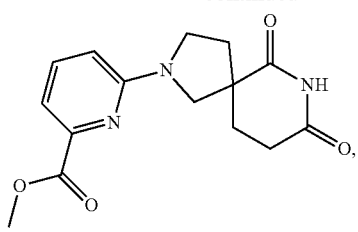
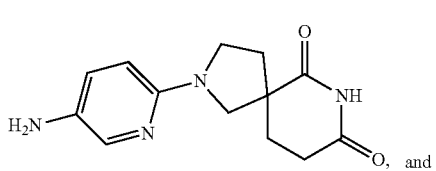
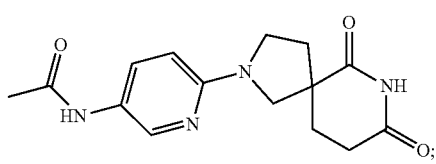
or a pharmaceutically acceptable salt thereof.
10. The compound of claim 1, wherein the compound is selected from:
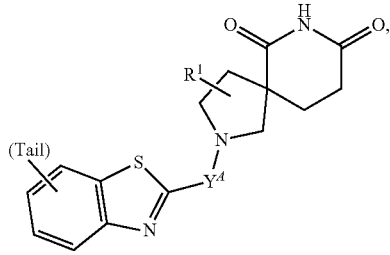
(XIV-d)
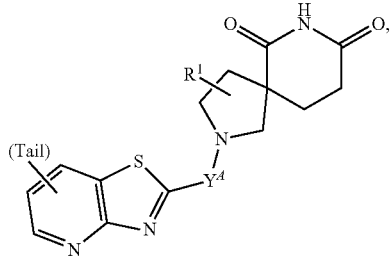
(XIV-e)
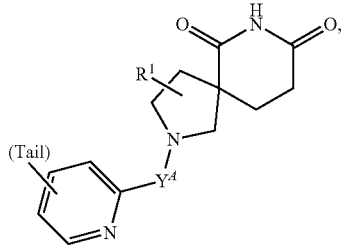
(XIV-f)

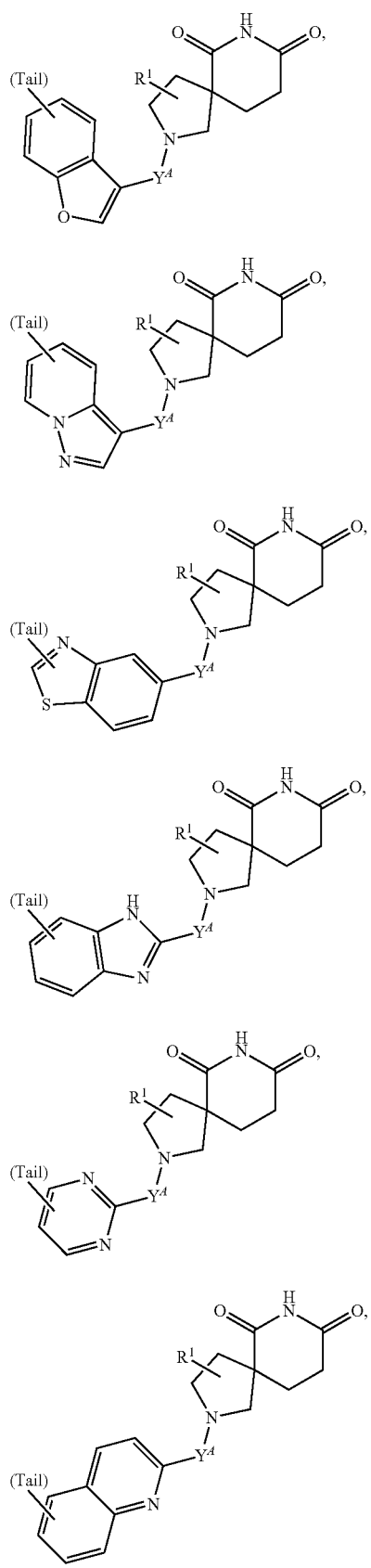
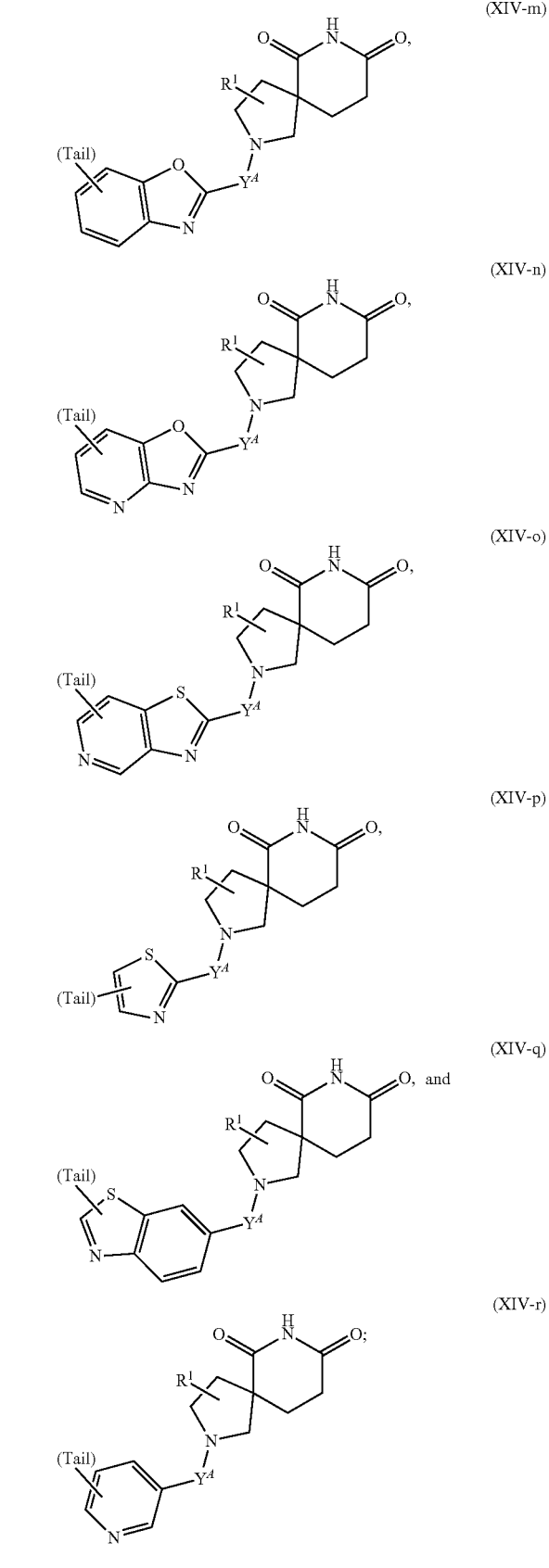
or a pharmaceutically acceptable salt thereof.

11. A pharmaceutical composition comprising an effective amount of a compound of claim 1, or a pharmaceutically acceptable salt thereof, in a pharmaceutically acceptable carrier.

* * * * *